(12) United States Patent
Fleischmann et al.

(10) Patent No.: US 6,355,450 B1
(45) Date of Patent: Mar. 12, 2002

(54) **COMPUTER READABLE GENOMIC SEQUENCE OF *HAEMOPHILUS INFLUENZAE* RD, FRAGMENTS THEREOF, AND USES THEREOF**

(75) Inventors: Robert D. Fleischmann, Gaithersburg; Mark D. Adams, N. Potomac; Owen White, Gaithersburg; Hamilton O. Smith, Towson; J. Craig Venter, Potomac, all of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 08/476,102

(22) Filed: Jun. 7, 1995

Related U.S. Application Data

(63) Continuation-in-part of application No. 08/426,787, filed on Apr. 21, 1995, now abandoned.

(51) Int. Cl.$^7$ .......................... C12P 21/06; C12N 1/20; C12N 15/00; C07H 21/04

(52) U.S. Cl. ................ 435/69.1; 435/252.3; 435/320.1; 435/851; 536/23.1; 536/23.7; 536/24.32; 536/24.33

(58) Field of Search .............................. 536/23.1, 23.7, 536/24.3, 24.32, 24.33; 435/69.1, 320.1, 252.3, 851

(56) References Cited

U.S. PATENT DOCUMENTS

| | | | |
|---|---|---|---|
| 5,064,754 A | 11/1991 | Mills | 435/6 |
| 5,202,231 A | 4/1993 | Drmanac et al. | 435/6 |
| 5,219,726 A | 6/1993 | Evans | 435/6 |
| 5,288,644 A | 2/1994 | Beavis et al. | 436/94 |

FOREIGN PATENT DOCUMENTS

| | | |
|---|---|---|
| CA | 2182046 | 1/1998 |
| EP | 0378929 A2 | 7/1990 |
| WO | 93/12230 | 6/1993 |
| WO | 93/19090 | 9/1993 |
| WO | 94/12641 | 6/1994 |
| WO | 9700697 | 1/1997 |
| WO | 9701638 | 1/1997 |
| WO | 9736914 | 1/1997 |

OTHER PUBLICATIONS

Cope, L. D. et al., "A Gene Cluster Involved in the Utilization of Both Free Heme and Heme:Hemopexin by *Haemophilus influenzae* Type B," *J. Bacteriol.* 177(10):2644–2653 (May 1995).

Cope, L. D. et al., "A Gene Cluster Involved in the Utilization of Both Free Heme and Heme:Hemopexin by *Haemophilus influenzae* type B," nucleotide sequence from Nucleotide Database on ENTREZ Release 15.0, published on CD–ROM by National Center for Biotechnology Information, National Library of Medicine, National Institutes of Health, Bethesda, MD (Feb. 1995).

Fleischmann, R. D. et al., "Whole–Genome Random Sequencing and Assembly of *Haemophilus influenzae* Rd," *Science* 269:496–512 (Jul. 1995).

Sanders, J. D. et al., "Identification of a Locus Involved in the Utilization of Iron by *Haemophilus influenzae*," *Infect. Immun.* 62(10):4515–4525 (Oct. 1994).

Watson, J. D. et al., eds., "Recombinant DNA in Medicine and Industry," in: *Recombinant DNA*, Second Edition, New York: Scientific American Books, W. H. Freeman and Company, pp. 453–470 (1992).

Weiser, J. N. et al., "Identification and characterization of oapA, a cell–envelope protein of *Haemophilus influenzae* contributing to phase variation in colony opacity and nasopharyngeal colonization," nucleotide sequence from Nucleotide Database on ENTREZ Release 15.0, published on CD–ROM by National Center for Biotechnology Information, National Library of Medicine, National Institutes of Health, Bethesda, MD (Feb. 1995).

International Search Report for PCT/US96/05320, mailed Aug. 27, 1996.

Adams et al., "A model for high–throughput automated DNA sequencing and analysis core facilities," *Nature* 368:474–475 (Mar. 31, 1994).

Bankier et al., "The DNA sequence of the human cytomegalovirus genome," *DNA Sequence—J. DNA Sequencing and Mapping* 2:1–12 (1991).

Goebel et al., "The Complete DNA Sequence of Vaccinia Virus," *Virology* 179:247–266 (1990).

Kauc et al., "Size and Physical Map of the Chromosome of *Haemophilus influenzae*," *J Bacteriol.* 171:2474–2479 (1989).

Lee et al., "Organization of the *Haemophilus influenzae* Rd Genome," *J Bacteriol.* 171:3016–3024 (1989).

Lee and Smith, "Sizing of the *Haemophilus influenzae* Rd Genome by Pulsed–Field Agarose Gel Electrophoresis," *J. Bacteriol.* 170(9):4402–4405 (1988).

Levy, J., "Sequencing the Yeast Genome: An International Achievement," *Yeast* 10:1689–1706 (Dec. 1994).

(List continued on next page.)

*Primary Examiner*—Bruce R. Campell

(57) ABSTRACT

The present invention provides the sequencing of the entire genome of *Haemophilus influenzae* Rd, SEQ ID NO: 1. The present invention further provides the sequence information stored on computer readable media, and computer-based systems and methods which facilitate its use. In addition to the entire genomic sequence, the present invention identifies over 1700 protein encoding fragments of the genome and identifies, by position relative to a unique Not I restriction endonuclease site, any regulatory elements which modulate the expression of the protein encoding fragments of the *Haemophilus* genome.

88 Claims, 47 Drawing Sheets

OTHER PUBLICATIONS

Nowak, R., "Genome Research: Venter Wins Sequencing Race–Twice," *Science 268*:1273 (Jun. 2, 1995).

Oda et al., "Gene Organization Deduced from the complete sequence of Liverwort *Marchantia polymorpha* Mitochondrial DNA," *J. Mol. Biol. 223*:1–7 (1992).

Ohyama et al., "Chloroplast gene organization deduced from the complete sequence of liverwort *Marchantia polymorpha* chloroplast DNA," *Nature 322*:572–574 (1986).

Redfield and Lee, "*Haemophilus influenzae* Rd," in Genetic Maps: Locus Maps of Complex Genomes, Fifth Edition, O'Brien, ed. Cold Springs Harbor Laboratory Press, New York, pp. II110–II112 (1990).

Sulston et al., "The *C. elegans* genome sequencing project: a beginning," *Nature 356*:37–41 (1992).

JF Tomb et al (1989) J Bacteriology 171: 3796–3802.

L Kauc et al (Dec. 1989) J Bacteriology 171: 6625–6628.

L Kauc et al (May 1989) J Bacteriology 171: 2474–2479.

RS Munson et al (1993) Infection and Immunity 61:4017–4020.

J Won et al (1993) Infection and Immunity 61: 2813–2821.

J. Weiser et al (1989) Cell 59: 657–665.

R Munson et al (1989) Infection and Immunity 57: 3300–3305.

RA Deich et al (1988) J Bacteriology 170: 489–498.

HAEMOPHILUS INFLUENZAE

COMPUTER READABLE GENOMIC SEQUENCE OF *HAEMOPHILUS INFLUENZAE* RD, FRAGMENTS THEREOF, AND USES THEREOF

CROSS REFERENCE TO RELATED APPLICATIONS

This application is a continuation-in-part of application Ser. No. 08/426,787, filed Apr. 21, 1995, abandoned which is hereby incorporated by reference.

Part of the work performed during development of this invention utilized U.S. Government funds. The government may have certain rights to this invention. NIH-5RO1GM48251.

FIELD OF THE INVENTION

The present invention relates to the field of bioinformatics. The present invention discloses the genomic sequence (the entire life-sustaining instructions and information) of *Haemophilus influenzae* Rd recorded on a computer readable medium, as well as computer-based systems and methods that employ said sequence.

BACKGROUND OF THE INVENTION

The complete genome sequence from a free living cellular organism has never been determined. The first mycobacterium sequence should be completed by 1996, while *E. coli* and *S. cervadase* are expected to be completed before 1998. These are being done by random and/or directed sequencing of overlapping cosmid clones. No one has attempted to determine sequences of the order of a megabase or more by a random shotgun approach.

*H. influenzae* is a small (approximately 0.4×1 micron) non-motile, non-spore forming, germ-negative bacterium whose only natural host is human. It is a resident of the upper respiratory mucosa of children and adults and causes otitis media and respiratory tract infections mostly in children. The most serious complication is meningitis, which produces neurological sequelae in up to 50% of affected children. Six *H. influenzae* serotypes (a through f) have been identified based on immunologically distinct capsular polysaccharide antigens. A number of non-typeable strains are also known. Serotype b accounts for the majority of human disease.

Interest in the medically important aspects of *H. influenzae* biology has focused particularly on those genes which determine virulence characteristics of the organism. A number of the genes responsible for the capsular polysaccharide have been mapped and sequenced (Kroll et al., *Mol. Microbiol*, 5(6):1549–1560 (1991)). Several outer membrane protein (OMP) genes have been identified and sequenced (Langford et al., *J. Gen. Microbiol.* 138:155–159 (1992)). The lipoligosaccharide (LOS) component of the outer membrane and the genes of its synthetic pathway are under intensive study (Weiser et al., *J. Bacteriol.* 172:3304–3309 (1990)). While a vaccine has been available since 1984, the study of outer membrane components is motivated to some extent by the need for improved vaccines. Recently, the catalase gene was characterized and sequenced as a possible virulene-related gene (Bishni et al., in press). Elucidation of the *H. influenzae* genome will enhance the understanding of how *H. influenzae* causes invasive disease and how best to combat infection.

*H. influenzae* possesses a highly efficient natural DNA transformation system which has been intensively studied in the non-encapsulated (R), serotype d strain (Kahn and Smith, *J. Membrane Biology* 81:89–103 (1984)). At least 16 transformation-specific genes have been identified and sequenced. Of these, four are regulatory (Redfield, *J. Bacteriol.* 173:5612–5618 (1991), and Chandler, *Proc. Natl. Acad. Sci. USA* 89:1626–1630 (1992)), at least two are involved in recombination processes (Barouki and Smith, *J. Bacteriol.* 163(2):629–634 (1985)), and at least seven are targeted to the membranes and periplasmic space (Tomb, et al., *Gene* 104:1–10 (1991), and Tomb, *Proc. Natl. Acad. Sci. USA* 89:1025–10256 (1992)), where they appear to function as structural components or in the assembly of the DNA transport machinery. *H. influenzae* Rd transformation shows a number of interesting features including sequence-specific DNA uptake, rapid uptake of several double-stranded DNA molecules per competent cell into a membrane compartment called the transformasome, linear translocation of a single strand of the donor DNA into the cytoplasm, and synapsis and recombination of the strand with the chromosome by a single-strand displacement mechanism. The *H. influenzae* Rd transformation system is the most thoroughly studied of the gram-negative systems and distinct in a number of ways from the gram-positive systems.

The size of *H. influenzae* Rd genome has been determined by pulsed-field agarose gel electrophoresis of restriction digests to be approximately 1.9 Mb, making its genome approximately 40% the size of *E. coli* (Lee and Smith, *J. Bacteriol.* 170:4402–4405 (1988)). The restriction map of *H. influenzae* is circular (Lee et al., *J. Bacteriol.* 171:3016–3024 (1989), and Redfield and Lee, "*Haemophilus influenzae* Rd", pp. 2110–2112, In O'Brien, S. J. (ed), Genetic Maps: Locus Maps of Complex Genomes, Cold Spring Harbor Press, New York). Various genes have been mapped to restriction fragments by Southern hybridization probing of restriction digest DNA bands. This map will be valuable in verification of the assembly of a complete genome sequence from randomly sequenced fragments. GenBank currently contains about 100 kb of non-redundant *H. influenzae* DNA sequences. About half are from serotype b and half from Rd.

SUMMARY OF THE INVENTION

The present invention if based on the sequencing of the *Haemophilus influenzae* Rd genome. The primary nucleotide sequence which was generated is provided in SEQ ID NO: 1.

The present invention provides the generated nucleotide sequence of the *Haemophilus influenzae* Rd genome, or a representative fragment thereof, in a form which can readily used, analyzed, and interpreted by a skilled artisan. In one embodiment, present invention is provided as a contiguous string of primary sequence information corresponding to the nucleotide sequence depicted in SEQ ID NO: 1.

The present invention further provides nucleotide sequences which are at least 99.9% identical to the nucleotide sequence of SEQ ID NO: 1.

The nucleotide sequence of SEQ ID NO: 1, a representative fragment thereof, or a nucleotide sequence which is at least 99.9% identical to the nucleotide sequence of SEQ ID NO: 1 may be provided in a variety of mediums to facilitate its use. In one application of this embodiment, the sequences of the present invention are recorded on computer readable media. Such media includes, but is not limited to: magnetic storage media, such as floppy disc, hard disc storage medium, and magnetic tape; optical storage media such as CD-ROM; electrical storage media such as RAM and ROM; and hybrids of these categories such as magnetic/optical storage media.

The present invention further provides systems, particularly computer-based systems which contain the sequence information herein described stored in a data storage means. Such systems are designed to identify commercially important fragments of the *Haemophilus influenzae* Rd genome.

Another embodiment of the present invention is directed to isolated fragments of the *Haemophilus influenzae* Rd genome. The fragments of the *Haemophilus influenzae* Rd genome of the present invention include, but are not limited to, fragments which encode peptides, hereinafter open reading frames (ORFs), fragments which modulate the expression of an operably linked ORF, hereinafter expression modulating fragments (EMFs), fragments which mediate the uptake of a linked DNA fragment into a cell, hereinafter uptake modulating fragments (UMFs), and fragments which can be used to diagnose the presence of *Haemophilus influenzae* Rd in a sample, hereinafter, diagnostic fragments (DFs).

Each of the ORF fragments of the *Haemophilus influenzae* Rd genome disclosed in Tables 1(a) and 2, and the EMF found 5' to the ORF, can be used in numerous ways as polynucleotide reagents. The sequences can be used as diagnostic probes or diagnostic amplification primers for the presence of a specific microbe in a sample, for the production of commercially important pharmaceutical agents, and to selectively control gene expression.

The present invention further includes recombinant constructs comprising one or more fragments of the *Haemophilus influenzae* Rd genome of the present invention. The recombinant constructs of the present invention comprise vectors, such as a plasmid or viral vector, into which a fragment of the *Haemophilus influenzae* Rd has been inserted.

The present invention further provides host cells containing any one of the isolated fragments of the *Haemophilus influenzae* Rd genome of the present invention. The host cells can be a higher eukaryotic host such as a mammalian cell, a lower eukaryotic cell such as a yeast cell, or can be a procaryotic cell such as a bacterial cell.

The present invention is further directed to isolated proteins encoded by the ORFs of the present invention. A variety of methodologies known in the art can be utilized to obtain any one of the proteins of the present invention. At the simplest level, the amino acid sequence can be synthesized using commercially available peptide synthesizers. In an alternative method, the protein is purified from bacterial cells which naturally produce the protein. Lastly, the proteins of the present invention can alternatively be purified from cells which have been altered express the desired protein.

The invention further provides methods of obtaining homologs of the fragments of the *Haemophilus influenzae* Rd genome of the present invention and homologs of the proteins encoded by the ORFs of the present invention. Specifically, by using the nucleotide and amino acid sequences disclosed herein as a probe or as primers, and techniques such as PCR cloning an colony/plaque hybridization, one skilled in the art can obtain homologs.

The invention further provides antibodies which selectively bind one of the proteins of the present invention. Such antibodies include both monoclonal and polyclonal antibodies.

The invention further provides hybridomas which produce the above-described antibodies. A hybridization is an immortalized cell line which is capable of secreting a specific monoclonal antibody.

The present invention further provides methods of identifying test samples derived from cells which express one of the ORF of the present invention, or homolog thereof. Such methods comprise incubating a test sample with one or more of the antibodies of the present invention, or one or more of the DFs of the present invention, under conditions which allow a skilled artisan to determine if the sample contains the ORF or product produced therefrom.

In another embodiment of the present invention, kits are provided which contain the necessary reagents to carry out the above-described assays.

Specifically, the invention provides a compartmentalized kit to receive, in close confinement, one or more containers which comprises: (a) a first container comprising one of the antibodies, or one of the DFs of the present invention; and (b) one or more other containers comprising one or more of the following: wash reagents, reagents capable of detecting presence of bound antibodies or hybridized DFs.

Using the isolated proteins of the present invention, the present invention further provides methods of obtaining and identifying agents capable of binding to a protein encoded by one of the ORFs of the present invention. Specifically, such agents include antibodies (described above), peptides, carbohydrates, pharmaceutical agents and the like. Such methods comprise the steps of:

(a) contacting an agent with an isolated protein encoded by one of the ORFs of the present invention; and (b) determining whether the agent binds to said protein.

The complete genomic sequence of *H. influenzae* will be of great value to all laboratories working with this organism and for a variety of commercial purposes. Many fragments of the *Haemophilus influenzae* Rd genome will be immediately identified by similarly searches against GenBank or protein databases and will be of immediate value to *Haemophilus* researchers and for immediate commercial value for the production of proteins or to control gene expression. A specific example concerns PHA synthase. It has been reported that polyhydroxybutyrate is present in the membrane of *Haemophilus influenzae* Rd and that the amount correlates with the level of competence for transformation. The PHA synthase that synthesizes this polymer has been identified and sequenced in a number of bacteria, none of which are evolutionarily close to *H. influenzae*. This gene has yet to be isolated from *Influenzae* by use of hybridization probes or PCR techniques. However, the genomic sequence of the present invention allows the identification of the gene by utilizing search means described below.

Developing the methodology and technology for elucidating the entire genomic sequence of bacterial and other small genomes has and will greatly enhance the ability to analyze and understand chromosomal organization. In particular, sequenced genomes will provide the models for developing tools for the analysis of chromosome structure and function, including the ability to identify genes within large segments of genomic DNA, the structure, position, and spacing of regulatory elements, the identification of genes with potential industrial applications, and the ability to do comparative genomic and molecular phylogeny.

DETAILED DESCRIPTION OF THE PREFERRED EMBODIMENTS

Figure 1:
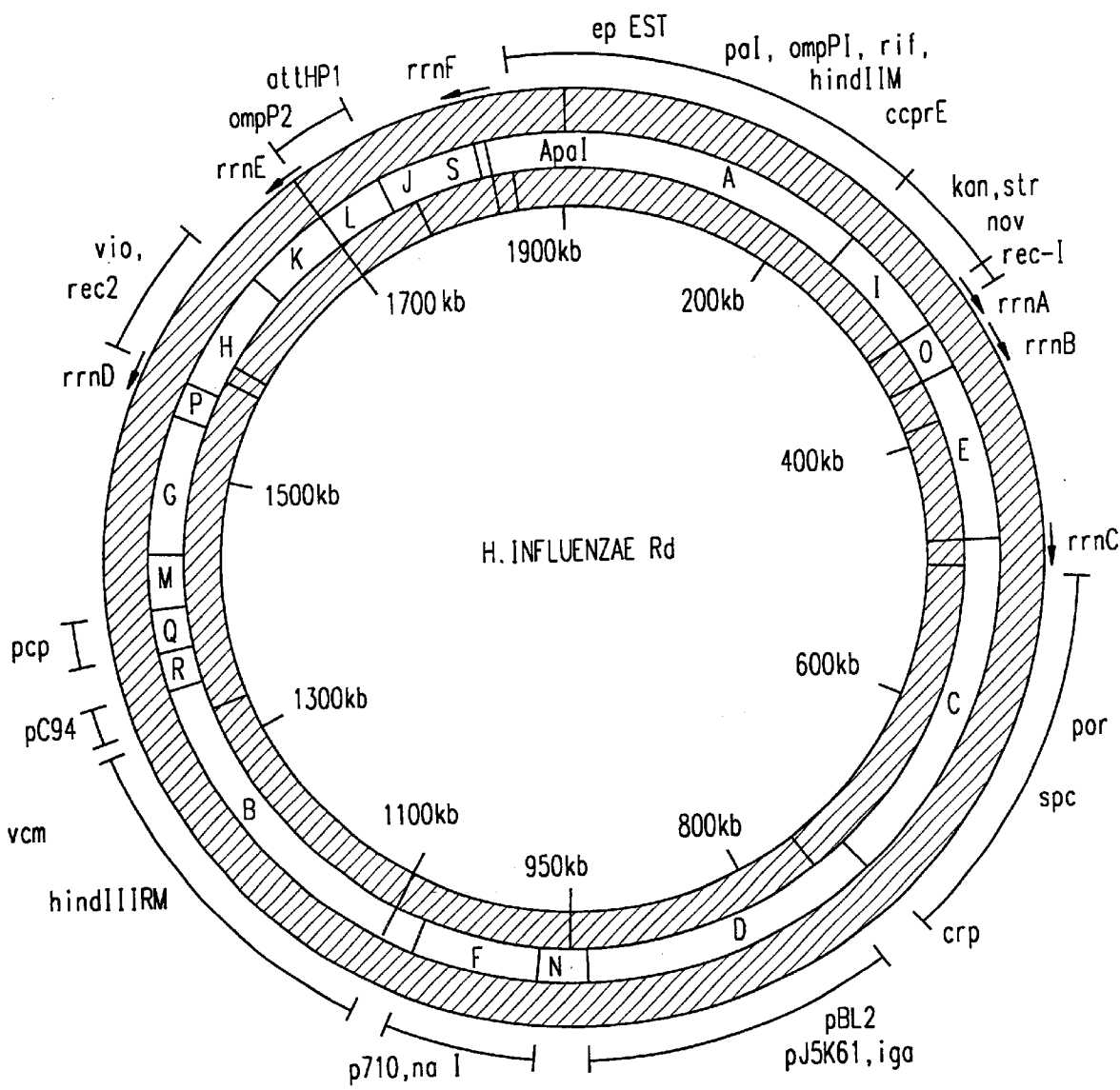
FIG. 1—restriction map of the *Haemophilus influenzae* Rd genome.

The present invention is based on the sequencing of the *H. influenzae* Rd genome. The primary nucleotide sequence which was generated is provided in SEQ ID NO: 1. As used herein, the "primary sequence" refers to the nucleotide sequence represented by the IUPAC nomenclature system.

The sequence provided in SEQ ID NO: 1 is oriented relative to a unique Not I restriction endonuclease site found in the *H. influenzae* Rd genome. A skilled artisan will readily recognize that this start/stop point was chosen for convenience and does not reflect a structural significance.

The present invention provides the nucleotide sequence of SEQ ID NO: 1, or a representative fragment thereof, in a form which can be readily used, analyzed, and interpreted by a skilled artisan. In one embodiment, the sequence is provided as a contiguous string of primary sequence information corresponding to the nucleotide sequence provided in SEQ ID NO: 1.

As used herein, a "representative fragment of the nucleotide sequence depicted in SEQ ID NO: 1" refers to any portion of SEQ ID NO: 1 which is not presently represented within a publicly available database. Preferred representative fragments of the present invention are *Haemophilus influenzae* open reading frames, expression modulating fragments, uptake modulating fragments, and fragments which can be used to diagnose the presence of *Haemophilus influenzae* Rd in sample. A non-limiting identification of such preferred representative fragments is provided in Tables 1(*a*) and and 2.

The nucleotide sequence information provided in SEQ ID NO: 1 was obtained by sequencing the *Haemophilus influenzae* Rd genome using a megabase shotgun sequencing method. Using three parameters of accuracy discussed in the Examples below, the present inventors have calculated that the sequence in SEQ ID NO: 1 has a maximum accuracy of 99.98%. Thus, the nucleotide sequence provided in SEQ ID NO: 1 is a highly accurate, although not necessarily a 100% perfect, representation of the nucleotide sequence of the *Haemophilus influenzae* Rd genome.

As discussed in detail below, using the information provided in SEQ ID NO: 1 and in Tables 1(a) and 2 together with routine cloning and sequencing methods, one of ordinary skill in the art will be able to clone and sequence all "representative fragments" of interest including open reading frames (ORFs) encoding a large variety of *Haemophilus influenzae* proteins. In very rare instances, this may reveal a nucleotide sequence error present in the nucleotide sequence disclosed in SEQ ID NO: 1. Thus, once the present invention is made available (i.e., once the information in SEQ ID NO: 1 and Tables 1(a) and 2 have been made available), resolving a rare sequencing error in SEQ ID NO: 1 will be well within the skill of the art. Nucleotide sequence editing software is publicly available. For example, Applied Biosystem's (AB) AutoAssembler™ can be used as an aid during visual inspection of nucleotide sequences.

Even if all of the very rare sequencing errors in SEQ ID NO: 1 were corrected, the resulting nucleotide sequence would still be at least 99.9% identical to the nucleotide sequence in SEQ ID NO: 1.

The nucleotide sequences of the genomes from different strains of *Haemophilus influenzae* differ slightly. However, the nucleotide sequence of the genomes of all *Haemophilus influenzae* strains will be at least 99.9% identical to the nucleotide sequence provided in SEQ ID NO: 1.

Thus, the present invention further provides nucleotide sequences which are at least 99.9% identical to the nucleotide sequence of SEQ ID NO: 1 in a form which can be readily used, analyzed and interpreted by the skilled artisan. Methods for determining whether a nucleotide sequence is at least 99.9% identical to the nucleotide sequence of SEQ ID NO: 1 are routine and readily available to the skilled artisan. For example, the well known fasts algorithm (Pearson and Lipman, *Proc. Natl. Acad. Sci. USA* 85:2444 (1988)) can be used to generate the percent identity of nucleotide sequences.

Computer Related Embodiments

The nucleotide sequence provided in SEQ ID NO: 1, a representative fragment thereof, or a nucleotide sequence at least 99.9% identical to SEQ ID NO: 1 may be "provided" in a variety of mediums to facilitate use thereof. As used herein, provided refers to a manufacture, other than an isolated nucleic acid molecule, which contains a nucleotide sequence of the present invention, i.e., the nucleotide sequence provided in SEQ ID NO: 1, a representative fragment thereof, of a nucleotide sequence at least 99.9% identical to SEQ ID NO: 1. Such a manufacture provides the *Haemophilus influenzae* Rd genome or a subset thereof (e.g., a *Haemophilus influenzae* Rd open reading frame (ORF)) in a form which allows a skilled artisan to examine the manufacture using means not directly applicable to examining the *Haemophilus influenzae* Rd genome or a subset thereof as it exists in nature or in purified form.

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCH file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NO: 1, a representative fragment thereof, or a nucleotide sequence at least 99.9% identical to SEQ ID NO: 1 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altaschul et al., *J. Mol. Biol.* 215:403–410 (1990)) and BLAZE (Brutlag et al., *Comp. Chem.* 17:203–207 (1993)) search algorithms on a Sybase system was used to identify open reading frames (ORFs) within the *Haemophilus influenzae* Rd genome which contain homology to ORFs or proteins from other organisms. Such ORFs are protein encoding fragments within the *Haemophilus influenzae* Rd genome and are useful in producing commercially important proteins such as enzymes and in fermentation sections and in the production of commercially useful metabolites.

The present invention further provides systems, particularly computer-based systems, which consists the sequence information described herein. Such systems are designed to identify commercially important fragments of the *Haemophilus influenzae* Rd genome.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of the *Haemophilus influenzae* Rd genome which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA). A skilled artisan can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments of the *Haemophilus influenzae* Rd genome, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymic active sites and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the *Haemophilus influenzae* Rd genome possessing varying degrees of homology to the target sequence or target motif. Such presentation provides skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the *Haemophilus influenzae* Rd genome. In the present examples, implementing software which implement the BLAST and BLAZE algorithms (Altschul et al., *J. Mol. Biol.* 215:403–410 (1990)) was used to identify open reading frames within the *Haemophilus influenzae* Rd genome. A skilled artisan can readily recognize that any one of the publicly available homology search programs can be used as the search means for the computer-based systems of the present invention.

Figure 2:
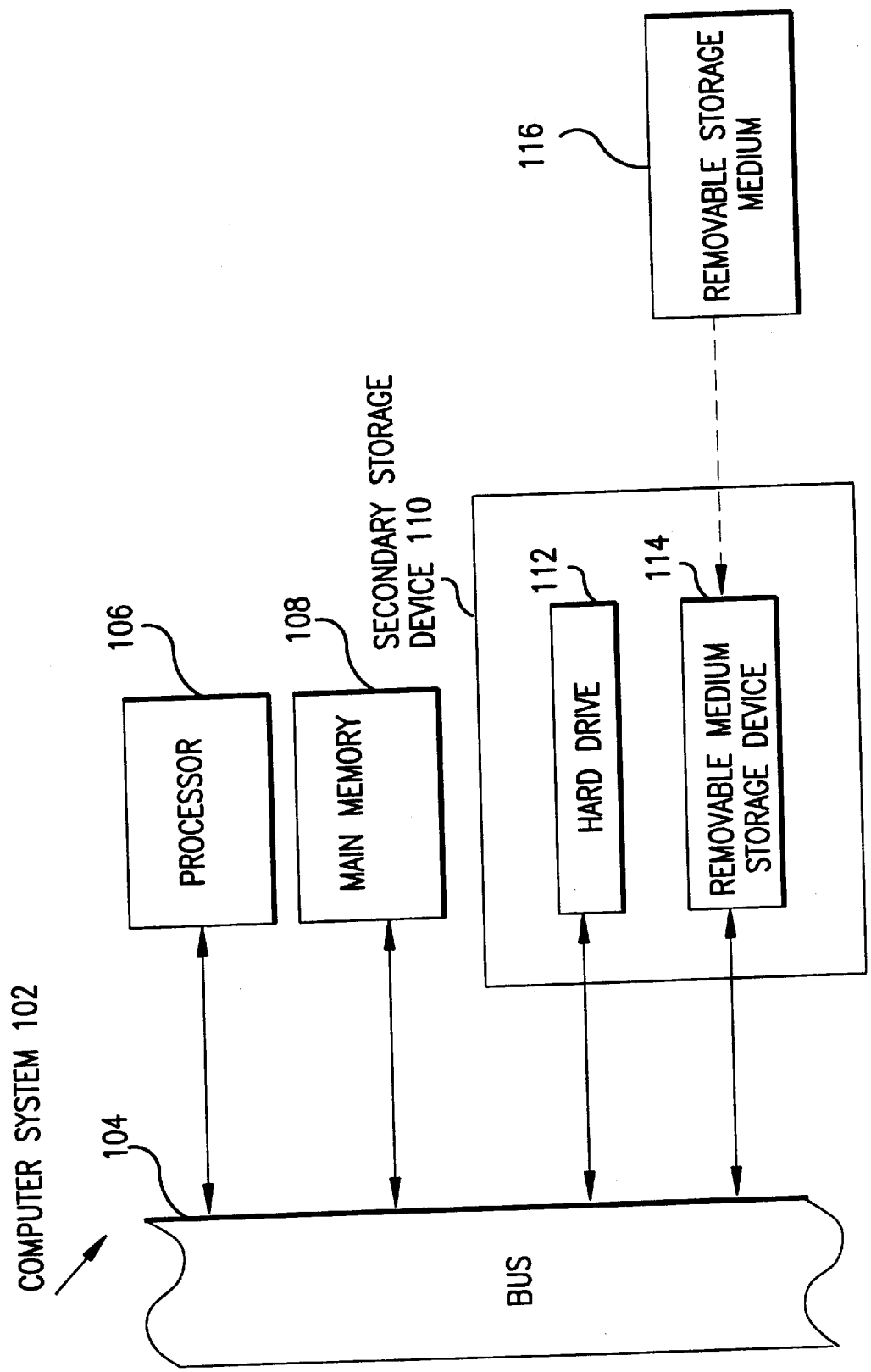
FIG. 2—Block diagram of a computer system 102 that can be used to implement the computer-based systems of present invention.

One application of this embodiment is provided in FIG. 2. FIG. 2 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, and magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114 once inserted in the removable medium storage device 114.

A nucleotide sequence of the present invention may be stored in a well known manner in the main memory 108, any of the secondary storage device 110, and/or a removable storage medium 116. Software for accessing and processing the genomic sequence (such as search tools, comparing tools, etc.) reside in main memory 108 during execution.

Biochemical Embodiments

Another embodiment of the present invention is directed to isolated fragments of the *Haemophilus influenzae* Rd genome. The fragments of the *Haemophilus influenzae* Rd genome of the present invention include, but are not limited to fragments which encode peptides, hereinafter open reading frames (ORFs), fragments which modulate the expression of an operably linked ORF, hereinafter expression modulating fragments (EMFs), fragments which mediate the uptake of a linked DNA fragment into a cell, hereinafter uptake modulating fragments (UMFs), and fragments which can be used to diagnose the presence of *Haemophilus influenzae* Rd in a sample, hereinafter diagnostic fragments (DFs).

As used herein, an "isolated nucleic acid molecule" or an "isolated fragment of the *Haemophilus influenzae* Rd genome" refers to a nucleic acid molecule possessing a specific nucleotide sequence which has been subjected to purification means to reduce, from the composition, the number of compounds which are normally associated with the composition. A variety of purification means can be used to generated the isolated fragments of the present invention. These include, but are not limited to methods which separate constituents of a solution based on charge, solubility, or size.

In one embodiment, *Haemophilus influenzae* Rd DNA can be mechanically sheared to produce fragments of 15–20 kb in length. These fragments can then be used to generate an *Haemophilus influenzae* Rd library by inserting them into labda clones as described in the Examples below. Primers flanking, for example, an ORF provided in Table 1(a) can then be generated using nucleotide sequence information provided in SEQ ID NO:1. PCR cloning can then be used to isolate the ORF from the lambda DNA library. PCR cloning is well known in the art. Thus, given the availability of SEQ ID NO:1, Table 1(a) and Table 2, it would be routine to isolate any ORF or other nucleic acid fragment of the present invention.

The isolated nucleic acid molecules of the present invention include, but are not limited to single stranded and double stranded DNA, and single stranded RNA.

As used herein, an "open reading frame," ORF, means a series of triplets coding for amino acids without any termination codons and is a sequence translatable into protein. Tables 1a, 1b and 2 identify ORFs in the *Haemophilus influenzae* Rd genome. In particular, Table 1a indicates the location of ORFs within the *Haemophilus influenzae* genome which encode the recited protein based on homology matching with protein sequences from the organism appearing in parentheticals (see the fourth column of Table 1(a)).

The first column of Table 1(a) provides the "GeneID" of a particular ORF. This information is useful for two reasons. First, the complete map of the *Haemophilus influenzae* Rd genome provided in FIGS. 6A–6N refers to the ORFs according to their geneID numbers. Second, Table 1(b) uses the GeneID numbers to indicate which ORFs were provided previously in a public database.

The second and third columns in Table 1(a) indicate an ORFs position in the nucleotide sequence provided in SEQ ID NO:1. One of ordinary skill will recognize that ORFs may be oriented in opposite directions in the *Haemophilus influenzae* genome. This is reflected in columns 2 and 3.

The fifth column of Table 1(a) indicates the percent identity of the protein encoded for by an ORF to the corresponding protein from the organism appearing in parentheticals in the fourth columns.

The sixth column of Table 1(a) indicates the percent similarity of the protein encoded for by an ORF to the corresponding protein from the organism appearing in parentheticals in the fourth column. The concepts of percent identity and percent similarity of two polypeptide sequences is well understood in the art. For example, two polypeptides 10 amino acids in length which differ at three amino acid positions (e.g., at positions 1, 3 and 5) are said to have a percent identity of 70%. However, the name two polypeptides would be deemed to have a percent similarity of 80% if, for example at position 5, the amino acids moieties, although not identical, were "similar" (i.e., possessed similar biochemical characteristics).

The seventh column in Table 1(a) indicates the length of the amino acid homology match.

Table 2 provides ORFs of the *Haemophilus influenzae* Rd genome which encode polypeptide sequences which did not elicit a "homology match" with a known protein sequence from another organism. Further details concerning the algorithms and criteria used for homology searches are provided in the Examples below.

A skilled artisan can readily identify ORFs in the *Haemophilus influenzae* Rd genome other than those listed in Tables 1(a), 1(b) and 2, such as ORFs which are overlapping or encoded by the opposite strand of an identified ORF in addition to those ascertainable using the computer-based systems of the present invention.

As used herein, an "expression modulating fragment," EMF, means a series of nucleotide molecules which modulates the expression of an operably linked ORF or EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event. A review of known EMFs from Haemophilus are described by (Tomb et al. *Gene* 104:1–10 (1991), Chandler, M. S., *Proc. Natl. Acad. Sci. USA* 89:1626–1630 (1992).

EMF sequences can be identified within the *Haemophilus influenzae* Rd genome by their proximity to the ORFs provided in Tables 1(a), 1(b) and 2. An intergenic segment, or a fragment of the intergenic segment, from about 10 to 200 nucleotides is length, taken 5' from any one of the ORFs of Tables 1(a), 1(b), or 2 will modulate the expression of an operably linked 3' ORF in a fashion similar to that found with the naturally linked ORF sequence. As used herein, an "intergenic segment" refers to the fragments of the Haemophilus genome which are between two ORF(s) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, a EMF will modulate the expression of an operably linked marker sequence. A more detailed discussion of various marker sequences is provided below.

A sequence which is suspected as being a EMF is cloned in all three reading frames in one or more restriction sites upstream from the marker sequence in the EMF trap vector. The vector is then transformed into an appropriate host using known procedures and the phenotype of the transformed host in examined under appropriate conditions. As described above, as EMF will modulate the expression of an operably linked marker sequence.

As used herein, an "uptake modulating fragment," UMF, means a series of nucleotide molecules which mediate the uptake of a linked DNA fragment into a cell. UMFs can be readily identified using known UMFs as a target sequence or target motif with the computer-based systems described above.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence. A review of DNA uptake in Haemophilus is provided by Goodgall, S. H., et al., *J. Bact.* 172:5924–5928 (1990).

As used herein, a "diagnostic fragment," DF, means a series of nucleotide molecules which selectively hybridize to *Haemophilus influenzae* sequences. DFs can be readily identified by identifying unique sequences within the *Haemophilus influenzae* Rd genome, or by generating and testing probes or amplification primers consisting of the DF sequence in an appropriate diagnostic format which determines amplification or hybridization selectivity.

The sequences falling within the scope of the present invention are not limited to the specific sequences herein described, but also include allelic and species variations thereof. Allelic and species variations can be routinely determined by comparing the sequence provided in SEQ ID NO:1, a representative fragment thereof, or a nucleotide sequence at least 99.9% identical to SEQ ID NO:1 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

Any specific sequence disclosed herein can be readily screened for errors by resequencing a particular fragment, such as an ORF, in both directions (i.e., sequence both strands). Alternatively, error screening can be performed by sequencing corresponding polynucleotides of *Haemophilus influenzae* origin isolated by using part or all of the fragments in question as a probe or primer.

Each of the ORFs of the *Haemophilus influenzae* Rd genome disclosed in Tables 1(a), 1(b), and 2, and the EMF found 5' to the ORF, can be used in numerous ways as polynucleotide reagents. The sequences can be used as diagnostic probes or diagnostic amplification primers to detect the presence of a specific microbe, such as *Haemophilus influenzae* RD, in a sample. This is especially the case with the fragments or ORFs of Table 2, which will be highly selective for *Haemophilus influenzae*.

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem,* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

The present invention further provides recombinant constructs comprising one or more fragments of the *Haemophilus influenzae* Rd genome of the present invention. The recombinant constructs of the present invention comprise a vector, such as a plasmid or viral vector, into which a fragment of the *Haemophilus influenzae* Rd has been inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBsKS, NH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include tacl, lacZ, T3, T7, gpt, lambda $P_R$, and trc. Eukaryotic promoters include CMV immediate early, HSV thymidine kinase, early and late SV40, LTRs from retrovirus, and mouse metallothionein-1. Selection of the appropriate vector and promoter is well within the level or ordinary skill in the art.

The present invention further provides host cells containing any one of the isolated fragments of the *Haemophilus influenzae* Rd genome of the present invention, wherein the fragment has been introduced into the host-cell using known transformulation methods. The host cell can be a high eukaryotic host cell, such as a mammalian cell, a lower eukaryotic host cell, such as a yeast cell, or the host cell can be a procaryotic cell, such as a bacterial cell. Introduction of the recombinant construct into the host cell can be effected by calcium phosphate transfection, DEAE, dextran mediated transfection, or electroporation (Davis, L. et al., *Basic Method sin Molecular Biology* (1986)).

The host cells containing one of the fragments of the *Haemophilus influenzae* Rd genome of the present invention, can be used in conventional manners to produce the gene product encoded by the isolated fragment (in the case of an ORF) or can be used to produce a heterologous protein under the control of the EMF.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragments of the present invention (e.g., an ORF) by nucleotide sequence but, due to the degeneracy of the Genetic Code, encode an identical polypeptide sequence. Preferred nucleic acid fragments of the present invention are the ORFs depicted in Table 1(a) which encode proteins.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level.

"Recombinant," as used herein, means that a polypeptide or protein is derived from recombinat (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern different from the expressed in mammalian cells.

"Nucleotide sequence" refers to a heteropolymer of deoxyribonucleotides. Generally, DNA segments encoding the polypeptides and proteins provided by this invention are assembled from fragments of the *Haemophilus influenzae*

Rd genome and short oligonucleotide linkers, or from a series of oligonucleotides, to provide a synthetic gene which is capable of being expressed in a recombinant transcriptional unit comprising regulatory elements derived from a microbial or viral operon.

"Recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or carry the recombinant transcriptional unit extra chromosomally. The cells can be prokaryotic or eukaryotic. Recombinant expression systems as defined herein will express heterologous polypeptides or proteins upon induction of the regulatory elements linked to the DNA segment or synthetic gene to be express.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryatic and eukaryotic hosts are described by Sambrook, et al., in *Molecular Cloning: A Laboratory Manual*, Second Edition, Cold Spring Harbor, New York (1989), the disclosure of which is hereby incorporated by reference.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a high-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled din appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombination product.

Useful expression vectors for bacterial use are constructed by inserting a structural DNA sequence encoding a desired protein together with suitable translation imitation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may, also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any accessory ribosome binding sites, polyadenylation site, splice donor and acceptor sites, transcriptional terminal sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant polypeptides and proteins produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The present invention further includes isolated polypeptides, proteins and nucleic acid molecules which are substantially equivalent to those herein described. As used herein, substantially equivalent can refer both to nucleic acid and amino acid sequences, for example a mutant sequence, that varies from a reference sequence by one or more substitutions, deletions, or additions, the net effect of which does not result in an adverse functional dissimilarity between reference and subject sequences. For purposes of the present invention, sequences having equivalent biological activity, and equivalent expression characteristics are considered substantially equivalent. For purposes of determining equivalence, truncation of the mature sequence should be disregarded.

The invention further provides methods of obtaining homologs from other strains of *Haemophilus influenzae*, of the fragments of the *Haemophilus influenzae* Rd genome of the present invention and homologs of the proteins encoded by the ORFs of the present invention. As used herein, a sequence or protein of *Haemophilus influenzae* is defined as a homolog of a fragment of the *Haemophilus Influenzae* Rd genome or a protein encoded by one of the ORFs of the present invention, if it share significant homology to one of the fragments of the *Haemophilus influenzae* Rd genome of the present invention or a protein encoded by one of the ORFs of the present invention. Specifically, by using the sequence disclosed herein as a probe or as primers, and techniques such as PCR cloning and colony/plaque hybridization, one skilled in the art can obtain homologs.

As used herein, two nucleic acid molecules or proteins are said to "share significant homology" if the two contain regions which process greater than 85% sequence (amino acid or nucleic acid) homology.

Region specific primers or probes derived from the nucleotide sequence provided in SEQ ID NO:1 or from a nucleotide sequence at last 99.9% identical to SEQ ID NO:1 can be used to prime DNA synthesis and PCR amplification, as well as to identify colonies containing closed DNA encoding a homolog using known methods (Innis et al., *PCR Protocols*, Academic Press, San Diego, Calif. (1990).

When using primers derived from SEQ ID NO:1 or from a nucleotide sequence at least 99.9% identical to SEQ ID NO:1, one skilled in the art will recognize that by employing high stringency conditions (e.g., annealing at 50–60° C.) only sequences which are greater than 75% homologous to the primer will be amplified. By employing lower stringency conditions (e.g., annealing at 35–37° C.), sequences which are greater than 40–50% homologous to the primer will also be amplified.

When using DNA probes derived from SEQ ID NO:1 or from a nucleotide sequence at least 99.9% identical to SEQ ID NO:1 for colony/plaque hybridization, one skilled in the art will recognize that by employing high stringency conditions (e.g., hybridizing at 50–60° C. in 5× SSPC and 50% formamide, and washing at 50–65° C. in 0.5× SSPC), sequences having regions which are greater than 90% homologous to the probe can be obtained, and that by employing lower stringency conditions (e.g., hybridizing at 35–37° C. in 5× SSPC and 40–45% formamide, and washing at 42° C. in SSPC), sequences having regions which are greater than 35–45% homologous to the probe will be obtained.

Any organism can be used as the source for homologs of the present invention so long as the organism naturally expresses such a protein or contains gene encoding the name. The most preferred organism for isolating homologs are bacterias which are closely related to *Haemophilus influenzae* Rd.

Uses for the Compositions of the Invention

Each ORF provided in Table 1(a) was assigned to one of 102 biological role categories adapted from Riley, M., *Mircobiology Reviews* 57(4):862 (1993)). This allows the skilled artisan to determine a use for each identified coding sequence. Tables 1(a) further provides an identification of the type of polypeptide which is encoded for by each ORF. As a result, one skilled in the art can use the polypeptides of the present invention for commercial, therapeutic and industrial purposes consistent with the type of putative identification of the polypeptide.

Such identifications permit one skilled in the art to use the *Haemophilus Influenzae* ORF's in a manner similar to the known type of sequences for which the identification is made; for example, to ferment a particular sugar source or to produce a particular metabolite. (For a review of enzymes used within the commercial industry, see *Biochemical Engineering and Biotechnology Handbook* 2nd, eds. Macmillan Publ. Ltd., NY (1991) and Biocatalysts in Organic Synthesis, ed. J. Tramper et al., Elsevier Science Publishers, Amsterdam, The Netherlands (1985)).

1. Biosynthetic Enzymes

Open reading frames encoding proteins involved in mediating the catalytic reactions involved in intermediary and macromolecular metabolism, the biosynthesis of small molecules, cellular processes and other functions includes enzymes involved in the degradation of the intermediary products of metabolism, enzymes involved in central intermediary metabolism, enzymes involved in respiration, both aerobic and anaerobic, enzymes involved in fermentation, enzymes involved in ATP proton motor force conversion, enzymes involved in broad regulatory function, enzymes involved in amino acid synthesis, enzymes involved in nucleotide synthesis, enzymes involved in cofactor and vitamin synthesis, can be used for industrial biosynthesis. The various metabolic pathways present in *Haemophilus* can be identified based on absolute nutritional requirements as well as by examining the various enzymes identified in Table 1(a).

Identified within the category of intermediary metabolism, a number of the proteins encoded by the identified ORF's in Tables 1(a) are particularly involved in the degradation of intermediary metabolites as well as non-macromolecular metabolism. Some of the enzymes identified include amylases, glucose oxidases, and catalase.

Proteolytic enzymes are another class of commercially important enzymes. Proteolytic enzymes find use in a number of industrial processes including the processing of flax and other vegetable fibers, in the extraction, clarification and depectinization of fruit juices, in the extraction of vegetables' oil and in the maceration of fruits and vegetables to give unicellular fruits. A detailed review of the proteolytic enzymes used in the food industry is provided by Rombouts et al., *Symbiosis* 21:79 (1986) and Voragen et al. in *Biocatalyst in Agricultural Biotechnology*, edited J. R. Whitaker et al., *American Chemical Society Symposium Series* 389:93 (1989)).

The metabolism of glucose, galactose, fructose, and xylose are important parts of the primary metabolism of *Haemophilus*. Enzymes involved in the degradation of these sugars can be used in industrial fermentation. Some of the important sugar transforming enzymes, from a commercial viewpoint, include sugar isomerases such as glucose isomerase. Other metabolic enzymes have found commercial use such as glucose oxidases which produces ketogulonic acid (KGA). KGA is an intermediate in the commercial production of ascorbic acid using the Reichstein's procedure (see Krueger et al., *Biotechnology* 6(A), Rhine, H. J. et al., eds., Veriag Press, Weinheim, Germany (1984)).

Glucose oxidase (GOD) is commercially available and has been used in purified form as well as in an immobolized form for the deoxygeneration of beer. See Hartmeir et al., *Biotechnology Letters* 1:21 (1979). The most important application of GOD is the industrial scale fermentation of gluconic acid. Market for gluconic acids which are used in the detergent, textile, leather, photographic, pharmaceutical, food, feed and concrete industry (see Bigellis in *Gene Manipulations and Fungi*, Bennett, J. W. et al., eds., Academic Press, New York (1985), p. 357). In addition to industrial applications, GOD has found applications in medicine for quantitative determination of glucose in body fluids recently in biotechnology for analyzing syrups from starch and cellulose hydrosylates. See Owuss et al., *Biochem. et Biophysica. Acta.* 872:83 (1986).

The main sweetener used in the world today is sugar which comes from sugar beets and sugar cane. In the field of industrial enzymes, the glucose isomerase process shows the largest expansion in the market today. Initially, soluble enzymes were used and later immobolized enzymes were developed (Krueger et al., *Biotechnology, The Textbook of Industrial Microbiology*, Sinauer Associated Incorporated, Sunderland, Mass. (1990)). Today, the use of glucose-produced high fructose syrups is by far the largest industrial business using immobilized enzymes. A review of the industrial use of these enzymes is provided by Jorgensen, *Starch* 40:307 (1988).

Proteinases, such as alkaline serine proteinases, are used in detergent additives and thus represent one of the largest volumes of microbial enzymes used in the industrial sector. Because of their industrial importance, there is a large body of published and unpublished information regarding the use of these enzymes in industrial processes. (See Faultman et al., *Acid Proteases Structure Function and Biology*, Tang, J., ed., Plenum Press, New York (1977) and Godfrey et al., *Industrial Enzymes*, MacMillan Publishers, Surrey, UK (1983) and Hepner et al., *Report Industrial Enzymes by 1990*, Hel Hepner & Associates, London (1986)).

Another class of commercially usable proteins of the present invention are the microbial lipases identified in Table 1 (see Macrae et al., *Philosophical Transactions of the Chiral Society of London* 310:227 (1985) and Poserke, *Journal of the American Oil Chemist Society* 61:1758 (1984). A major use of lipases is in the fat and oil industry for the production of neutral glycerides using lipase catalyzed inter-esterification of readily available triglycerides. Application of lipases include the use as a detergent additive to facilitate the removal of fats from fabrics in the course of the washing procedures.

The use of enzymes, and in particular microbial enzymes, as catalyst for key steps in the synthesis of complex organic molecules is gaining popularity at a great rate. One area of great interest is the preparation of chiral intermediates. Preparation of chiral intermediates is of interest to a wide range of synthetic chemists particularly those scientists involved with the preparation of new pharmaceuticals, agrochemicals, fragrances and flavors. (See Davies et al., *Recent Advances in the Generation of Chiral Intermediates Using Enzymes*, CRC Press, Boca Raton, Fla. (1990)). The following reactions catalyzed by enzymes are of interest to organic chemists: hydrolysis of carboxylic acid esters, phosphate esters, amides and nitriles, esterification reactions, trans-esterification reactions, synthesis of amides, reduction of alkanones and oxoalkanates, oxidation of alcohols to carbonyl compounds, oxidation of sulfides to sulfoxides, and carbon bond forming reactions such as the aldol reaction. When considering the use of an enzyme encoded by one of the ORF's of the present invention for biotransformation and organic synthesis it is sometimes necessary to consider the respective advantages and disadvantages of using a microorganism as opposed to an isolated enzyme. Pros and cons of using a whole cell system on the one hand or an isolated partially purified enzyme on the other hand, has been described in detail by Bud et al., *Chemistry in Britain* (1987), p. 127.

Amino transferases, enzymes involved in the biosynthesis and metabolism of amino acids, are useful in the catalytic production of amino acids. The advantages of using microbial based enzyme systems is that the amino transferase enzymes catalyze the stereo-selective synthesis of only 1-amino acids and generally possess uniformly high catalytic rates. A description of the use of amino transferases for amino acid production is provided by Roselle-David, *Methods of Enzymology* 136:479 (1987).

Another category of useful proteins encoded by the ORF's of the present invention include enzymes involved in nucleic acid synthesis, repair, and recombination. A variety of commercially important enzymes have previously been isolated from members of *Haemophilus* sp. These include the Hine II, Hind III, and Hind I restriction enconucleases. Table 1(a) identifies a wide array of enzymes, such as restriction enzymes, ligases, gyrases and methylases, which have intermediate use in the biotechnology industry.

2. Generation of Antibodies

As described here, the proteins of the present invention, as well as homologs thereof, can be used in a variety procedures and methods known in the art which are currently applied to other proteins. The proteins of the present invention can further be used to generate an antibody which selectively binds the protein. Such antibodies can be either monoclonal or polyclonal antibodies, as well fragments of these antibodies, and humanized forms.

The invention further provides antibodies which selectively bind to one of the proteins of the present invention and hybridomas which produce these antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (Campbell, A. M., *Monoclonal Antibody Technology: Laboratory Techniques in Biochemistry and Molecular Biology*, Elsevier Science Publishers, Amsterdam, The Netherlands (1984): St. Groth et al., *J. Immunol. Methods* 35:1–21 (1980): Kohler and Milstein, *Nature* 256:495–497 (1975)), the trioma technique, the human B-cell hybridoma technique (Kozbor et al., *Immunology Today* 4:72 (1983): Cole et al., in *Monoclonal Antibodies and Cancer Therapy*, Alan R. Liss, Inc. (1985), pp. 77–96.

Any animal (mouse, rabbit, etc.) which is known to produce antibodies can be immunized with the pseudogene polypeptide. Methods for immunization are well known in the art. Such methods include subcutaneous or interperitoneal injection of the polypeptide. One skilled in the art will recognize that the amount of the protein encoded by the ORF of the present invention used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to coupling the antigen with a heterologous protein (such as glubolin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western block analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

Techniques described for the production of single chain antibodies (U.S. Pat. No. 4,946,778) can be adapted to produce single chain antibodies to proteins of the present invention.

For polyclonal antibodies, antibody containing antisera is isolated from the immunized animal and is screened for the presence of antibodies with the desired specificity using one of the above-described procedures.

The present invention further provides the above-described antibodies in detectably labelled form. Antibodies can be detectably labelled through the use of radioisotopes, affinity labels (such as biotin, avidin, etc.), enzymatic labels (such as horseradish peroxidase, alkaline phosphotase, etc.) fluorescent labels (such as FITC or rhodamine, etc.), paramagnetic atoms, etc. Procedures for accomplishing such labelling are well-known in the art, for example see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

The labeled antibodies of the present invention can be used for in vitro, in vivo, and in situ assays to identify cells or tissues in which a fragment of the *Haemophilus influenzae* Rd genome is expressed.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., *"Handbook of Experimental Immunology"* 4th Ed., Blackwell Scientific Publications, Oxford, England, Chapter 10 (1986): Jacoby, W. D. et al., *Meth. Enzym.* 34 Academic Press, N.Y. (1974)). The immunized antibodies of the present invention can be used for in vitro, in vivo, and in situ assays as well as for immunoaffinity purification of the proteins of the present invention.

3. Diagnostic Assays and Kits

The present invention further provides methods to identify the expression of one of the ORF's of the present invention, or homolog thereof, in a test sample, using one of the DFs or antibodies of the present invention.

In detail, such methods comprise incubating a test sample with one or more of the antibodies or one or more of the DFs of the present invention and assaying for binding of the DFs or antibodies to components within the test sample.

Conditions for incubating a DF or antibody with a test sample vary. Incubation conditions depend on the format employed in the assay, the detection methods employed, and the type and nature of the DF or antibody used in the assay. One skilled in the art will recognize that any one of the commonly available hybridization, amplification or immunological assay formats can readily be adapted to employ the DFs or antibodies of the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the DFs or antibodies of the present invention; and (b) one or more other containers comprising one or more of the following: wash reagents, reagents capable of detecting presence of a bound DF or antibody.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or DF.

Types of detection reagents include labelled nucleic acid probes, labelled secondary antibodies, or in the alternative, if the primary antibody is labelled, the enzymatic, or antibody binding reagents which are capable of reacting with the labelled antibody. One skilled in the art will readily recognize that the disclosed DFs and antibodies of the present invention can be readily incorporated into one of the established kit formats which are well known in the art.

4. Screening Assay for Binding Agents

Using the isolated proteins of the present invention, the present invention further provides methods of obtaining and identifying agents which bind to a protein encoded by one of the ORFs of the present invention or to one of the fragments and the *Haemophilus* genome herein described.

In detail, said method comprises the steps of:
(a) contacting an agent with an isolated protein encoded by one of the ORFs of the present invention, or an isolated fragment of the *Haemophilus* genome; and
(b) determining whether the agent binds to said protein or said fragment.

The agents screened in the above assay can be, but are not limited to, peptides, carbohydrates, vitamin derivatives, or other pharmaceutical agents. The agents can be selected and screened at random or rationally selected or designed using protein modelling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In *Synthetic Peptides, A User's Guide*, W. H. Freeman, NY (1992), pp. 289–307, and Kaspczak et al., *Biochemistry* 28:9230–8 (1989), or pharmaceutical agents or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control.

One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., *Nucl. Acids. Res.* 6:3073 (1979); Cooney et al., *Science* 241:456 (1988); and Dervan et al., *Science* 251:1360 (1991)) or to the mRNA itself (antisense—Okano, j. *Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition for use in controlling *Haemophilus* growth and infection.

5. Vaccine and Pharmaceutical Composition

The present invention further provides pharmaceutical agents which can be used to modulate the growth of *Haemophilus influenzae*, or another related organism, in vivo or in vitro. As used herein, a "pharmaceutical agent" is defined as a composition of matter which can be formulated using known techniques to provide a pharmaceutical compositions. As used herein, the "pharmaceutical agents of the present invention" refers the pharmaceutical agents which are derived from the proteins encoded by the ORFs of the present invention or are agents which are identified using the herein described assays.

As used herein, a pharmaceutical agent is said to "modulate the growth of *Haemophilus* sp., or a related organism, in vivo or in vitro," when the agent reduces the rate of growth, rate of division, or visability of the organism in question. The pharmaceutical agents of the present invention can modulate the growth of an organism in many fashions, although an understanding of the underlying mechanism of action is not needed to practice the use of the pharmaceutical agents of the present invention. Some agents will modulate the growth by binding to an important protein thus blocking the biological activity of the protein, while other agents may bind to a component of the outer surface of the organism blocking attachment or rendering the organism more prone to act the bodies nature immune system. Alternatively, the agent may be comprise a protein encoded by one of the ORFs of the present invention and serve as a vaccine. The development and use of a vaccine based on outer membrane components, such as the LPS, are well known in the art.

As used herein, a "related organism" is a broad term which refers to any organism whose growth can be modulated by one of the pharmaceutical agents of the present invention. In general, such an organism will contain a homolog of the protein which is the target of the pharmaceutical agent or the protein used as a vaccine. As such, related organism do not need to be bacterial but may be fungal or viral pathogens.

The pharmaceutical agents and compositions of the present invention may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The agents of the present invention can be used in native form or can be modified to form a chemical derivative. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980).

For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

The therapeutic effects of the agents of the present invention may be obtained by providing the agent to a patient by any suitable means (i.e., inhalation, intravenously, intramuscularly, subcutaneously, enterally, or parenterally). It is preferred to administer the agent of the present invention so as to achieve an effective concentration within the blood or tissue in which the growth of the organism is to be controlled.

To achieve an effective blood concentration, the preferred method is to administer the agent by injection. The administration may be by continuous infusion, or by single or multiple injections.

In providing a patient with one of the agents of the present invention, the dosage of the administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered. The therapeutically effective dose can be lowered by using combinations of the agents of the present invention or another agent.

As used herein, two or more compounds or agents are said to be administered "in combination" with each other when either (1) the physiological effects of each compound, or (2) the serum concentrations of each compound can be measured at the same time. The composition of the present invention can be administered concurrently with, prior to, or following the administration of the other agent.

The agents of the present invention are intended to be provided to recipient subjects in an amount sufficient to decrease the rate of growth (as defined above) of the target organism.

The administration of the agent(s) of the invention may be for either a "prophylactic" or "therapeutic" purpose. When provided prophylactically, the agent(s) are provided in advance of any symptoms indicative of the organisms growth. The prophylactic administration of the agent(s) serves to prevent, attenuate, or decrease the rate of onset of any subsequent infection. When provided therapeutically, the agent(s) are provided at (or shortly after) the onset of an indication of infection. The therapeutic administration of the compound(s) serves to attenuate the pathological symptoms of the infection and to increase the rate of recovery.

The agents of the present invention are administered to be mammal in a pharmaceutically acceptable form and in a therapeutically effective concentration. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton, Pa. (1980)). In order to form a pharmaceutically acceptable composition suitable for effective administration, such compositions will contain an effective amount of one or more of the agents of the present invention, together with a suitable amount of carrier vehicle.

Additional pharmaceutical methods may be employed to control the duration of action. Control release preparations may be achieved through the use of polymers to complex or absorb one or more of the agents of the present invention. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate agents of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacrylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The invention further provides a pharmaceutical pack or kit comprising one or more containers filled with one or more of the ingredients of the pharmaceutical compositions of the invention. Associated with such container(s) can be a notice in the form prescribed by a governmental agency regulating the manufacture and/or sale of pharmaceuticals or biological products, which notice reflects approval by the agency of manufacture, use or sale for human administration. In addition, the agents of the present invention may be employed in conjunction with other therapeutic compounds.

6. Shot-Gun Approach to Megabase DNA Sequencing

The present invention further provides the first demonstration that a sequence of greater than one megabase can be sequenced using a random shotgun approach. This procedure, described in detail in the examples that follow, has eliminated the up front cost of isolating and ordering overlapping or contiguous subclones prior to the start of the sequencing protocols.

Certain aspects of the present invention are described in greater detail in the non-limiting Examples that follow.

EXAMPLES

Experimental Design and Methods

1. Shotgun Sequencing Strategy

The overall strategy for a shotgun approach to whole genome sequencing is outlined in Table 3. The theory of shotgun sequencing follows from the Lander and Waterman (Landerman and Waterman, Genomics 2: 231 (1988)) application of the equation for the Poisson distribution $p_x = m^x e^{-m}/x!$, where x is the number of occurrences of an event, m is the mean number of occurrences, and $p_x$ is the probability that any given base is not sequenced after a certain amount of random sequence has been generated. If L is the genome length, n is the number of clone insert ends sequenced, and w is the sequencing read length, then m=nw/L, and the probability that no clone originates at any of the w bases preceding a given base, i.e., the probability that the base is not sequenced, is $p_o = e^{-m}$. Using the fold coverage as the unit for m, one sees that after 1.8 Mb of sequence has been randomly generated, m=1, representing 1× coverage. In this case, $p_o = e^{-1} = 0.37$, thus approximately 37% is unsequenced. For example, 5× coverage (approximately 9500 clones sequenced from both insert ends and an average sequence read length of 460 bp) yields $p_o = e^{-5} = 0.0067$, or 0.67% unsequenced. The total gap length is $Le^{-m}$, and the average gap size is L/n. 5× coverage would leave about 128 gaps averaging about 100 bp in size. The treatment is essentially that of Lander and Waterman, Genomics 2:231 (1988). Table 4 illustrates the coverage for a 1.9 Mb genome with an average fragment size of 460 bp.

2. Random Library Construction

In order to approximate the random model described above during actual sequencing, a nearly ideal library of cloned genomic fragment is required. The following library construction procedure was developed to achieve this.

H. influenzae Rd KW20 DNA was prepared by phenol extraction. A mixture (3.3 ml) containing 600 μg DNA, 300 mM sodium acetate, 10 mM Tris-HCl, 1 mM Na-EDTA, 30% glycerol was sonicated (Branson Model 450 Sonicator) at the lowest energy setting for 1 min. at 0° using a 3 mm probe. The DNA was ethanol precipitated and redissolved in 500 μl TE buffer. To create blunt-ends, a 100 μl aliquot was digested for 10 min at 30° in 200 μl BAL31 buffer with 5 units BAL31 nuclease (New England BioLabs). The DNA was phenol-extracted, ethanol-precipitated, redissolved in 100 μl TE buffer, electrophoresed on a 1.0% low melting agarose gel, and the 1.6–2.0 kb size fraction was excised, phenol-extracted, and redissolved in 20 μl TE buffer. A two-step ligation procedure was used to produce a plasmid library with 97% insert of which >99% were single inserts. The first ligation mixture (50 μl) contained 2 μg of DNA fragments, 2 μg SmaI/BAP pUC18 DNA (Pharmacia), and 10 units T4 ligase (GIBCO/BRL), and incubation was at 14° for 4 hr. After phenol extraction and ethanol precipitation, the DNA was dissolved in 20 μl TE buffer and electrophoresed on a 1.0% low melting agarose gel. A ladder of ethidium bromide-stained linear bands, identified by size as insert (i), vector (v), v+i, v+2i, v+3i, . . . was visualized by 360 nm UV light, and the v+i DNA was excised and recovered in 20 μl TE. The v+i DNA was blunt-ended by T4 polymerase treatment for 5 min. at 37° in a reaction mixture (50 μl) containing the v+i linears, 500 μM each of the 4 dNTP's, and 9 units of T4 polymerase (New England BioLabs) uner recommended buffer conditions. After phenol extraction and ethanol precipitation the repaired v+i linears were dissolved in 20 μl TE. The final ligation to produce circles was carried out in a 50 μl reaction containing 5 μl of v+i linears and 5 units of T4 ligase at 14° overnight. After 10 min. at 70° the reaction mixture was stored at −20°.

This two-stage procedure resulted in a molecularly random collection of single-insert plasmid recombinants with minimal contamination from double-insert chimeras (<1%) or free vector (<3%). Since deviation from randomness is most likely to occur during cloning. E. coli host cells deficient in all recombination and restriction functions (A. Greener, *Strategies* 3 (1):5 (1990)) were used to prevent rearrangements, deletions, and loss of clones by restriction. Transformed cells were plated directly on antibiotic diffusion plates to avoid the usual broth recovery phase which allows multiplication and selection of the most rapidly growing cells. Plating occured as follows:

A 100 μl aliquot of Epicurian Coli SURE II Supercompetent Cells (Stratagene 200152) was thawed on ice and transferred to a chilled Falcon 2059 tube on ice. A 1.7 μl aliquot of 1.42 M β-mercaptoethanol was added to the aliquot of cells to a final concentration of 25 mM. Cells were incubated on ice for 10 min. A 1 μl aliquot of the final ligation was added to the cells and incubated on ice for 30 min. The cells were heat pulsed for 30 sec. at 42° and placed back on ice for 2 min. The outgrowth period in liquid culture was eliminated from this protocol in order to minimize the preferential growth of any given transformed cell. Instead the transformation were plated directly on a nutrient rich SOB plate containing a 5 ml bottom layer of SOB agar (1.5% SOB agar: 20 g tryptone, 5 g yeast extract, 0.5 g NaCl, 1.5% Difco Agar/L). The 5 ml bottom layer is supplemented with 0.4 ml ampicillin (50 mg/ml)/100 ml SOB agar. This 15 ml top layer of SOB agar is supplemented with 1 ml X-Gal (2%), 1 ml MgCl$_2$ (1 M), and 1 ml MgSO$_4$/100 ml SOB agar. The 15 ml top layer was poured just prior to plating. Our titer was approximately 100 colonies/10 μl aliquot of transformation.

All colonies were picked for template preparation regardless of size. Only clones lost due to "poison" DNA or deleterious gene products would be deleted from the library, resulting in a slight increase in gap number over that expected.

Figure 3:
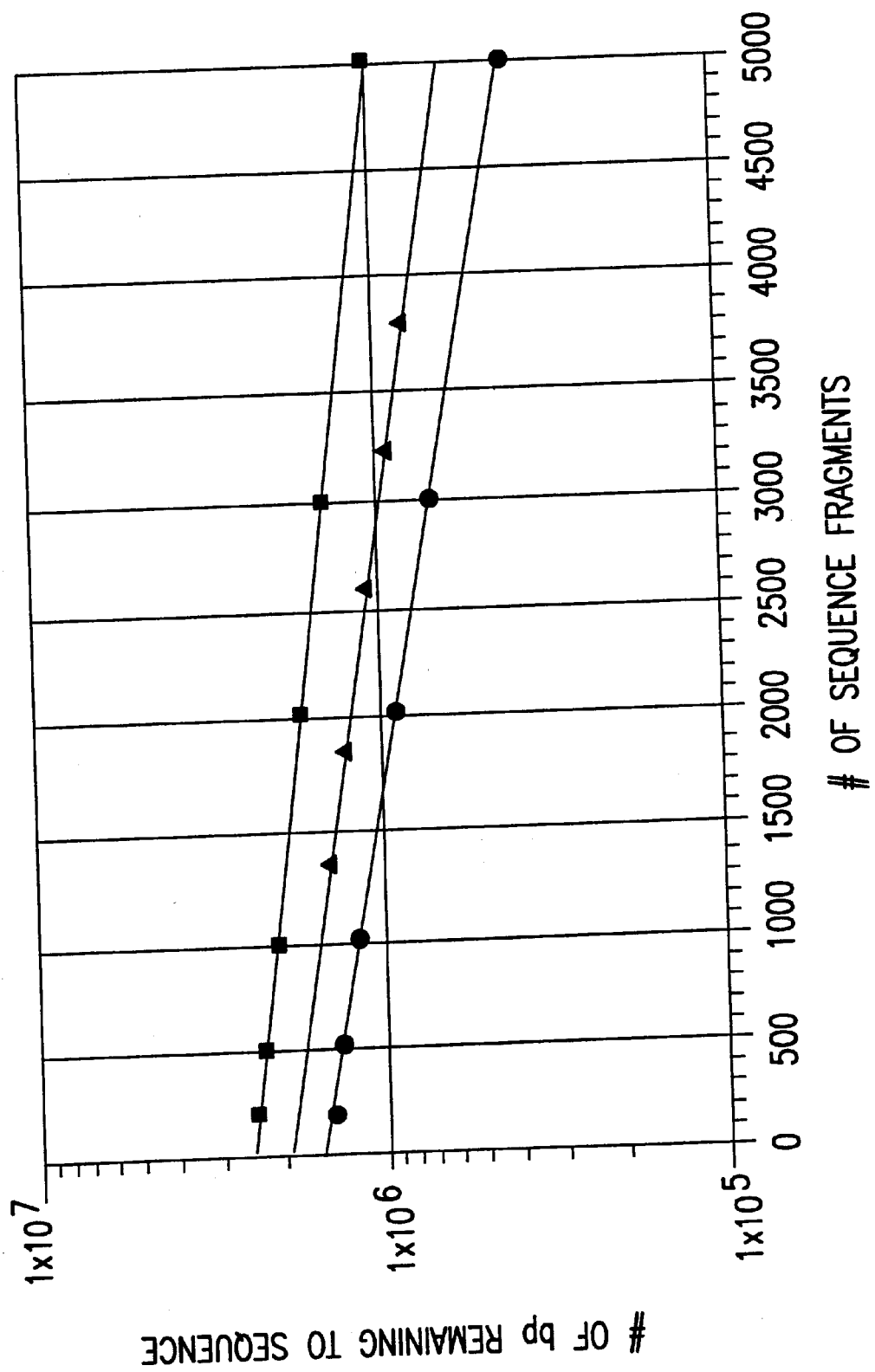
FIG. 3—A comparison of experimental coverage of up to approximately 4000 random sequence fragments assembled with AutoAssembler (squares) as compared to Lander-Waterman prediction for a 2.5 Mb genome (triangles) and a 1.6 Mb genome (circles) with a 400 bp average sequence length and a 25 bp overlap.

In order to evaluate the quality of the *H. influenzae* library, sequence data were obtained from approximately 4000 templates using the M13-21 primer. The random sequence fragments were assembled using the AutoAssembler™ software (Applied Biosystems division of Perkin-Elmer (AB)) after obtaining 1300, 1800, 2500, 3200, and 3800 sequence fragments, and the number of unique assembled base pairs was determined. Based on the equations described above, an ideal plot of the number of base pairs remaining to be sequenced as a function of the # of sequenced fragments obtained with an average read length of 460 bp for a $2.5\times10^4$ and a $1.9\times10^4$ bp genome was determined (FIG. 3). The progression of assembly was plotted using the actual data obtained from the assembly of up to 3800 sequence fragments and compared the data that is provided in the ideal plot (FIG. 3). FIG. 3 illustrates that there was essentially no deviation of the actual assembly data from the ideal ploat, indicating that we had constructed close to an ideal random library with minimal contamination from double insert chimeras and free of vector.

3. Random DNA Sequencing

High quality double stranded DNA plasmid templates (19,687) were prepared using a "boiling bead" method developed in collaboration with Advanced Genetic Technology Corp. (Gathersburg, Md.) (Adams et al., *Science* 252:1651 (1991); Adams et al., *Nature* 355:632 (1992)). Plamid preparation was performed in a 96-well format for all stages of DNA preparation from bacterial growth through final DNA purification. Template concentration was determined using Hoechst Dye and a Millipore Cytofluor. DNA concentrations were not adjusted, but low-yielding templates were identified where possible and not sequenced. Templates were also prepared from two *H. influenzae* lambda genomic libraries. An amplified library was constructed in vector Lambda GEM-12 (Promega) and an unamplified library was constructed in Lambda DASH II (Stratagene). In particular, for the unamplified lambda library, *H. influenzae* Rd KW20 DNA (>100 kb) was partially digested in a reaction mixture (200 μl) containing 50 μg DNA, 1× Sau3Al buffer, 20 units Sau3Al for 6 min. at 23°. The digested DNA was phenol-extracted and electrophoresed on a 0.5% low melting agarose gel at 2V/cm for 7 hours. Fragments from 15 to 25 kb were excised and recovered in a final volume of 6 μl. One μl of fragments was used with 1 μl of DASHII vector (Stratagene) in the recommended ligation reaction. One μl of the ligation mixture was used per packaging reaction following the recommended protocol with the Gigapack II XL Packaging Extract (Stratagene, #227711). Phage were plated directly without amplification from the packaging mixture (after dilution with 500 μl of recommended SM buffer and chloroform treatment). Yield was about $2.5\times10^3$ pfu/μl. The amplified library was prepared essentially as above except the lambda GEM-12 vector was used. After packaging, about $3.5\times10^4$ pfu were plated on the restrictive NM539 host. The lysate was harvested in 2 ml of SM buffer and stored frozen in 7% dimethylsulfoxide. The phage titer was approximately $1\times10^9$ pfu/ml.

Liquid lysates (10 ml) were prepared from randomly selected plaques and template was prepared on an anion-exchange resin (Qiagen). Sequencing reactions were carried out on plasmid templates using the AB Catalyst LabStation with Applied Biosystems PRISM Ready Reaction Dye Primer Cycle Sequencing Kits for the M13 forward (M13-21) and the M13 reverse (M13RP1) primers (Adams et al., *Nature* 368:474 (1994)). Dye terminator sequencing reactions were carried out on the lambda templates on a Perkin-Elmer 9600 Thermocycler using the Applied Biosystems Ready Reaction Dye Terminator Cycle Sequencing kits. T7 and SP6 primers were used to sequence the ends of the inserts from the Lambda GEM-12 library and T7 and T3 primers were used to sequence the ends of the inserts from the Lambda DASH II library. Sequencing reactions (28,643) were performed by eight individuals using an average of fourteen AB 373 DNA Sequencers per day over a 3 month period. All sequencing reactions were analyzed using the Stretch modification of the AB 373, primarily using a 34 cm well-to-read distance. The overall sequencing success rate was 84% for M13-21 sequences, 83% for M13RP1 sequences and 65% for dye-terminator reactions. The average usable read length was 485 bp for M13-21 sequences, 444 bp for M13RP1 sequences, and 375 bp for dye-terminator reactions. Table 5 summarizes the high-throughput sequencing phase of the invention.

Richards, et al. (Richards et al., *Automated DNA sequencing and Analysis*, M. D. Adams, C. Fields, J. C. Venter, Eds. (*Academic Press, London,* 1994), Chap. 28.) described the value of using sequence from both ends of sequencing templates to facilitate ordering of contigs in shotgun assembly projects of lambda and cosmid clones. We balanced the desirability of both-end sequencing (including the reduced cost of lower total number of templates) against shorter read-lengths for sequencing reactions performed with the M13RP1 (reverse) primer compared to the M13-21 (forward) primer. Approximately one-half of the templates were sequenced from both ends. In total, 9,297 M13RP1 sequencing reactions were done. Random reverse sequencing reactions were done based on successful forward sequencing reactions. Some M13RP1 sequences were obtained in a semi-directed fashion: M13-21 sequences pointing outward at the ends of contigs were chosen for M13RP1 sequencing in an effort to specifically order contigs. The semi-directed strategy was effective, and clone-based ordering formed an integral part of assembly and gap closure (see below).

4. Protocol for Automated Cycle Sequencing

The sequencing consisted of using eight ABI Catalyst robots and fourteen AB 373 Automated DNA Sequencers. The Catalyst robot is a publicly available sophisticated pipetting and temperature control robot which has been developed specifically for DNA sequencing reactions. The Catalyst combines pre-aliquoted templates and reaction mixes consisting of deoxy- and dideoxynucleotides, the Taq thermostable DNA polymerase, fluorescently-labelled sequencing primers, and reaction buffer. Reaction mixes and templates were combined in the wells of an aluminum 96-well thermocycling plate. Thirty consecutive cycles of linear amplification (e.g., one primer synthesis) steps were performed including denaturation, annealing of primer and template, and extension of DNA synthesis. A heated lid with rubber gaskets on the thermocycling plate prevented evaporation without the need for an oil overlay.

Two sequencing protocols were used: dye-labelled primers and dye-labelled dideoxy chain terminators. The shotgun sequencing involves use of four dye-labelled sequencing primers, one for each of the four terminator nucleotide. Each dye-primer is labelled with a different fluorescent dye, permitting the four individual reactions to be combined into one lane of the 373 DNA Sequencer for electrophoresis, detection, and base-calling. AB currently supplies pre-mixed reaction mixes in bulk packages containing all the necessary non-template reagents for sequencing. Sequencing can be done with both plasmid and PCR-generated templates with both dye-primers and dye-terminators with approximately equal fidelity, although plasmid templates generally give longer usable sequences.

Thirty-two reactions were loaded per 373 Sequencer each day, for a total of 960 samples. Electrophoresis was run overnight following the manufacture's protocols, and the data was collected for twelve hours. Following electrophoresis and fluorescence detection, the AB 373 performs automatic lane tracking and base-calling. The lane-tracking was confirmed visually. Each sequence electropherogram (or fluorescence lane trace) was inspected visually and assessed for quality. Trailing sequences of low quality were removed and the sequence itself was loaded via software to a Sybase database (archived daily to a 8 mm tape). Leading vector polylinker sequence was removed automatically by software program. Average edited lengths of sequences from the standard ABI 373 were around 400 bp and depended mostly on the quality of the template used for the sequencing reaction. All of the ABI 373 Sequencers were converted to Stretch Liners, which provided a longer electrophoresis path prior to fluorescence detection, thus increasing the average number of usable bases to 500–600 bp.

Informatics

1. Data Management

Figure 4:
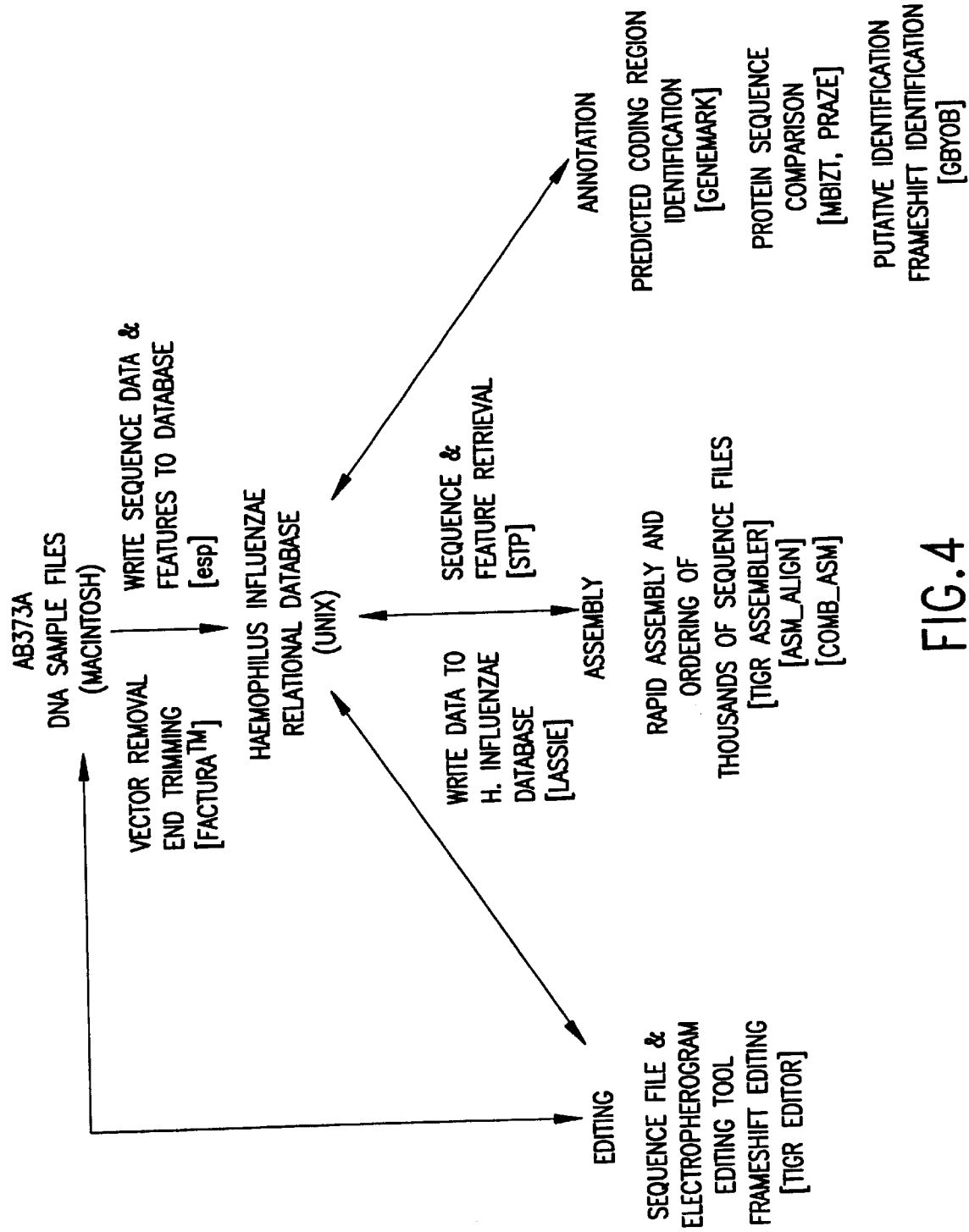
FIG. 4—Data flow and computer programs used to manage, assemble, edit, and annotate the *H. influenzae* genome. Both Macintosh and Unix platforms, are used to handle the AB 373 sequence data files (Kerlavage et al., *Proceedings of the Twenty-Sixth Annual Hawaii International Conference on System Sciences*, IEEE Computer Society Press, Washington D.C., 585 (1993)). Fracture (AB) is a Macintosh program designed for automatic vector sequence removal and end trimming of sequence files. The program esp runs on a Macintosh platform to the Unix based *H. influenzae* relational database. Assembly is accomplished by retrieving a specific set of sequence files and their associated features using stp, an X-windows graphical interface and control program which can retrieve sequences from the *H. influenzae* database using user-defined or standard SQL queries. The sequence files were assembled using TIGR Assembler, an assembly engine designed at TIGR for rapid and accurate assembly of thousands of sequence fragments. TIGR Editor is a graphical interface which can parse the aligned sequence files from TIGR Assembler output and display the alignment and associated electropherograms for contig editing. Identification of putative coding regions was performed with Genemark (Borodovsky and McIninch, *Computers Chem.* 17(2): 123 (1993)), a Markov and Bayes modeled program for predicting gene locations, and trained on a *H. influenzae* sequence data net. Peptide searches were performed against the three reading frames of each Genemark predicted coding region using blaze (Brutlag et al., *Computers Chem.* 17:203 (1993)) run on a Maspar MP-2 massively parallel computer with 4096 microprocessors. Results from each frame were combined into a single output file by subtext, Optimal protein alignments were obtained using the program prane which extends alignments across potential frameshifts. The output was inspected using a custom graphic viewing program, gbyeb, that interacts directly with the *H. influenzae* database. The alignments were further used to identify potential frameshift errors and were targeted for additional editing.

A number of information management systems (LIMA) for a large-scale sequencing lab have been developed (Kerlavage et al., *Proceedings of the Twenty-Sixth Annual Hawaii International Conference on System Sciences*, IEEE Computer Society Press, Washington D.C., 585 (1993)). The system used to collect and assemble the sequence data was developed using the Sybase relational data management system and was designed to automate data flow whereever possible and to reduce user error. The database stores and correlates all information collected during the entire operation from template preparation to final analysis of the genome. Because the raw output of the AB 373 Sequencers was based on a Macintosh platform and the data management system chosen was based on a Unix platform, it was necessary to design and implement a variety of multi-user, client server applications which allow the raw data as well as analysis results to flow seamlessly into the database with a minimum of user effort. A description of the software programs used for large sequence assembly and managment is provided in FIG. 4.

2. Assembly

An assembly engine (TIGR Assembler) was developed for the rapid and accurate assembly of thousands of sequence fragments. The AB AutoAssembler™ was modified (and named TIGR Editor) to provide a graphical interface to the electropherogram for the purpose of editing data associated with the aligned sequence file output of TIGR Assembler. TIGR Editor maintains synchrony between the electropherogram files on the Macintosh platform and the sequence data in the *H. influenzae* database on the Unix platform.

The TIGR assembler simultaneously clusters and assembles fragments of the genome. In order to obtain the speed necessary to assemble more than $10^4$ fragments, the algorithm builds a hash table of 10 bp oligonucleotide subsequences to generate a list of potential sequence fragment overlaps. The number of potential overlaps for each fragment determines which fragments are likely to fall into repetitive elements. Beginning with a single seed sequence fragment, TIGR Assembler extends the current contig by attempting to add the best matching fragment based on oligonucleotide content. The current contig and candidate fragment are aligned using a modified version of the Smith-Waterman algorithm (Waterman, M. S., *Methods in Enzymology* 164:765 (1988)) which provides for optimal gapped alignments. The current contig is extended by the fragment only if strict criteria for the quality of the match are met. The match criteria include the minimum length of overlap, the maximum length of all unmatched end, and the minimum percentage match. These criteria are automatically lowered by the algorithm in regions of minimal coverage and raised in regions with a possible repetitive element. The number of potential overlaps for each fragment determines which fragments are likely to fall into repetitive elements. Fragments representing the boundaries of repetitive elements and potentially chimeric fragments are often rejected based on partial mismatches at the ends of alignments and excluded from the current contig. TIGR Assembler is designed to take advantage of clone size information coupled with sequencing from both ends of each template. It enforces the constraint that sequence fragments from two ends of the same template point toward one another in the contig and are located within a certain ranged of base pairs (definable for each clone based on the known clone size range for a given library). Assembly of 24,304 sequence fragments of *H. influenzae* required 30 hours of CPU time using one processor on a SPARCenter 2000 with 512 Mb of RAM. This process resulted in approximately 210 contigs. Because of the high stringency of the TIGR Assembler, all contigs were searched against each other using grasta (a modified fasta (Person and Lipman, *Proc. Natl. Acad. Sci. U.S.A.* 85:2444 (1988)). In this way, additional overlaps were detected which enabled compression oof the data set into 140 contigs. The location of each fragment in the contigs and extensive information about the consensus sequence itself were loaded into the *H. influenzae* relational database.

3. Ordering Assembled Contigs

After assembly the relative positions of the 140 contigs were unknown. The contigs were ordered by asm.align. Asm.align uses a number of relationships to identify and align contigs that are adjacent to each other. Using the algorithm, the 140 contigs were placed into 42 groups totaling 42 physical gaps (no template DNA for the region) and 98 sequence gaps (template available for gap closure).

Ordering Contigs Separated by Physical Gaps and Achieving Closure

Four integrated strategies were developed to order contigs separated by physical gaps. Oligonucleotide primers were designed and synthesized from the end of each contig group. These primers were then available for use in one or more of the strategies outlined below:

1. Southern analysis was done to develop a unique "fingerprint" for a subset of 72 of the above oligonucleotides. This procedure was based upon the supposition that labeled oligonucleotides homologous to the ends of adjacent contigs should hybridize to common DNA restriction fragments, and thus share a similar or identical hybridization pattern or "fingerprint". Oligonucleotides were labeled using 50 pmoles of each 20 mer and 250 mCl of $[\gamma-^{33}P]$ATP and T4 polynucleotide kinase. The labeled oligonucleotides were purified using Sephadex G-25 superfine (Pharmacia) and $10^7$ cpm of each was used in a Southern hybridization analysis of *H. influenzae* Rd chromosomal DNA digested with one frequent cutters (AseI) and five less frequent cutters (BglII, EcoRI, PstI, XbaI, and PvuII). The DNA from each digest was fractionated on a 0.7% agarose gel and transferred to Nytran Plus nylon membranes (Schleicher & Schuell). Hybridization was carried out for 16 hours at 40°. To remove non-specific signals, each blot was sequentially washed at room temperature with increasingly stringent conditions up to 0.1× SSC+0.5% SDS. Blots were exposed to a PhosphorImager cassette (Molecular Dynamics) for several hours and hybridization patterns were visually compared.

Adjacent contigs identified in this manner were targeted for specific PCR reactions.

2. Peptide links were made by searching each contig end using blasts (Altschul et al., *J. Mol. Biol.* 215:403 (1990)) against a peptide database. If the ends of two contigs matched the same database sequence in an appropriate manner, then the two contigs were tentatively considered to be adjacent to each other.

3. The two lambda libraries constructed from *H. influenaze* genomic DNA were probed with oligonucleotides designed from the ends of contig groups (Kirkness et al., *Genomics* 10:985 (1991)). The positive plaques were then used to prepare templates and the sequence was determined from each end of the lambda clone insert. These sequence fragments were searched using grasta against a database of all contigs. Two contigs that matched the sequence from the opposite ends of the same lambda clone were ordered. The lambda clone then provided the template for closure of the sequence gap between the adjacent contigs. The lambda clones were especially valuable for solving repeat structures.

4. To confirm the order of contigs found by the other approaches and establish the order of non-ordered contigs, standard and long range (XL) PCR reactions were performed as follows.

Standard PCR was performed in the following manner. Each reaction contained a 37 µl cocktail; 16.5 µl $H_2O$, 3 µl 25 mM $MgCl_2$, 8 µl of a dNTP mix (1.25 mM each dNTP), 4.5 µl 10× PCR core buffer II (Perkin Elmer), 25 ng *H. influenzae* Rd KW20 genomic DNA. The appropriate two primers (4 µl, 3.2 pmole/µl) were added to each reaction. A hot start was performed at 95° for 5 min followed by a 75° hold. During the hold Amplitaq DNA polymerase (Perkin Elmer) 0.3 µl in 4.3 µl $H_2O$, 0.5 µl 10× PCR core buffer II, was added to each reaction. The PCR profile was 25 cycles of 94°/45 sec., denature; 55°/1 min, anneal; 72°/3 min, extension. All reactions were performed in a 96 well format on a Perkin Elmer GeneAmp PCR System 9600.

Long range PCR (XL PCR) was performed as follows: Each reaction contained a 35.2 µl cocktail; 12.0 µl $H_2O$, 2.2 µl 25 mM $Mg(OAc)_2$, 4 µl of a dNTP mix (200 µM final concentration), 12.0 µl 3.3× PCR buffer, 25 ng *H. influenzae* Rd KW20 genomic DNA. The appropriate two primers (5 µl, 3.2 pmoles/µl) was added to each reaction. A hot start was performed at 94° for 1 minute. rTth polymerase, 2.0 µl (4 U/reaction) in 2.8 µl 3.3× PCR buffer II was added to each reaction. The PCR profile was 18 cycles of 94°/15 sec., denature; 62°/8 min., anneal and extend followed by 12 cycles 94°/15 sec., denature; 62°/8 min. (increase 15 sec./cycle), anneal and extend; 72°/10 min., final extension. All reactions were performed in a 96 well format on a Perkin Elmer GeneAmp PCR System 9600.

Although a PCR reaction was performed for essentially every combination of physical gap ends, techniques such as Southern fingerprinting, database matching, and the probing of large insert clones were particularly valuable in ordering contigs adjacent to each other and reducing the number of combinatorial PCR reactions necessary to achieve complete gap closure. Employing these strategies to an even greater extent in future genome projects will increase the overall efficiency of complete genome closure. The number of physical gaps ordered and closed by each of these techniques is summarized in Table 5.

Figure 5:
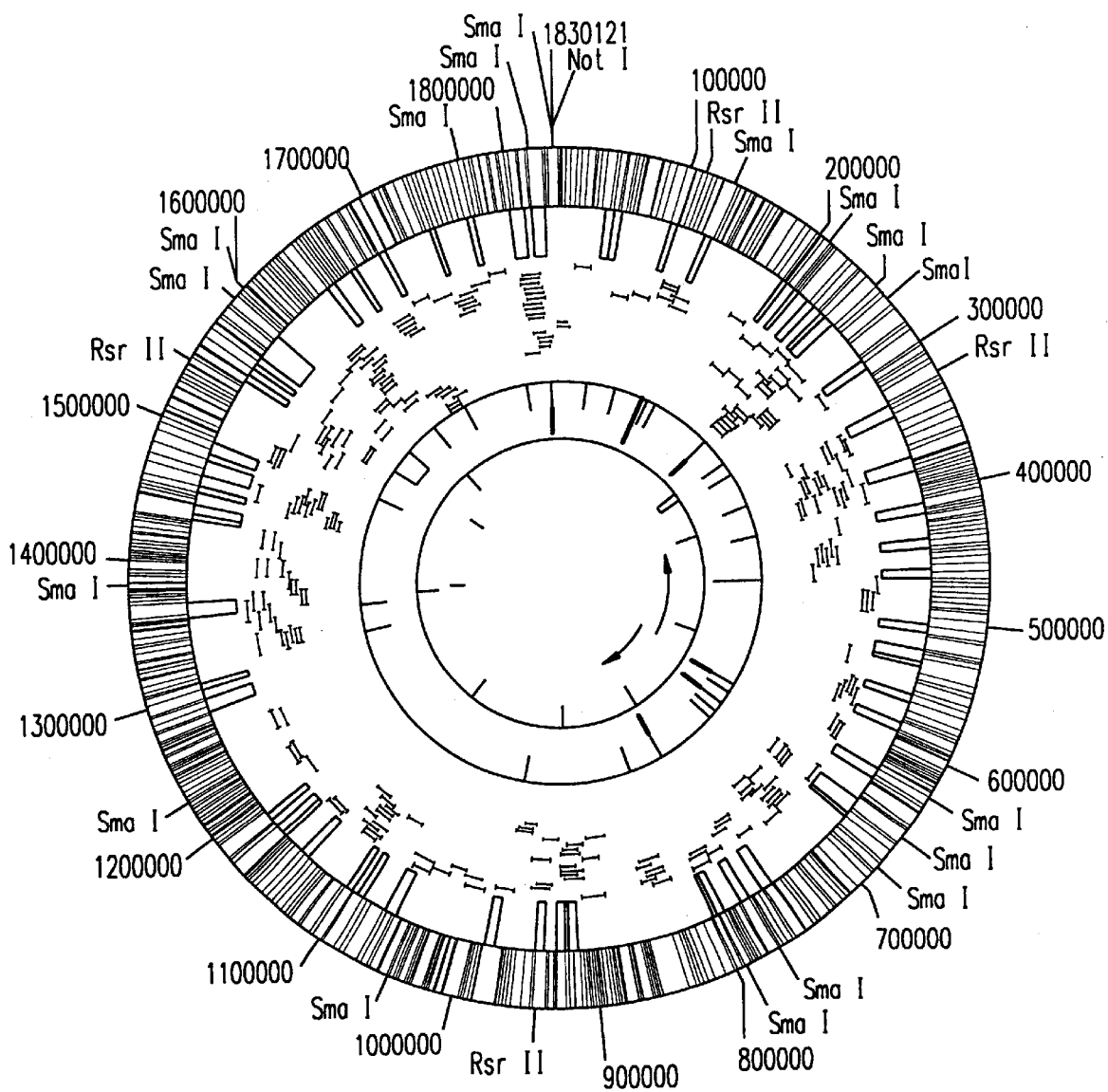
FIG. 5—A circular representation of the *H. influenzae* Rd chromosome illustrating the location of each predicted coding region containing a database match as well as selected global features of the genome. Outer perimeter: The location of the unique NotI restriction site (designated as nucleotide I), the RsrII sites, and the SmaI sites. Outer concentric circle: The location of each identified coding region for which a gene identification was made. Each coding region location is coded as to role in FIG. 6A–6N. Second concentric circle: Regions of high G/C content and high A/T content. High G/C content regions are specifically associated with the 6 ribosomal operons and the mu-like prophage. Third concentric circle: Coverage by lambda clones. Over 300 lambda clones were sequenced from each end to confirm the overall structure of the genome and identify the 6 ribosomal operons. Fourth concentric circle: The locations of the 6 ribosomal operons, the tRNAs and the cryptic mu-like prophage. Fifth concentric circle: Simple tandem repeats. The locations of the following repeats are shown: CTGGCT, GTCT, ATT, AATGGC, TTGA, TTGG, TTTA, TTATC, TGACC, TCGTC, AACC, TTGC, CAAT, CCAA. The putative origin of replication is illustrated by the outward pointing arrows originating near base 603,000. Two potential termination sequences are shown near the opposite midpoint of the circle.

Sequence information from the ends of 15–20 kb clones is particularly suitable for gap closure, solving repeat structures, and providing general confirmation of the overall genome assembly. We were also concerned that some fragments of the *H. influenaze* genome would be non-clonable in a high copy plasmid in *E. coli*. We reasoned that lytic lambda clones would provide the DNA for these segments. Approximately 100 random plaques were picked from the amplified lambda library, templates prepared, and sequence information obtained from each end. These sequences were searched (grasta) against the contigs and linked in the database to their appropriate contig, thus providing a scaffolding of lambda clones contributing additional support to the accuracy of the genome assembly (FIG. 5). In addition to confirmation of the contig structure, the lambda clones provided closure for 23 physical gaps. Approximately 78% of the genome is covered by lambda clones.

Lambda clones were also useful for solving repeat structures. Repeat structures identified in the genome were small enough to be spanned by a single clone from the random insert library, except for the six ribosomal RNA operons and one repeat (2 copies) which was 5,340 bp in length. Oligonucleotide probes were designed from the unique flanks at the beginning of each repeat and hybridized to the lambda libraries. Positive plaques were identified for each flank and the sequence fragments from the ends of each clone were used to correctly orient the repeats within the genome.

The ability to distinguish and assemble the six ribosomal RNA (rRNA) operons of *H. influenaze* (16S subunit-23S subunit-5S subunit) was a test of our overall strategy to sequence and assemble a complex genome which might contain a significant number of repeat regions. The high degree of sequence similarity and the length of the six operons caused the assembly process to cluster all the underlying sequences into a few indistinguishable contigs. To determine the correct placement of the operons in the sequence, a pair of unique flanking sequences was required for each. No unique flanking sequences could be found at the left (16S rRNA) ends. This region contains the ribosomal promoter and appeared to be non-clonable in the high copy number pUC18 plasmid. However, unique sequences could be identified at the right (5S) ends. Oligonucleotide primers were designed from these six flanking regions and used to probe the two lambda libraries. For each of the six rRNA operons at least one positive plaque was identified which completely spanned the rRNA operon and combined unique flanking sequence at the 16S and 5S ends. These plaques provided the templates for obtaining the unique sequence for each of the six rRNA operons.

An additional confirmation of the global structure of the assembled circular genome was obtained by comparing a computer generated restriction map based on the assembled sequence for the enzymes ApaI, SmaI, and RsrII with the predicted physical map of Redfield and Lee (*Genetic Maps: locus maps of complex genomes*, S. J. O'Brien, Ed. Cold Spring Harbor Laboratory Press, New York, N.Y., 1990, 2110.). The restriction fragments from the sequence-derived map matched those from the physical map in size and relative order (FIG. 5).

Editing

Simultaneous with the final gap filling process, each contig was edited visually by reassembling overlapping 10 kb sections of contigs using the AB AutoAssembler™ and the First Data Finder™ hardware. AutoAssembler™ provides a graphical interface to electropherogram data for editing. The electropherogram data was used to assign the most likely base at each position. Where a discrepancy could not be resolved or a clear assignment made, the automatic base calls were left unchanged. Individual sequence changes were written to the electropherogram files and a replication protocol (crash) was used to maintain the synchrony of sequence data between the *H. influenzae* database and the electropherogram files. Following editing, contigs were reassembled with TIGR Assembler prior to annotation.

Potential frameshifts identified in the course of annotating the genome were saved as reports in the database. These reports include the coordinates in a contig which the alignment software (praze) predicts to be the most likely location of a missing or inserted base and a representation of the sequence alignment containing the frameshift. Apparent frameshifts were used to indicate areas of the sequence which may require further editing. Frameshifts were not corrected in cases where clear electropherogram data disagreed with a frameshift. Frameshift editing was performed with TIGR Editor.

The rRNA and other repeat regions precluded complete assembly of the circular genome with TIGR Assembler. Final assembly of the genome was accomplished using comb_asm which splices together contigs based on short overlaps.

Accuracy of the Genome Sequence

The accuracy of the *H. influenaze* genome sequence is difficult to quantitate because there is very little previously determined *H. influenaze* sequence and most of these sequences are from other strains. There are, however, three parameters of accuracy that can be applied to the data. First, the number of apparent frameshifts in predicted *H. influenaze* genes, based on database similarities, is 148. Some of these apparent frameshifts may be in the database sequences rather than in ours, particularly considering that 49 of the apparent frameshifts are based on matches to hypothetical proteins from other organisms. Second, there are 188 bases in the genome that remain as N ambitguities (1/9,735 bp). Combining these two types of "known" errors, we can calculate a maximum sequence accuracy of 99.98%. The average coverage is 6.5× and less than 1% of the genome is single-fold coverage.

Identifying Genes

An attempt was made to predict all of the coding regions of the *H. influenzae* Rd genome and identify genes, tRNAs and rRNAs, as well as other features of the DNA sequence (e.g., repeats, regulatory sites, replication origin sites, nucleotide composition). A description of some of the readily apparent sequence features is provided below.

The *H Influenaze* Rd genome is a circular chromosome of 1,830,121 bp. The overall G/C nucleotide content is approximately 38% (A=31%, C=19%, G=19%, T=31%, IUB=0.035%). The G/C content of the genome was examined with several window lengths to look for global structural features. With a window of 5,000 bp, the G/C content is relatively even except for 7 large G/C-rich regions and several A/T-rich regions (FIG. 5). The G/C rich regions correspond to six rRNA operons and the location of a cryptic mu-like prophage. Genes for several proteins with similarity to proteins encoded by bacteriophage mu are located at approximately position 1.56–1.59 Mbp of the genome. This area of the genome has a markedly higher G/C content than average for *H. influenaze* (~50% G/C compared to ~38% for the rest of the genome). No significance has yet been ascertained for the source or importance of the A/T rich regions.

The minimal origin of replication (oriC) in *E. coli* is a 245 bp region defined by three copies of a thirteen base pair repeat containing a GATC core sequence at one end and four copies of a nine base pair repeat containing a TTAT core sequence at the other end. The GATC sites are methylation targets and control replication while the TTAT sites provide the binding sites for DnaA, the first step in the application process (*Genes* V. B. Lewin Ed. (Oxford University Press, N.Y., 1994), chap. 18–19). An approximately 281 bp sequence (602,483–602,764) whose limits are defined by these same core sequences appears to define the origin of replication in *H Influenaze* Rd. These coordinates lie between sets of ribosomal operons rrnF, rrnE, rrnD and rrnA, rrnB, rrnC. These two groups of ribosomal operons are transcribed in opposite directions and the placement of the origin is consistent with their polarity for transcription. Termination of *E. coli* replication is marked by two 23 bp termination sequences located ~100 kb on either side of the midway point at which the two replication forks meet. Two potential termination sequences sharing a 10 bp core sequence with the *E. coli* termination sequence were identified in *H. Influenaze* at coordinates 1,375,949–1,375,958 and 1,558,759–1,558,768. These two sets of coordinates are offset approximately 100 kb from the point 180° opposite of the proposed origin of *H. influenaze* replication.

Six rRNA operons were identified. Each rRNA operon contains three rRNA subunits and a variable spacer region in the order: 16S—spacer region—23S subunit—5S subunit. The subunit lengths are 1539 bp, 2653 bp, and 116 bp, respectively. The G/C content of the three ribosomal subunits (50%) is higher than the genome as a whole. The G/C content of the spacer region (38%) is consistent with the remainder of the genome. The nucleotide sequence of the three rRNA subunits is 100% identical in all six ribosomal operons. The rRNA operons can be grouped into two classes based on the spacer region between the 16S and 23S sequences. The shorter of the two spacer regions is 478 bp in length (rrnB, rrnE, and rrnF) and contents of gene for tRNA Glu. The longer spacer is 723 bp in length (rrnA, rrnC, and RRnD) and contains the genes for tRNA Ile and tRNA Ala. The two sets of spacer regions are also 100% identical across each group of three operons. tRNA genes are also present at the 16S and 5S ends of two of the rRNA operons. The genes for tRNA Arg, tRNA His, and tRNA Pro are located at the 16S end of rnnE while the genes for tRNA Trp, and tRNA Asp are located at the 5S end of rrnA.

The predicted coding regions of the *H influenaze* genome were initially defined by evaluating their coding potential with the program Genemark (Borodovsky and McInich, *Computers Chem* 17(2):123 (1993)) using codon frequency matrices derived from 122 *H. influenzae* coding sequences in Genbank. The predicted coding region sequences (plus 300 bp of flanking sequence) were used in searches against a database of non-redundant bacterial proteins (NRSP) created specifically for the annotation. Redundancy was removed from NRBP at two stages. All DNA coding sequences were extracted from GenBank (release 85), and sequences from the same species were searched against each other. Sequences having >97% similarity over regions >100 nucleotides were combined. In addition, the sequences were translated and used in protein comparisons with all sequences in Swiss-Prot (release 30). Sequences belonging to the same species and having >98% similarity over 33 amino acids were combined. NRBP is composed of 21,445 sequences extracted from 23,751 GenBank sequences and 11,183 Swiss-Prot sequences from 1,099 different species.

A total of 1,749 predicted coding regions were identified. Searches of the *H. influenaze* predicted coding regions were performed using an algorithm that translates the query DNA sequences in the three plus-strand reading frame for searching against NRBP, identifies the protein sequences that match the query, and aligns the protein-protein matches using prase, a modified Smith-Waterman (Pearson and Lipman, *Proc. Natl. Acad. Sci. U.S.A.* 85:2444 (1988)) algorithm. In cases where insertion or deletions in the DNA sequence produced a frameshift error, the alignment algorithm started with protein regions of maximum similarity and extended the alignment to the same database match in alternative frames using the 300 bp flanking region. Regions known to contain frameswft errors were saved in the database and evaluation for possible correction. Unidentified predicted coding regions and the remaining intergenic sequences were searched against a dataset of all available peptide sequences from Swiss-Prot, PIR, and GenBank. Identification of operon structures will be facilitated by experimental determination of transcription promoter and termination sites.

Each putatively identified *H. influenaze* gene was assigned to one of 102 biological role categories adapted from Riley (Riley, M., *Microbiology Reviews* 57(4):862 (1993)). Assignments were made by linking the protein sequence of the predicted coding regions with the Swiss-Prot sequences in the Riley database. Of the 1,749 predicted coding regions, 724 have no role assignment. Of these, no database match was found for 384, while 340 matched "hypothetical proteins" in the database. Role assignments were made for 1,025 of the predicted coding regions. A compilation of all the predicted coding regions, their unique identifiers, a three letter gene identifier, percent identity, percent similarity, and amino acid match length are presented in Table 1(a).

Figure 6A:
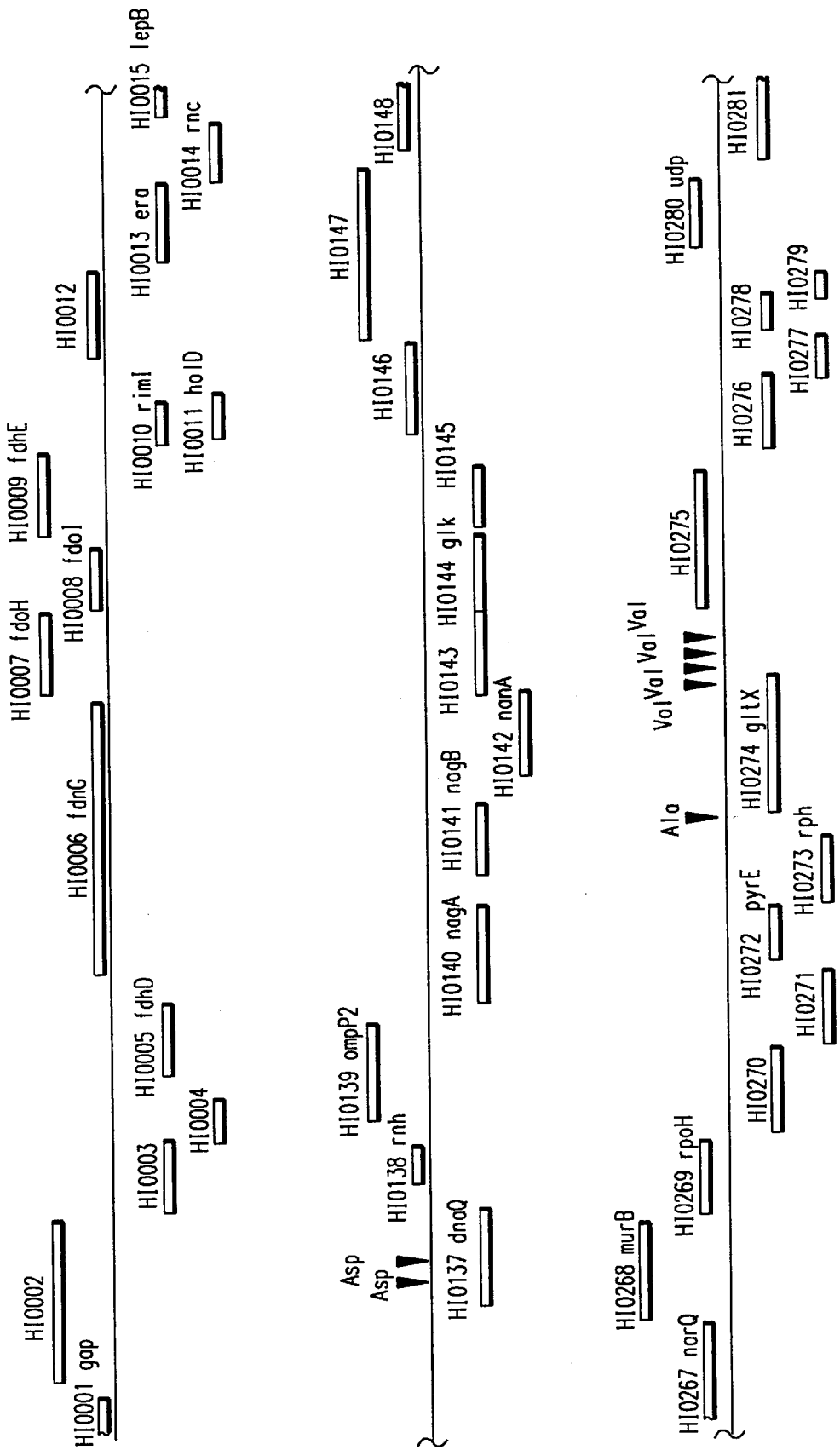
FIGS. 6A–6N Complete map of the *H. influenzae* Rd genome. Predicated coding regions are shown on each strand. rRNA and tRNA genes are shown in lines and triangles, respectively. GeneID numbers correspond to those in Tables 1(*a*), 1(*b*) and 2. Where possible, three-letter designations are also provided.
Figure 6B:
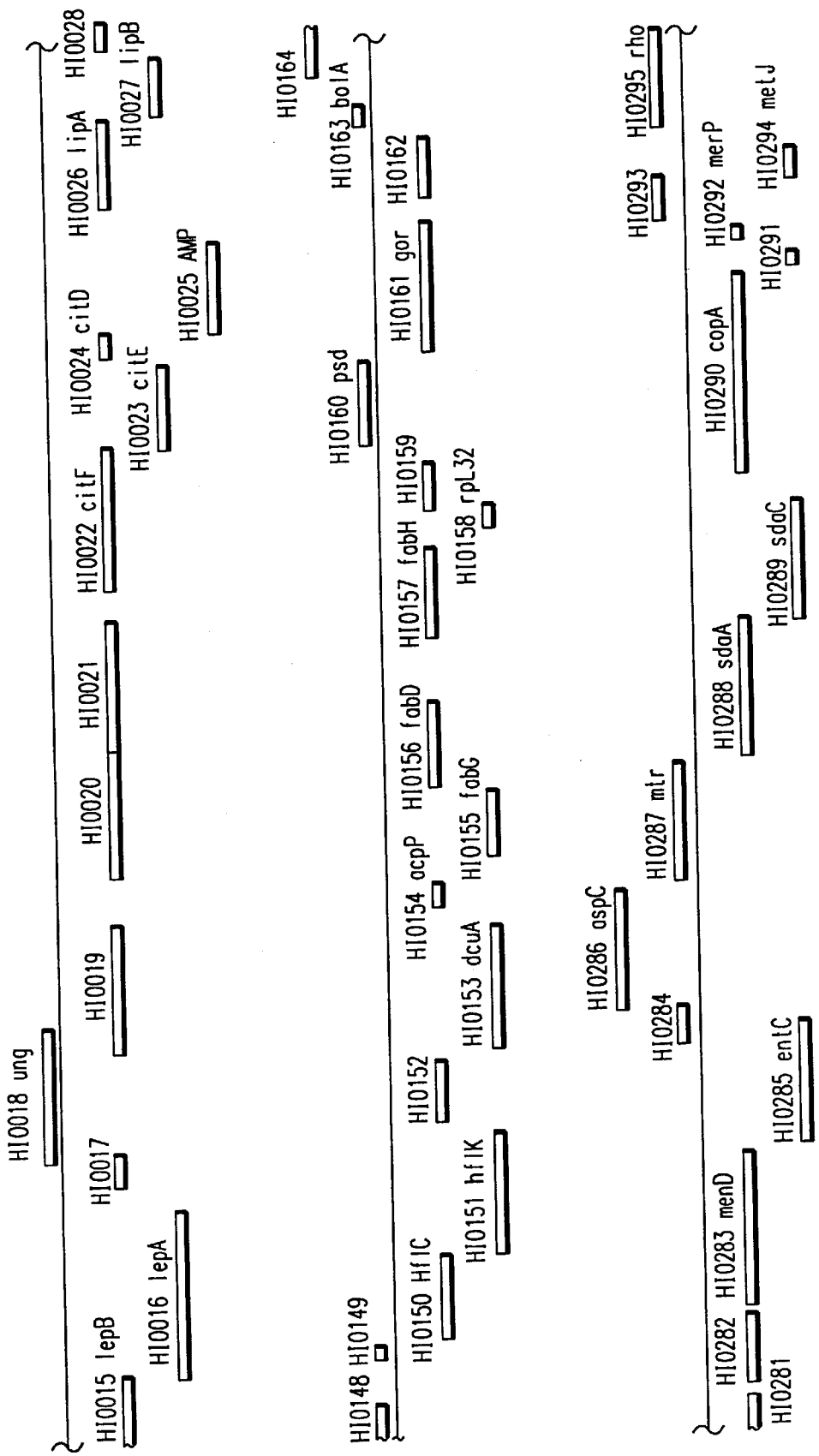
Figure 6C:
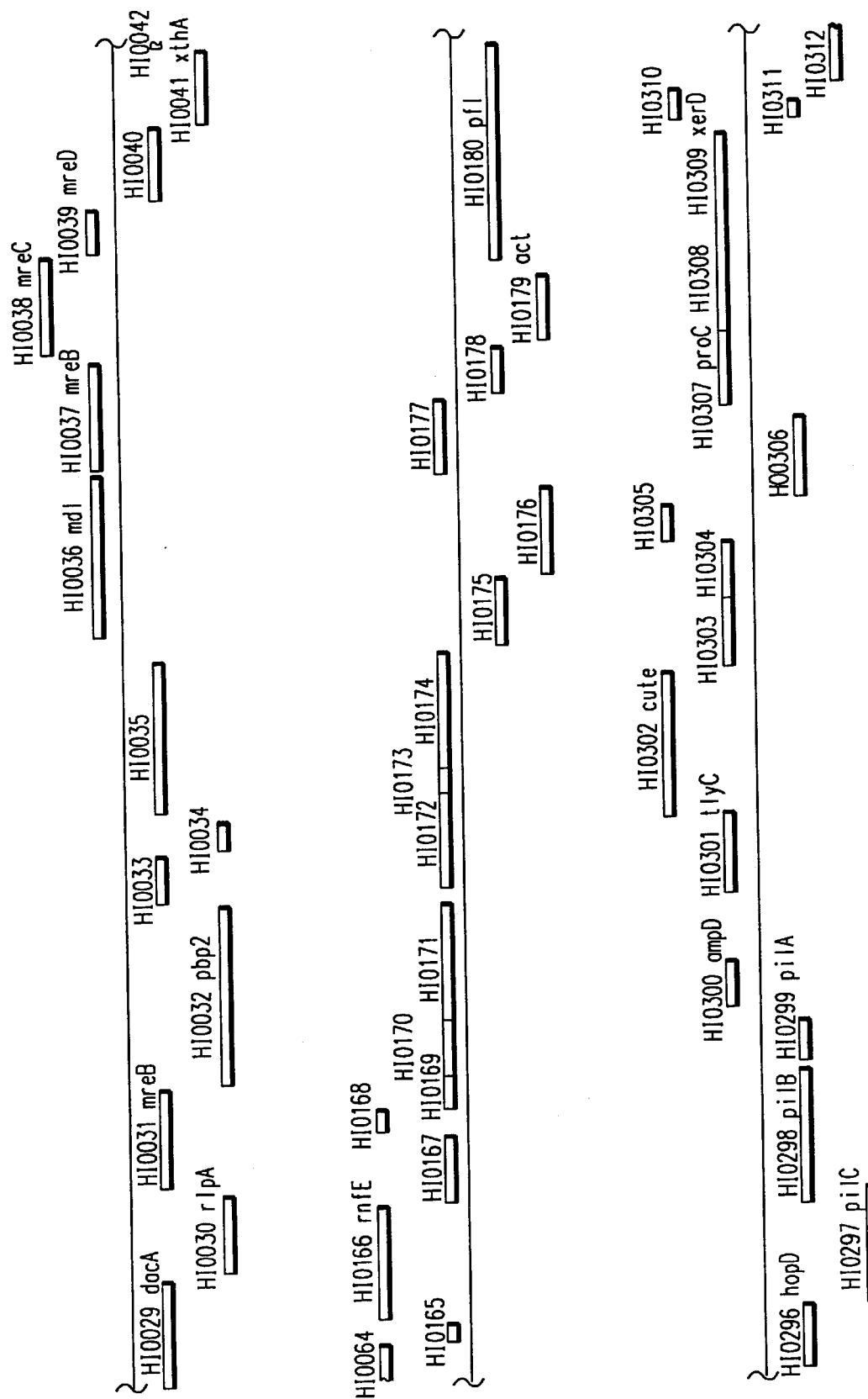
Figure 6D:
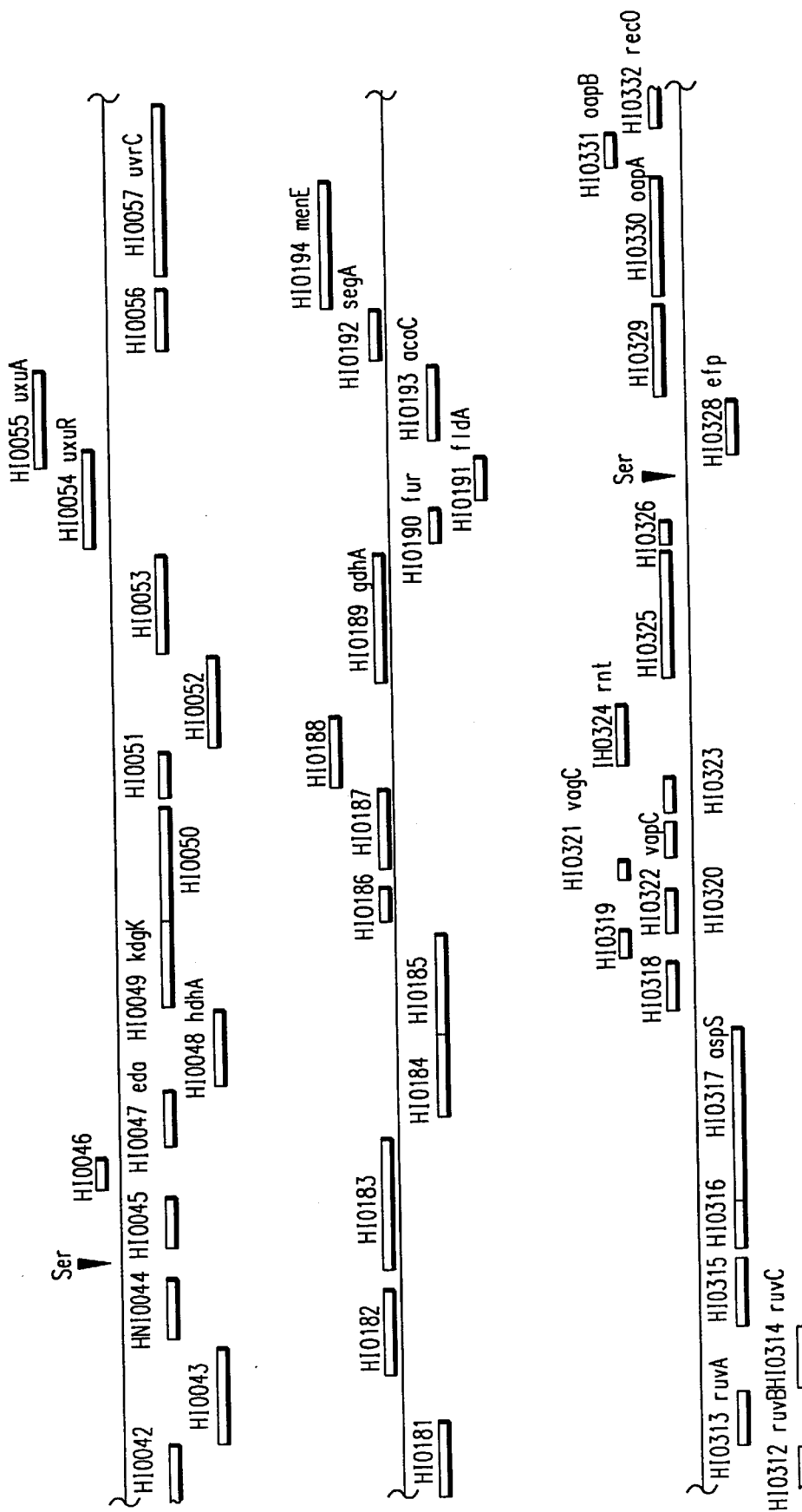
Figure 6E:
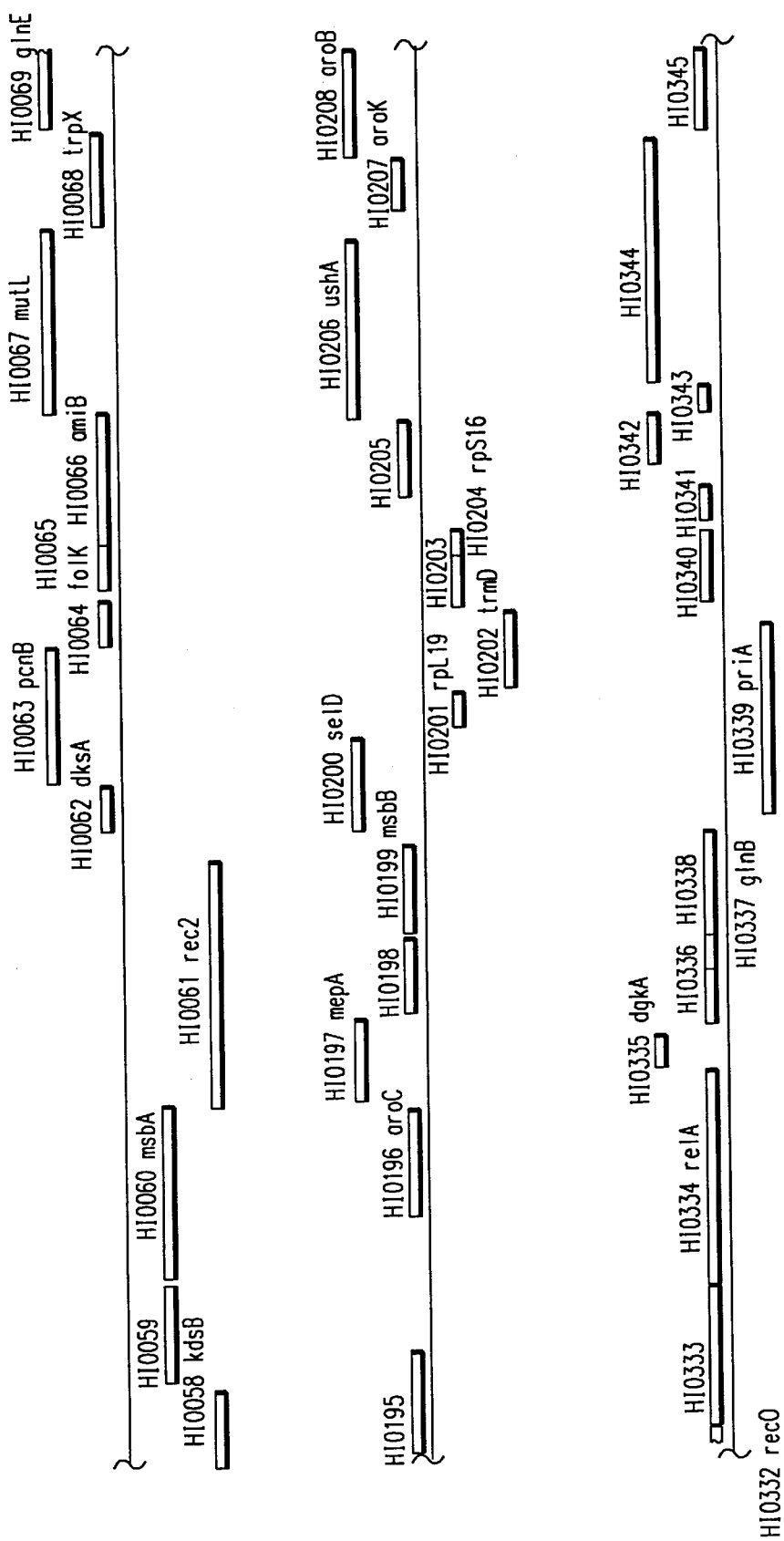
Figure 6F:
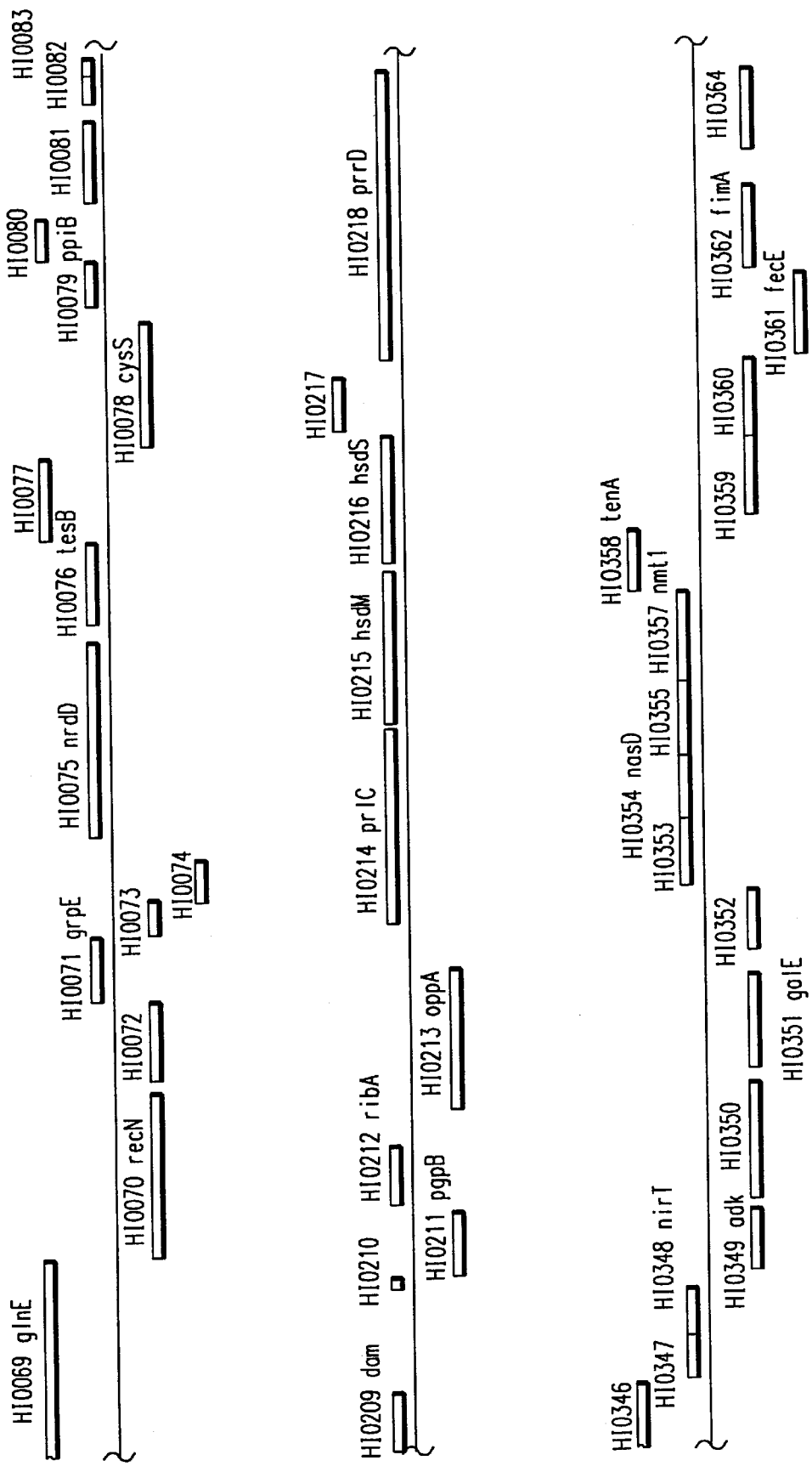
Figure 6G:
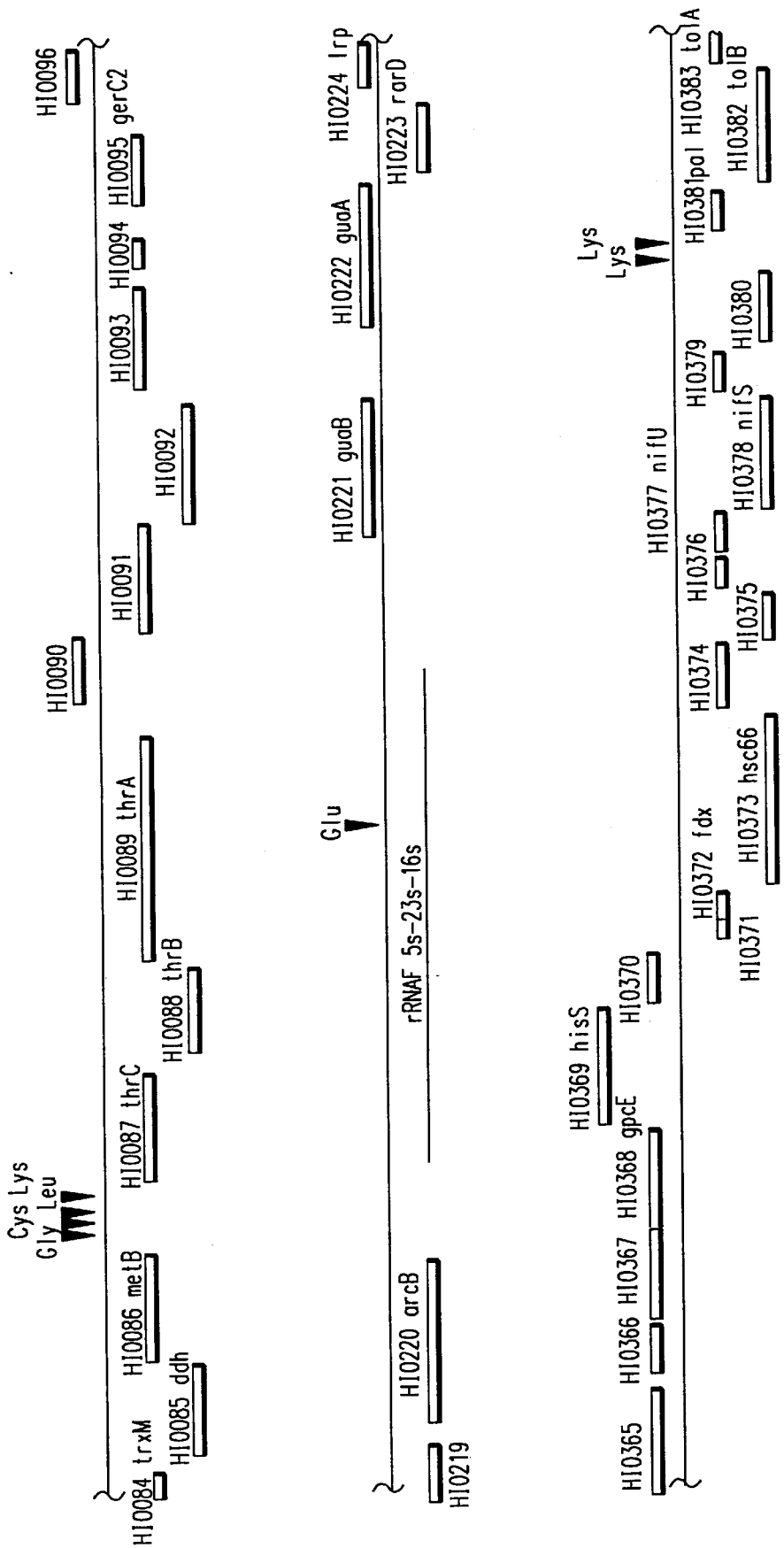
Figure 6H:
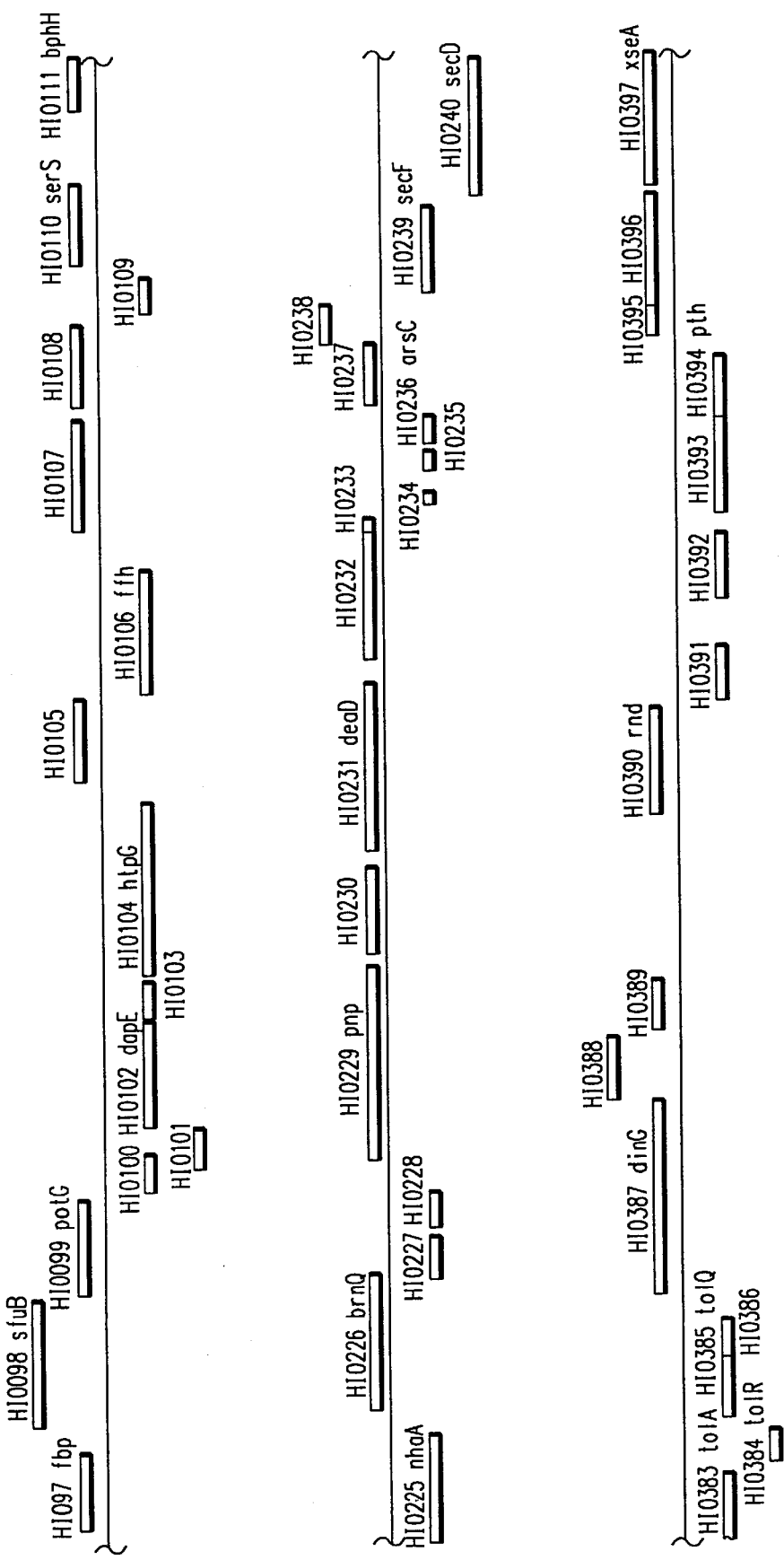
Figure 61:
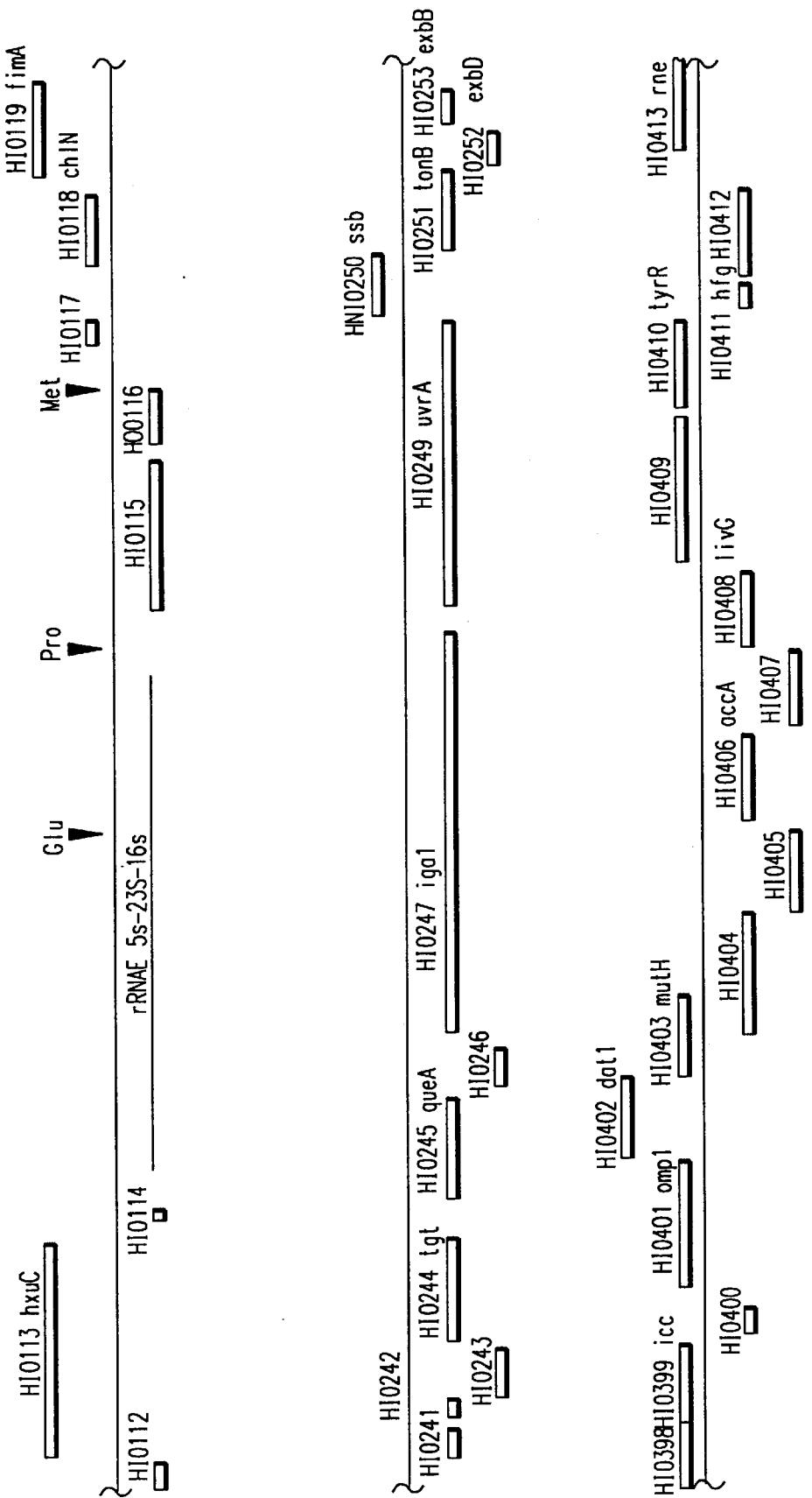
Figure 6J:
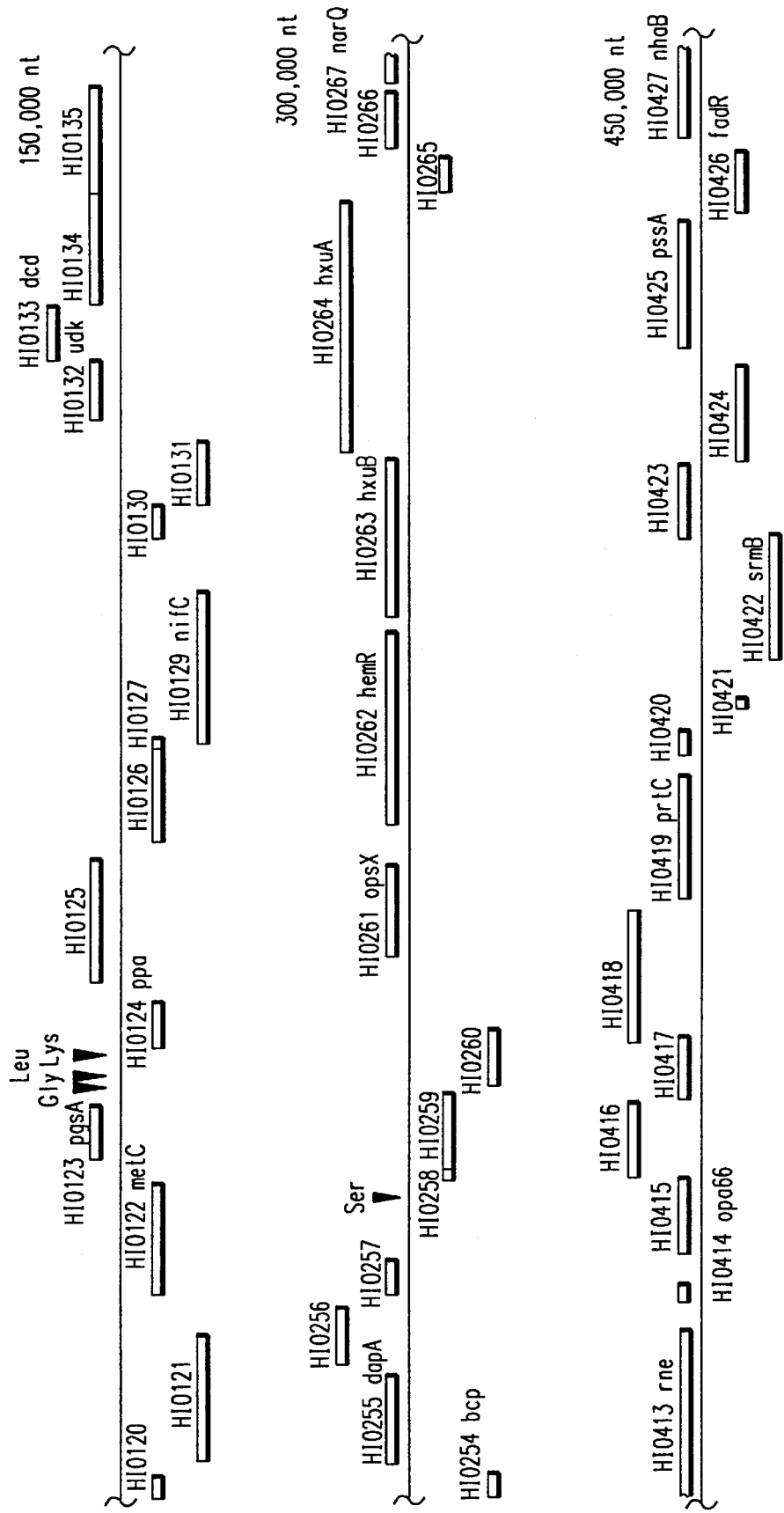
Figure 6K:
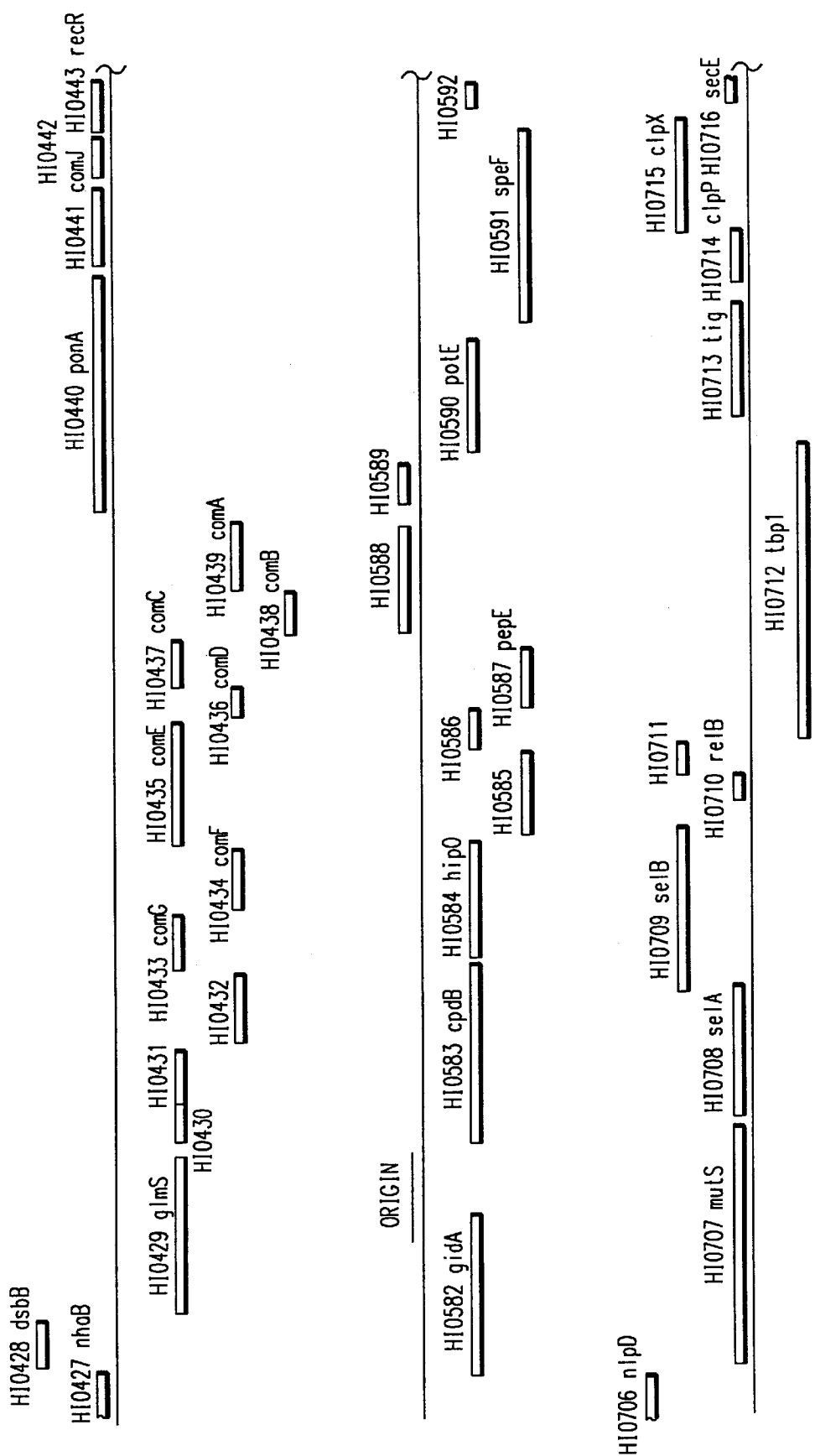
Figure 6L:
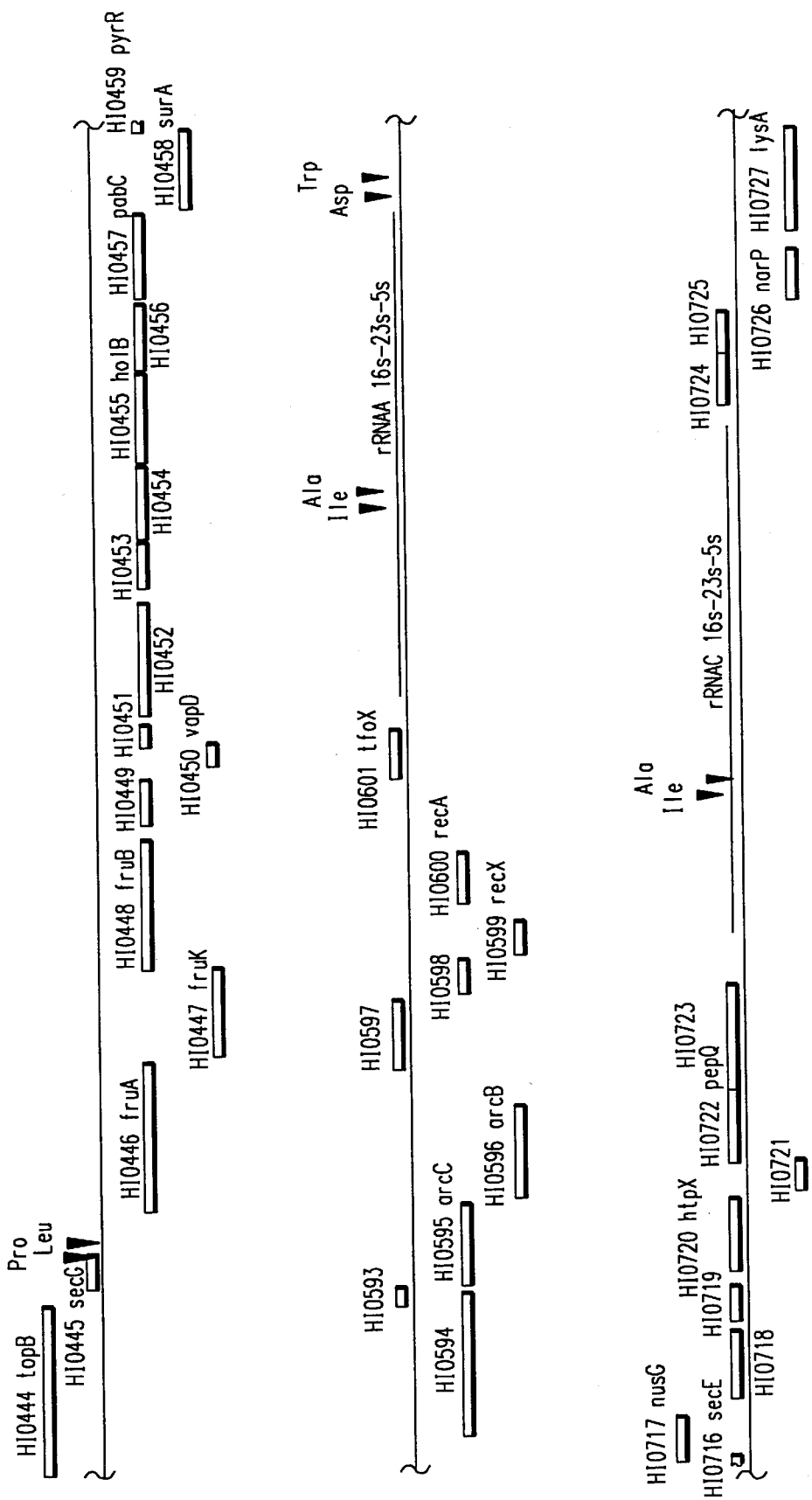
Figure 6M:
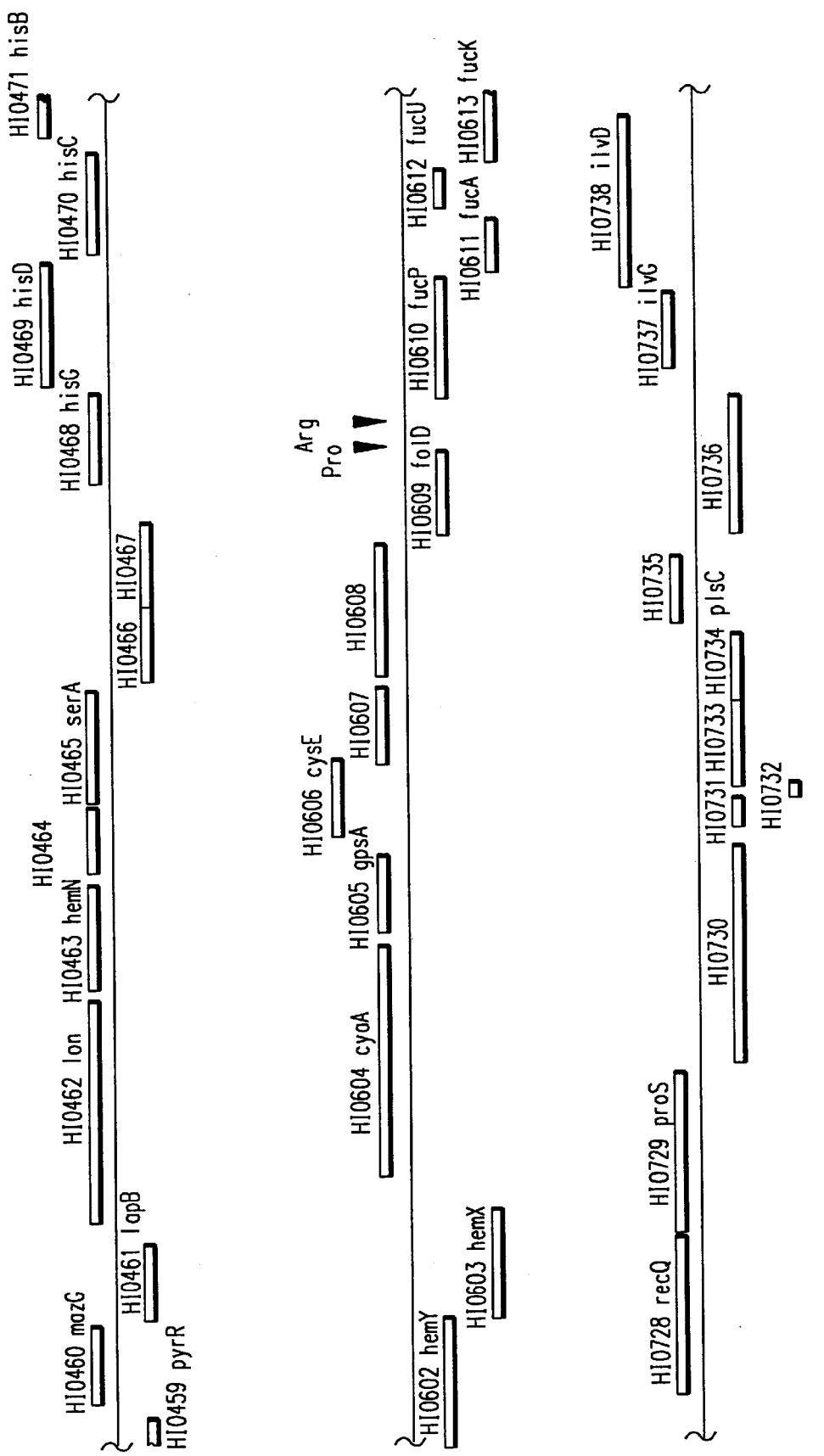
Figure 6N:
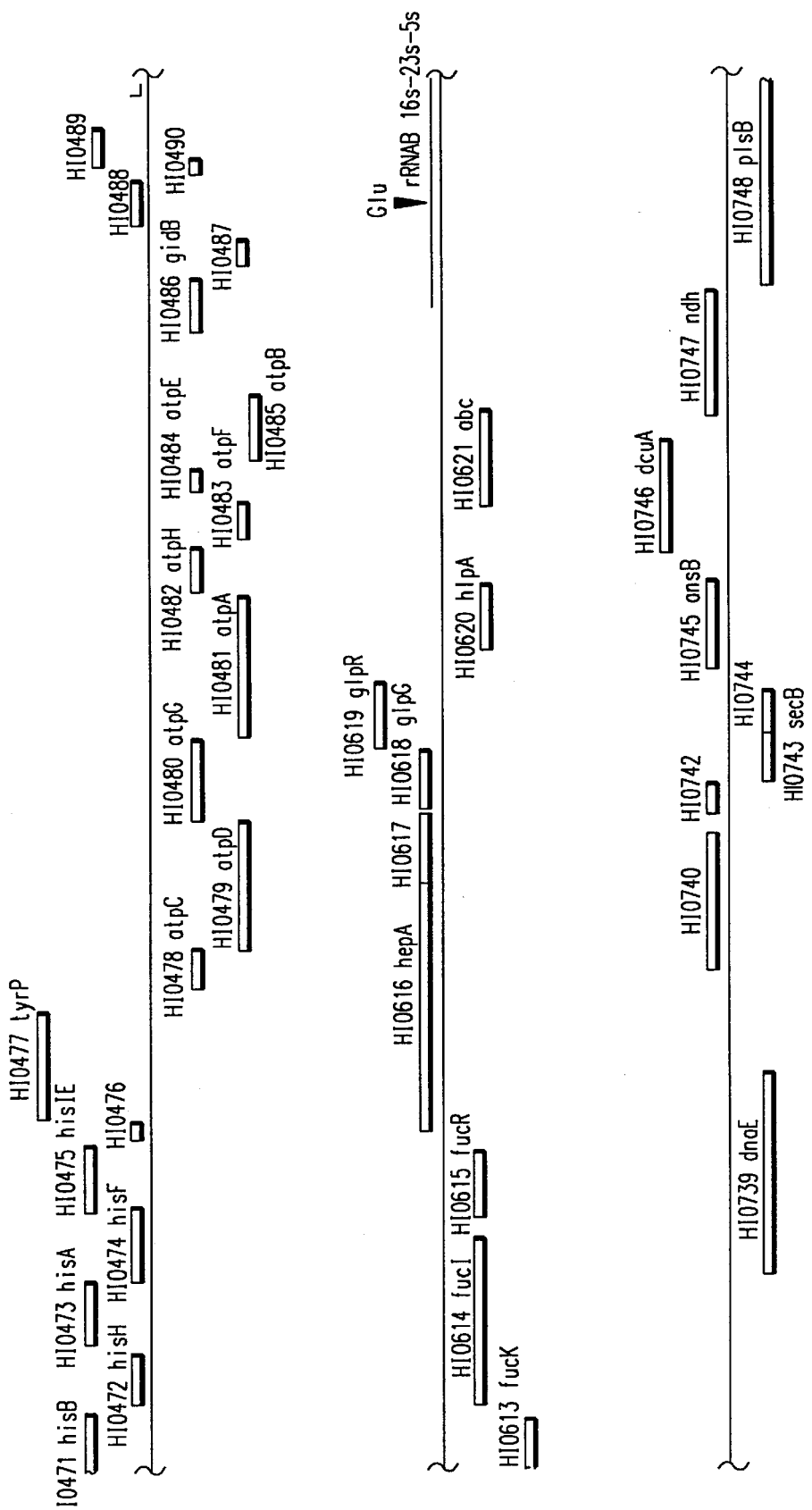
Figure 60:
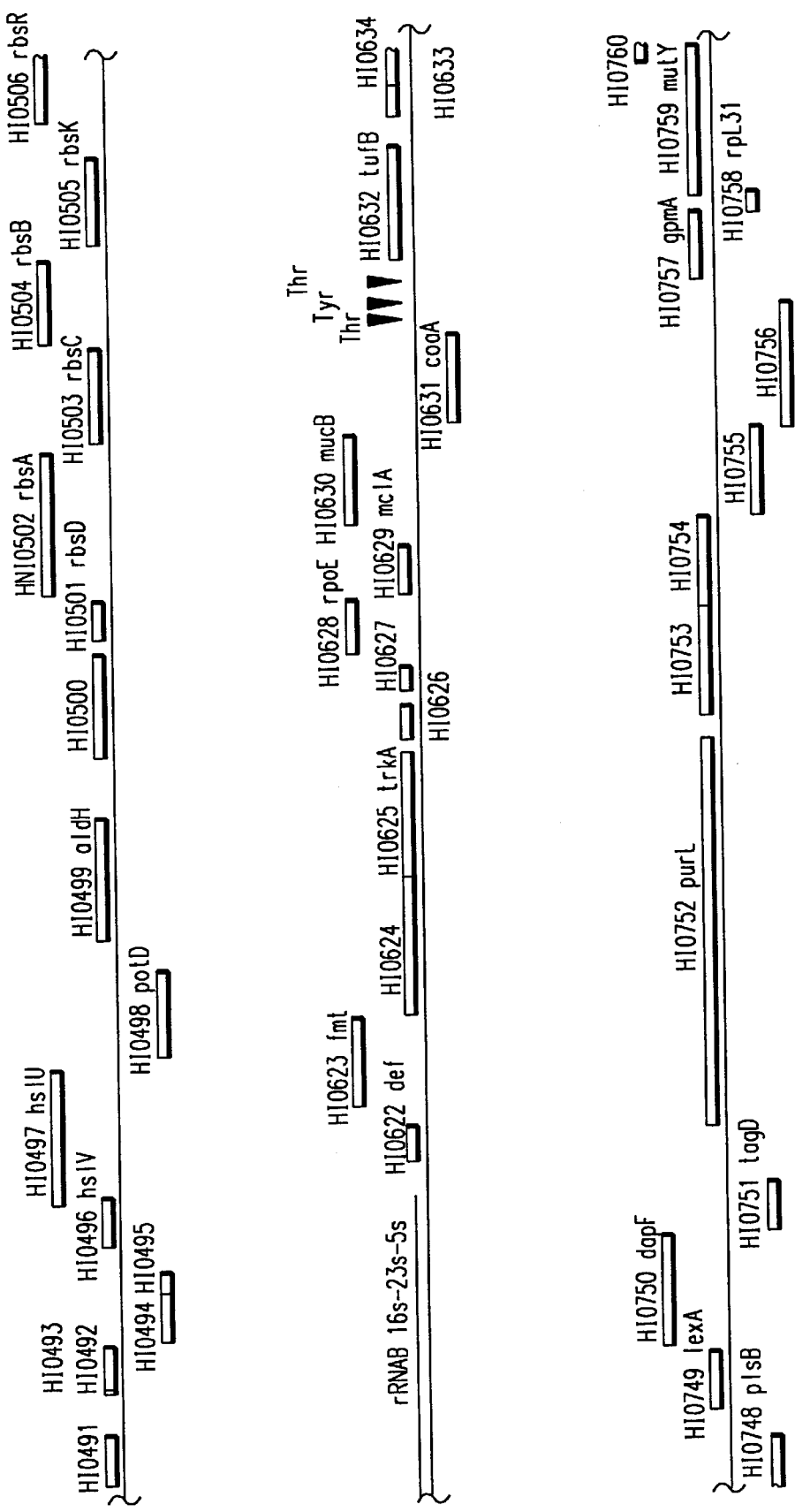
Figure 6P:
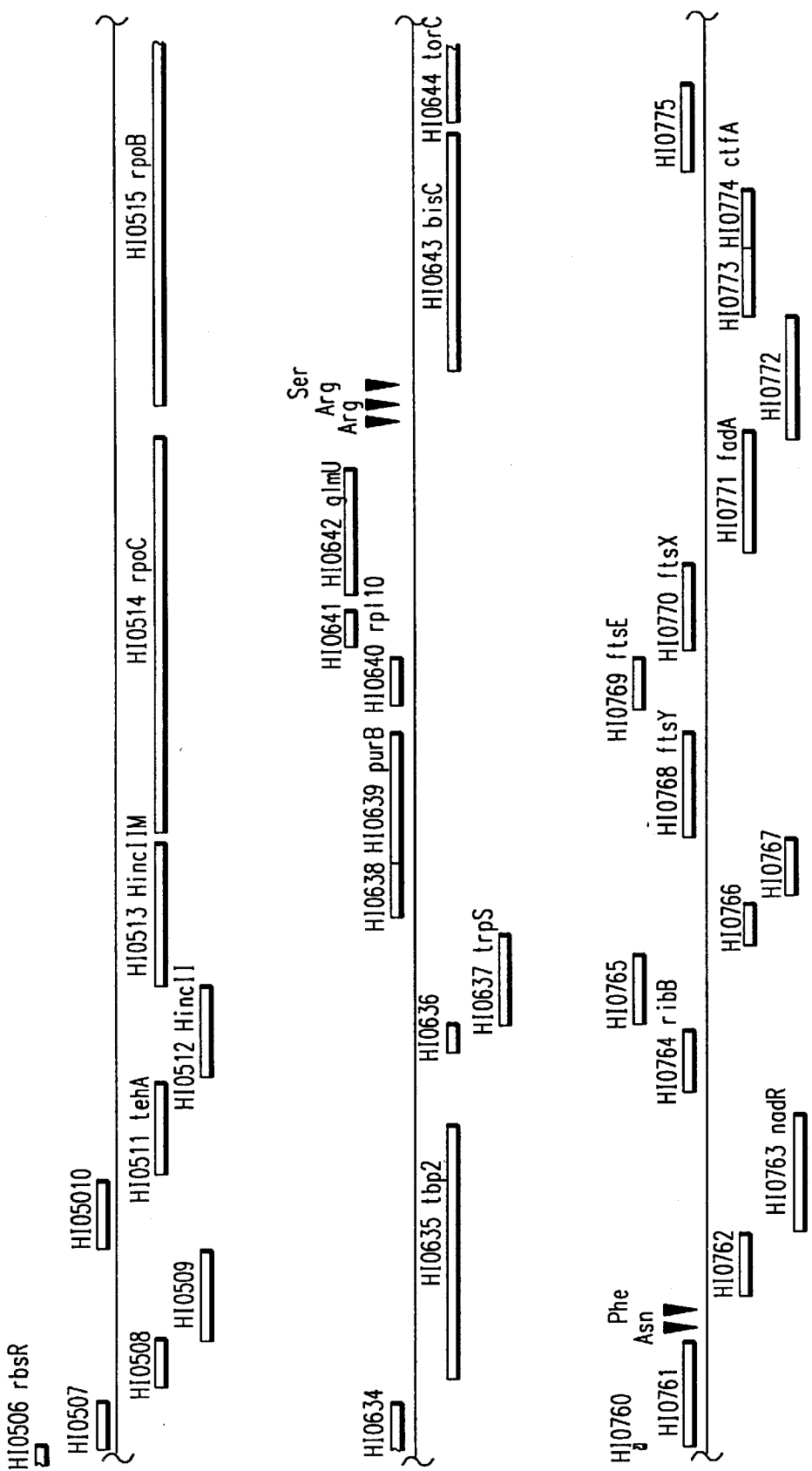
Figure 6Q:
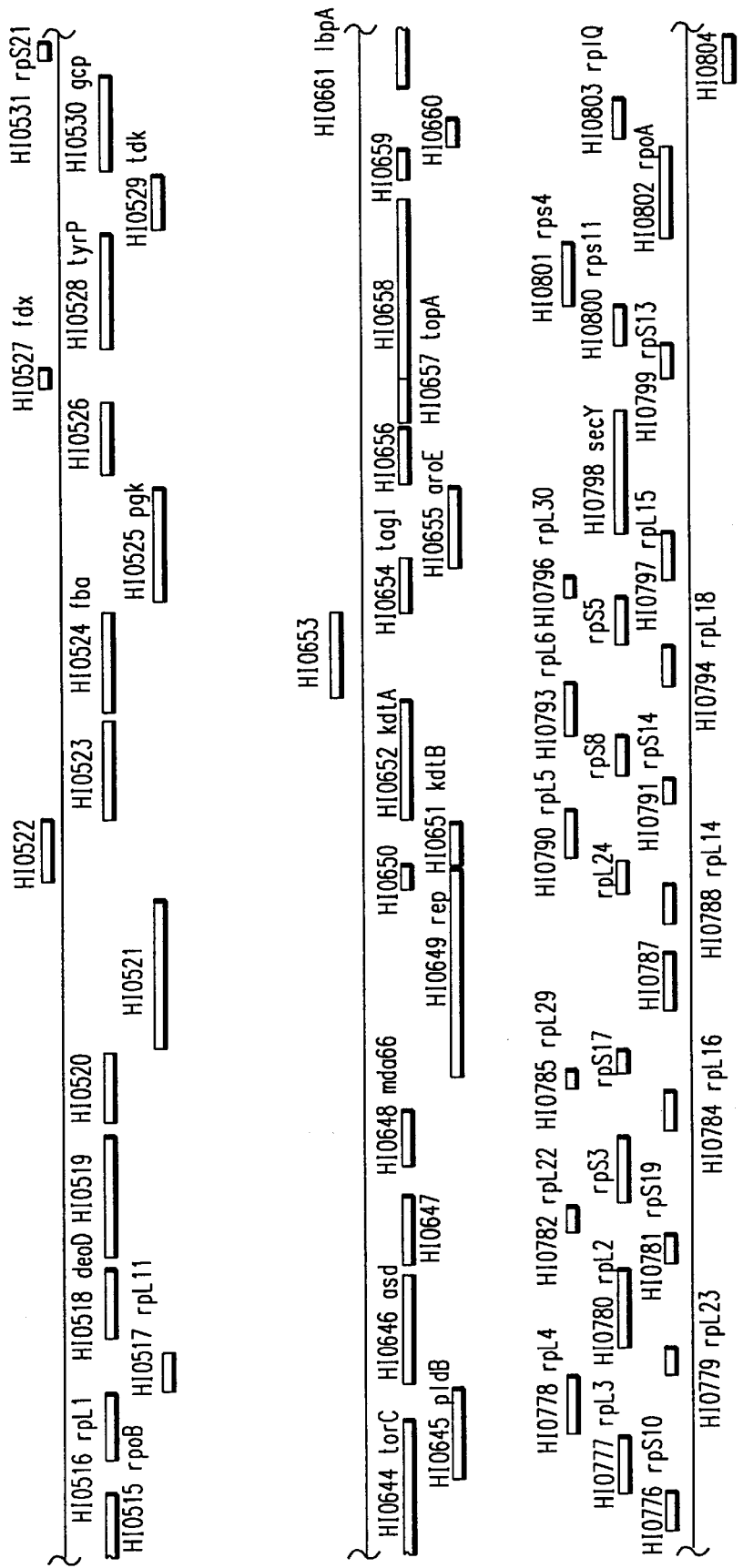
Figure 6R:
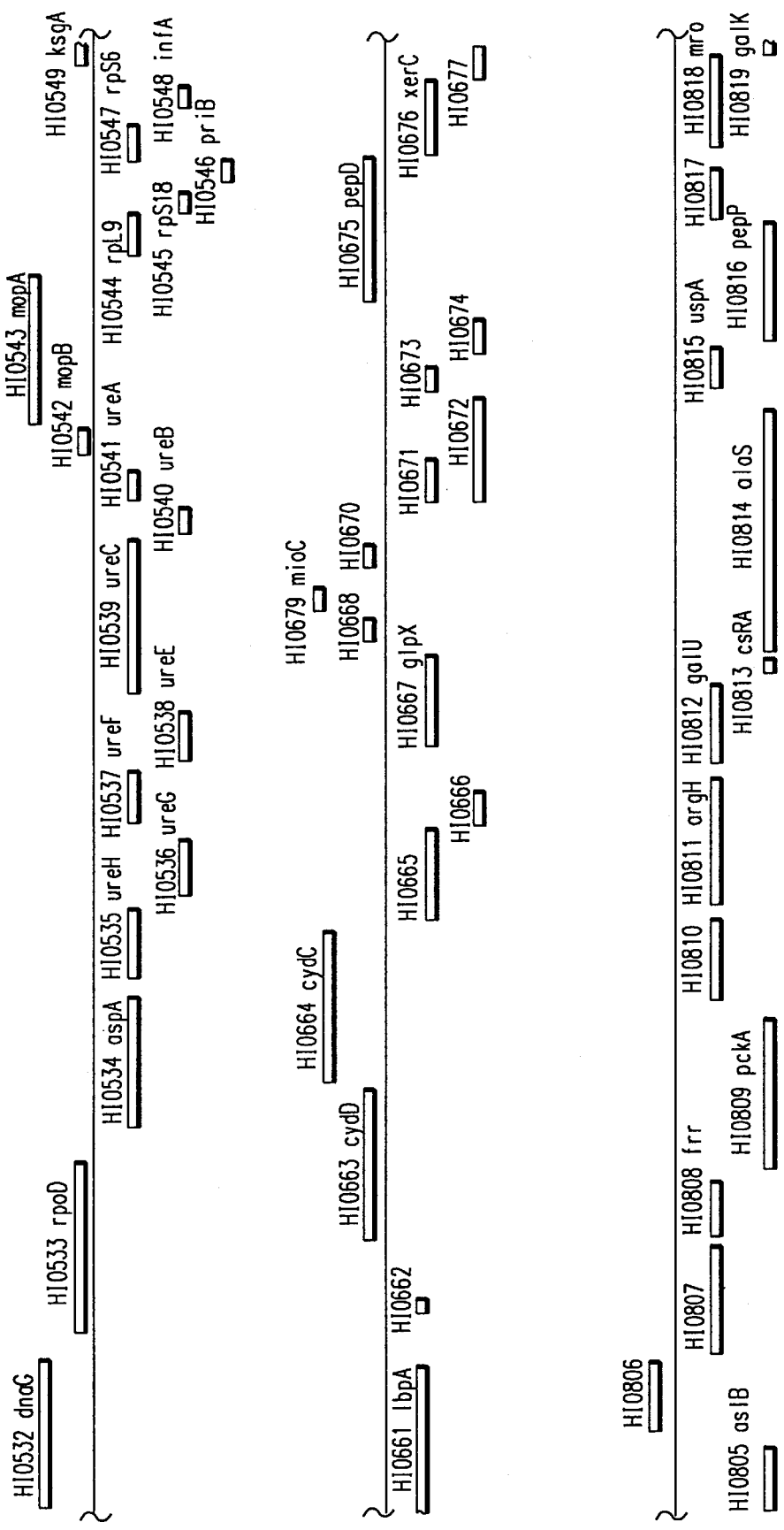
Figure 6S:
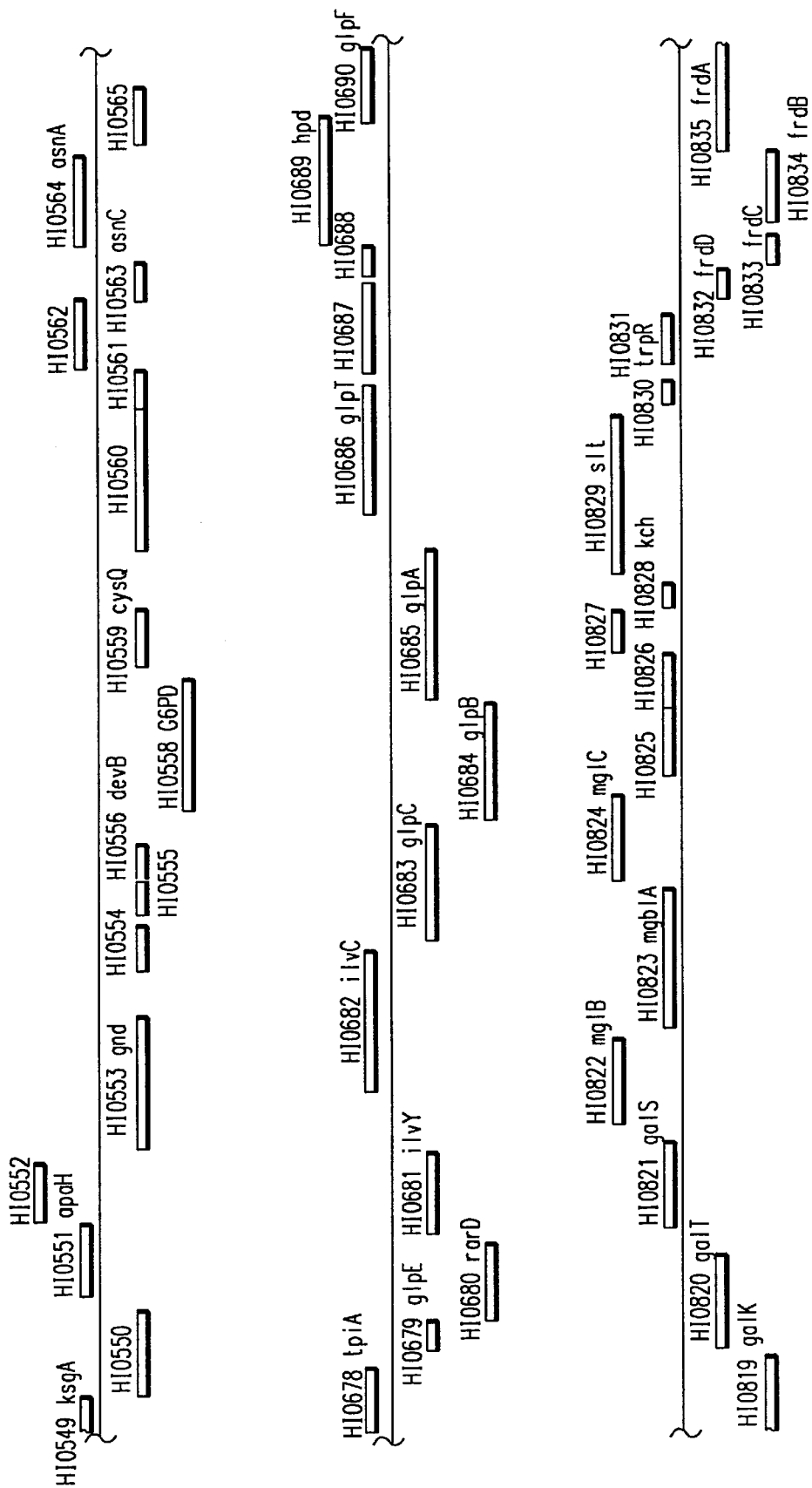
Figure 6T:
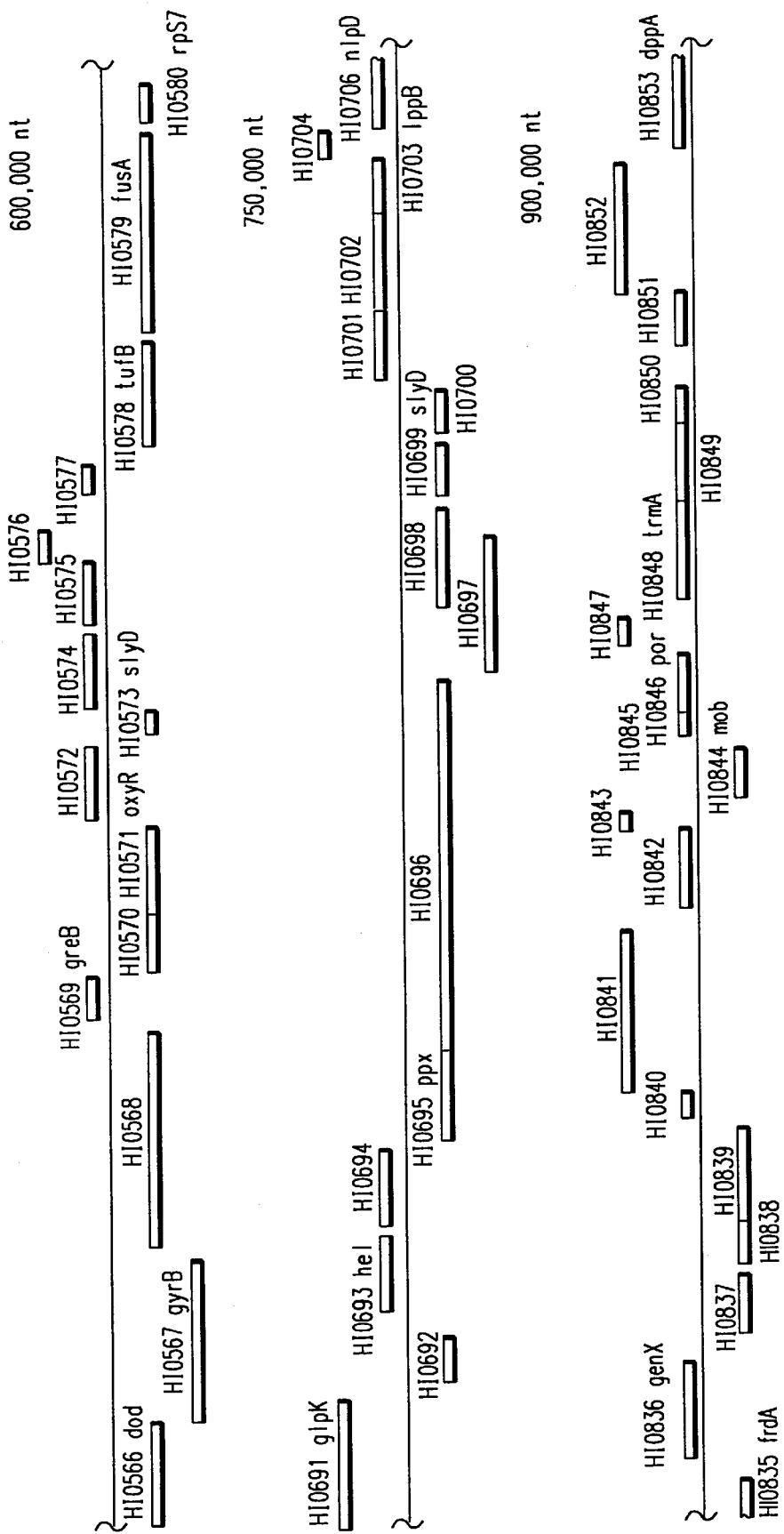
Figure 6U:
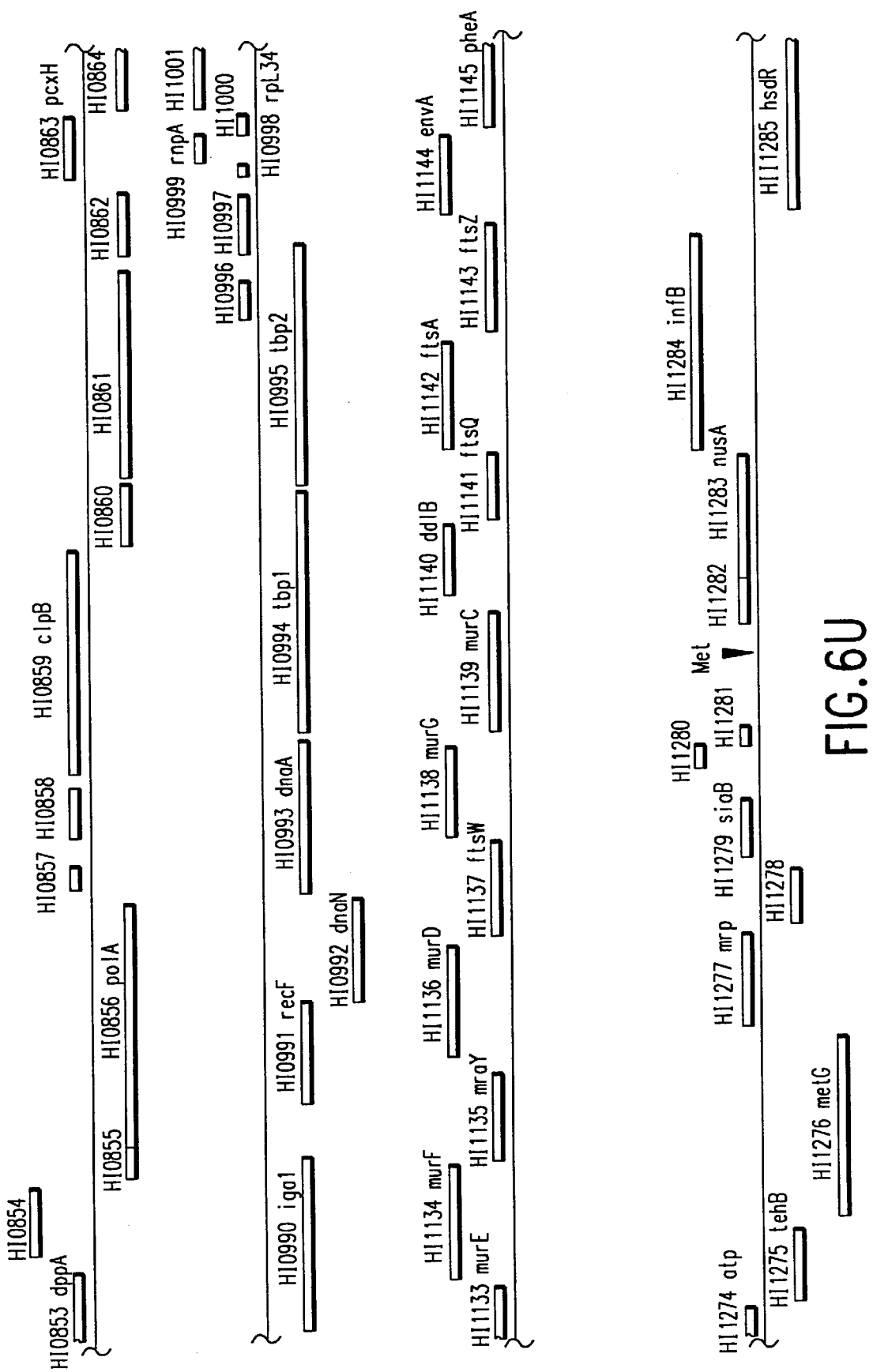
Figure 6V:
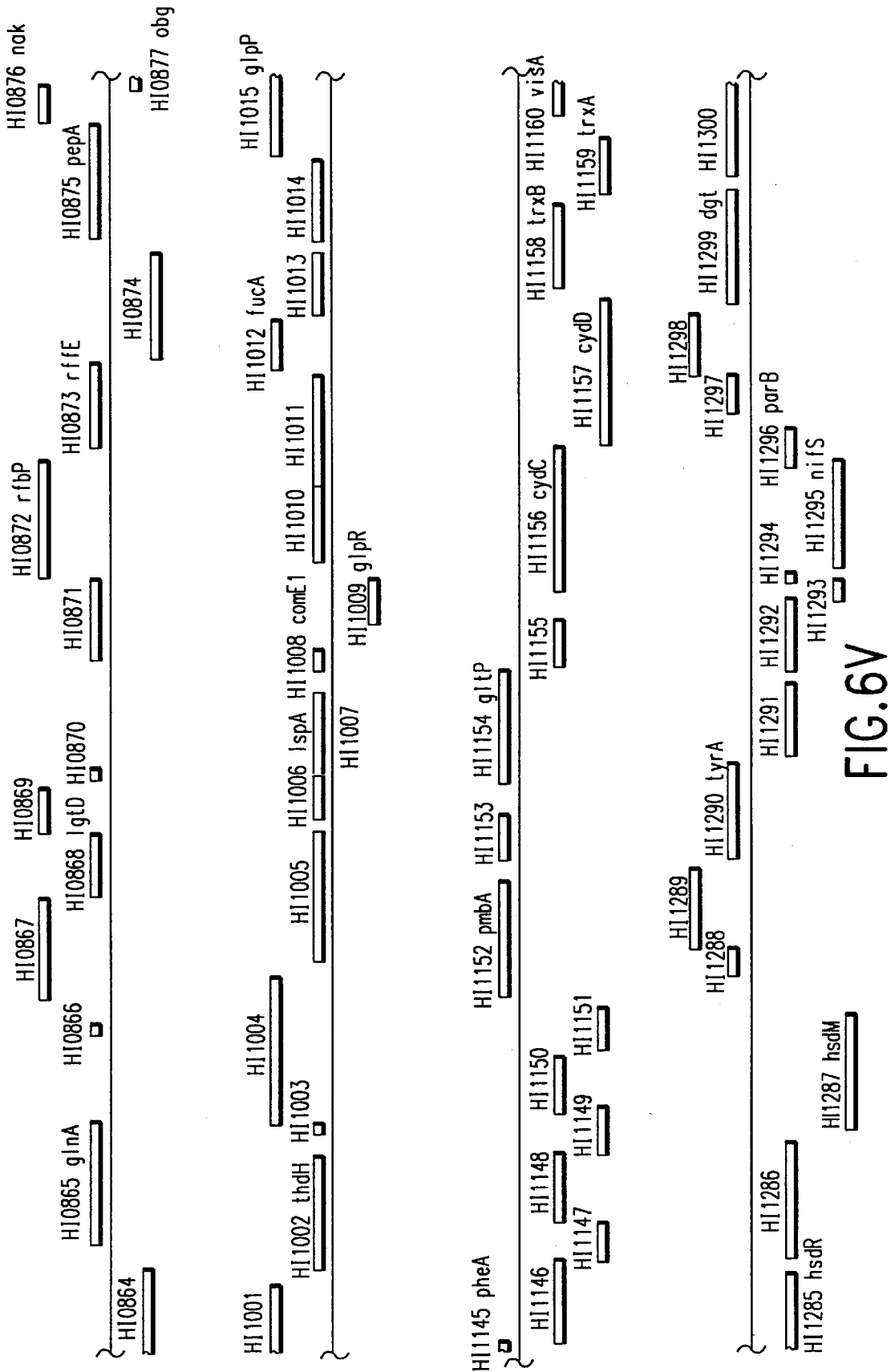
Figure 6W:
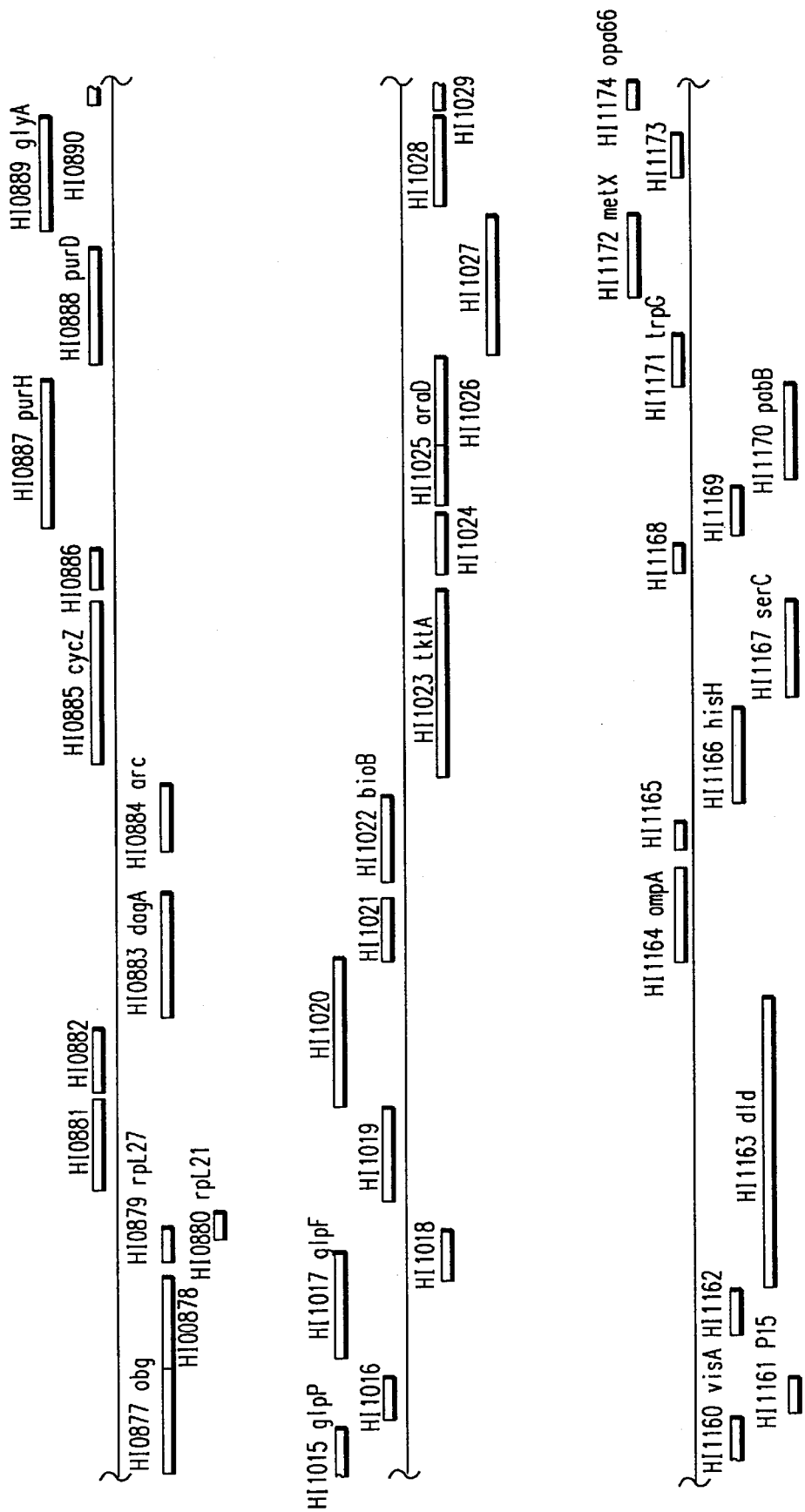
Figure 6X:
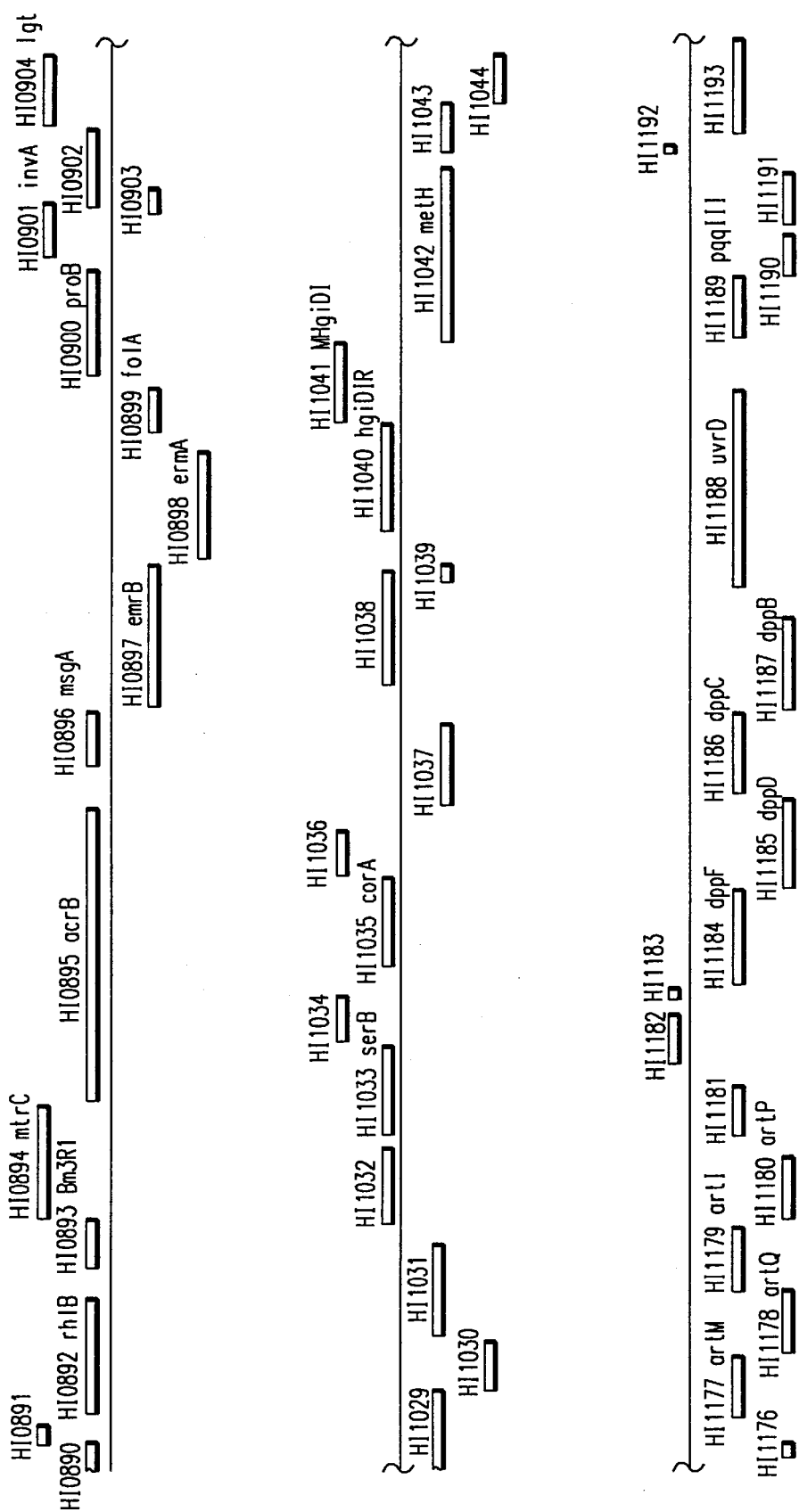
Figure 6Y:
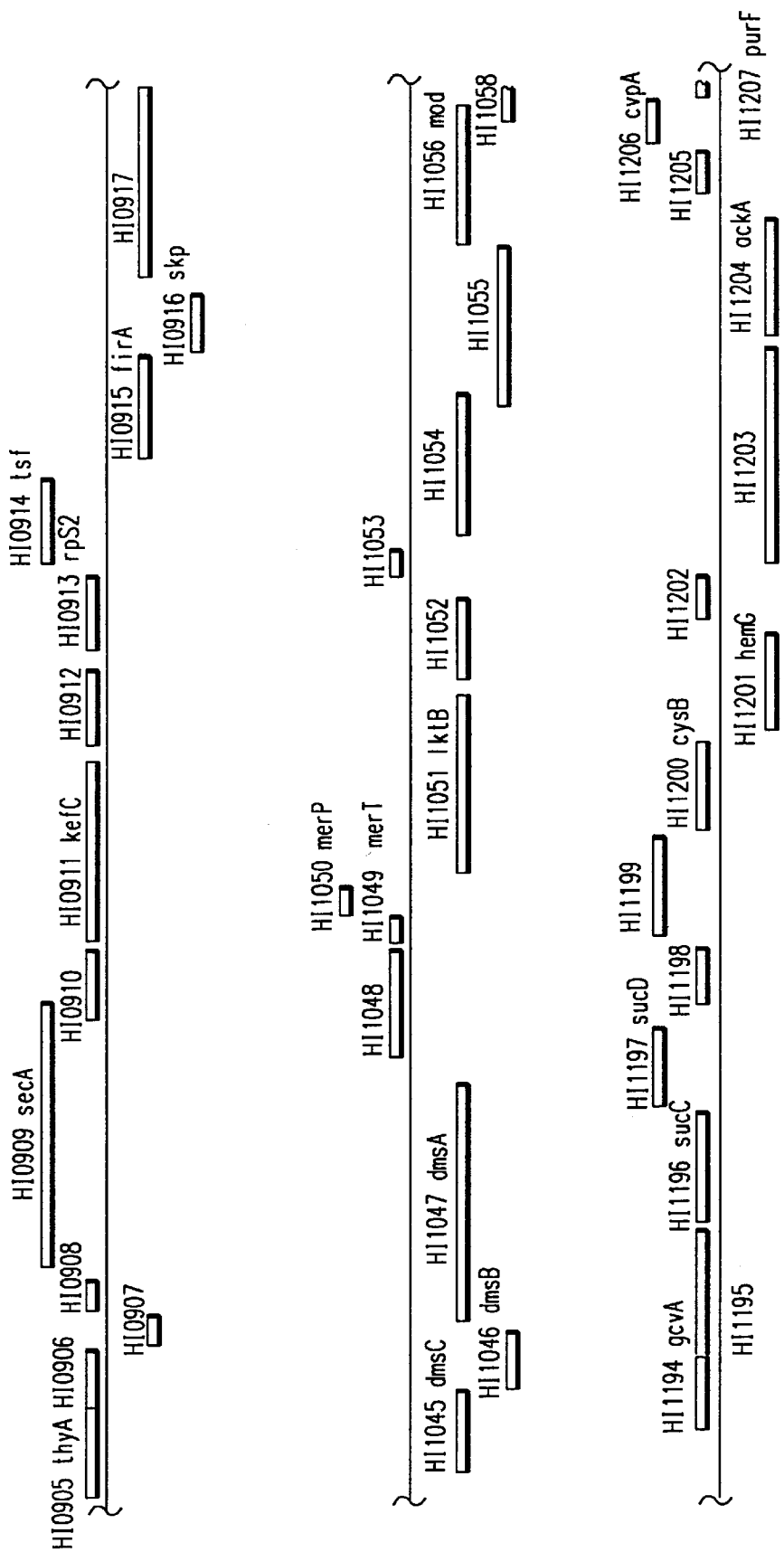
Figure 6Z:
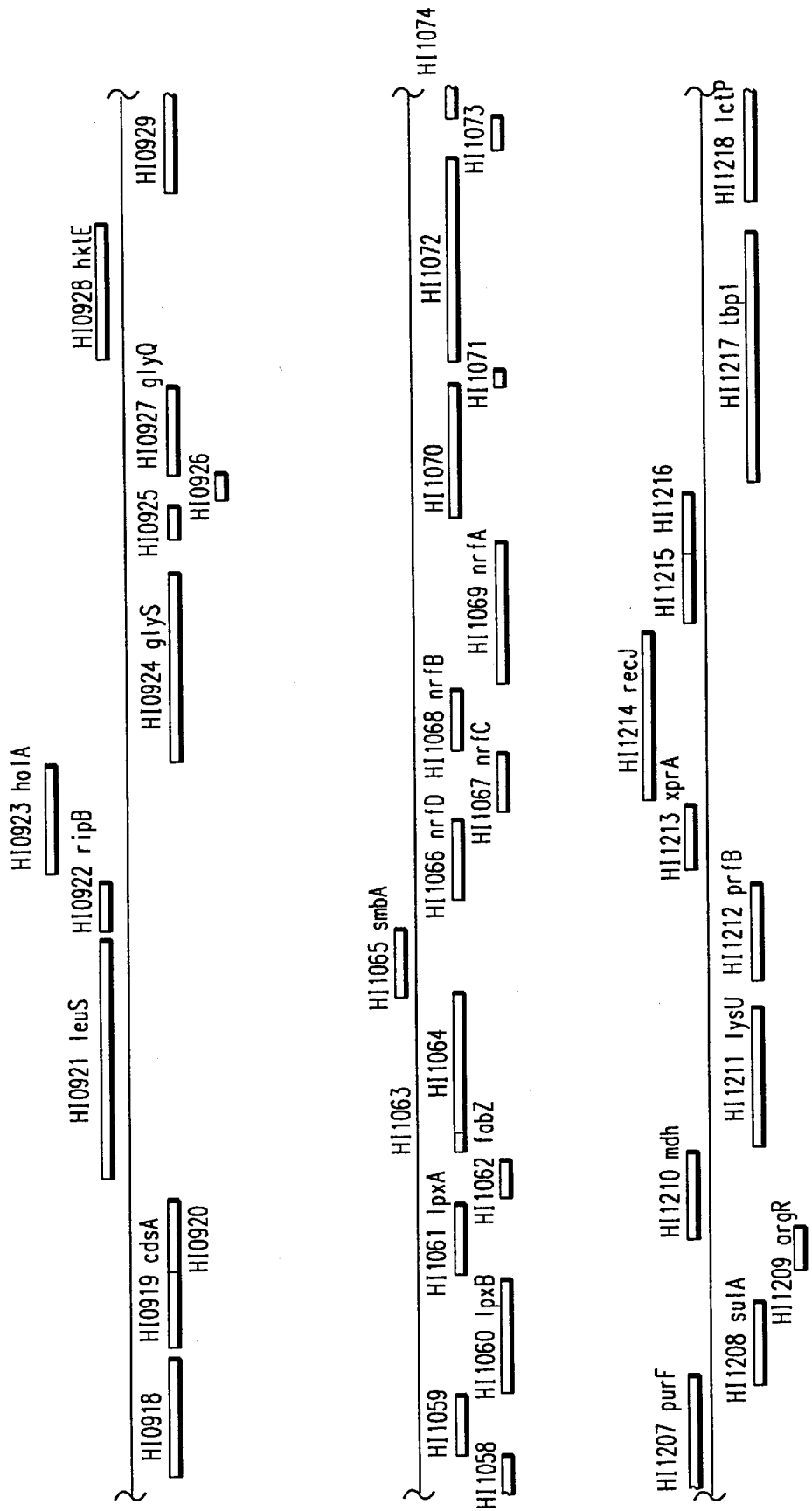
Figure 6A:
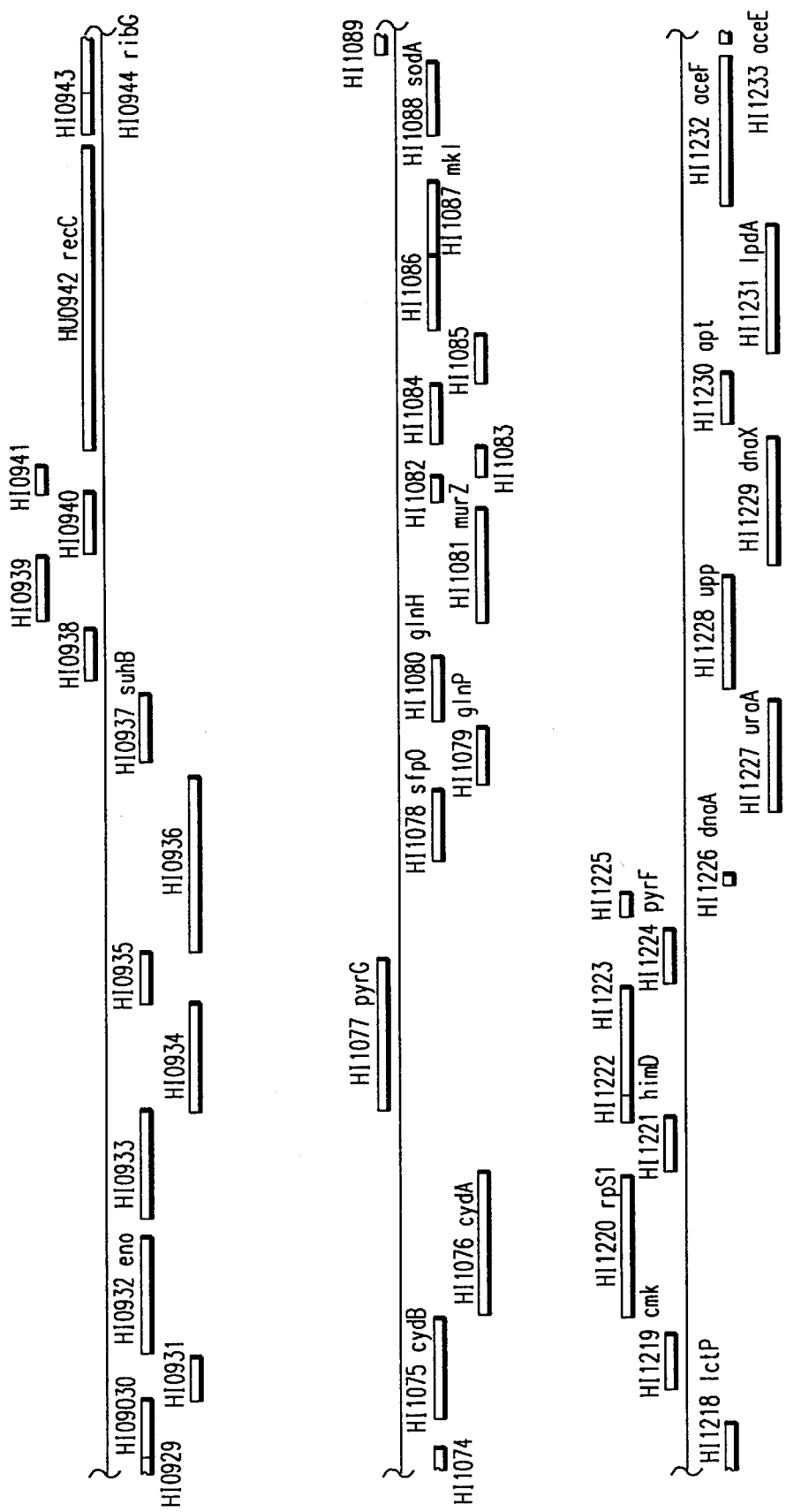
Figure 6A:
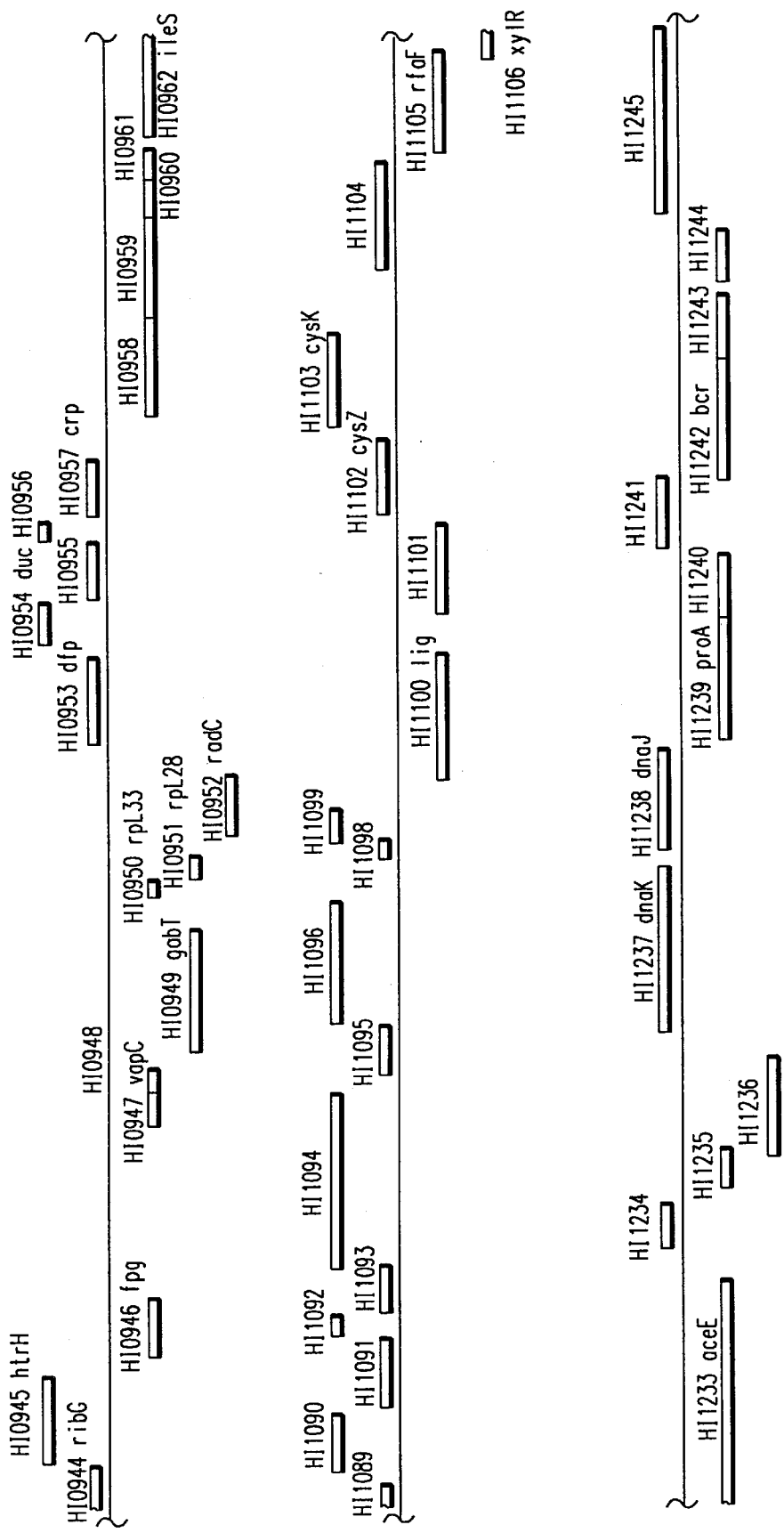
Figure 6A:
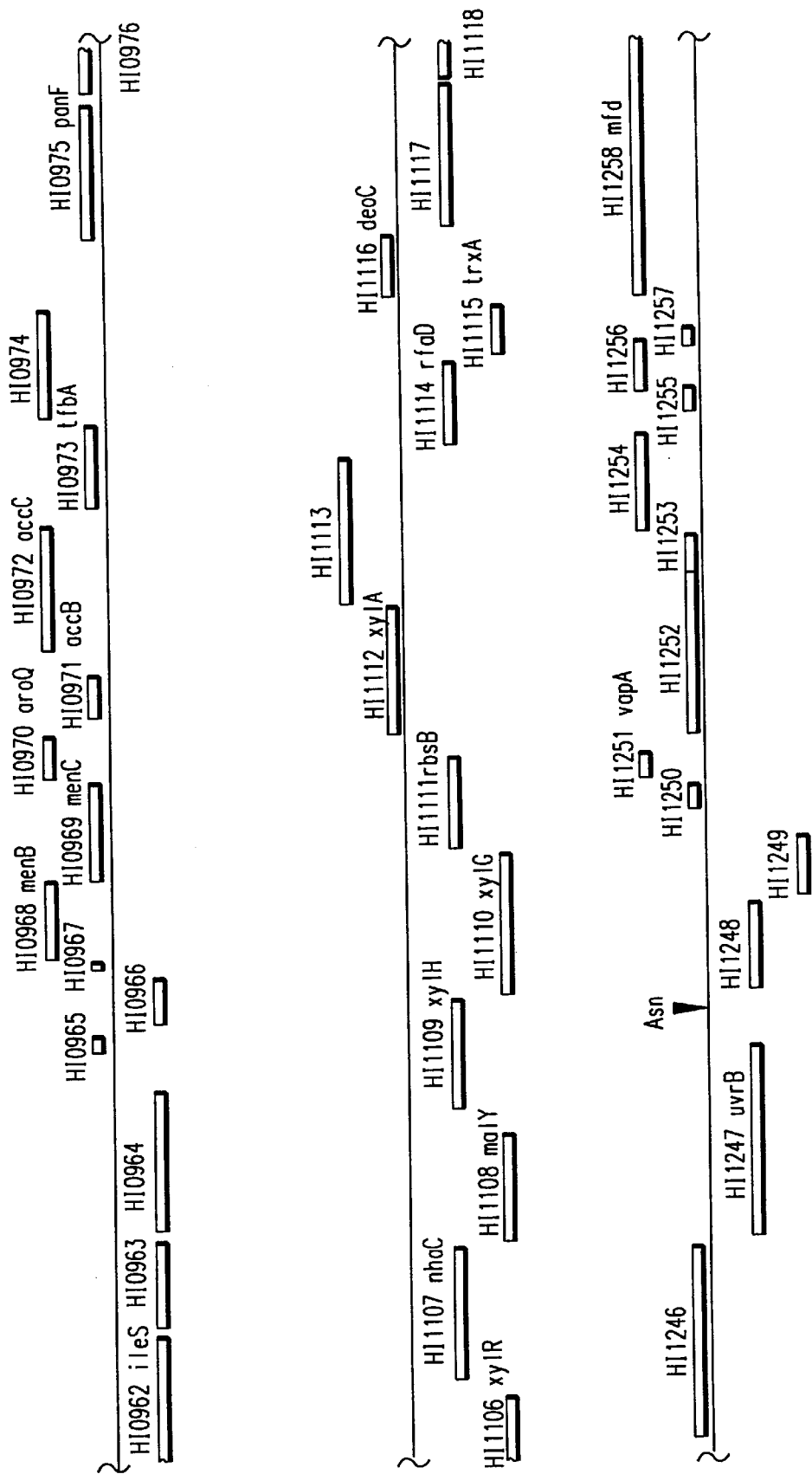
Figure 6A:
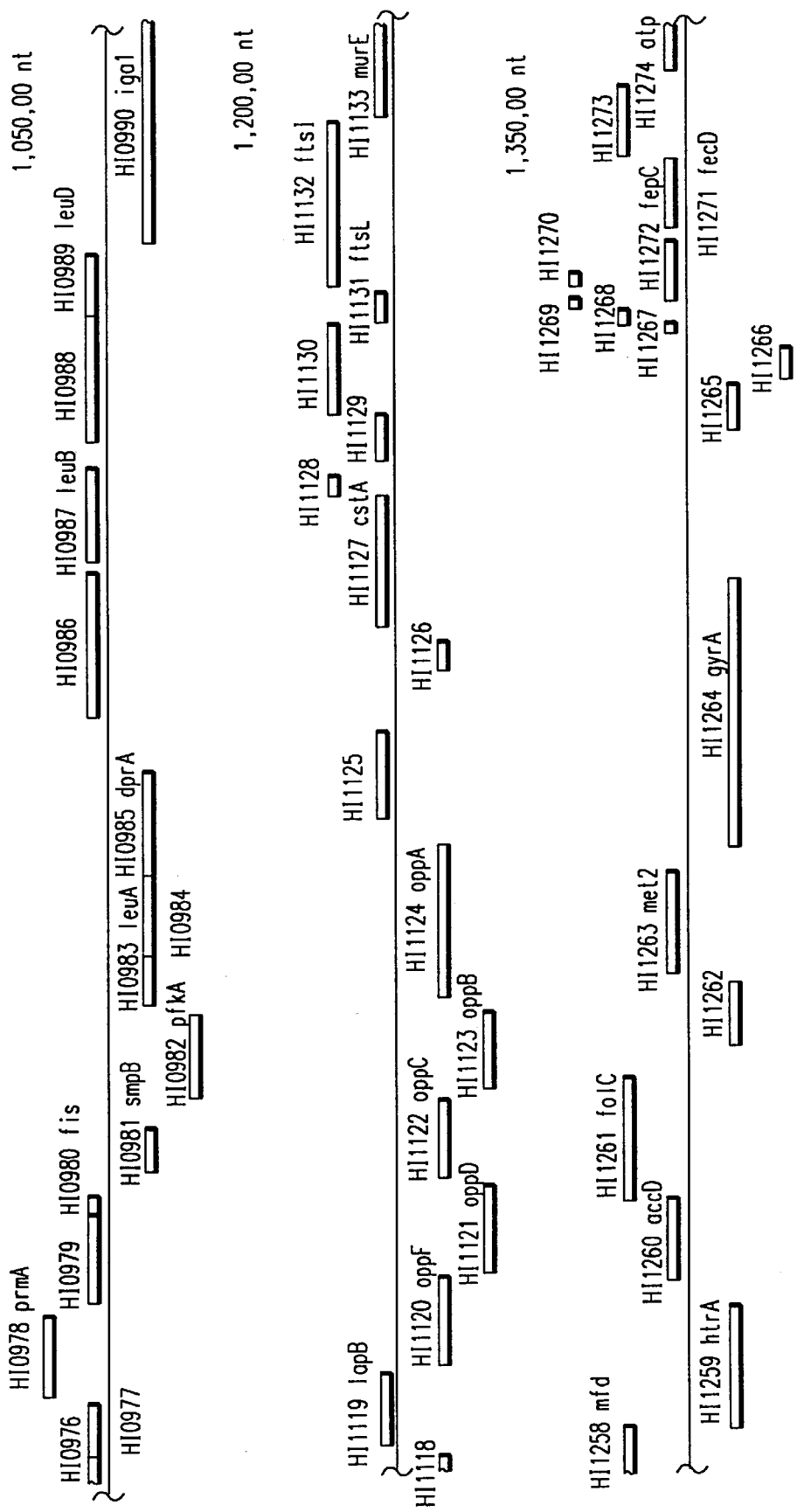
Figure 6A:
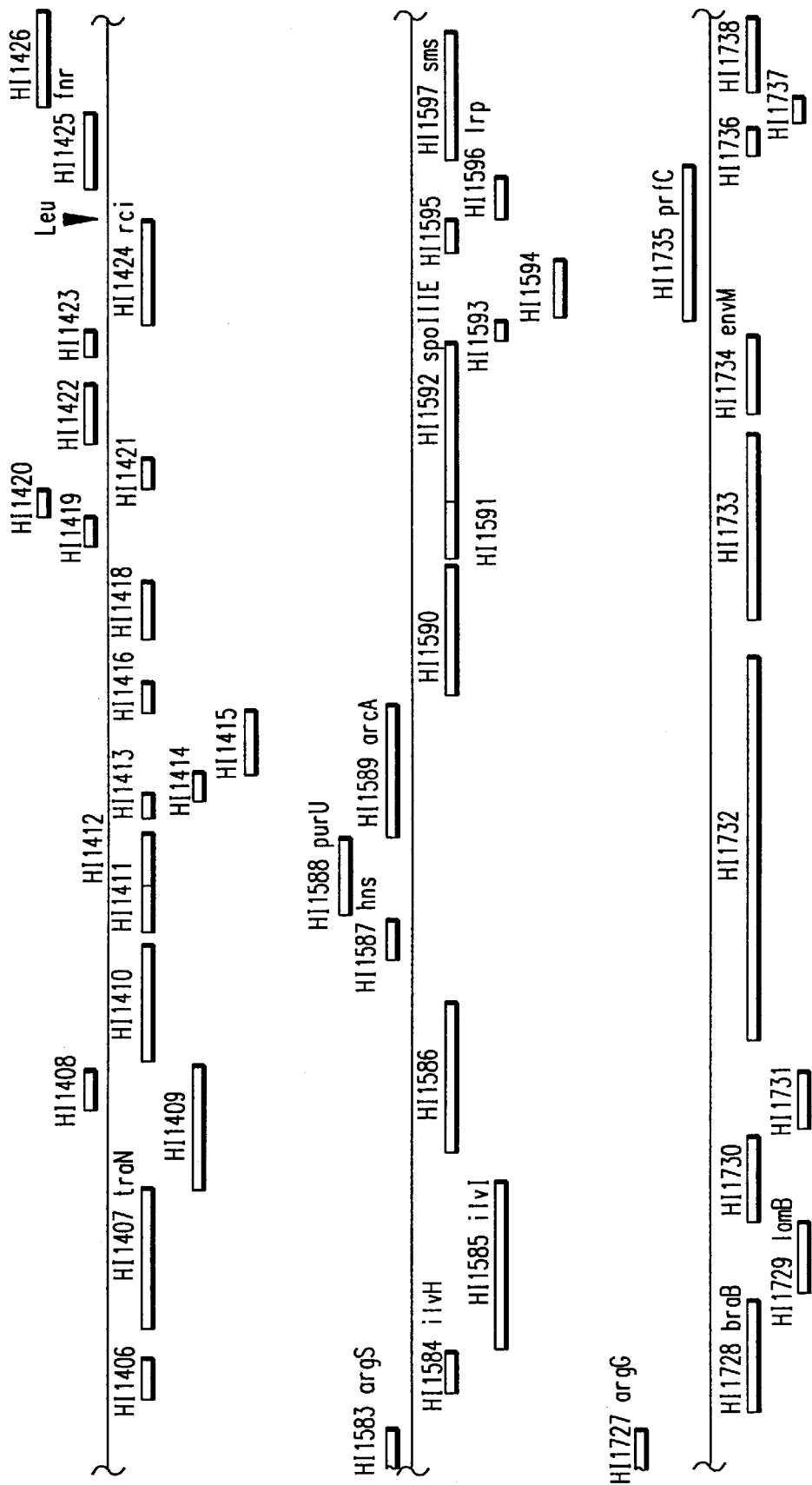
Figure 6A:
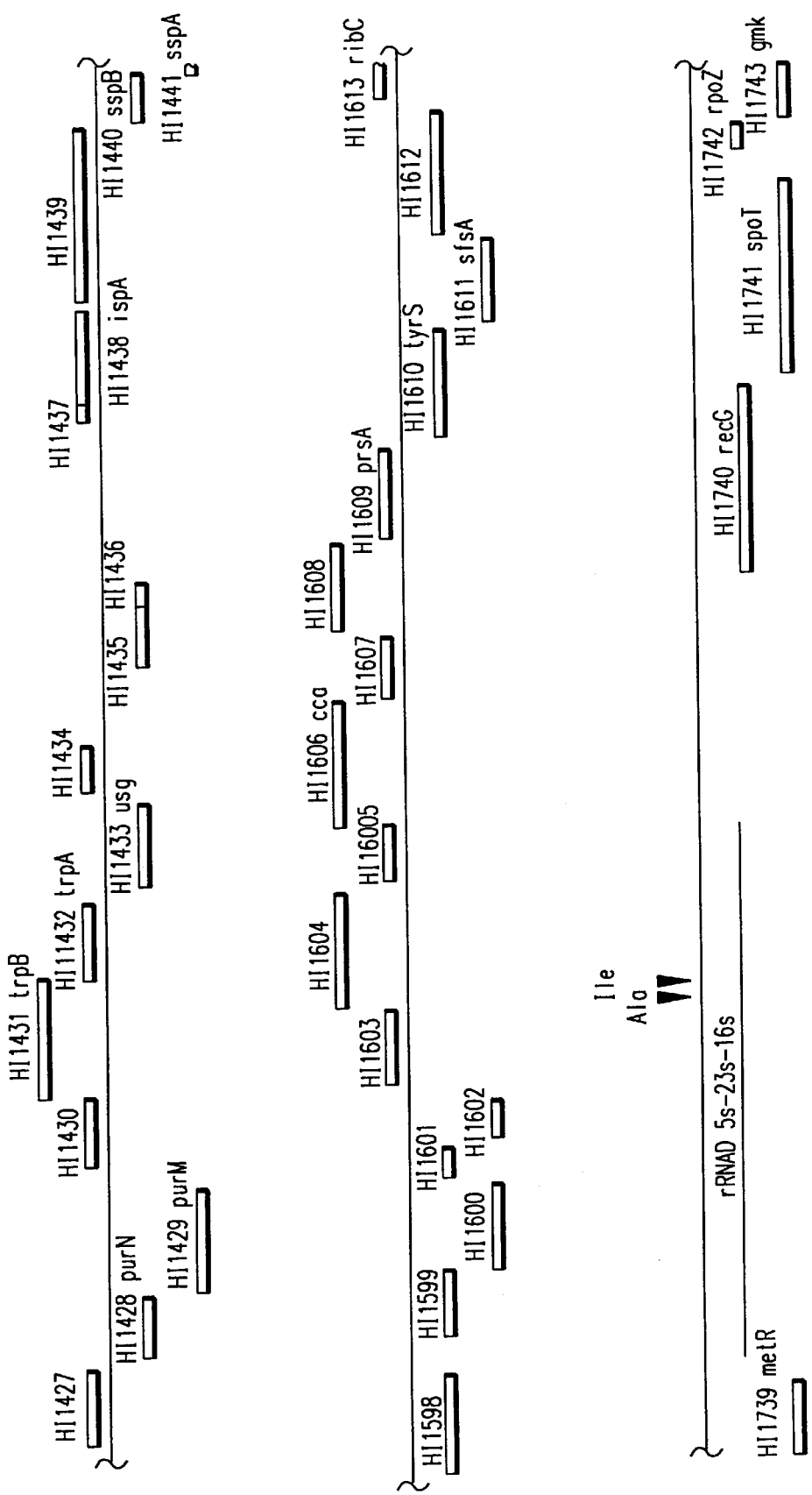
Figure 6A:
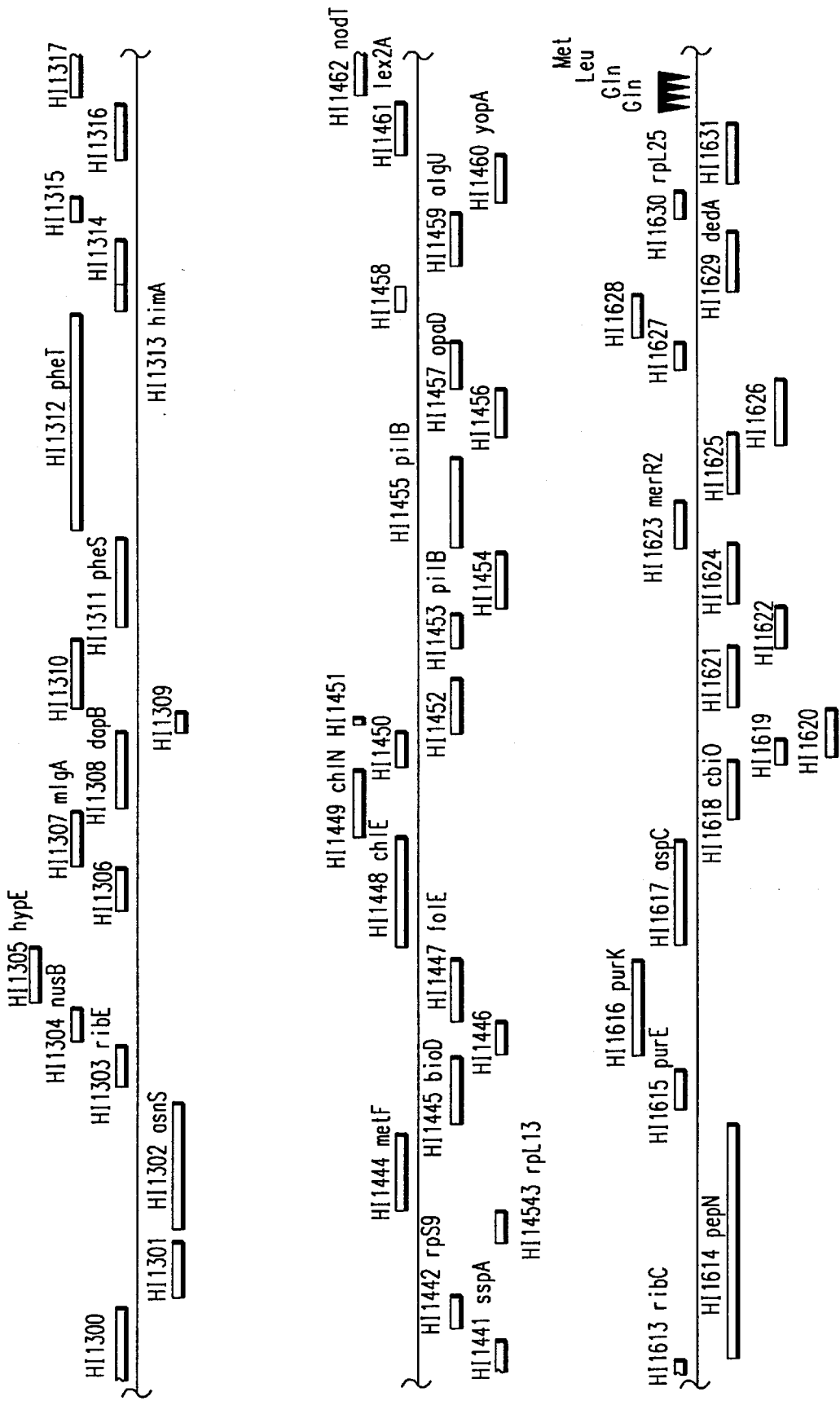
Figure 6A:
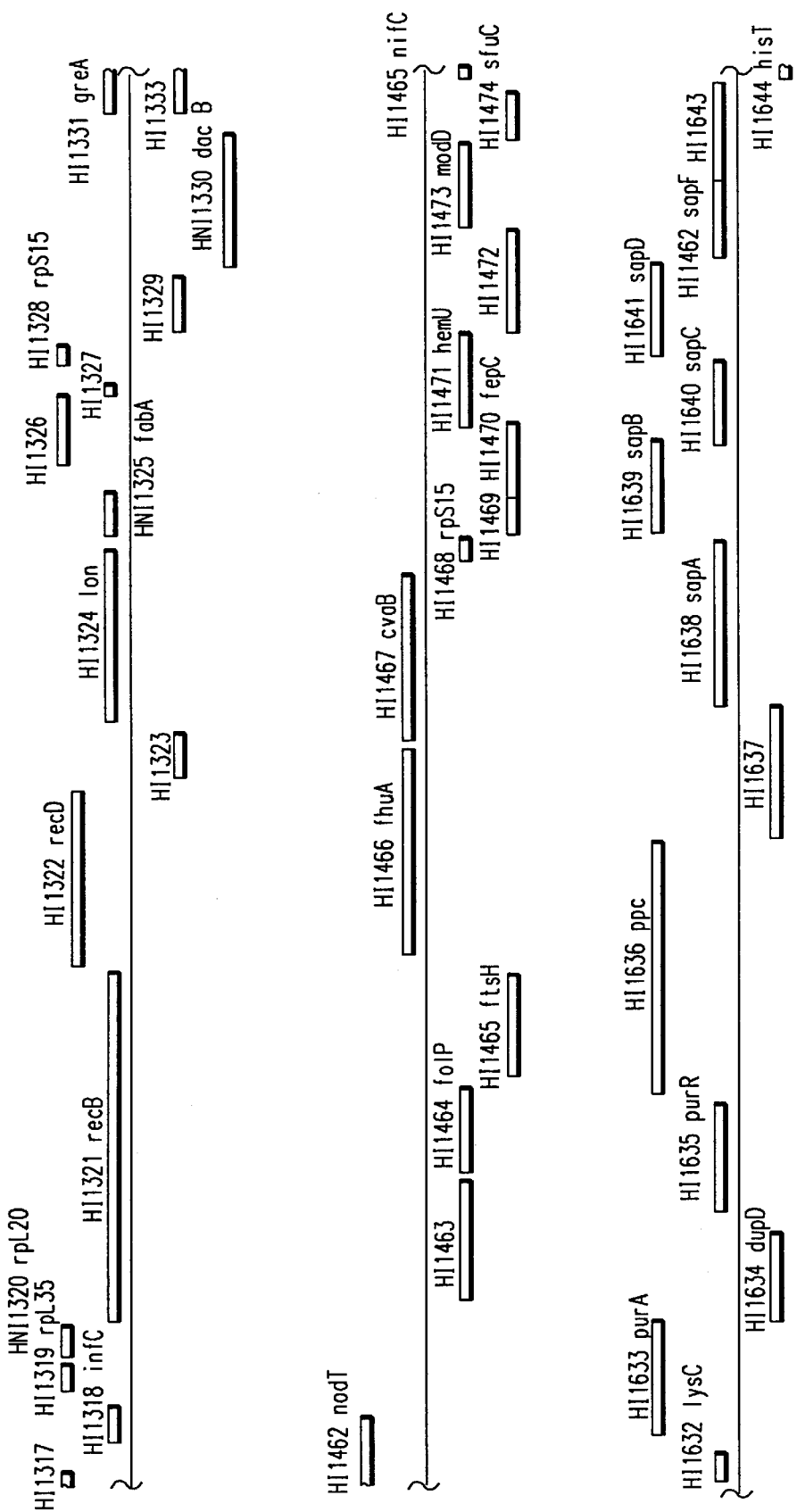
Figure 6A:
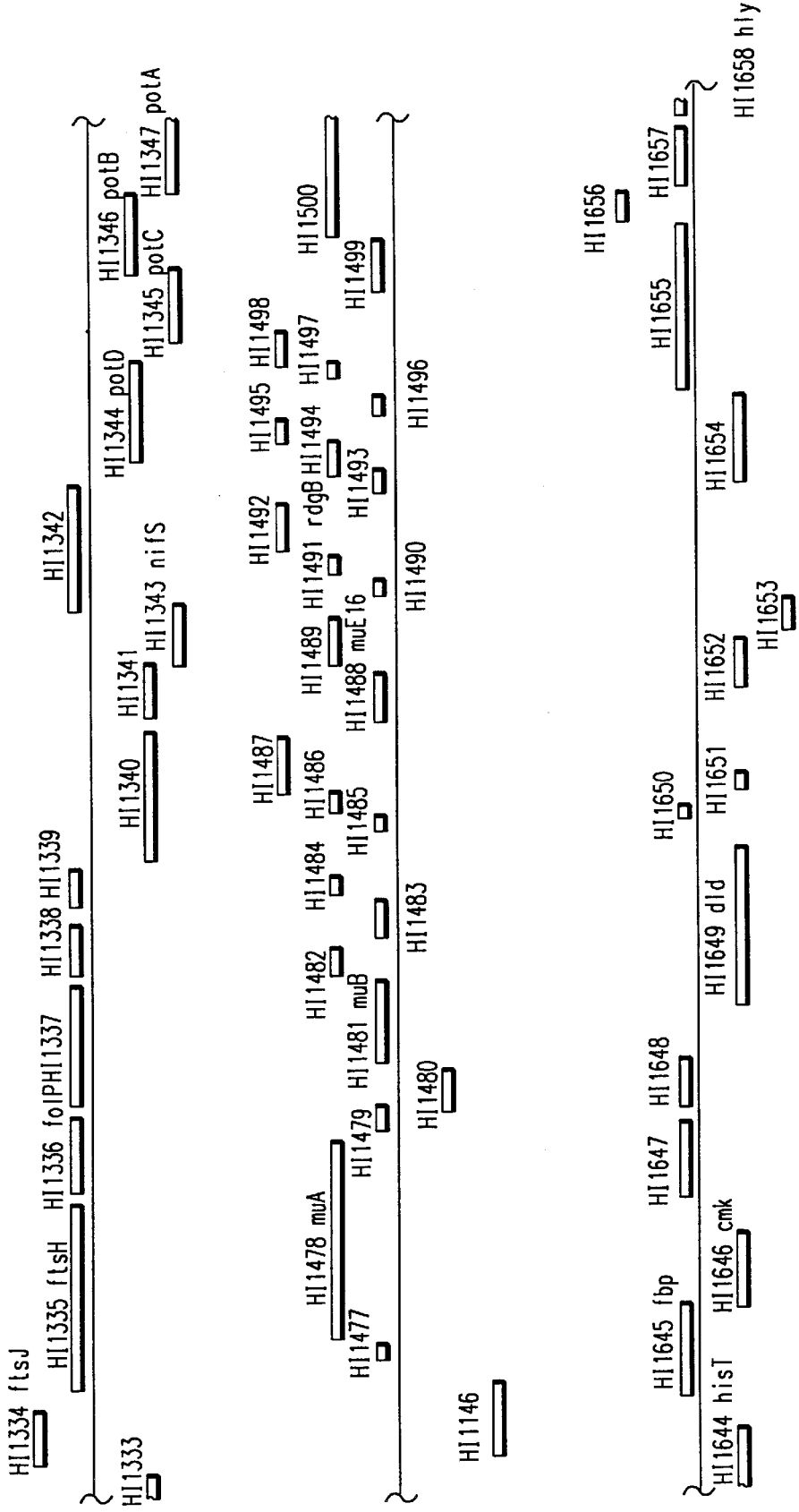
Figure 6A:
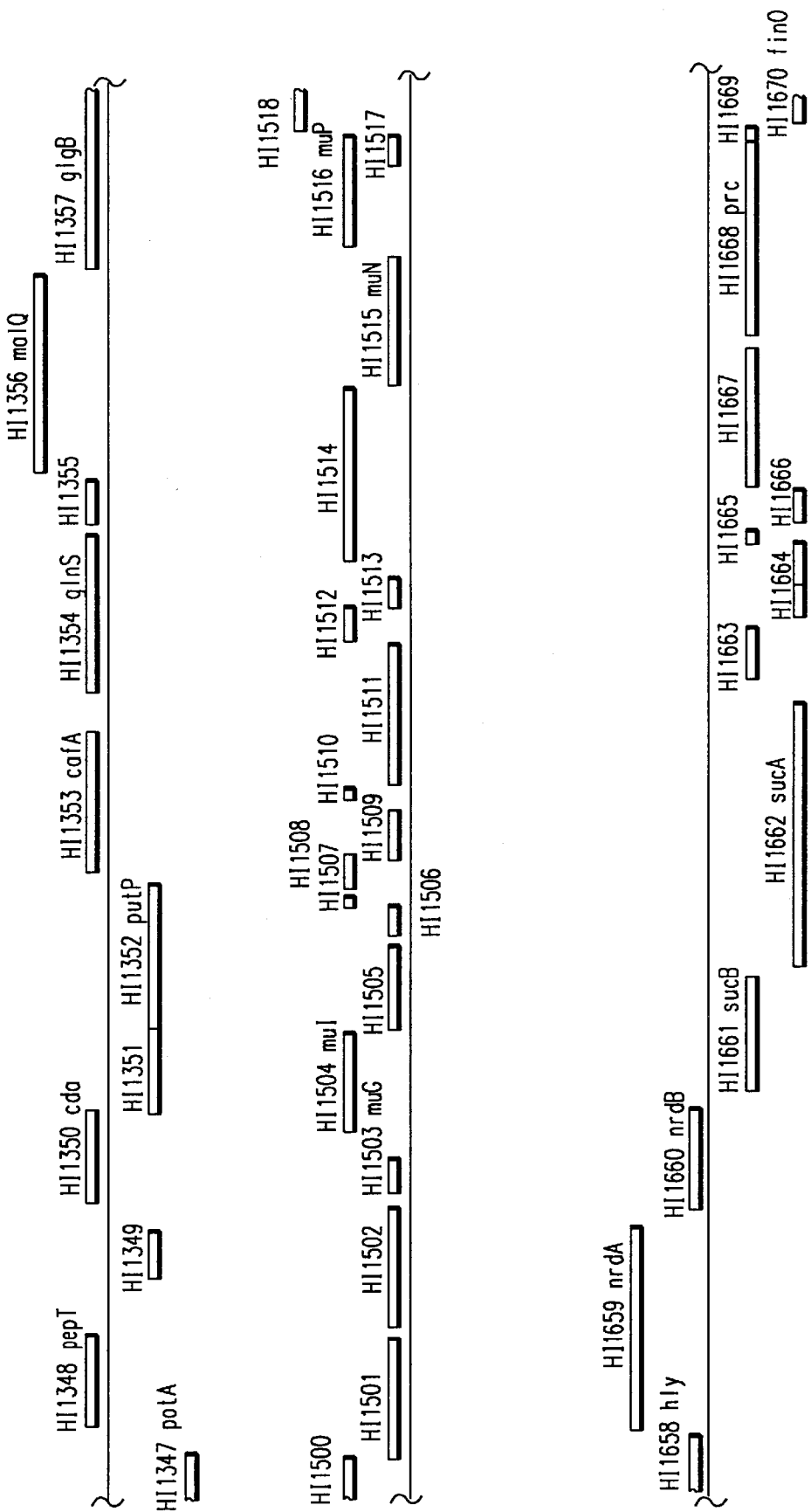
Figure 6A:
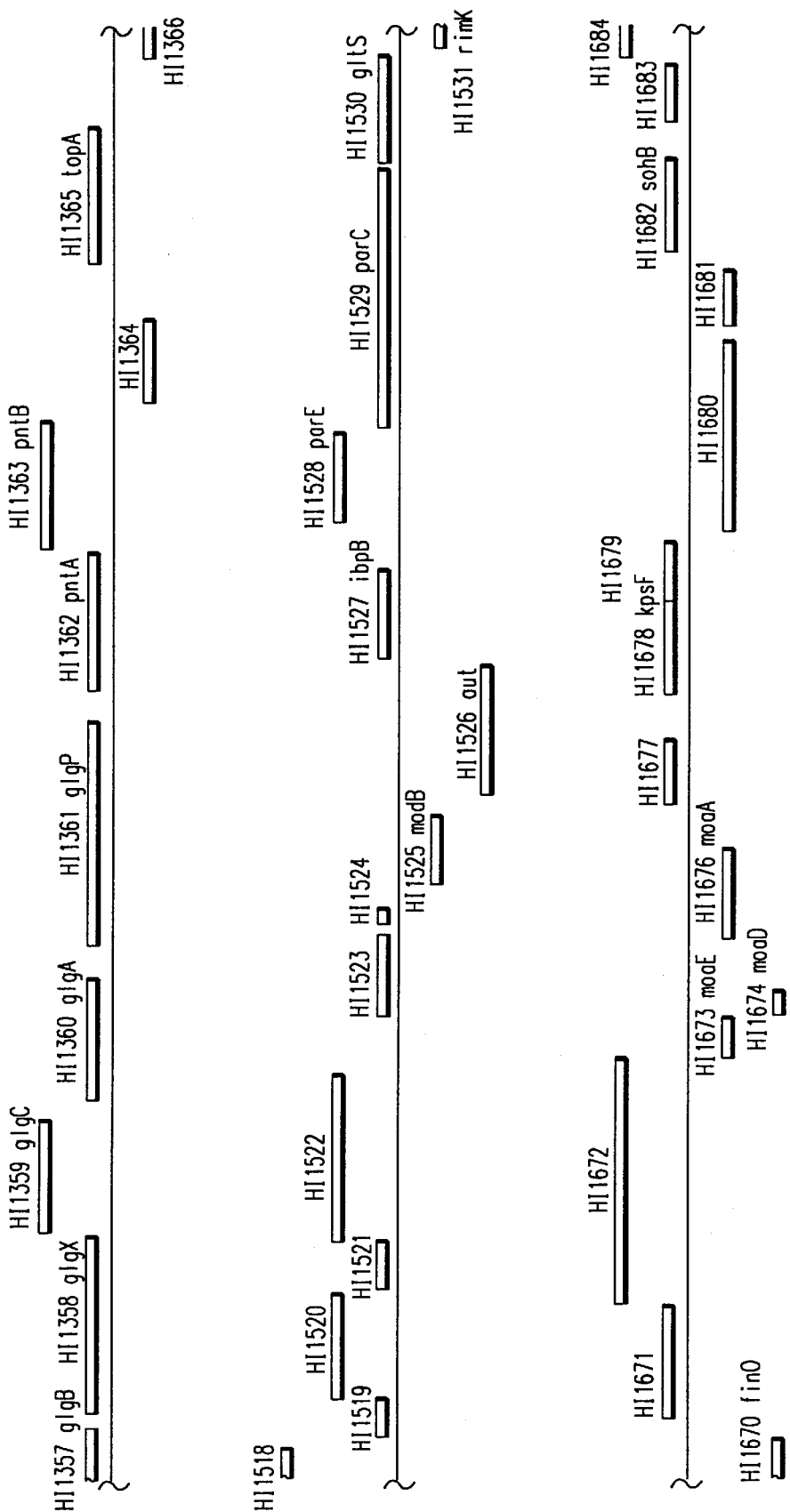
Figure 6A:
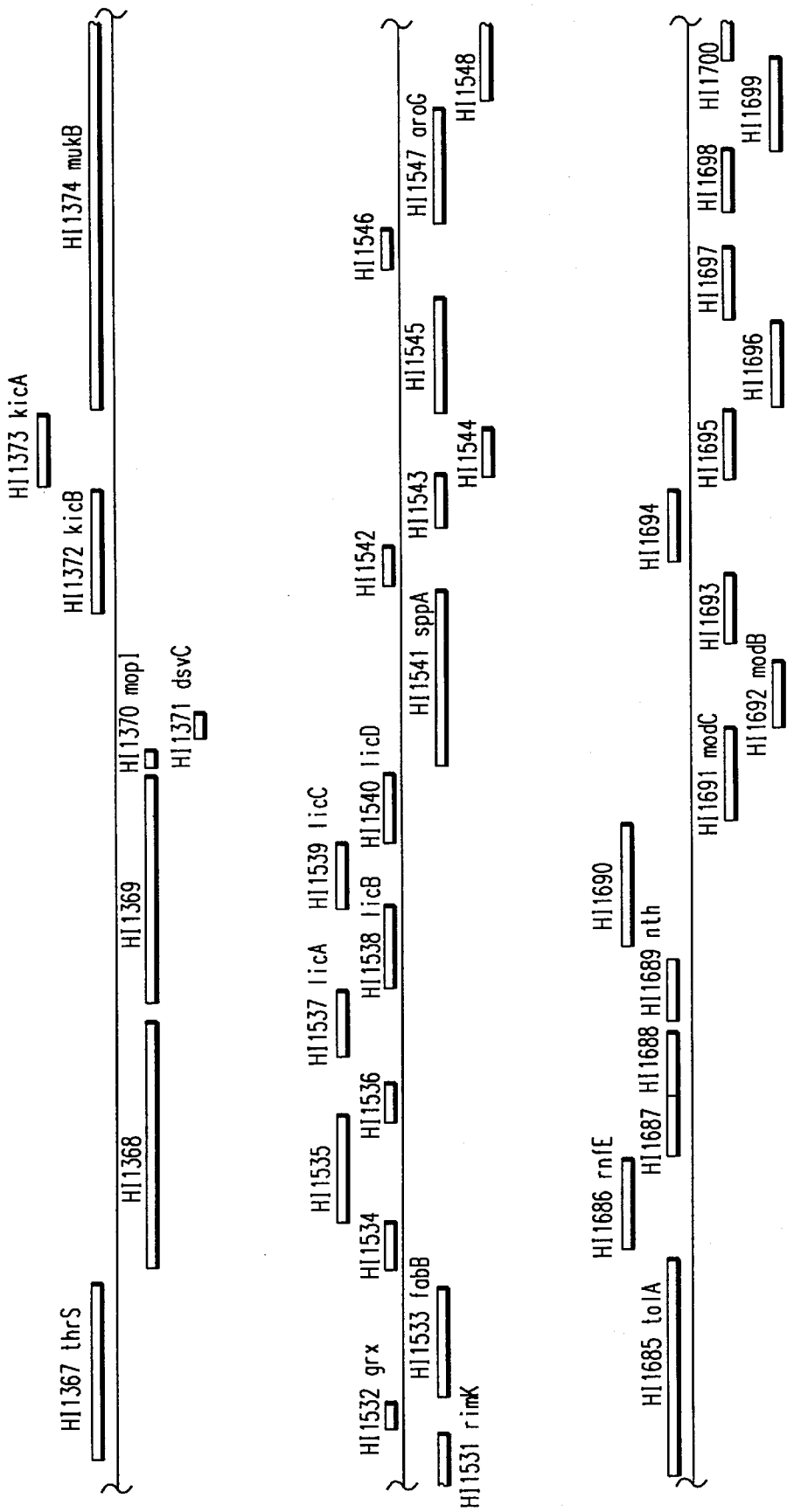
Figure 6A:
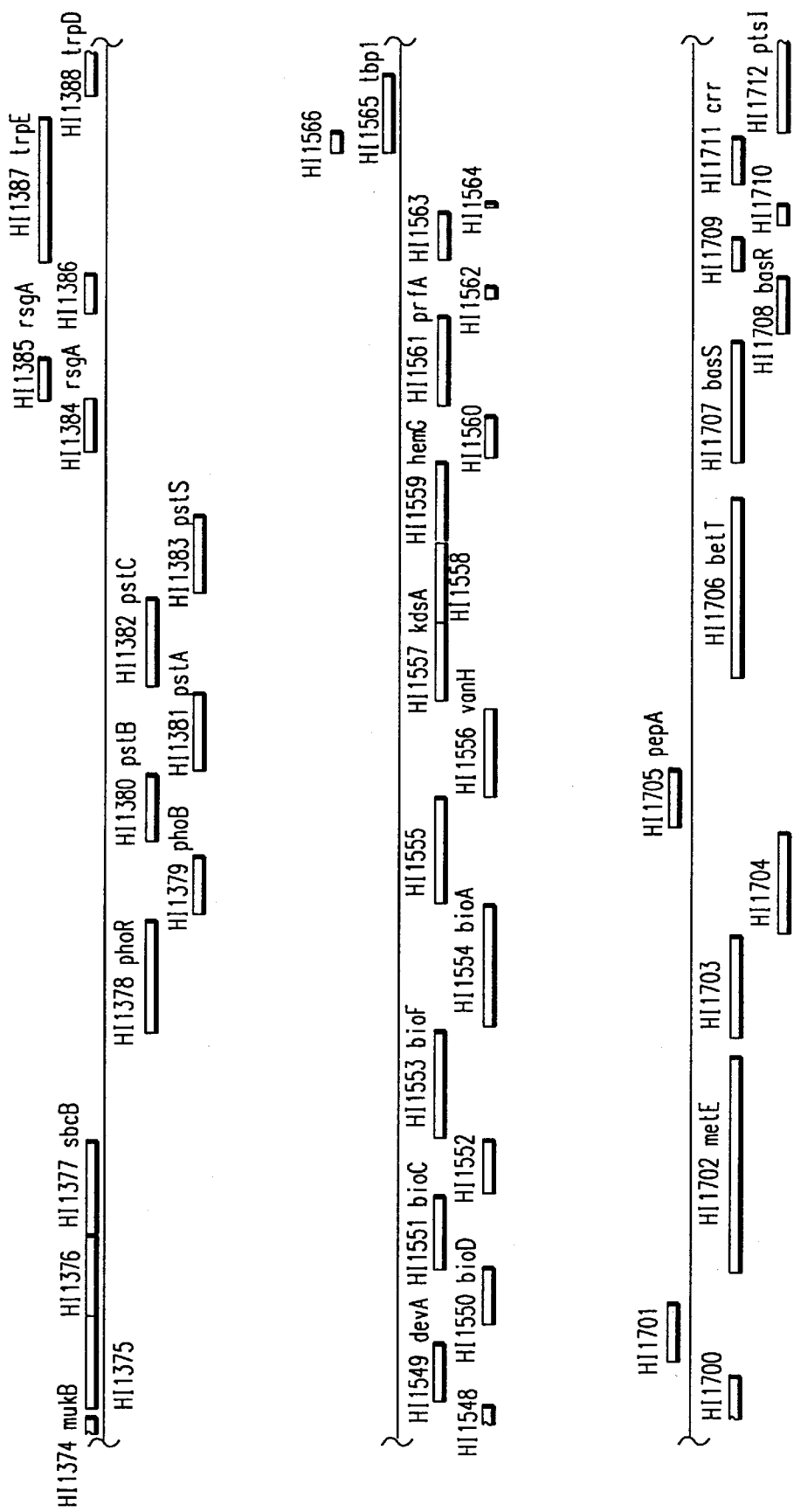
Figure 6A:

An annotated complete genome map of *H. influenaze* Rd is presented in FIGS. 6A–N. The map places each predicted coding region on the *H. influenaze* chromosome, indicates its direction of transcription and color codes its role assignment. Role assignments are also represented in FIG. 5.

A survey of the genes and their chromosomal organization in *H. influenaze* Rd make possible a description of the metabolic processes *H. influenaze* requires for survival as a free living organism, the nutritional requirements for its growth in the laboratory, and the characteristics which make it unique from other organisms specifically as it relates to its pathogenicity and virulence. The genome would be expected to have complete complements of certain classes of genes known to be essential for life. For example, there is a one-to-one correspondence of published *E. coli* ribosomal protein sequences to potential homologs in the *H. influenaze* database. Likewise, as shown in Table 1(a), an aminoacyl tRNA-synthetase is present in the genome for each amino acid. Finally, the location of tRNA genes was mapped onto the genome. There are 54 identified tRNA genes, including representatives of all 20 amino acids.

In order to survive as a free living organism, *H. influenaze* must produce energy in the form of ATP via fermentation and/or electron transport. As a facultative annerobe, *H. influenaze* Rd is known to ferment glucose, fructose, galactose, ribose, xylose and fucos. (Dorocicz et. al., *J. Bacteriol.* 175:7142 (1993)). The genes identified in Table 1(a) indicate that transport systems are available for the uptake of these sugars via the phosphoenolpyruvate-phosphotransferase system (PTS), and via non-TPS mechanisms. Genes that specify the common phosphate-carriers Enzyme I and Hpr (ptsI and ptsH) of the PTS system were identified as well as the glucose specific crr gene. The ptsH, ptsI, and crr genes constitute the pts operon. We have not however identified the gene encoding membrane-bound glucose specific Enzyme II. The latter enzyme is required for transport of glucose by the PTS system. A complete PTS system for fructose was identified.

Genes encoding the complete glycolytic pathway for the production of fermentative end products were identified. Growth utilizing anserobic respiratory mechanisms were found by identifying genes encoding functional electron transport systems using inorganic electron acceptors such as nitrates, nitrites, and dimethylsulfoxide. Genes encoding three enzymes of the tricarboxylic acid (TCA) cycle appear to be absent from the genome. Citrate synthase, isocitrate dehydrogenase, and acordtase were not found by searching the predicted coding regions or by using the *E. coli* enzymes as peptide queries against the entire genome in translation. This provides an explanation for the very high level of glutamate (Ig/L) which is required in defined culture media (Klein and Luginbuhi, *J. Gen. Microbiol.* 113:409 (1979)). Glutamate can be directed into the TCA cycle via conversion to alpha-ketoglutarate by glutamate dehydrogenase. In the absence of a complete TCA cycle, glutamate presumably serves as the source of carbon for biosynthesis of amino acids using precursors, which branch from the TCA cycle. Functional electron transport systems are available for the production of ATP cycle. Functional electron transport systems are available for the production of ATP using oxygen as a terminal electron acceptor.

Previously unanswered questions regarding pathogenicity and virulence can be addressed by examining certain classes of genes such as adhesions and the lipooligosaccharide biogenesis genes. Mozon and co-workers (Weiser et al., *Cell* 59:657 (1989)) have obtained evidence that a number of these virulence-related genes contain tandem tetramer repeats which undergo frequent addition and deletion of one or more repeat units during replication such that the reading frame of the gene is changed and its expression thereby altered. It is now possible, using the complete genome sequence, to locate all such tandem repeat tracts (FIG. 5) and to begin to determine their roles in phase variation of such potential virulence genes.

*H. influenzae* Rd possess a highly efficient natural DNA transformation system (Kahn and Smith, *J. Membrane Biol.* 138:155 (1984). A unique DNA uptake sequence site, 5'AAGTGCGGT, present in multiple copies in the genome, has been shown to be necessary for efficient DNA uptake. It is now possible to locate all of these sites and completely describe their distribution with respect to genic and intergenic regions. Fifteen genes involved in transformation have already been described and sequenced (Redfield, R., *J. Bacteriol.* 173:5612 (1991); Chandler, M., *Proc. Natl. Acad. Sci. U.S.A.* 89:1616 (1992); Barouki and Smith, *J. Bacteriol.* 163(2):629 (1985); Tomb et al., *Gene* 104:1 (1991); Tomb, *J. Proc. Natl. Acad. Sci. U.S.A.* 89:10252 (1992)). Six of the genes, comA to comF, comprise an operon which is under positive control by a 22-bp palindromic competence regulatory element (CRE) about one helix turn upstream of the promoter. The rec-2 transformation gene is also controlled by this element. It is now possible to locate additional copies of CRE in the genome and discover potential transformation genes under CRE control. In addition, it may now be possible to discover other global regulatory elements with an ease not previously possible.

One well-described gene regulatory system in bacteria is the "two-component" system composed of a sensor molecule that detects some sort of environmental signal and a regulator molecule that is phosphorlated by the activated form of the sensor. The regulator protein is generally a transcription factor which, when activated by the sensor, turns on or off expression of a specific set of genes (for review, see Albright et al., *Ann. Rev. Genet.* 23:311 (1989); Parinson and Kofold, *Ann. Rev. Genet.* 26:71 (1992). It has been estimated that *E. coli* harbors 40 sensor-regulator pairs (Albright et al., *Ann. Rev. Genet.* 23:311 (1989); Parkinson and Kofold, *Ann. Rev. Genet.* 26:71 (1992)). The *H. influenaze* genome was searched with representative proteins from each family of sensor and regulator proteins using tblasts and tfasta. Four sensor and five regulator proteins were identified with similarity to proteins from other species (Table 6). There appears to be a corresponding sensor for each regulator protein except CpxR. Searches with the CpxA protein from *E. coli* identified three of the four sensors listed in Table 6, but no additional significant matches were found. It is possible that the level of sequence similarity is low enough to be undetectable with tfasts. No representatives of the NtrC-class of regulators were found. This class of proteins interacts directly with the sigma-54 subunit of RNA polymerase, which is not present in *H. influenaze*. All of the regulator proteins fall into the OmpR subclass (Albright et al., *Ann. Rev. Genet.* 23:311 (1989); Parkinson and Kofold, *Ann. Rev. Genet.* 26:71 (1992)). The phoBR and basRS genes of *H. influenaze* are adjacent to one another and presumably form an operon. The nar and arc genes are not located adjacent to one another.

Figure 7:
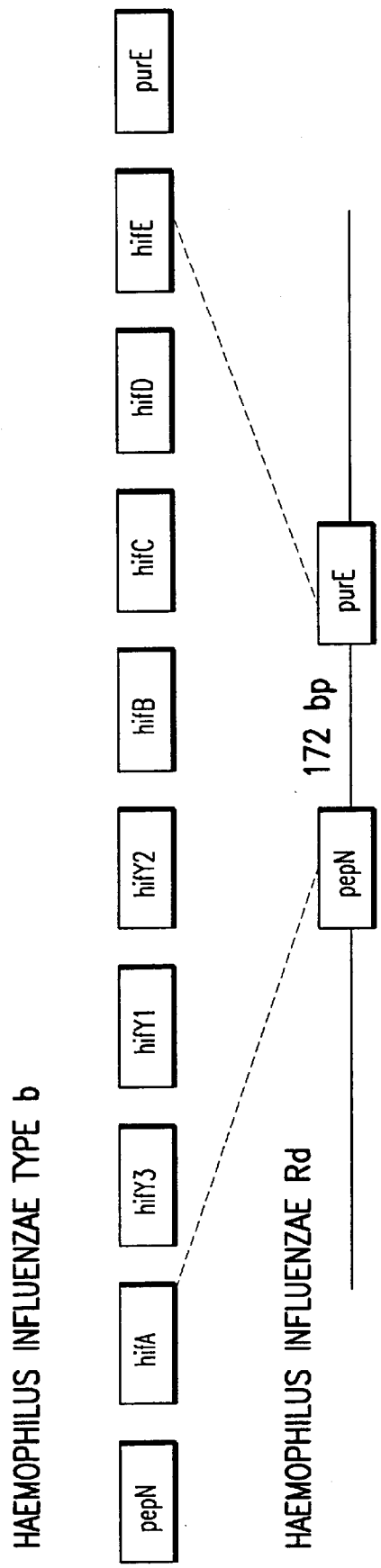
FIG. 7—A comparison of the region of the *H. influenzae* chromosome containing the 8 genes of the fimbrial gene cluster present in *H. influenzae* type b and the same region in *H. influenzae* Rd. The region is flanked by the pepN and purE genes in both organisms. However in the non-infectious Rd strain the 8 genes of the fimbrial gene cluster have been excised. A 172 bp spacer region is located in this region in the Rd strain and continues to be flanked by the pepN and purE genes.

Some of the most interesting questions that can be answered by a complete genome sequence relate to what genes or pathways are absent. The non-pathogenic *H. influenaze* Rd strain varies significantly from the pathogenic serotype b strains. Many of the differences between these two strains appear in factors affecting infectivity. For example, the eight genes which make up the fimbrial gene cluster (vanHam et al., *Mol. Microbio.* 13:673 (1994)) involved in adhesion of bacteria to host cells are now shown to be absent in the Rd strain. The pepN and purE genes which flank the fimbrial cluster in *H. Influenaze* type b strains are adjacent to one another in the Rd strain (FIG. 7), suggesting that the entire fimbrial duster was excised. On a broader level, we determined which *E. coli* proteins are not in *H. influenaze* by taking advantage of a non-redundant set of protein coding genes from *E. coli*, namely the University of Wisconsin Genome Project contigs in GenBank: 1,216 predicted protein sequences from GenBank accessions D10483, L10328, U00006, U00039, U14003, and U18997 (Yurs, etl al., *Nucleic Acids Research* 20:3305 (1992); Burland et al., *Genomics* 16:551 (1993)). The minimum threshold for matches was set so that even weak matches would be scored as positive, thereby giving a minimal estimate of the *E. coli* genes not present in *H. influenaze*. tBlasts was used to search each of the *E. coli* proteins against the complete genome. All blast scores >100 were considered matches. Altogether 62 *E. coli* proteins matched at least one region of the *H. influenaze* genome and 589 proteins did not. The 589 non-matching proteins were examined and found to contain a disproportionate number of hypothetical proteins from *E.* coli. Sixty-eight percent of the identified *E. coli* proteins were matched by an *H. influenaze* sequence whereas only 38% of the hypothetical proteins were matches. Proteins are annotated as hypotetical based on a lack of matches with any other known protein (Yurs et al., *Nucleic Acids Research* 20:3305 (1992); Burland et al., *Genomics* 16:551 (1993)). At least two potential explanations can be offered for the over representations of hypothetical proteins among those without matches: some of the hypothetical proteins are not, in fact, translated (at least in the annotated frame), or these are *E. coli*-specific proteins that are unlikely to be found in any species except those most closely related to *E. coli*, for example *Salmonella typhimurium*.

A total of 384 predicted coding regions did not display significant similarity with a six-frame translation of GenBank release 87. Several novel gene families were identified. For example, two predicted coding regions without database matches (H10591, H10852) share 75% identity over almost their entire lengths (139 and 143 amino acid residues respectively). Their similarity to each other but failure to match any protein available in the current databases suggest that they could represent a novel cellular function.

Figure 8:
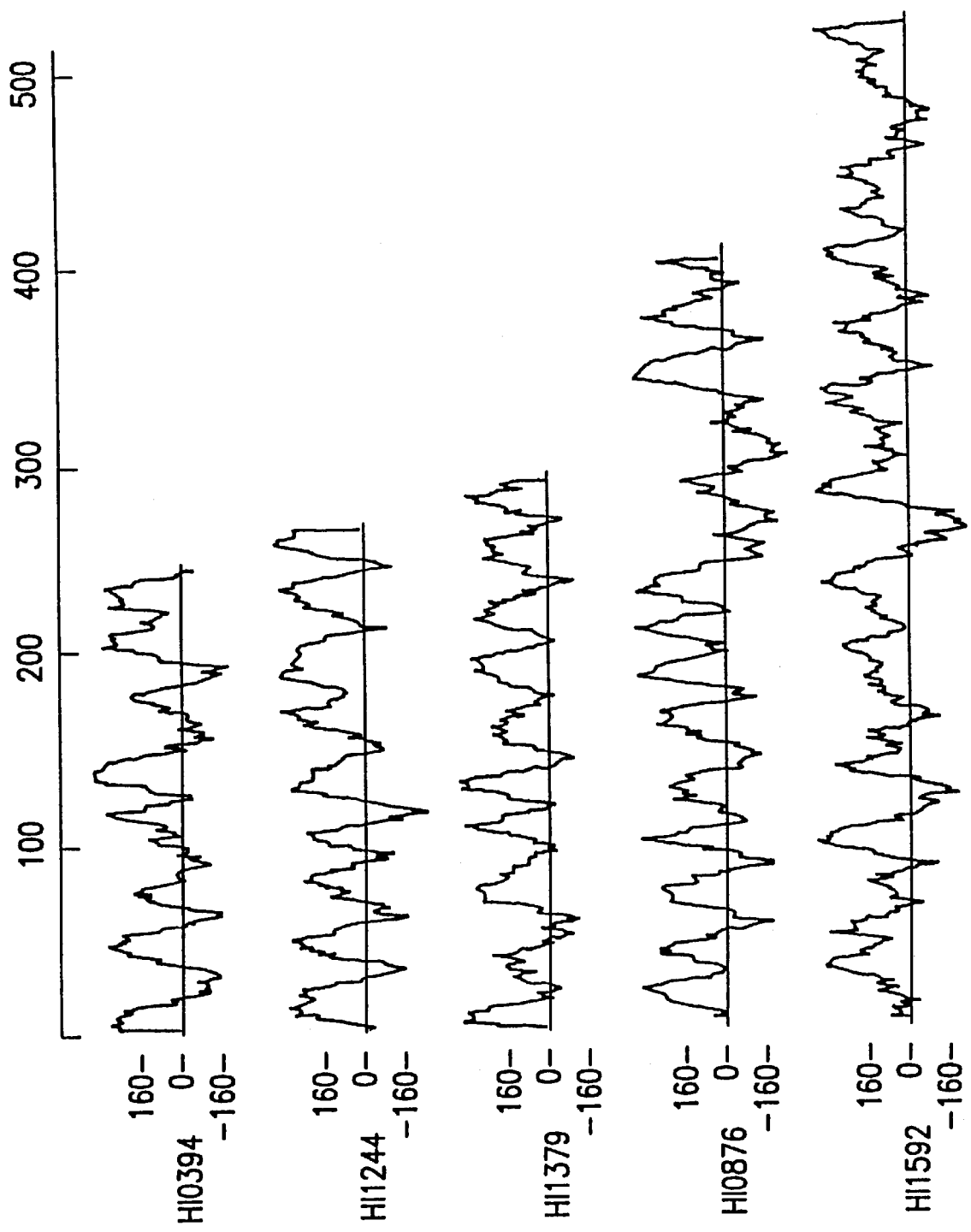
FIG. 8—Hydrophobicity analysis of five predicted channel-proteins. The amino acid sequences of five predicted coding regions that do not display homology with known peptide sequences (GenBank release 87), such exhibit multiple hydrophobic domains that are characteristic of channel-forming proteins. The predicted coding region sequences were analyzed by the Kyte-Doolittle algorithm (Kyte and Doolittle, *J. Mol. Biol.* 157:105 (1982)) (with a range of 11 residues) using the GeneWorks software package (Intelligenetics).

Other types of analyses can be applied to the unidentified coding regions, including hydropathy analysis, which indicates the patterns of potential membrane-spanning domains that are often conserved between members of receptor and transporter gene families, even in the absence of significant amino acid identity. Five examples of unidentified predicted coding regions that display potential transmembrane domains with a periodic pattern that is characteristic of membrane-bound channel proteins are shown in FIG. 8. Such information can be used to focus on specific aspects of cellular function that are affected by targeted deletion or mutation of these genes.

Interest in the medically important aspects of *H. influenaze* biology has focused particularly on those genes which determine virulence characteristics of the organism. Recently, the catalase gene was characterized and sequenced as a possible virulence-related gene (Bishai et al., *J. Bacteriol.* 176:2914 (1994)). A number of the genes responsible for the capsular polysaccharide have been mapped and sequenced (Kroll et al., *Mol. Microbiol.* 5(6):1549 (1991)). Several outer membrane protein genes have been identified and sequenced (Langford et al., *J. Gen. Microbiol.* 138:155 (1992)). The lipooligosaccharide component of the outer membrane and the genes of its synthetic pathway are under intensive study (Weiser et al., *J. Bacteriol.* 173:3304 (1990)). While a vaccine is available, the study of outer membrane components is motivated to some extent by the need for improved vaccines.

Data Availability

The *H. influenaze* genome sequence has been deposited in the Genome Sequence DataBase (GSDA) with the accession number L42023. The nucleotide sequence and peptide translation of each predicted coding region with identified start and stop condons have also been accessioned by GSDB.

Production of an Antibody to a *Haemophilus influenzae* Protein

Substantially pure protein or polypeptide is isolated from the transfected or transformed cells using any one of the methods known in the art. The protein can also be produced in a recombinant prokaryotic expression system, such as *E. coli*, or can by chemically synthesized. Concentration of protein in the final preparation is adjusted, for example, by concentration on an Amicon filter device, to the level of a few micrograms/ml. Monoclonal or polyclonal antibody to the protein can then be prepared as follow:

Monoclonal Antibody Production by Hybridoma Fusion

Monoclonal antibody to epitopes of any of the peptides identified and isolated as described can be prepared from murine hybridomas according to the classical method of Kohler, G. and Milstein, C., *Nature* 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopteria (HAT media). The successfully fused cells are diluted and aliquots of the dilution placed in wells of a microtiter plate where growth of the culture is continued. Antibody producing clones are identified by detection of antibody in the supernatant fluid of the wells by immunoassay procedures, such as ELISA, as originally described by Engvall, E., *Meth. Enzymol.* 70:419 (1980), and modified methods thereof. Selected positive clones can be expanded and their monoclonal antibody product harvested for use. Detailed procedures for monoclonal antibody production are described in Davis, L. et al. Basic Method in Molecular Biology Elsevier, N.Y. Section 21-2 (1989).

Polyclonal Antibody Production by Immunization

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic that other and may require the use of carriers and adjuvant. Also, host animals vary in response to site of inoculations and dose, with both inadequate or excessive doses of antigen resulting in low titer antisers. Small doses (ng level) of antigen administered at multiple intradermal sites appears to be most reliable. An effective immunization protocol for rabbits can be found in Vaitukaitis, J. et al., *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology*, Wier, D., ed, Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology*, second edition, Rose and Friedman, eds., Amer. Soc. For Microbiology, Washing D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample Preparation of PCR Primers and Amplification of DNA Various fragments of the *haemophilus influenzae* Rd genome, such as those disclosed in Tables 1(a) and 2 can be used, in accordance with the present invention, to prepare PCR primers for a variety of uses. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers and amplified DNA of this Example find use in the Examples that follow.

Gene expression from DNA Sequences Corresponding to ORFs

A fragment of the *Haemophilus influenzae* Rd genome provided in Tables 1(a) or 2 is introduced into an expression vector using conventional technology. (Techniques to transfer cloned sequences into expression vectors that direct protein translation in mammalian, yeast, insect or bacterial expression systems are well known in the art.) Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism, as explained by Hatfield et al., U.S. Pat. No. 5,082,767, incorporated herein by this reference.

The following is provided as one exemplary method to generate polypeptide(s) from cloned ORFs of the Haemophilus genome fragment. Since the ORF lacks a poly A sequence because of the bacterial origin of the ORF, this sequence can be added to the construct by, for example, splicing out the poly A sequence from pSG5 (Stratagene) using BglI and SalI restriction endonclease enzymes and incorporating it into the mammalian expression vector pXTI (Stratagene) for use in eukaryotic expression systems. pXTI contains the LTRs and a portion of the gag gene from Moloney Murine Leukemia Virus. The position of the LTRs in the construct allow efficient stable transfection. The vector includes the Herpes Simplex thymidine kinase promoter and the selectable neomycin gene. The Haemophilus DNA is obtained by PCR from the bacterial vector using oligonucleotide primers complementary to the Haemophilus DNA and containing restriction endonuclease sequences for PstI incorporated into the 5' primer and BglII at the 5' end of the corresponding Haemophilus DNA 3' primer, taking care to ensure that the Haemophilus DNA is positioned such that its followed with the poly A sequence. The purified fragment obtained from the resulting PCR reaction is digested with PstI, blunt ended with an exonuclease, digested with BglII, purified with ligated to pXTI, now containing a poly A sequence and digested BgtII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). The protein is preferably released into the supernatant. However if the protein has membrane binding domains, the protein may additionally be retained within the cell or expression may be restricted to the cell surface.

Since it may be necessary to purify and locate the transfected product, synthetic 15-mer peptides synthesized from the predicted Haemophilus DNA sequence are injected into mice to generate antibody to the polypeptide encoded by the Haemophilus DNA.

If antibody production is not possible, the Haemophilus DNA sequence is additionally incorporated into eukaryotic expression vectors and expressed as a chimeric with for example, β-globin. Antibody to β-globin is used to purify the chimeric. Corresponding protease cleavage sites engineered between the β-globin gene and the Haemophilus DNA are then used to separate the two polypeptide fragments from one another after translation. One useful expression vector for generating β-globin chimerics in P6G5 (Stragagene). This vector encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al. and many of the methods are available from the technical assistance representatives from Stratagene, Life Technologies, Inc., or Promega. Polypeptide may additionally be produced from either construct using in vitro translation systems such as in vitro Express™ Translation Kit (Stratagene).

While the present invention has been described in some detail for purposes of clarity and understanding, one skilled in the art will appreciate that various changes in form and detail can be made without departing from the true scope of the invention.

All patents, patent applications and publications referred to above are hereby incorporated by reference.

Amino acid biosynthesis

Glutamate family

| | | | | | | |
|---|---|---|---|---|---|---|
| HI0190 | 202698 | 204044 | flutamate dehydrogenase (gdhA) (*Escherichia coli*) | 74.1 | 84.4 | 446 |
| HI0667 | 915793 | 917833 | glutamine synthetase (glnA) (*Proteus vulgens*) | 70.7 | 85.9 | 467 |
| HI1725 | 1792409 | 1799821 | undylyl transferase (glnD) (*Escherichia coli*) | 46.6 | 67.8 | 854 |
| HI0613 | 661610 | 860240 | argininosuccinate lyase (arginosuccinase) (seal) (argH) (*Escherichia coli*) | 73.5 | 84.5 | 457 |
| HI1733 | 1799112 | 1800443 | argininosuccinate synthetase (argG) (*Escherichia coli*) | 78.6 | 87.5 | 738 |
| HI0598 | 618753 | 617752 | ornithine carbemoyltransferase (arcB) (*Pseudornones sreuginoes*) | 62.3 | 90.7 | 334 |
| HI1242 | 1313013 | 1311753 | gamma-glutamyl phosphate reductase (proA) (*Escherichia coli*) | 61.7 | 79.4 | 406 |
| HI0902 | 955516 | 956621 | glutamate 5-kinase (gmma-glutamyl lunase) (proB) (*Escherichia coli*) | 65.7 | 80.2 | 363 |

Asperate family

| | | | | | | |
|---|---|---|---|---|---|---|
| HI0288 | 319209 | 320419 | aspartate amminotransferase (aspC) (*Bacillus* sp.) | 31.1 | 53.8 | 349 |
| HI1623 | 1684147 | 1685334 | aspartate anubitrabsferase (aspC) (*Escherichia coli*) | 62.6 | 79.0 | 396 |
| HI0566 | 582379 | 583366 | asparagine synthetase A (asnA) (*Escherichia coli*) | 63.3 | 77.0 | 330 |
| HI0648 | 690744 | 689632 | aspartate-semialdehyde dehydrogenese (aes) (*Escherichia coli*) | 71.9 | 84.9 | 367 |
| HI1311 | 1385700 | 1386509 | dehydrodipicolnate reductse (dapB) (*Escherichia coli*) | 70.3 | 82.5 | 269 |
| HI0729 | 779456 | 778212 | diaminopomelete decarboxylase (dep decarboxylase) (lysA) (*Pseudomones seruginose*) | 57.6 | 78.6 | 413 |
| HI0752 | 810250 | 811071 | diaminopimelete epimerase (dapF) (*Escherichia coli*) | 77.0 | 85.8 | 274 |
| HI0258 | 284972 | 285865 | dehydrodapicotnate synthetase (dapA) (*Escherichia coli*) | 85.2 | 79.8 | 292 |

-continued

| | | | | | | |
|---|---|---|---|---|---|---|
| HI1638 | 1693968 | 1694330 | lysine-senarine aspartokinase ill (lysC) (*Escherichia coli*) | 55.3 | 73.2 | 449 |
| HI0102 | 109226 | 106096 | succinyl-diaminopimalate desuccinylase (dagE) (*Echerichia coli*) | 61.6 | 79.7 | 374 |
| HI1640 | 1696728 | 1695820 | tetrahydrodipirolinate N-succinyltransferase (dspD) (*Actinobacillus pleuropneumonase* | 96.7 | 98.5 | 273 |
| HI0089 | 96280 | 93836 | sapertokinase-homoserine dehydrogenese (xhrA) (*Serratia merceacene*) | 62.2 | 77.4 | 814 |
| HI0068 | 93820 | 92879 | homosenne lonase (thrR) (*Serratia mercescens*) | 61.8 | 80.6 | 306 |
| HI0087 | 92833 | 91559 | threonine synthase (thrC) (*Serratia mercescens*) | 67.0 | 80.9 | 425 |
| HI1044 | 1107725 | 1105876 | B12-dependent homocysteine-N5-methyltetrahydrofolate transmethylase (metH) (*Escherchia coli*) | 54.2 | 70.4 | 1217 |
| HI0122 | 137942 | 136745 | beta-cystathionase (metC) (*Escherichia coli*) | 65.4 | 84.1 | 390 |
| HI0066 | 90743 | 69601 | cystathione gamma-synthase (metB) (*Escherichia coli*) | 41.9 | 62.2 | 374 |
| HI1266 | 1339983 | 1341056 | homosenne acetyltransferase (met2) (*Saccharomyces careviase*) | 38.1 | 57.1 | 387 |
| HI1708 | 1773485 | 1771221 | tetrahydropteroyltriglutamate methyltransferase (metE) (*Escherichia coli*) | 52.4 | 68.0 | 747 |
| Senne family | | | | | | |
| HI0891 | 942366 | 943628 | senne hydroxymethyltransferase (senne methylase) (glyA) (*Actinobacillus actinomycetemcomitans*) | 85.7 | 93.6 | 419 |
| HI0467 | 486594 | 487823 | phosphoglycerate dehydrogenase (serA) (*Escherichia coli*) | 71.1 | 83.9 | 408 |
| HI1170 | 1238587 | 1237502 | phosphosenne aminotransferase (serC) (*Escherichia coli*) | 53.4 | 72.3 | 358 |
| HI1035 | 1097573 | 1096814 | phosphosenne phosphatase (o-phosphosenne phosphohydrolase) (serB) (*Escherichia coli*) | 52.3 | 69.5 | 303 |
| HI1105 | 1165130 | 1166077 | cysteine synthetase (cysK) (*Escherichia coli*) | 70.0 | 83.9 | 309 |
| HI0608 | 636187 | 636987 | serine acetyltransferase (cysE) (*Escherichia coli*) | 73.0 | 88.3 | 256 |
| Aromatic amino acid family | | | | | | |
| HI0972 | 1026936 | 1027382 | 3-dehydroquinase (aroQ) (*Actinobacillus pleuropneumoniase*) | 67.1 | 82.5 | 143 |
| HI0209 | 222169 | 223254 | 3-dehydroquinate synthase (aroB) (*Escherichia coli*) | 62.1 | 76.7 | 356 |
| HI0197 | 211424 | 212494 | chorismate synthase (aroC) (*Escherichia coli*) | 77.3 | 88.4 | 350 |
| HI0609 | 637000 | 637812 | dehydroquinase shilumate dehydrogenase (*Nicotiana tabacum*) | 30.0 | 51.5 | 242 |
| HI1595 | 1656463 | 1657758 | enolpyruvylshilumatephosphatesynthase (aroA) (*Haemophilus influenzae*) | 97.7 | 98.4 | 432 |
| HI0857 | 698939 | 698124 | shilumate 5-dehydrogenase (aroE) (*Escherichia coli*) | 49.1 | 70.1 | 270 |
| HI0206 | 221607 | 222146 | shilomic acid lanase I (aroK) (*Escreichia coli*) | 75.0 | 87.5 | 104 |
| HI1148 | 1213767 | 1214921 | chonamate mutase/prophonate dehydratase phsA polypeptide (phsA) (*Escherichia coli*) | 54.3 | 74.7 | 375 |
| HI1553 | 1618339 | 1617254 | DAHP synthetase (phenylalanine repressible) (aroG) (*Escherichia coli*) | 72.0 | 83.8 | 345 |
| HI1293 | 1370448 | 1371578 | chorismate mutase (tyrA) (*Erwina herbicola*) | 59.6 | 76.8 | 366 |
| HI1392 | 1481917 | 1483470 | anthranilate synthase component I (trpE) (*Escherichia coli*) | 52.9 | 73.2 | 494 |
| HI1393 | 1483718 | 1495554 | anthranilate synthase component II (trpD) (*Escherichia coli*) | 56.6 | 74.2 | 452 |
| HI1174 | 1240757 | 1241335 | antrhanilate synthase glutamine amindotransferase )trpG) (*Acimetobacter calcoacebcus*) | 34.0 | 59.0 | 191 |
| HI1437 | 1519794 | 1520597 | tryptophan synthase alpha chain (trpA) (*Salmonella typhimunum*) | 57.8 | 72.6 | 267 |
| HI1436 | 1518601 | 1519791 | trytpophan synthase beta chain (trpB) (*Escherichia coli*) | 82.4 | 90.3 | 391 |
| HI0474 | 494758 | 495354 | amedotransferase (hrsH) (*Escherichia coli*) | 55.9 | 70.3 | 195 |
| HI0470 | 490033 | 490941 | ATP phosphonbosyltransferase (hisG) (*Escherichia coli*) | 72.2 | 82.0 | 295 |
| HI0476 | 496124 | 496897 | hisF cyclase )hisF) (*Escherichia coli*) | 82.0 | 91.0 | 256 |
| HI0472 | 492389 | 493469 | hisbidinol-phosphate aminotransferase (hisC) (*Escherichia coli*) | 60.1 | 77.5 | 351 |
| HI1169 | 1237411 | 1236314 | histindinol-phosphate aminotransferase (hisH) (*Bacillus subtidis*) | 38.7 | 61.0 | 354 |
| HI0473 | 493604 | 494689 | imisaxoleglycerol-phosphate dehydratase (hisB) (*Escherichia coli*) | 65.0 | 80.5 | 353 |
| HI0477 | 496900 | 497562 | phosphorboxyl-AMP cyclohydrolase (hisE) (*Escherichia coli*) | 60.7 | 77.0 | 195 |
| HI0475 | 495393 | 496139 | phosphonbosylformamino-5aminoimidazole carboxamide ribotide momerase (hisA) (*Escherichia coli*) | 62.9 | 77.1 | 245 |
| Pyruvate family | | | | | | |
| HI1581 | 1642613 | 1643692 | slanine racemase, biosynthetic (air) (*Escherichia coli*) | 56.3 | 74.9 | 358 |
| Branched clain family | | | | | | |
| HI0739 | 791174 | 791968 | acetohydroxy acid synthase II (ilvG) (*Escherichia coli*) | 63.6 | 78.5 | 386 |
| HI1591 | 1652923 | 1651205 | acetolactate synthase III large chain (ilvI) (*Escherichia coli*) | 69.1 | 83.9 | 527 |
| HI1590 | 1651202 | 1650714 | acetolactate synthase III small chain (ilvH) (*Escherichia coli*) | 65.6 | 85.0 | 160 |
| HI1196 | 1259031 | 1258003 | branched-chain-amino-acid transamnase (*Salmonella typhimunum*) | 32.9 | 49.6 | 298 |
| HI0740 | 791969 | 793960 | dihydroxyscid dehydrase (ilvD) (*Escherichia coli*) | 77.9 | 89.4 | 614 |
| HI0684 | 723320 | 724795 | ketol-acid reductoisomerase (ilvC) (*Escherichia coli*) | 81.7 | 89.6 | 491 |
| HI0991 | 1047074 | 1047673 | 3-isopropylmalate dehydratase (isopropylmalate isomerase) (leuD) (*Salmonella typhimunum*) | 71.1 | 86.3 | 197 |
| HI0989 | 1044390 | 1045463 | 3-isopropylmalate dehydrogenase (beta-IPM dehydrogenase) (leuB) (*Salmonella typhimunum*) | 68.0 | 80.1 | 353 |
| HI0985 | 1040319 | 1039578 | leuA protein (leuA) (*Haemophilus influenzae*) | 99.5 | 100.0 | 193 |
| Biosynthesis of cofactors, prosthetic groups, carriers | | | | | | |
| Biotin | | | | | | |
| HI1560 | 1625092 | 1623403 | 7,6-diamino-pelargonic acid aminotransferase (bioA) (*Escherichia coli*) | 58.0 | 74.1 | 420 |
| HI1559 | 1623791 | 1622652 | 7-keto-8-aminopelargonic acid synthetase (bioF) (*Bacillus sphaericus*) | 33.5 | 56.3 | 370 |
| HI1557 | 1622004 | 1621225 | biotin biosynthesis; reaction prior to primeloyl CoA (bioC) (*Escherichia coli*) | 28.6 | 48.8 | 151 |
| HI0645 | 687346 | 684672 | biotin sulfoxide reductase (BDS reductase) (bisC) (*Escherichia coli*) | 54.0 | 71.8 | 734 |
| HI1024 | 1085536 | 1056535 | biotin synthetase (bioB) (*Escherichia coli*) | 59.6 | 77.5 | 307 |
| HI1556 | 1621212 | 1620640 | dethiobiotin synthase (bioD) (*Bacillus sphaericu*) | 42.1 | 59.6 | 175 |
| HI1449 | 1532932 | 1532207 | dethiobiotin synthase (bioD) (*Escherichia coli*) | 41.3 | 62.4 | 217 |

-continued

Folic acid

| | | | | | | |
|---|---|---|---|---|---|---|
| HI1448 | 1531237 | 1532112 | 5,10 methylenetetrahydrofolate reductase (metF) (*Escherichia coli*) | 72.8 | 83.4 | 290 |
| HI0611 | 640325 | 639480 | 5,10-methylene-tetrahydrofolate dehydrogenase (folD) (*Escherichia coli*) | 67.6 | 82.0 | 278 |
| HI0064 | 67257 | 67760 | 7,8-dehydro-6-hydroxymethylpterin-pyrophosphokinase (folK) (*Escherichia coli*) | 56.3 | 77.8 | 158 |
| HI0459 | 478432 | 477392 | aminodeoxychonamate lyase (pabC) (*Escherichia coli*) | 40.1 | 66.5 | 243 |
| HI1635 | 1691986 | 1691351 | dedA protein )dedA) (*Escherichia coli*) | 30.4 | 55.1 | 158 |
| HI0901 | 955417 | 954938 | dehydrolotate reductase, type I (totA) (*Echerichia coli*) | 83.2 | 99.4 | 158 |
| HI1338 | 1412130 | 1412954 | dihydropieroate synthase (folP) (*Escherichia coli*) | 54.5 | 70.9 | 275 |
| HI1468 | 1547398 | 1548370 | dihydropieroate synthase (folP) (*Escherichia coli*) | 54.5 | 70.9 | 275 |
| HI1264 | 1337544 | 1338854 | folylpolyglutamate synthase (folC) (*Escherichia coli*) | 51.7 | 68.4 | 409 |
| HI1451 | 1534018 | 1533365 | GTP cyclohydrolase I (folE) (*Escherichia coli* | 63.9 | 79.0 | 219 |
| HI1173 | 1240715 | 1239732 | p-aminobenzoate synthetase (pabB) (*Escherichia coli*) | 31.0 | 53.6 | 257 |

Lipoate

| | | | | | | |
|---|---|---|---|---|---|---|
| HI0026 | 28810 | 27651 | lipoate biosynthesis protein A (lipA) (*Escherichia coli*) | 73.8 | 84.1 | 321 |
| HI0027 | 29302 | 28667 | lipoate biosynthesis protein B (lipB) (*Escherichia coli*) | 86.7 | 84.2 | 181 |

Molybdoptenn

| | | | | | | |
|---|---|---|---|---|---|---|
| HI1661 | 1743523 | 1743044 | moe C protein (moeC) (*Escherichia coli*) | 79.1 | 89.2 | 157 |
| HI1882 | 1744628 | 1743618 | molybdenum cofactor biosynthesis proten A (mosA) (*Escherichia coli*) | 61.8 | 78.3 | 327 |
| HI1373 | 1461582 | 1461376 | molybdenum-plenn binding protein (mopI) (*Clostridum pesteurianum*) | 51.5 | 74.2 | 66 |
| HI1680 | 1743078 | 1742797 | molybdoplenn (MPT) converting factor, subunit 1 (mobD) (*Escherichia coli*) | 59.3 | 79.0 | 81 |
| HI1452 | 1534156 | 1535367 | molybdopleen biosynthesis protein (chiE) (*Escherichia coli*) | 56.4 | 72.5 | 403 |
| HI0118 | 132351 | 133133 | molybdopleen biosynthesis protein (chiE) (*Escherichia coli*) | 27.9 | 52.9 | 135 |
| HI1453 | 1535374 | 1536102 | molybdopleen biosynthesis protein (chiE) (*Escherichia coli*) | 63.9 | 75.4 | 241 |
| HI1679 | 1742793 | 1742344 | molybdopleen converting factor, subunit 2 (mosE) (*Escherichia coli*) | 58.0 | 75.0 | 150 |
| HI0646 | 692779 | 692204 | molybdopleen-guanine dinucleotide (mob) (*Escherichia coli*) | 39.4 | 61.7 | 187 |

Pantothenate

| | | | | | | |
|---|---|---|---|---|---|---|
| HI0633 | 670482 | 669530 | antothenate lanase (cosA) (*Escherichia coli*) | 64.1 | 78.2 | 314 |

Pyndoxine

| | | | | | | |
|---|---|---|---|---|---|---|
| HI0665 | 913165 | 913851 | pyndoxamine phosphate oxxdase (pdxH) (*Escherichia coli*) | 46.0 | 55.3 | 213 |

Riboflavin

| | | | | | | |
|---|---|---|---|---|---|---|
| HI0766 | 827249 | 827893 | 3,4-dihydroxy-2-butanone 4-phosphate sunthase (nbB) (*Escherichia coli*) | 69.6 | 82.7 | 213 |
| HI0213 | 225991 | 226662 | GTP cyclohydrolase II (rbA) (*Escherichia coli*) | 68.0 | 81.4 | 193 |
| HI0946 | 1002768 | 1003883 | riboflavin biosynthesis protein RtBG (rbD) (*Escherichia coli*) | 87.9 | 76.5 | 361 |
| HI1619 | 1678899 | 1679510 | riboflavin synthase alha chain (ribC) (*Escherichia coli*) | 65.5 | 82.3 | 203 |
| HI1306 | 1382553 | 1383071 | riboflavin synthase beta chain (ribE) (*Escherichia coli*) | 76.3 | 69.7 | 158 |

Thioredoxin, glutaredoxin, glutathione

| | | | | | | |
|---|---|---|---|---|---|---|
| HI0152 | 177496 | 176129 | glutathinone reductase (gor) (*Escherichia coli*) | 74.2 | 85.0 | 450 |
| HI1118 | 1181697 | 1181197 | thioredoxin (trzA) (*Anabeens* sp.) | 36.6 | 58.5 | 82 |
| HI1162 | 1228652 | 1228002 | thioredoxin (trzA) (*Anabeens* sp.) | 33.3 | 61.5 | 39 |
| HI0064 | 88470 | 88150 | thioredoxin n (trxM) (*Anecystis redulena*) | 53.3 | 79.4 | 107 |

Manequinons, ubiquinone

| | | | | | | |
|---|---|---|---|---|---|---|
| HI0265 | 317768 | 316062 | 2-succinyl-6-hydroxy-2,4-cyclohexadiene-1-carbosyalte synthase (menD) (*Escherichia coli*) | 46.8 | 64.4 | 551 |
| HI0971 | 1025835 | 1026875 | 4-(2'-carboxyphenyl)-4-oxybutyric acid synthase (menC) (*Escherichia coli*) | 57.3 | 74.2 | 312 |
| HI1192 | 1256548 | 1255916 | coenzyme PQQ synthesis protein III (pqq#1) (*Acinetobacter celcosostious*) | 25.4 | 49.6 | 211 |
| HI0970 | 1024963 | 1025817 | DHNA synthase (menB) (*Escherichia coli*) | 56.7 | 95.1 | 285 |
| HI1442 | 1525823 | 1526707 | laurnesyldiphosphate synthase (ispA) (*Escherichia coli*) | 53.8 | 71.2 | 297 |
| HI0195 | 206694 | 208049 | o-succinylbenzoate-CoA synthase (menE) (*Escherichia coli*) | 46.0 | 56.8 | 426 |

Heme, prophyrin

| | | | | | | |
|---|---|---|---|---|---|---|
| HI1163 | 1229908 | 1228940 | lerrocheistase (visA) (*Escherichia coli*) | 31.8 | 69.4 | 315 |
| HI0113 | 119848 | 122079 | leme ublization protein (hzuC) (*Haemophilus influenzae*) | 26.4 | 46.1 | 695 |
| HI0265 | 293930 | 285624 | heme-hemopexin ulinaztion (hzuB) (*Heamophilus influenzae*) | 96.1 | 96.9 | 565 |
| HI0804 | 831034 | 829751 | hernY Protein (hemY) (*Escherichia coli*) | 38.9 | 64.4 | 365 |
| HI0485 | 484621 | 485769 | oxygen-independent coproporphyrinogen III oxidase (hemN) (*Salmonella typhimunium*) | 31.5 | 52.3 | 241 |
| HI1204 | 1267418 | 1256477 | protoporphyrinogen oxidase (hemG) (*Escherichia coli*) | 36.1 | 56.8 | 153 |
| HI1565 | 1629849 | 1628974 | protoprophtrinogen oxidase (hemG) (*Escherichia coli*) | 59.1 | 72.6 | 203 |
| HI0605 | 631035 | 632562 | uroporphytrinogen III methylase (hemX) (*Escherichia coli*) | 39.9 | 60.3 | 358 |

Cell envelope

Membranes, lipoproteins, ponne

| | | | | | | |
|---|---|---|---|---|---|---|
| HI1585 | 1647711 | 1647247 | 15 kd peptidoglycan-associated lipoprotein (lpp) (pi Heamophilus influenzae) | 94.6 | 95.5 | 154 |
| HI0622 | 653682 | 652864 | 28 kDa membrane protein (hlpA) (*Haemophilus influenzae*) | 99.6 | 100.0 | 273 |
| HI0304 | 335684 | 337249 | apolipoprotein N-acyltransferase (cuts) (*Escherichia coli*) | 45.2 | 64.1 | 497 |
| HI0362 | 384880 | 384035 | hydrophobic membrane protein (*Streptococcus gordorm*) | 37.2 | 66.5 | 266 |
| HI0409 | 428260 | 427478 | hydrophobic membrane protein (*Streptococcus gordorm*) | 34.4 | 61.3 | 254 |
| HI1573 | 1634553 | 1636106 | iron-regulated outer membrane protein A (iroA) (*Neissene meningitidis*) | 28.9 | 50.9 | 398 |
| HI0695 | 736825 | 737846 | lipoprotein (hel) (*Haemophilus influenzae*) | 99.6 | 99.6 | 274 |

-continued

| | | | | | | |
|---|---|---|---|---|---|---|
| HI0707 | 749215 | 750429 | lipoprotein (nlpD) (*Escherichia coli*) | 48.6 | 84.8 | 364 |
| HI0705 | 748419 | 748994 | lipoprotein B (lppB) (*Haemophilus somnus*) | 72.3 | 589.5 | 191 |
| HI0896 | 946675 | 947916 | membrane fusion protein (mtrC) (*Neiseene gonorrhosse*) | 30.9 | 53.6 | 337 |
| HI0403 | 421547 | 422923 | outer membrane protein P1 (ompP1) (*Haemophilus influenzae*) | 93.0 | 97.2 | 459 |
| HI0140 | 153446 | 154522 | outer membrane protein P2 (ompP2) (*Haemophilus influenzae*) | 96.7 | 97.5 | 361 |
| HI1167 | 1234699 | 1235757 | outer membrane protein P5 (ompA) (*Haemophilus influenzae*) | 94.1 | 95.8 | 353 |
| HI0906 | 958203 | 958901 | prolipoprotein diacylglyceryl transferase (lgt) (*Escherichia coli*) | 62.5 | 80.1 | 285 |
| HI0030 | 31698 | 30838 | rare lipoprotein A (rlpA) (*Escherichia coli*) | 34.5 | 57.8 | 288 |
| HI0924 | 979182 | 979727 | rare lipoprotein B (rlpB) (*Escherichia coli*) | 33.5 | 62.1 | 163 |
| Surface polysaccharides, lipopolysaccharides & antigens | | | | | | |
| HI1582 | 1628153 | 1627302 | 2-dehydro-3-deoxyphosphooctonate aklolase (kdsA) (*Escherichia coli*) | 81.3 | 91.5 | 283 |
| HI0654 | 696743 | 695463 | 2-deoxy-d-manno-octuloeonic-acid transferase (kdtA) (*Escherichia coli*) | 50.7 | 69.9 | 420 |
| HI1108 | 1169716 | 1168139 | ADP-heptose-lps heptosyltransferase II (rlsF) (*Escherichia coli*) | 63.6 | 78.9 | 345 |
| HI1117 | 1181141 | 1180218 | ADP-L-glycero-D-mannoheptose-6-epimerase (rfaD) (*Escherichia coli*) | 78.2 | 87.7 | 308 |
| HI0058 | 59659 | 58898 | CTP:CMP-3-deoxy-D-manno-octulosonate-cylidylyl-transferase (kdsB) (*Escherichia coli*) | 65.0 | 81.7 | 245 |
| HI0917 | 970233 | 969211 | firA protein (firA) (*Pasteurella mulocula*) | 84.9 | 91.1 | 338 |
| HI0870 | 919974 | 920723 | glycosyl transferase (lgtD) (*Nerseens gonorrhosse*) | 30.3 | 55.3 | 200 |
| HI1584 | 1646090 | 1647058 | glycosyl transferase (lgtD) (*Nerseens gonorrhosse*) | 47.3 | 64.0 | 328 |
| HI0653 | 695453 | 694996 | KDTB protein (kdtD) (*Escherichia coli*) | 52.3 | 75.8 | 153 |
| HI1684 | 1746281 | 1747291 | kpaF protein (kpaF) (*Escherichia coli*) | 49.3 | 70.8 | 294 |
| HI1543 | 1607986 | 1608967 | lic-1 operon protein (licA) (*Haemophilus influenzae*) | 99.7 | 100.0 | 321 |
| HI1544 | 1608970 | 1609885 | lic-1 operon protein (licB) (*Haemophilus influenzae*) | 99.0 | 99.3 | 303 |
| HI1545 | 1609845 | 1610543 | lic-1 operon protein (licC) (*Haemophilus influenzae*) | 96.5 | 99.5 | 198 |
| HI1546 | 1610546 | 1611340 | lic-1 operon protein (licD) (*Haemophilus influenzae*) | 88.7 | 94.0 | 265 |
| HI1062 | 1125450 | 1124254 | lipid A disaccharide synthetase (fpxB) (*Escherichia coli*) | 63.2 | 77.3 | 382 |
| HI0552 | 571001 | 570096 | lipooligosaccharide biosynthesis protein (*Haemophilus influenzae*) | 96.3 | 99.0 | 298 |
| HI0767 | 627911 | 628758 | lipooligosaccharide biosynthesis protein (*Haemophilus influenzae*) | 36.4 | 59.5 | 267 |
| HI0869 | 916779 | 919990 | lag locus hypothetical protein (GB:M94855_1) (*Haemophilus influenzae*) | 80.5 | 82.5 | 400 |
| HI1706 | 1770127 | 1768916 | lag locus hypothetical protein (GB:M94855_1) (*Haemophilus influenzae*) | 99.3 | 100.0 | 401 |
| HI1705 | 1788457 | 1768005 | lag locus hypothetical protein (GB:M94855_2) (*Haemophilus influenzae*) | 98.4 | 98.7 | 304 |
| HI1704 | 1768000 | 1767322 | lag locus hypothetical protein (GB:M94855_3) (*Haemophilus influenzae*) | 96.0 | 97.4 | 226 |
| HI1703 | 1766957 | 1766157 | lag locus hypothetical protein (GB:M94855_4) (*Haemophilus influenzae*) | 96.1 | 98.4 | 257 |
| HI1702 | 1766142 | 1765261 | lag locus hypothetical protein (GB:M94855_5) (*Haemophilus influenzae*) | 96.9 | 98.3 | 294 |
| HI1701 | 1765256 | 1764456 | lag locus hypothetical protein (GB:M94855_6) (*Haemophilus influenzae*) | 98.9 | 99.3 | 267 |
| HI1700 | 1763577 | 1764341 | lag locus hypothetical protein (GB:M94855_7) (*Haemophilus influenzae*) | 98.4 | 98.4 | 256 |
| HI1899 | 1763439 | 1762678 | lag locus hypothetical protein (GB:M94855_8) (*Haemophilus influenzae*) | 98.8 | 98.0 | 209 |
| HI0283 | 290317 | 291387 | opsX locus protein (opsX) (*Xanthomones carnpestris*) | 35.2 | 56.7 | 261 |
| HI1722 | 1788457 | 1787483 | rle (CGSC No 294) protein (*Escherichia coli*) | 59.0 | 77.2 | 344 |
| HI1147 | 1212723 | 1213637 | UDP-3-0-acyl N-acetylglcosamine descetylase (envA) *Escherichia coli*) | 77.3 | 88.2 | 304 |
| HI1083 | 1126276 | 1125493 | UDP-N-acetylgluocosemine acetyltransferase (lpsA) (*Escherichia coli*) | 86.0 | 79.4 | 262 |
| HI0675 | 925083 | 926096 | UDP-N-acetylglucosamine epimersase (rlfE) (*Escherichia coli*) | 65.5 | 79.5 | 336 |
| HI0674 | 923609 | 925021 | undecaprenyl-phosphate galactosephosphotransferase (ribP) (*Salmonella typhimunum*) | 57.9 | 75.1 | 495 |
| Surface structures | | | | | | |
| HI1736 | 1806251 | 1804281 | adhesin (andA-I) (*Escherichia coli*) | 29.3 | 45.8 | 1196 |
| HI0119 | 133314 | 134324 | adhesin B precursor (fimA) (*Streptococcus parasanguis*) | 24.5 | 48.3 | 309 |
| HI0364 | 386685 | 385807 | adhesin B precursor (fimA) (*Streptococcus parasanguis*) | 34.6 | 61.6 | 302 |
| HI0332 | 356770 | 368062 | cellenvelope protein (cepA) (*Haemophilus influenzae*) | 99.8 | 100.0 | 431 |
| HI0713 | 757120 | 757425 | flagellar switch protein (ftiM) (*Salmonella typhimunum*) | 34.1 | 61.0 | 41 |
| HI1484 | 1542848 | 1542294 | invesin precursor (outer membrane adhesin) (yopA) (*Yersinia enterocoluica*) | 38.5 | 62.1 | 291 |
| HI0333 | 358125 | 358526 | opacity associated protein (oapB) (*Haemophilus influenzae*) | 99.2 | 99.2 | 132 |
| HI0418 | 436627 | 436636 | opacity protein (opa66) (*Neisseria gonorrhosse*) | 74.5 | 90.9 | 55 |
| HI1177 | 1243585 | 1243947 | opacity protein (opa66) (*Neisseria gonorrhosse*) | 37.7 | 59.0 | 181 |
| HI1461 | 1540805 | 1540272 | opacity protein (opaD) (*Neisseria meningitidis*) | 34.5 | 55.8 | 230 |
| HI0300 | 333052 | 331661 | plin biogeneers protein (pilB) (*Pseudomones seruginosa*) | 44.1 | 64.8 | 485 |
| HI0919 | 973373 | 970950 | protective surface antigen D15 (*Haemophilus influenzae*) | 96.6 | 99.5 | 797 |
| Murein, secculus, peptidoglycan | | | | | | |
| HI1674 | 1737564 | 1735481 | carbosy-terminal protease, penicillin-binding protein 3 (prc) (*Escherichia coli*) | 52.3 | 69.5 | 660 |
| HI1143 | 1208355 | 1209272 | D-alanine-D-sterine ligase (ddB) (*Escherichia coli*) | 58.9 | 75.8 | 303 |
| HI1333 | 1408296 | 1406850 | D-alanyl-D-alanine carbosypeptidase (decB) (*Escherichia coli*) | 43.9 | 68.2 | 454 |
| HI0066 | 68323 | 69618 | N-acetylmuramoyl-L-alanine amidase (amiB) (*Escherichia coli*) | 59.5 | 77.0 | 221 |
| HI0383 | 401990 | 401532 | PC protein (15kd peptidoglycan-associated outer membrane lipoprotein) (pal) (*Haemophilus influenzae*) | 100.0 | 100.0 | 153 |
| HI1731 | 1795566 | 1797908 | penicillin-binding protein 1B (ponB) (*Escherichia coli*) | 47.0 | 67.5 | 767 |
| HI0032 | 34810 | 32858 | penicillin-binding protein 2 (pbp2) (*Escherichia coli*) | 58.8 | 73.8 | 609 |
| HI0029 | 30819 | 29641 | penicillin-binding protein 5 (decA) (*Escherichia coli*) | 54.8 | 68.4 | 362 |
| HI0198 | 212582 | 213439 | penicillin-insensitive murein endopeptidse (mapA) (*Escherichia coli*) | 49.3 | 56.7 | 269 |
| HI1138 | 1201927 | 1203006 | phospho-N-acetylmuramoyl-pentapeptide-transferes E (mrsY) (*Escherichia coli*) | 76.7 | 88.9 | 360 |
| HI0036 | 40689 | 41741 | rod shape-determining protein (mrsC) (*Escherichia coli*) | 50.3 | 74.5 | 293 |
| HI0031 | 32865 | 31753 | rod shape-determining protein (mrsB) (*Escherichia coli*) | 63.1 | 80.7 | 358 |
| HI0037 | 39473 | 40606 | rod shape-determining protein (mrsB) (*Escherichia coli*) | 79.8 | 89.9 | 347 |
| HI0039 | 41744 | 42229 | rod shape-determining protein (mrsD) (*Escherichia coli*) | 40.8 | 71.8 | 154 |
| HI0631 | 878792 | 880570 | soluable lytic mureine transglycosylase (slt) (*Escherichia coli*) | 40.4 | 59.3 | 378 |

| | | | -continued | | | |
|---|---|---|---|---|---|---|
| HI1141 | 1205663 | 1206715 | transferase, peptidoglycan synthesis (murG) (*Escherichia coli*) | 61.7 | 78.0 | 350 |
| HI1137 | 1200560 | 1201930 | UDP-murnec-pentapeptide synthetase (murF) (*Escherichia coli*) | 51.4 | 68.2 | 452 |
| HI1136 | 1199080 | 1200543 | UDP-MurNac-tripeptide synthetase (murE) (*Escherichia coli*) | 55.7 | 72.6 | 463 |
| HI0270 | 301245 | 302267 | UDP-N-acetylenotypruvoylglucosamine reductase (murB) (*Escherichia coli*) | 57.6 | 75.6 | 340 |
| HI1083 | 1148434 | 1147163 | UDP-N-acetylglucosamine enolpyrubyl transferase (murZ) (*Escherichia coli*) | 72.4 | 64.5 | 419 |
| HI1142 | 1206856 | 1208280 | UDP-N-acetylmuramate-alanine ligase (murC) (*Escherichia coli*) | 68.2 | 81.8 | 470 |
| HI1139 | 1203132 | 1204442 | UDP-N-acetylmursmoylalanine-D-glutamate ligase (murD) (*Escherichia coli*) | 61.0 | 73.7 | 437 |
| HI1498 | 1569479 | 1569626 | N-acetylmuramoyl-L-alanine amidase (Bacteriophage T3) | 42.9 | 62.2 | 87 |
| Central intermediary metabolism | | | | | | |
| Phosphorus compounds | | | | | | |
| HI0697 | 739608 | 738640 | exopolyphophatase (ppx) (*Escherichia coli*) | 55.2 | 76.7 | 318 |
| HI0124 | 139861 | 139334 | inorganic pyrophosphatase (ppa) (*Escherichia coli*) | 36.3 | 50.3 | 157 |
| HI0647 | 689574 | 688637 | lysophosphotipase LP (pidB) (*Escherichia coli*) | 31.2 | 53.1 | 217 |
| Sulfur metabolism | | | | | | |
| HI1374 | 1462019 | 1461683 | desulfoviridin gamma subunit (devC) (*Desulfovibrio vulgaris*) | 34.0 | 58.0 | 99 |
| HI0807 | 854438 | 853741 | putative arylsulfatase regulatory protein (salB) (*Escherichia coli*) | 47.4 | 67.0 | 381 |
| HI0561 | 578539 | 577856 | sulfite synthesis pathway protein (cysO) (*Escherichia coli*) | 36.9 | 56.0 | 265 |
| Polyamine biosynthesis | | | | | | |
| HI0099 | 106307 | 107374 | nucleotide binding protein (potG) (*Escherichia coli*) | 42.6 | 66.9 | 340 |
| HI0593 | 614187 | 612028 | ornithine decarboxylase (spoF) (*Escherichia coli*) | 66.4 | 80.2 | 717 |
| Polysaccharides - (cytoplasmic) | | | | | | |
| HI1360 | 1436170 | 1438359 | 1,4-alpha-glucan branching enzyme (glgB) (*Escherichia coli*) | 64.5 | 80.1 | 723 |
| HI1362 | 1440427 | 1441758 | ADP-glucose synthetase )glgC) (*Escherichia coli*) | 55.0 | 74.3 | 407 |
| HI1364 | 1443545 | 1446007 | alpha-glucan phosphorylase (glgC) (*Escherichia coli*) | 61.1 | 79.1 | 809 |
| HI1361 | 1438458 | 1440434 | glycogen operon protein(glgX) (*Escherichia coli*) | 54.3 | 67.8 | 501 |
| HI1363 | 1441868 | 1443296 | glycogen synthease (glgA) (*Escherichia coli*) | 56.2 | 71.2 | 475 |
| Degradation of polysaccharides | | | | | | |
| HI1359 | 1434061 | 1436157 | amylomaltase (malO) (*Escherichia coli*) | 72.1 | 84.3 | 609 |
| HI1420 | 1507662 | 1507063 | emdochitinase (*Oryza saliva*) | 38.9 | 50.9 | 106 |
| Amino sugars | | | | | | |
| HI0431 | 452989 | 451160 | glutamine amidotransferase (glmB) (*Escherichia coli*) | 72.1 | 84.3 | 609 |
| HI0141 | 155859 | 154717 | N-acetylglucosamine-6-phosphate danoetylase (negA) (*Escherichia coli*) | 54.5 | 72.1 | 376 |
| HI0142 | 156944 | 156135 | negB protein (negB) (*Escherichia coli*) | 74.2 | 88.1 | 260 |
| Other | | | | | | |
| HI0048 | 49257 | 48403 | 7-alpha-hydroxysteroid dehydrogenase (hdhA) (*Escherichia coli*) | 32.4 | 55.1 | 24 |
| HI1207 | 1271536 | 1270334 | secrete kinase (ackA) (*Escherichia coli*) | 69.1 | 83.9 | 396 |
| HI0981 | 1009728 | 1008367 | GABA transerminase (gabT)(*Escherichia coli*) | 34.4 | 55.8 | 420 |
| HI0111 | 118858 | 119484 | glutathione transferase (bphH) (*Pseudomones* sp.) | 37.6 | 57.4 | 200 |
| HI0693 | 734488 | 735996 | glycerol kinase (glpK) (*Escherichia coli*) | 76.9 | 89.2 | 502 |
| HI0596 | 608429 | 605161 | hippuricase (hipO) (*Campylobacter jejuni*) | 27.8 | 49.6 | 276 |
| HI0643 | 584874 | 584575 | urease (ureA) (*Helicobacter hetlmannii*) | 62.4 | 76.2 | 101 |
| HI0639 | 581666 | 561087 | urease accessory protein (UraF) (*Bacillus* sp.) | 31.8 | 54.9 | 194 |
| HI0541 | 564179 | 562464 | urease alpha subunit (urea amidohydrolase) (ureC) (*Bacillus* sp.) | 67.3 | 82.1 | 588 |
| HI0640 | 562333 | 561779 | urease protein (ureE) (*Helicobacter pylori*) | 31.01 | 56.9 | 155 |
| HI0538 | 560961 | 560307 | urease protein (ureG) (*Helicobacter pylori*) | 70.7 | 86.9 | 129 |
| HI0537 | 580229 | 559447 | urease protein (ureH) (*Helicobacter pylori*) | 31.5 | 53.9 | 213 |
| HI0542 | 564180 | 546574 | urease subunit B (ureB) (*Escherichia coli*) | 61.6 | 77.6 | 103 |
| Energy metabolism | | | | | | |
| Amino acids, amines | | | | | | |
| HI0536 | 559266 | 557842 | aspertase (aspA) (*Escherichia coli*) | 78.2 | 89.1 | 408 |
| HI0597 | 617739 | 616810 | carbamate kinase (sroC) (*Pseudomones seruginosa*) | 78.3 | 67.7 | 309 |
| HI0747 | 802651 | 803897 | L-aspargainase II (ansB) (*Escherichia coli*) | 70.5 | 81.2 | 329 |
| HI0280 | 323270 | 321807 | L-serine deseminase (sdsA) (*Escherichia coli*) | 68.6 | 83.3 | 454 |
| Sugars | | | | | | |
| HI0620 | 669307 | 868288 | aldose 1-apimerase precursor (mutarotase) (mro) (*Acinetobacter calcoaceticus*) | 36.8 | 54.7 | 326 |
| HI0055 | 55016 | 56197 | D-mannonate hydrolase (uxuA) (*Escherichia coli*) | 72.8 | 85.8 | 394 |
| HI1119 | 1181808 | 1182476 | deoxyribose aldolase (deoC) (*Mycoplasma hominis*) | 49.0 | 68.5 | 200 |
| HI0615 | 644708 | 643299 | fucokinase (fucK) (*Escherichia coli*) | 41.1 | 64.5 | 459 |
| HI0613 | 642828 | 642181 | fuculose-1-phosphate aidolase (fucA) (*Escherichia coli*) | 64.7 | 81.4 | 215 |
| HI1014 | 1075981 | 1076610 | fuculose-1-phosphate aidolase (fucA) (*Escherichia coli*) | 32.9 | 51.8 | 163 |
| HI0821 | 870510 | 869320 | galactokinase (galK) (*Haemophilus influenzae*) | 98.4 | 99.0 | 384 |
| HI0145 | 159883 | 158984 | glucose lunase (gik) (*Streptomyces coelicolor*) | 33.6 | 53.2 | 303 |
| HI0615 | 646595 | 644784 | L-fucoso isomerase (fuci) (*Escherichia coli*) | 69.5 | 84.5 | 583 |
| HI1027 | 1090247 | 1089519 | L-ribulose-phosphate 4-epimerase (arsD) (*Escherichia coli*) | 72.3 | 81.8 | 231 |
| HI1111 | 1173107 | 1171938 | mal inducer biosynthesis blocker (malY) (*Escherichia coli*) | 28.1 | 51.6 | 375 |
| HI0143 | 158111 | 157233 | N-acetylneuraminals tyase (nanA) (*Escherichia coli*) | 36.2 | 61.4 | 291 |
| HI0507 | 521330 | 522247 | ribokinase (rbsK) (*Escherichia coli*) | 58.0 | 74.8 | 302 |

-continued

| | | | | | | |
|---|---|---|---|---|---|---|
| HI1115 | 1177307 | 1178823 | xylose isomerase (xylA) (*Escherichia coli*) | 71.3 | 87.2 | 439 |
| HI1116 | 1178629 | 1180161 | xylulose lunase (xylulonase) (*Escherichia coli*) | 33.1 | 50.0 | 479 |
| Glycolysis | | | | | | |
| HI0449 | 470260 | 469342 | 1-phosphofructokinase (fruK) (*Escherichia coli*) | 55.4 | 74.1 | 304 |
| HI0984 | 1039579 | 1038817 | 6-phosphofructokinase (pfkA) (*Escherichia coli*) | 74.4 | 84.4 | 319 |
| HI0934 | 990636 | 989329 | anoisse (ano) (*Bacilius subtilis*) | 65.9 | 78.5 | 413 |
| HI0526 | 547668 | 546592 | fructose-bisphosphate aidolase (fba) (*Escherichia coli*) | 71.3 | 85.8 | 359 |
| HI1592 | 1643750 | 1645438 | glucose-6-phosphate isomerase (pgi) (*Escherichia coli*) | 76.9 | 88.7 | 546 |
| HI0001 | 1 | 600 | glyceraldehyde-3-phosphate dehydrogenase (gapdH) (*Escherichia coli*) | 85.8 | 90.3 | 133 |
| HI0527 | 648939 | 547782 | phosphoglycerate kinase (pgk) (*Escherichia coli*) | 81.1 | 90.7 | 387 |
| HI0759 | 820852 | 821533 | phosphoglyceromutase (gpmA) (*Zymomonas mobius*) | 58.9 | 74.8 | 222 |
| HI1579 | 1639619 | 1641052 | pyruvate kinase type II (pykA) (*Escherichia coli*) | 77.2 | 87.5 | 480 |
| HI0680 | 719664 | 720452 | triosephosphate isomerase (tpiA) (*Escherichia coli*) | 74.4 | 80.7 | 253 |
| Pyruvate dehydrogenase | | | | | | |
| HI1235 | 1303195 | 1301495 | dihydroliposmide acetyltransferase (aceF) (*Escherichia coli*) | 72.8 | 82.4 | 526 |
| HI0194 | 206108 | 203248 | dihydroliposmide acetyltransferase (acoC) (*Pseudemorias pulida*) | 27.8 | 49.1 | 235 |
| HI1234 | 1301378 | 1299945 | liposmide dehydrogenase (lpdA) (*Escherichia coli*) | 81.8 | 91.6 | 474 |
| HI1238 | 1305918 | 1303261 | pyruvate dehydrogenase (aceE) (*Escherichia coli*) | 68.6 | 84.0 | 888 |
| TCA cycle | | | | | | |
| HI1668 | 1731748 | 1728899 | 2-oxogluterate dehydrogenase (sucA) (*Escherichia coli*) | 69.0 | 80.7 | 930 |
| HI0025 | 27397 | 26393 | acetate:SH-citrate lyase ligase (AMP) (*Klebsiella pneumonise*) | 46.9 | 88.4 | 321 |
| HI0022 | 25179 | 23680 | citrate lyase alpha chain (acyl lyase subunit) (citF) (*Klebsiella pneumonise*) | 72.1 | 86.1 | 469 |
| HI0023 | 26068 | 25457 | citrate lyase beta chain (acyl lyase subunit) (*Klebsiella pneumonise*) | 62.3 | 81.9 | 203 |
| HI0024 | 26352 | 25088 | citrate lyase gamma chain (acyl lyase subunit) (citD) (*Klebsiella pneumonise*) | 52.1 | 71.9 | 97 |
| HI1667 | 1728793 | 1727567 | dihydroliposmide succinyltransferase (sucB) (*Escherichia coli*) | 73.6 | 84.5 | 403 |
| HI1403 | 1493925 | 1495316 | fumarate hydratase class II (fumarase) (fumC) (*Escherichia coli*) | 81.8 | 74.2 | 460 |
| HI1215 | 1275907 | 1276839 | malate dehydrogenase (mdh) (*Escherichia coli*) | 78.5 | 85.1 | 303 |
| HI1248 | 1317431 | 1319690 | malic acid enzyme (*Bacillus stearothermophilus*) | 49.5 | 68.3 | 376 |
| HI1200 | 1262687 | 1263585 | succinyl-CoA synthetase alpha-subunit (sucD) (*Escherichia coli*) | 83.4 | 91.7 | 289 |
| HI1199 | 1261518 | 1262684 | succinyl-CoA synthetase beta-subunit (sucC) (*Escherichia coli*) | 64.7 | 80.2 | 388 |
| Pentose phosphate pathway | | | | | | |
| HI0556 | 574158 | 572708 | 6-phosphogluconate dehydrogenase, decarboxylating (gnd) (*Escherichia coli*) | 54.0 | 71.1 | 464 |
| HI0560 | 577777 | 576296 | glucose-6-phosphate 1-dehydrogenase (G6PD) (*Synechococous sp.*) | 46.2 | 65.3 | 483 |
| HI1025 | 1088660 | 1086566 | transluetolese 1 (TK 1) (tktA) (*Escherichia coli*) | 77.1 | 87.5 | 664 |
| Entner-Doudoroff | | | | | | |
| HI0047 | 45381 | 47745 | 2-keto-3-deoxy-6-phosphogluconate aldolase (eda) (*Escherichia coli*) | 37.3 | 63.2 | 193 |
| HI0049 | 50201 | 49260 | 2-keto-3-deoxy-D-gluconate lanase (kdgK) (*Eninnis chrysanthemi*) | 44.2 | 64.5 | 300 |
| Aerobic | | | | | | |
| HI1655 | 1715678 | 1713987 | D-lactate dehydrogenase (dld) (*Escherichia coli*) | 59.5 | 77.7 | 560 |
| HI1166 | 1234330 | 1231250 | D-lactate dehydrogenase (dld) (*Saccharomyces cerevisiae*) | 27.6 | 47.7 | 427 |
| HI0607 | 635168 | 636172 | glycerol-3-phosphate dehydrogenase (gpsA) (*Escherichia coli*) | 66.6 | 81.5 | 335 |
| HI0749 | 805382 | 806713 | NADH dehydrogenase (ndh) (*Escherichia coli*) | 57.8 | 75.4 | 430 |
| Anaerobic | | | | | | |
| HI1049 | 1112944 | 1110527 | anaerobic dimethyl sulfoxide reductase A (dmsA) (*Escherichia coli*) | 74.0 | 86.3 | 785 |
| HI1048 | 1110513 | 1109899 | anaerobic dimethyl sulfoxide reductase B (dmsB) (*Escherichia coli*) | 72.1 | 84.8 | 204 |
| HI1047 | 1109894 | 1109058 | anaerobic dimethyl sulfoxide reductase C (dmsC) (*Escherichia coli*) | 41.0 | 65.0 | 287 |
| HI0648 | 688485 | 687382 | cytochrome C-type protein (torC) (*Escherichia coli*) | 37.4 | 54.7 | 365 |
| HI0350 | 374535 | 375134 | denitrification system component (nirT) (*Pseudomones stutzen*) | 51.7 | 71.6 | 176 |
| HI0009 | 9878 | 10783 | ldhE protein (ldhE) (*Escherichia coli*) | 50.8 | 71.6 | 307 |
| HI0006 | 5067 | 8158 | lormate dehydrogenase, nitrate-inducible major subunit (fdnG) (*Escherichia coli*) | 64.4 | 79.2 | 1015 |
| HI0005 | 4802 | 3993 | formate dehydrogenase-N affector (fdhD) (*Escherichia coli*) | 57.7 | 71.0 | 249 |
| HI0008 | 9035 | 9805 | formate dehydrogenase-O gamma subunit (fdoI) (*Escherichia coli*) | 52.8 | 72.1 | 195 |
| HI0007 | 8161 | 9096 | formate dehydrogenase-O beta subunit (fdoH) (*Escherichia coli*) | 72.2 | 85.6 | 297 |
| HI1071 | 1133439 | 1131826 | formate-dependent nitrite reductase (cytochrome C552) (nrfC) (*Escherichia coli*) | 56.7 | 75.3 | 450 |
| HI1070 | 1131779 | 1131102 | formate-dependent nitrite reductase (nrfB) (*Escherichia coli*) | 50.0 | 66.9 | 134 |
| HI1069 | 1131102 | 1130428 | formate-dependent nitrite reductase protein Fe—S centers (nrfC) (*Escherichia coli*) | 64.2 | 81.2 | 217 |
| HI1068 | 1130428 | 1129466 | formate-dependent nitrite reductase transmembrane protein (nrfD) (*Escherichia coli*) | 48.2 | 68.4 | 312 |
| HI0835 | 882094 | 882529 | fumerate reductase (frdC) (*Escherichia coli*) | 49.2 | 72.3 | 129 |
| HI0834 | 882093 | 881752 | fumerate reductase 13 kDa hydrophobic protein (frdD) (*Escherichia coli*) | 53.0 | 76.5 | 119 |
| HI0837 | 885089 | 883293 | fumarate reductase, flavoprotein subunit (frdA) (*Escherichia coli*) | 75.4 | 87.2 | 602 |
| HI0636 | 883357 | 882530 | fumarate reductase, iron-sulfur protein (frdB) (*Escherichia coli*) | 75.5 | 85.3 | 244 |
| HI0681 | 720855 | 720541 | glpE protein (glpE) (*Escherichia coli*) | 43.3 | 63.5 | 103 |
| HI0620 | 651184 | 651759 | glpG protein (glpG) (*Escherichia coli*) | 39.1 | 64.8 | 178 |
| HI0687 | 729160 | 727492 | glycerol-3-phosphate dehydrogenase, subunit A (glpA) (*Escherichia coli*) | 69.9 | 52.7 | 531 |
| HI0686 | 727529 | 726204 | glycerol-3-phosphate dehydrogenase, subunit B (glpB) (*Escherichia coli*) | 42.3 | 60.3 | 414 |
| HI0685 | 726189 | 724912 | glycerol-3-phosphate dehydrogenase, subunit C (glpC) (*Escherichia coli*) | 58.8 | 76.0 | 393 |

-continued

| | | | | | | |
|---|---|---|---|---|---|---|
| HI1395 | 1487087 | 4187358 | hydrogenase isoenzymes formation protein (hypC) (*Escherichia coli*) | 53.2 | 81.6 | 76 |

Electron transport

| | | | | | | |
|---|---|---|---|---|---|---|
| HI0887 | 936816 | 938552 | C-type cytochrome biogenesis protein (copper tolerance) (cycZ) (*Escherichia coli*) | 48.8 | 57.7 | 557 |
| HI1078 | 1141318 | 1139756 | cytochrome oxidase d subunit I (cydA) (*Escherichia coli*) | 84.3 | 82.4 | 515 |
| HI1077 | 1139738 | 1138605 | cytochrome oxidase d subunit II (cydB) (*Escherichia coli*) | 60.9 | 78.4 | 379 |
| HI0629 | 549672 | 550341 | ferrodoxin )fdx) (*Chromatium vinosum*) | 59.5 | 77.2 | 78 |
| HI0374 | 394564 | 394226 | ferrodoxin (fdx) (*Escherichia coli*) | 64.5 | 83.6 | 110 |
| HI0192 | 205148 | 204627 | Flavodixin (fldA (*Escherichia coli*) | 76.9 | 87.3 | 173 |
| HI1365 | 1446272 | 1447807 | AND(P) transhydrogenas subunit alpha (pntA) (*Escherichia coli*) | 73.7 | 84.1 | 509 |
| HI1366 | 1447821 | 1449242 | AND(P) transhydrogenase subunit beta (pntB) (*Escherichia coli*) | 80.5 | 87.7 | 462 |
| HI1281 | 1355273 | 1354614 | AND(P)H-flavin oxidorductase (*Vibrio fischeri*) | 33.3 | 54.8 | 211 |

Fermentation

| | | | | | | |
|---|---|---|---|---|---|---|
| HI0601 | 514365 | 515657 | aldehyde dehydrogenase (aklH) (*Escherichia coli*) | 41.2 | 61.8 | 236 |
| HI0776 | 836764 | 836114 | butyrate-acetoacetate cos-transferase subunit A (ctlA) (*Clostridium acetobutylicum*) | 53.3 | 75.2 | 214 |
| HI0186 | 200017 | 198884 | glutathione-dependent formaldehyde dehydrogenase )gd-laidH) (*Paracoccus denitrificans*) | 58.5 | 77.6 | 375 |
| HI1308 | 1383529 | 1384583 | hydrogenase gene region (hypE) (*Alcaligenes eutrophus*) | 28.1 | 48.2 | 237 |
| HI1642 | 1698196 | 1700833 | phosphoenolpytuvate carboxylase (ppc) (*Escherichia coli*) | 64.8 | 80.0 | 983 |
| HI0181 | 193936 | 191621 | pyruvate formate-lyase (pfl) (*Escherichia coli*) | 86.1 | 82.9 | 760 |
| HI0180 | 191487 | 190750 | pyruvate formate-lyase activating enzyme (act) (*Escherichia coli*) | 74.0 | 85.4 | 246 |
| HI1435 | 1517826 | 1518581 | short chain alcohol dehydrogenase (ORFB) (*Dichelobacter nodoeus*) | 51.9 | 69.2 | 104 |

Gluconeogenesis

| | | | | | | |
|---|---|---|---|---|---|---|
| HI1651 | 1709919 | 1710917 | fructose-1-6-bisphosphatase (fbp) (*Escherichia coli*) | 70.5 | 84.0 | 331 |
| HI0811 | 859038 | 857425 | phosphoenolpyruvate carboxylinase (pckA) (*Escherichia coli*) | 71.7 | 83.0 | 444 |

ATP-proton motive force interconversion

| | | | | | | |
|---|---|---|---|---|---|---|
| HI0466 | 504824 | 504573 | ATP synthease C chain (atpE) (*Vibrio alginolyticus*) | 62.7 | 81.9 | 83 |
| HI0467 | 505668 | 504883 | ATP synthase F0 subunit a (stpB) (*Escherichia coli*) | 58.2 | 78.1 | 261 |
| HI0485 | 504520 | 504053 | ATP synthase F0 subunit b (stpF) (*Escherichia coli*) | 63.5 | 79.5 | 156 |
| HI0483 | 503491 | 501953 | ATP synthase F1 subunit (stpA) (*Escherichia coli*) | 86.5 | 94.7 | 513 |
| HI0481 | 501081 | 499678 | ATP synthase F1 beta subunit (atpD) (*Escherichia coli*) | 89.3 | 96.1 | 460 |
| HI0484 | 504037 | 503507 | ATP synthase F1 delta subunit (atpH) (*Escherichia coli*) | 58.0 | 78.4 | 176 |
| HI0480 | 499645 | 499220 | ATP synthase F1 ipsilon subunit (atpC) (*Escherichia coli*) | 59.6 | 75.7 | 136 |
| HI0482 | 501934 | 501068 | ATP synthase F1 gamma subunit (stpG) (*Escherichia coli*) | 65.3 | 83.0 | 287 |
| HI1277 | 1349508 | 1350221 | ATP synthase subunit 3 region protein (atp) (*Rhodpseudomonas blastics*) | 31.9 | 50.0 | 237 |

Fatty acid/phospholipid metabolism

| | | | | | | |
|---|---|---|---|---|---|---|
| HI0773 | 834230 | 832896 | acetyl coenzyme A acetyltransferase (thiolase) (fadA) (*Clostndium acetobuylicum*) | 63.0 | 80.4 | 391 |
| HI0428 | 448891 | 448169 | fdR protein involved in fatty acid metabolism (fadR) (*Escherichia coli*) | 47.4 | 68.4 | 234 |
| HI1064 | 1126738 | 1126295 | (3R)-hydroxymynatol acyl carner protein dehydrase )fabZ) (*Escherichia coli*) | 68.1 | 85.1 | 141 |
| HI0156 | 171552 | 170827 | 3-ketoacyl-acyl carner protein reductase (fabG) (*Escherichia coli*) | 73.4 | 88.4 | 241 |
| HI0408 | 427385 | 426441 | acetyl-CoA carboxylase (accA) (*Escherichia coli*) | 75.8 | 88.3 | 318 |
| HI0155 | 170568 | 170341 | acyl carrier protein (acpP) (*Escherichia coli*) | 82.7 | 90.7 | 75 |
| HI0076 | 82175 | 83032 | acyl-CoA thioesterase II (tesB) (*Escherichia coli*) | 52.3 | 73.1 | 283 |
| HI1539 | 1605754 | 1604537 | beta-katoacyl-ACP synthase I (labB) (*Escherichia coli*) | 72.8 | 83.7 | 403 |
| HI0158 | 174085 | 173138 | beta-katoacyl-acyl carrier protein synthase III (labH) (*Escherichia coli*) | 65.9 | 79.8 | 317 |
| HI0973 | 1027538 | 1028002 | biotin carboxyl carrier protein (accB) (*Escherichia coli*) | 71.2 | 82.7 | 156 |
| HI0974 | 1028180 | 1029523 | biotin carboxylase (accC) (*Escherichia coli*) | 81.5 | 91.3 | 448 |
| HI1328 | 1404041 | 1404571 | D-3-hydroxydecanoyl-(acyl carrier-protein) dehydratase (labA) (*Escherichia coli*) | 79.2 | 91.7 | 168 |
| HI0337 | 362881 | 363234 | diacylglycerol kinase (dgkA) (*Escherichia coli*) | 50.9 | 71.8 | 110 |
| HI0002 | 601 | 2421 | long chain fatty acid coA ligase (*Homo sapiens*) | 29.5 | 52.8 | 575 |
| HI0157 | 172507 | 171572 | maionyl coenzyme A-acyl carrier protein transacylase (labO) (*Escherichia coli*) | 71.0 | 81.6 | 308 |
| HI1740 | 1811556 | 1810672 | short chain alcohol dehydrogenase homolog (envM) (*Escherichia coli*) | 75.3 | 84.9 | 259 |
| HI1438 | 1521691 | 1520741 | USG-1 protein (usg) (*Escherichia coli*) | 32.7 | 53.9 | 334 |
| HI0738 | 788371 | 787652 | 1-acyl-glycerol-3-phosphate acyltransferase (pisC) (*Escherichia coli*) | 62.2 | 78.2 | 238 |
| HI0921 | 975561 | 974698 | CDP-diglyceride synthetase (cdsA) (*Escherichia coli*) | 48.4 | 66.5 | 248 |
| HI0750 | 809228 | 806799 | glycerol-3-phosphate acyltransferase (plaB) (*Escherichia coli*) | 57.3 | 75.7 | 804 |
| HI0212 | 225946 | 225224 | phosphatidylglycerophosphate phosphatase B (pgpB) (*Escherichia coli*) | 35.7 | 60.3 | 220 |
| HI0123 | 138207 | 138761 | phosphatidylglycerophosphate synthase (pgsA) (*Escherichia coli*) | 66.5 | 83.0 | 182 |
| HI0161 | 175145 | 176014 | phosphatidylsenne decarboxylase proenzyme (ped) (*Escherichia coli*) | 57.6 | 75.5 | 280 |
| HI0427 | 446754 | 448118 | phosphatidylsenne synthase (pssA) (*Escherichia coli*) | 49.2 | 70.8 | 452 |
| HI0691 | 732349 | 733440 | protein D (hpd) (*Haemophilus influenzae*) | 98.4 | 99.2 | 364 |

Purines, pynmidines, nucleosides and nucleotides

Punne ribonucleotide biosynthesis

| | | | | | | |
|---|---|---|---|---|---|---|
| HI1522 | 1582920 | 1684005 | 5'-phosphonbosyl-5-amino-4-imidazole carboxylase II (purK) (*Escherichia coli*) | 56.8 | 71.9 | 351 |
| HI1434 | 1517646 | 1516615 | 5'-phosphonbosyl-5-aminoimidazole synthetase (purM) (*Escherichia coli*) | 76.5 | 86.7 | 344 |
| HI1749 | 1829283 | 1828660 | 5'guanylate kinase (gmk) (*Escherichia coli*) | 64.7 | 81.6 | 206 |

-continued

| | | | | | | |
|---|---|---|---|---|---|---|
| HI0351 | 375941 | 375300 | adeynlate kinase (ATP-AMP transphosphorylase) (adk) (*Haemophilus influenzae*) | 99.5 | 99.5 | 214 |
| HI0641 | 579574 | 581094 | adenylosuccinate lyase (purB) (*Escherichia coli*) | 76.5 | 87.9 | 456 |
| HI1639 | 1694462 | 1695757 | adenylosuccinate synthetase (purA) (*Escherichia coli*) | 75.7 | 87.3 | 432 |
| HI1210 | 1272783 | 1274297 | amidophosphonbosyltransferase (purF) (*Escherichia coli*) | 69.1 | 84.0 | 504 |
| HI0754 | 812369 | 816326 | formylglycineamide ribonucleotide synthetase (purL) (*Escherichia coli*) | 59.7 | 82.0 | 1290 |
| HI1594 | 1655627 | 1658480 | formylietishydrololate hydrolase (purU) (*Escherichia coli*) | 72.6 | 85.2 | 277 |
| HI0223 | 250532 | 252100 | guaA protein (guaA) (*Escherichia coli*) | 75.1 | 57.6 | 525 |
| HI0222 | 248355 | 249818 | inosine-5'-monophosphate dehydrogenase (guaB) (*Acinetobacter calcoaceocus*) | 62.7 | 80.9 | 487 |
| HI0878 | 928811 | 929233 | nucleoside diphosphale kinase (ndk) (*Escherichia coli*) | 63.0 | 73.9 | 138 |
| HI0890 | 940953 | 942239 | phosphonbosylamino-glycine ligase (purD) (*Escherichia coli*) | 75.2 | 84.5 | 427 |
| HI1621 | 1582355 | 1682847 | phosphonbosylimidazole carboxylase catalytic subunit (purE) (*Haemophilu influenzae*) | 94.4 | 96.9 | 161 |
| HI0889 | 939259 | 940854 | phosphonbosylaminoimidazolecarboxamide formyltransferase (purH) (*Escherichia coli*) | 77.2 | 86.5 | 525 |
| HI1433 | 1516567 | 1515922 | phosphonbosylglycinamide formyltransferase (purN) (*Escherichia coli*) | 51.9 | 71.4 | 210 |
| HI1615 | 1674317 | 1675261 | phosphonbosylpyrophosphate synthetase (prsA) (*Salmonella typhimurium*) | 84.1 | 91.1 | 314 |
| HI1732 | 1798036 | 1798953 | SAICAR synthetase (purC) (*Streptococcus pneumonae*) | 29.5 | 54.8 | 204 |
| Pyrimidine ribonucleotide biosyn | | | | | | |
| HI1406 | 1497997 | 1496981 | dihydroorotate dehydrogenase (dihydroorotate oxidase) (pyrD) (*Escherichia coli*) | 80.7 | 77.4 | 334 |
| HI0274 | 305799 | 305161 | orotate phosphonbosyltransferase (pyrE) (*Escherichia coli*) | 69.0 | 83.8 | 213 |
| HI1228 | 1293955 | 1294282 | pyrF opeion encoding orobdine 5'-monophosphate (OMP) decarboxylase (*Escherichia coli*) | 77.1 | 87.6 | 105 |
| HI1227 | 1293266 | 1293955 | pyrF protein (pyrF) (*Escherichia coli*) | 62.3 | 79.4 | 228 |
| HI0461 | 480053 | 479517 | uracil phosphonbosyltransferase (pyrR) (*Bacillus caldolyticus*) | 52.2 | 73.9 | 179 |
| 2'-deoxyribonucleotide metabolism | | | | | | |
| HI0075 | 79934 | 82054 | anaerobic ribonucleoside-triphosphate reductase (nrdD) (*Escherichia coli*) | 77.4 | 88.2 | 702 |
| HI0133 | 146656 | 147240 | deoxycyladine triphosphate deaminase (dcd) (*Escherichia coli*) | 75.6 | 86.5 | 193 |
| HI0956 | 1012787 | 1013239 | deoxyundinetriphosphatase (dut) (*Escherichia coli*) | 75.5 | 90.7 | 151 |
| HI1838 | 1604204 | 1604464 | glutaredoxin (grx) (*Escherichia coli*) | 69.9 | 79.5 | 83 |
| HI1666 | 1726318 | 1727448 | nrdB protein (nrdB) (*Escherichia coli*) | 85.4 | 82.6 | 376 |
| HI1665 | 1723831 | 1726173 | ribonucleoside-diphosphate reductase 1 alpha chain (nrdA) (*Escherichia coli*) | 83.4 | 92.2 | 761 |
| HI1161 | 1227925 | 1226972 | thioradoxin reductase (trxB) (*Escherichia coli*) | 75.9 | 85.8 | 316 |
| HI0907 | 958914 | 959762 | thymidylate synthetase (thyA) (*Escherichia coli*) | 35.3 | 55.0 | 254 |
| Salvage of nucleosides and nucleotides | | | | | | |
| HI0585 | 805064 | 803094 | 2',3'-cyclic-nucleotide 2'-phosphodiesterase (cpdB) (*Escherichia coli*) | 62.4 | 77.7 | 641 |
| HI1233 | 1299794 | 1299255 | adeninephosphoribosyltransferase (apt) (*Escherichia coli*) | 66.1 | 83.1 | 177 |
| HI0653 | 571120 | 571943 | adenosine-tetrephosphatase (apsH) (*Escherichia coli*) | 52.4 | 73.1 | 271 |
| HI1353 | 1426390 | 1427265 | cytidine deaminase (cytidine aminohydroises) (cds) (*Escherichia coli*) | 50.0 | 63.4 | 253 |
| HI1222 | 1258579 | 1289628 | cytidylate kinase (cmk) (*Escherichia coli*) | 64.5 | 79.3 | 217 |
| HI1652 | 1711636 | 1710842 | cytidylate kinase (cmk) (*Escherichia coli*) | 63.5 | 76.6 | 202 |
| HI0620 | 540879 | 540188 | purine-nucleoside phosphorylase (deoD) (*Escherichia coli*) | 84.3 | 90.2 | 235 |
| HI0631 | 552177 | 551599 | thymidine kinase (tdk) (*Escherichia coli*) | 68.6 | 82.4 | 188 |
| HI1231 | 1297060 | 1296427 | uracil phosphonbosyltransferase (upp) (*Escherichia coli*) | 83.2 | 93.6 | 208 |
| HI0676 | 716559 | 718095 | xanthine guanine phosphoribosyl transferase gpt (xgprt) (*Escherichia coli*) | 72.1 | 87.7 | 152 |
| HI0694 | 736541 | 736077 | xanthine-guanine phosphonbosyltransferase (xprt) (*Salmonells typhimurium*) | 74.0 | 67.7 | 152 |
| HI1280 | 1353404 | 1354561 | putative ATOase (mrp) (*Escherichia coli*) | 66.0 | 79.0 | 353 |
| Sugar-nucleotide biosynthesis, conversions | | | | | | |
| HI0207 | 219511 | 221319 | 5'-nucleotidase (ushA0 *Homo sapiens*) | 34.5 | 54.8 | 487 |
| HI1282 | 1355378 | 1358061 | CMP-NeuNAc synthetase (sisB) (*Neisseris meningtidis*) | 47.1 | 64.3 | 221 |
| HI0822 | 871597 | 870551 | galactose-1-phosphate undylyltransferase (galT) (*Haemophilus influenzae*) | 99.1 | 100.0 | 349 |
| HI0814 | 862832 | 861748 | glucosephosphate undylyltransferase (galU) (*Escherichia coli*) | 74.0 | 86.1 | 287 |
| HI0353 | 378461 | 377448 | udp-glucose 4-epimerase (galactowaldenase) (galE) (*Haemophilus influenzae*) | 99.1 | 99.1 | 338 |
| HI0644 | 662446 | 683813 | UDP-N-acetylglucocamine pyrophosphorylase (glmU) (*Escherichia coli*) | 68.6 | 83.1 | 456 |
| Nucleotide and nucleoside interconversions | | | | | | |
| HI1302 | 1376759 | 1378139 | deoxyguanosine triphosphate triphosphohydrolase (dgt) (*Escherichia coli*) | 38.2 | 57.6 | 469 |
| HI1079 | 1141970 | 1143603 | pyrG protein (pyrG) (*Escherichia coli*) | 80.4 | 90.5 | 545 |
| HI0132 | 148006 | 146644 | uridine kinase (undine monophokinase) (udk) (*Escherichia coli*) | 67.8 | 84.7 | 202 |
| Regulatory functions | | | | | | |
| HI0806 | 632583 | 635094 | adenylate cyclase (cysA) (*Haemophilus influenzae*) | 100.0 | 100.0 | 843 |
| HI0886 | 936824 | 935917 | aerobic respiration control protein ARCA (DYE resistance protein) (arcA) (*Escherichia coli*) | 77.2 | 87.8 | 237 |
| HI0221 | 238723 | 248354 | aerobic respiration control sensor protein (arcB) (*Escherichia coli*) | 45.7 | 70.4 | 768 |
| HI1054 | 1117672 | 1116979 | araC-like transcription regulator (*Streptomyces lividans*) | 25.7 | 47.7 | 303 |
| HI1212 | 1275700 | 1275246 | arginine repressor protein (argR) (*Escherichia coli*) | 69.1 | 81.2 | 149 |
| HI0237 | 265657 | 265310 | arsC protein (arsC) (Plasmid R773) | 38.3 | 56.5 | 114 |
| HI0454 | 482094 | 484602 | ATP-dependent proteinase (lon) (*Escherichia coli*) | 74.5 | 87.9 | 769 |
| HI0336 | 360836 | 362863 | ATP:GTP 3'-pyrophosphotransferase (relA) (*Escherichia coli*) | 62.9 | 80.5 | 741 |
| HI1130 | 1193658 | 1195126 | carbon starvation protein (cstA) (*Escherichia coli*) | 32.1 | 53.5 | 499 |

-continued

| | | | | | | |
|---|---|---|---|---|---|---|
| HI0815 | 862845 | 862657 | carbon storage regulator (cstA) (*Escherichia coli*) | 68.4 | 91.2 | 57 |
| HI0906 | 863619 | 853063 | cyclic AMP receptor protein (crp) (*Haemophilus influenzae*) | 27.2 | 46.7 | 174 |
| HI0959 | 1014161 | 1014832 | cyclic AMP receptor protein (crp) (*Haemophilus influenzae*) | 100.0 | 100.0 | 224 |
| HI1203 | 1265444 | 1266412 | cys regulon transcriptional activator (cysB) (*Escherichia coli*) | 63.3 | 79.3 | 324 |
| HI0191 | 204595 | 204158 | ferric uptake regulation protein (fur) (*Escherichia coli*) | 61.4 | 75.0 | 139 |
| HI1457 | 1537858 | 1537391 | limbrial transcription regulation repressor (pilB) (*Neiasoria gonorrhoaes*) | 32.3 | 53.2 | 124 |
| HI1459 | 1539614 | 1538556 | limbrial transcription regulation repressor (pilB) (*Neiasoria gonorrhoaes*) | 59.0 | 72.6 | 325 |
| HI1263 | 1336881 | 1337548 | folyipolyglutamate-dihydrofolate synthetase expression regulator (accD) (*Escherichia coli*) | 69.5 | 62.5 | 290 |
| HI1430 | 1512975 | 1513745 | fumerate (and nitrate) reduction regulatory protein (fnr) (*Escherichia coli*) | 78.8 | 88.8 | 240 |
| HI0823 | 871805 | 872800 | galactose operon repressor (galS) (*Haemophilus influenzae*) | 99.1 | 99.4 | 332 |
| HI0756 | 817661 | 818559 | glucolonase regulator (*Rattus norvegicus*) | 31.8 | 56.1 | 512 |
| HI0621 | 651792 | 652556 | glycerol-3-phosphate regulon repressor (glpR) (*Escherichia coli*) | 61.5 | 77.4 | 252 |
| HI1011 | 1073676 | 1073047 | glycerol-3-phosphate regulon repressor (glpR) (*Escherichia coli*) | 28.6 | 50.3 | 198 |
| HI1197 | 1259493 | 1260395 | glcine cleavage system transcriptional activator (gcvA) (*Escherichia coli*) | 51.7 | 69.1 | 298 |
| HI0013 | 13742 | 12837 | GTP-binding protein (era) (*Escherichia coli*) | 77.9 | 87.0 | 299 |
| HI0879 | 930478 | 929309 | GTP-binding protein (obg) (*Bacillus subtilis*) | 47.7 | 70.9 | 332 |
| HI0673 | 592001 | 591099 | hydrogen percade-inducible activator (oxyR) (*Escherichia coli*) | 71.1 | 85.9 | 298 |
| HI0617 | 647526 | 646780 | L-lucose operon activator (leoR) (*Escherichia coli*) | 35.1 | 56.1 | 229 |
| HI0401 | 420131 | 420952 | lacZ exression regulator (ioc) (*Escherichia coli*) | 52.9 | 71.3 | 261 |
| HI0225 | 253133 | 253638 | leucine responsive regulatory protein (lrp) (*Escherichia coli*) | 29.6 | 52.8 | 152 |
| HI1602 | 1663150 | 1862653 | leucine responsive regulatory protein (lrp) (*Escherichia coli*) | 77.2 | 86.7 | 155 |
| HI0751 | 809477 | 810103 | LEXA repressor (lexA) (*Escherichia coli*) | 66.1 | 85.3 | 202 |
| HI1465 | 1542848 | 1542810 | lipooligosaccharide protein (lex2A) (*Haemophilus influenzae*) | 44.4 | 66.7 | 9 |
| HI1466 | 1542849 | 1543428 | lipooligosaccharide protein (lex2A) (*Haemophilus influenzae*) | 50.0 | 66.7 | 48 |
| HI0296 | 328190 | 327878 | metF aporepressor (metJ) (*Escherichia coli*) | 81.9 | 93.3 | 105 |
| HI1478 | 1558154 | 1557312 | molybdenum transport system alternative nitrogenae regulator (modD) (*Rhodobacter capsulatus*) | 31.8 | 51.7 | 259 |
| HI0200 | 214274 | 215227 | msbB protein (msbB) (*Escherichia coli*) | 45.3 | 67.0 | 301 |
| HI0411 | 429238 | 430662 | msbB protein (msbB) (*Escherichia coli*) | 50.9 | 69.3 | 284 |
| HI0712 | 756824 | 757117 | negative regulator of translation (retB) (*Escherichia coli*) | 28.3 | 48.3 | 60 |
| HI0631 | 667822 | 668406 | negative rpo regulator(mclA) (*Escherichia coli*) | 40.1 | 62.9 | 199 |
| HI0269 | 299532 | 301232 | nitrate sensor protein (narO) (*Escherichia coli*) | 38.6 | 63.0 | 555 |
| HI0728 | 778003 | 777380 | nitrate/nitrite response regulator protein (narP) (*Escherichia coli*) | 59.6 | 79.3 | 205 |
| HI0339 | 363915 | 364250 | nitrogen regulatory protein P-H (glnB) (*Escherichia coli*) | 77.7 | 93.8 | 112 |
| HI1747 | 1828067 | 1826037 | penta-phosphate guanosine-J pyrophosphohydrolase (spoT) (*Escherichia coli*) | 58.8 | 76.8 | 675 |
| HI0200 | 214274 | 215227 | phosphate regulon sensor protein (phoR) (*Escherichia coli*) | 41.8 | 66.8 | 335 |
| HI1382 | 1475709 | 1475017 | phosphate regulon transcriptional regulatory protein (phoB) (*Escherichia coli*) | 52.9 | 71.8 | 227 |
| HI0765 | 827030 | 825768 | probably nadAB transcriptional regulator (nedR) (*Escherichia coli*) | 54.6 | 75.1 | 349 |
| HI1641 | 1697003 | 1698115 | punne necletide synthesis repressor protein (purR) (*Escherichia coli*) | 55.9 | 74.5 | 326 |
| HI0164 | 178405 | 178713 | putativo murein geno regulator (bolA) (*Escherichia coli*) | 47.1 | 65.7 | 102 |
| HI0508 | 522278 | 523273 | rbs repressor (rbsR) (*Escherichia coli*) | 48.8 | 71.0 | 329 |
| HI0565 | 582225 | 581776 | regulatory protein (asnC) (*Escherichia coli*) | 68.0 | 81.0 | 147 |
| HI1617 | 1677452 | 1676583 | regulatory protein sfs1 involved in meltose metabolism (srsA) (*Escherichia coli*) | 54.3 | 71.2 | 218 |
| HI0995 | 946128 | 946688 | repressor for sytochrome P450 (Bm3R1) (*Bacillus magatenum*) | 23.3 | 50.5 | 182 |
| HI0271 | 302396 | 303238 | RNA polymerase sigma-32 factor (heat shock regulatory protein F334) (rpoH) (*Escherichia coli*) | 70.8 | 86.8 | 281 |
| HI0535 | 555646 | 557532 | RNA polymerase sigma-70 factor (rpoD) (*Escherichia coli*) | 68.9 | 80.8 | 608 |
| HI0630 | 667228 | 667794 | RNA polymerase sigma-E factor (rpoE) (*Escherichia coli*) | 73.0 | 87.8 | 189 |
| HI1713 | 1781137 | 1779785 | sensor protein for basR (basS) (*Escherichia coli*) | 30.0 | 55.7 | 253 |
| HI1444 | 1529117 | 1528668 | stringent starvation protein (sspB) (*Escherichia coli*) | 63.2 | 81.1 | 106 |
| HI1445 | 1529755 | 1529120 | stringent starvation protein A (sspA) (*Haemophilus somnus*) | 76.9 | 87.3 | 212 |
| HI1745 | 1815630 | 1814704 | trans-activator of metE and metH (metR) (*Escherichia coli*) | 39.5 | 60.8 | 294 |
| HI0360 | 382477 | 383121 | transcription activator (tenA) (*Bacillus subtilis*) | 27.8 | 48.3 | 208 |
| HI0883 | 722643 | 721766 | transcriptional activator protein (xlvY) (*Escherichia coli*) | 47.4 | 70.3 | 293 |
| HI1714 | 1781799 | 1781137 | transcriptional regulatory protein (basR) (*Escherichia coli*) | 43.5 | 59.7 | 216 |
| HI0412 | 430780 | 431783 | transcriptional regulatory protein (tyrR) (*Escherichia coli*) | 48.2 | 65.8 | 306 |
| HI0832 | 880611 | 880913 | tryptophan repressor (trpR) (*Emerobacter aerogenea*) | 38.8 | 67.0 | 88 |
| HI0054 | 54188 | 54965 | uxu operon regulator (uxuR) (*Escherichia coli*) | 50.0 | 72.1 | 246 |
| HI1109 | 1170415 | 1169255 | xylose operon regulatory protein (xylR) (*Escherichia coli*) | 57.3 | 75.3 | 384 |

Replication

DNA - replication, realr/modification, recombination

| | | | | | | |
|---|---|---|---|---|---|---|
| HI0751 | 822003 | 823136 | A/G-specific adenine glycosylase (mulY) (*Escherichia coli*) | 81.9 | 75.1 | 341 |
| HI0895 | 1056874 | 1055313 | chromosomal replication initiator protein (dnaA) (*Escherichia coli*) | 61.7 | 79.7 | 464 |
| HI1229 | 1294415 | 1294317 | chromosomal replication initiator protein (dnaA) (*Escherichia coli*) | 50.0 | 75.0 | 12 |
| HI0316 | 345720 | 345151 | crossover junction endodioxyribonuclease (ruvC) (*Escherichia coli*) | 78.5 | 88.3 | 163 |
| HI0955 | 1011537 | 1012736 | dtp protein (dtp) (*Escherichia coli*) | 61.1 | 76.8 | 402 |
| HI0210 | 223259 | 224116 | DNA adenine methylase (dam) (*Escherichia coli*) | 55.4 | 71.4 | 268 |
| HI1267 | 1343755 | 1341116 | DNA gyrase, subunit A (gyrA) (*Escherichia coli*) | 70.6 | 84.8 | 859 |
| HI0569 | 587397 | 584980 | DNA gyrase, subunit B (gyrB) (*Escherichia coli*) | 74.7 | 85.9 | 803 |
| HI1191 | 1255302 | 1253122 | DNA helicase II (uvrD) (*Haemophilus influenzae*) | 96.8 | 97.5 | 727 |
| HI1102 | 1162989 | 1160953 | DNA ligase (lig) (*Escherichia coli*) | 63.7 | 79.9 | 666 |
| HI0405 | 423539 | 424207 | DNA mismatch protein (mutH) (*Escherichia coli*) | 60.4 | 80.7 | 212 |
| HI0709 | 750565 | 753147 | DNA mismatch repair protein (mutS) (*Escherichia coli*) | 71.0 | 84.0 | 853 |

-continued

| | | | | | | |
|---|---|---|---|---|---|---|
| HI0067 | 69622 | 71508 | DNA mismatch repair protein MUTL (mutL) (*Escherichia coli*) | 50.2 | 67.3 | 612 |
| HI0858 | 904919 | 902130 | DNA polymerase I (polA) (*Escherichia coli*) | 63.1 | 77.0 | 928 |
| HI0994 | 1055297 | 1054200 | DNA polymerase III beta-subunit (dnaN) (*Escherichia coli*) | 62.6 | 80.3 | 366 |
| HI0457 | 476761 | 475763 | DNA polymerase III delta prime subunit (holB) (*Escherichia coli*) | 35.3 | 57.4 | 316 |
| HI0925 | 979730 | 980761 | DNA polymerase III delta subunit (holA) (*Escherichia coli*) | 45.2 | 62.0 | 332 |
| HI0138 | 152669 | 151902 | DNA polymerase III epsilon subunit (dnaO) (*Escherichia coli*) | 61.3 | 76.5 | 236 |
| HI0741 | 799019 | 795544 | DNA polymerase III, alpha chain (dnaE) (*Escherichia coli*) | 71.9 | 85.7 | 1159 |
| HI1402 | 1493690 | 1493259 | DNA polymerase III, chi subunit (holC) (*Haemophilus influenzae*) | 95.9 | 98.9 | 88 |
| HI0011 | 11672 | 11271 | DNA polymerase III, psi subunit (holD) (*Escherichia coli*) | 34.4 | 59.2 | 123 |
| HI0534 | 553659 | 555645 | DNA primase (dnaG) (*Escherichia coli*) | 56.5 | 73.8 | 571 |
| HI1746 | 1826037 | 1823959 | DNA recombinase (recG) (*Escherichia coli*) | 68.5 | 80.1 | 893 |
| HI0070 | 77166 | 75493 | DNA repair protein (recN) (*Escherichia coli*) | 48.6 | 67.3 | 833 |
| HI0659 | 699507 | 700058 | DNA toporsomerase I (topA) (*Bacillus subtilis*) | 34.2 | 55.0 | 110 |
| HI0656 | 698124 | 697570 | DNA-3-methyladenine glycosidase I (lagI) (*Escherichia coli*) | 62.6 | 76.0 | 179 |
| HI0730 | 779457 | 781969 | DNA-dependent ATPase, DNA helicase (recO) (*Escherichia coli*) | 62.9 | 77.6 | 589 |
| HI0568 | 584850 | 584159 | DOD protein (dod) (*Serratia marcascans*) | 81.4 | 93.3 | 210 |
| HI0062 | 65230 | 65664 | dosage-dependent dnaK supressor protein (dksA) (*Escherichia coli*) | 73.9 | 83.8 | 142 |
| HI0948 | 1005798 | 1004986 | lormamidopyrimidine-DNA glycosylase (lpg) (*Escherichia coli*) | 57.8 | 74.7 | 269 |
| HI0584 | 602405 | 600519 | glucose inhibited division protein (gidA) (*Escherichia coli*) | 76.1 | 87.3 | 627 |
| HI0488 | 506816 | 506208 | glucose inhibited division protein (gidB) (*Escherichia coli*) | 64.0 | 78.0 | 200 |
| HI0982 | 1037496 | 1037792 | Hin recombinational enhancer binding protein (Iis) (*Escherichia coli*) | 81.6 | 92.9 | 97 |
| HI0514 | 528338 | 527565 | HineII endonuclease (HineII) (*Haemophilus influenzae*) | 98.4 | 98.4 | 258 |
| HI1397 | 1491189 | 1490263 | HindIII modification methyltransferase (hindIIIM) (*Haemophilus influenzae*) | 99.4 | 99.4 | 309 |
| HI1398 | 1492072 | 1491173 | HindIII restriction endonuclease (hindIIIR) (*Haemophilus influenzae*) | 99.7 | 99.7 | 300 |
| HI0315 | 345085 | 344474 | Holiday junction DNA helicase (ruvA) (*Escherichia coli*) | 58.8 | 79.9 | 203 |
| HI0314 | 344483 | 343459 | Holiday junction DNA helicase (ruvB) (*Escherichia coli*) | 80.9 | 90.0 | 330 |
| HI0678 | 719084 | 718180 | integrase/recombinase protein (xerC) (*Escherichia coli*) | 58.0 | 74.0 | 293 |
| HI1316 | 1391102 | 1391389 | integration host factor alpha-subunit (himA) (*Escherichia coli*) | 63.8 | 83.0 | 94 |
| HI1224 | 1291400 | 1291581 | integration host factor beta-subunit (IHF-beta) (himD) (*Escherichia coli*) | 56.5 | 77.2 | 92 |
| HI0404 | 422970 | 423539 | metylated-DNA--protein-cysteine methyltranferase (dall) (*Bacillus subtilis*) | 40.1 | 61.7 | 163 |
| HI0671 | 713369 | 713806 | mioC protein (mioC) (*Escherichia coli*) | 53.6 | 71.5 | 144 |
| HI1043 | 1104813 | 1105724 | modification methylase HgiDl (MHgiDl) (*Herpelosipnon aurantiscus*) | 56.4 | 70.5 | 297 |
| HI0515 | 529891 | 528338 | modification methylase HincII (hincIIM) (*Haemophilus influenzae*) | 98.2 | 96.6 | 502 |
| HI0912 | 963611 | 964312 | mutator mutT (AT-GC transversion) (*Escherichia coli*) | 48.8 | 72.0 | 125 |
| HI0193 | 206098 | 206688 | negative modulator of initiation of replication (seqA) (*Escherichia coli*) | 53.1 | 71.8 | 177 |
| HI0548 | 568202 | 567879 | primosomal protein n precursor (priB) (*Escherichia coli*) | 57.4 | 75.2 | 101 |
| HI0341 | 367532 | 365343 | primosomal protein replication factor (priA) (*Escherichia coli*) | 52.3 | 70.2 | 729 |
| HI0389 | 406402 | 408321 | probable ATP-dependent helicase (dinG) (*Escherichia coli*) | 32.2 | 51.1 | 860 |
| HI0993 | 1054243 | 1053119 | recF protein (recF) (*Escherichia coli*) | 57.0 | 75.8 | 356 |
| HI0334 | 358532 | 359239 | recO protein (recO) (*Escherichia coli*) | 64.6 | 75.5 | 226 |
| HI0502 | 621957 | 620896 | recombinase (recA) (*Haemophilus influenzae*) | 100.0 | 100.0 | 354 |
| HI0061 | 64971 | 62573 | recombination protein (rec2) (*Haemophilus influenzae*) | 99.9 | 99.9 | 800 |
| HI0445 | 464118 | 464717 | recR protein (recR) (*Escherichia coli*) | 74.9 | 88.4 | 199 |
| HI0601 | 620735 | 620358 | regulatory protein (recX) (*Pseudomones fluorescans*) | 26.6 | 50.4 | 117 |
| HI0651 | 694862 | 692768 | rep helicase (rep) (*Escherichia coli*) | 66.9 | 82.7 | 669 |
| HI1232 | 1299240 | 1297177 | replication protein (dnaX) (*Escherichia coli*) | 52.9 | 69.8 | 643 |
| HI1580 | 1641089 | 1642600 | replicative DNA helicase (dnaB) (*Escherichia coli*) | 68.6 | 82.8 | 482 |
| HI1042 | 1103812 | 1104813 | restriction enzyme (hgiDIR) (*Herpetosiphon gigantsus*) | 44.2 | 83.9 | 350 |
| HI1175 | 1241423 | 1242574 | S-adenosylmethionine synthetase 2 (metX) (*Escherichia coli*) | 82.3 | 91.7 | 383 |
| HI1429 | 1512163 | 1511552 | shufflon-specific DNA recombinase (rci) (*Escherichia coli*) | 31.1 | 55.5 | 259 |
| HI0251 | 281830 | 282333 | single-stranded DNA binding protein (sab) (*Haemophilus influenzae*) | 95.8 | 98.2 | 168 |
| HI1576 | 1639113 | 1638016 | site-specific recombinase (rcd) (*Escherichia coli*) | 36.3 | 57.0 | 268 |
| HI1368 | 1450325 | 1452928 | topoisomerase I (topA) (*Escherichia coli*) | 72.0 | 84.3 | 855 |
| HI0446 | 464736 | 466688 | topoisomerase III (tpoB) (*Escherichia coli*) | 65.9 | 79.4 | 645 |
| HI1535 | 1598641 | 1601881 | topoisomerase IV subunit A (parC) (*Escherichia coli*) | 71.4 | 65.4 | 727 |
| HI1534 | 1597767 | 1599571 | topoisomerase IV subunit B (parE) (*Escherichia coli*) | 76.5 | 88.6 | 630 |
| HI1261 | 1331575 | 1335011 | transcription-repair coupling factor (trcF) (mld) (*Escherichia coli*) | 64.3 | 82.7 | 1134 |
| HI0217 | 232884 | 234038 | type I restriction enzyme ecokI specificity protein (hsdS) (*Escherichia coli*) | 36.1 | 58.6 | 394 |
| HI0216 | 231281 | 232797 | type I restriction enzyme ECOR124/3 I M protein (hsdM) (*Escherichia coli*) | 81.2 | 89.3 | 512 |
| HI1290 | 1368549 | 1367223 | type I restriction enzyme ECOR124/3 I M protein (hsdM) (*Escherichia coli*) | 30.4 | 53.7 | 332 |
| HI1288 | 1365756 | 1362592 | type I restriction enzyme ECOR124/3 R protein (hsdR) (*Escherichia coli*) | 30.4 | 52.7 | 991 |
| HI1059 | 1123091 | 1121206 | type III restriction-modification ECOP15 enzyme (mod) (*Escherichia coli*) | 36.5 | 55.5 | 384 |
| HI0018 | 18087 | 18743 | uracil DNA glycosylase (ung) (*Escherichia coli*) | 70.2 | 79.5 | 215 |
| HI0311 | 342051 | 342941 | aprB protein (merD) (*Escherichia coli*) | 68.9 | 84.8 | 296 |
| Degradation of DNA | | | | | | |
| HI1698 | 1756680 | 1759312 | endonuclease III (nth) (*Escherichia coli*) | 83.4 | 91.9 | 211 |
| HI0250 | 278526 | 281829 | excinuclease ABC subunit A (uvrA) (*Escherichia coli*) | 81.2 | 91.0 | 940 |
| HI1250 | 1323924 | 1321888 | excinuclease ABC subunit B (uvrB) (*Escherichia coli*) | 78.0 | 87.7 | 669 |
| HI0057 | 68893 | 67067 | excinuclease ABC subunit C (uvrC) (*Escherichia coli*) | 65.9 | 80.0 | 588 |
| HI0380 | 1471626 | 1473044 | exodeoxyribonuclease I (abcB) (*Escherichia coli*) | 57.5 | 74.9 | 462 |
| HI1324 | 1395898 | 1399530 | exodeoxyribonuclease V (recB) (*Escherichia coli*) | 37.1 | 58.2 | 1165 |
| HI0944 | 998895 | 1002257 | exodeoxyribonuclease V (recC) (*Escherichia coli*) | 40.1 | 61.2 | 1114 |
| HI1325 | 1399533 | 1401452 | exodeoxyribonuclease V (recD) (*Escherichia coli*) | 40.0 | 59.3 | 570 |
| HI0041 | 43872 | 43072 | exonuclease III (xthA) (*Escherichia coli*) | 71.9 | 83.9 | 267 |
| HI0399 | 417972 | 419288 | exonuclease VII, large subunit (xseA) (*Escherichia coli*) | 57.8 | 74.4 | 437 |
| HI1217 | 1280795 | 1282519 | single-stranded-DNA-specific exonuclease (recJ) (*Escherichia coli*) | 59.2 | 77.3 | 554 |

-continued

Transcription

RNA synthesis, modification and DNA transcription

| | | | | | | |
|---|---|---|---|---|---|---|
| HI0618 | 647724 | 650492 | ATP-dependent helicase HEPA (hepA) (*Escherichia coli*) | 53.6 | 73.6 | 968 |
| HI0424 | 444751 | 443435 | ATP-dependent RNA helicase (srmB) (*Escherichia coli*) | 39.8 | 60.9 | 448 |
| HI0232 | 260978 | 262816 | ATP-dependent RNA helicase DEAD (deaD) (*Escherichia coli*) | 64.0 | 78.6 | 613 |
| HI0604 | 851485 | 852468 | DNA-directed RNA polymerase alpha chain (rpoA) (*Escherichia coli*) | 91.8 | 97.0 | 329 |
| HI0517 | 534212 | 538670 | DNA-directed RNA polymerase beta chain (rpoB) (*Salmonella typhimunum*) | 83.3 | 91.9 | 1342 |
| HI0516 | 534211 | 529967 | DNA-directed RNA polymerase beta' chain (rpoC) (*Escherichia coli*) | 83.0 | 90.7 | 1399 |
| HI1307 | 1383078 | 1383509 | N utilization sustance protein B (nusB) (*Escherichia coli*) | 54.9 | 71.4 | 133 |
| HI0063 | 65915 | 67269 | plasmid copy number control protein (pcnB) (*Escherichia coli*) | 55.7 | 73.4 | 404 |
| HI0230 | 257702 | 259828 | polynucleotide phosphorylase (pnp) (*Escherichia coli*) | 74.2 | 86.7 | 708 |
| HI0694 | 944630 | 945883 | putative ATP-dependent RNA helicase (rhlB) (*Escherichia coli*) | 73.9 | 84.1 | 410 |
| HI1748 | 1828594 | 1828331 | RNA polymerase omega subunit (rpoZ) (*Escherichia coli*) | 64.8 | 76.1 | 88 |
| HI1463 | 1542205 | 1541024 | sigma factor (algU) (*Pseudomones seruginosa*) | 27.6 | 48.8 | 168 |
| HI0719 | 764847 | 765401 | transcription antitermination protein (nutG) (*Escherichia coli*) | 73.7 | 64.4 | 179 |
| HI0671 | 569932 | 590405 | transcription elongation factor (graB) (*Escherichia coli*) | 61.5 | 79.5 | 156 |
| HI1266 | 1358486 | 1360006 | transcription factor (nusA) (*Salmonella typhimunum*) | 70.8 | 84.1 | 499 |
| HI0297 | 328437 | 329696 | transcription termination factor rho (rho) (*Escherichia coli*) | 87.4 | 95.2 | 419 |

Degradation of RNA

| | | | | | | |
|---|---|---|---|---|---|---|
| HI0219 | 234848 | 234923 | anticodon nuclease meeting-agent (prrD) (*Escherichia coli*) | 72.9 | 85.6 | 291 |
| HI1739 | 1810586 | 1809610 | exoribonuclease II (RNeeell) (*Escherichia coli*) | 50.8 | 68.0 | 586 |
| HI0392 | 411354 | 412550 | ribonuclease D (rnd) (*Escherichia coli*) | 41.3 | 65.5 | 365 |
| HI0415 | 433540 | 436392 | ribonuclease E (rne) (*Escherichia coli*) | 60.3 | 72.3 | 1058 |
| HI0139 | 152730 | 153181 | ribonuclease H (rnh) (*Escherichia coli*) | 64.9 | 78.0 | 154 |
| HI1061 | 1124258 | 1123668 | ribonuclease HII (EC 31264) (RNASE H12) (*Escherichia coli*) | 73.7 | 82.8 | 135 |
| HI0014 | 14422 | 13742 | ribonuclease III (rnc) (*Escherichia coli*) | 65.3 | 80.2 | 221 |
| HI0275 | 306539 | 305826 | ribonuclease PH 9rph) (*Escherichia coli*) | 79.9 | 87.8 | 237 |
| HI1001 | 1063336 | 1063743 | RNase P (rnpA) (*Escherichia coli*) | 69.7 | 80.7 | 119 |
| HI0326 | 351726 | 352412 | RNase T (rnt) (*Escherichia coli*) | 65.7 | 80.9 | 204 |

Translation

Ribosomal proteins - synthesis, modification

| | | | | | | |
|---|---|---|---|---|---|---|
| HI0516 | 539557 | 538871 | ribosomal protein L1 (rpL1) (*Escherichia coli*) | 85.6 | 93.4 | 229 |
| HI0642 | 681369 | 681857 | ribosomal protein L10 (rpL10) (*Salmonella typhimunum*) | 80.5 | 89.0 | 165 |
| HI0519 | 539990 | 539565 | ribosomal protein L11 (rpL11) (*Escherichia coli*) | 86.6 | 94.4 | 142 |
| HI0960 | 1035484 | 1036371 | ribosomal protein L11 methyltransferase (prmA) (*Escherichia coli*) | 69.2 | 83.2 | 291 |
| HI1447 | 1530773 | 1530348 | ribosomal protein L13 (rpL13) (*Haemophilus somnus*) | 94.4 | 95.8 | 142 |
| HI0790 | 844379 | 844747 | ribosomal protein L14 (rpL14) (*Escherichia coli*) | 94.3 | 98.4 | 123 |
| HI0799 | 847996 | 848427 | ribosomal protein L15 (rpL15) (*Escherichia coli*) | 82.6 | 91.0 | 144 |
| HI0786 | 842244 | 842651 | ribosomal protein L16 (rpL16) (*Escherichia coli*) | 89.7 | 95.6 | 136 |
| HI0805 | 852512 | 852695 | ribosomal protein L17 (rpTQ) (*Escherichia coli*) | 89.8 | 92.1 | 127 |
| HI0796 | 846938 | 847288 | ribosomal protein L18 (rpL18) (*Escherichia coli*) | 84.6 | 91.5 | 117 |
| HI0202 | 216787 | 216440 | ribosomal protein L19 (rpL19) (*Escherichia coli*) | 89.5 | 98.2 | 114 |
| HI0782 | 840039 | 840857 | ribosomal protein L2 (rpL2) (*Escherichia coli*) | 85.7 | 93.4 | 273 |
| HI1323 | 1395432 | 1395782 | ribosomal protein L20 (rpL20) (*Escherichia coli*) | 94.0 | 96.6 | 117 |
| HI0682 | 932097 | 931789 | ribosomal protein L21 (rpL21) (*Escherichia coli*) | 79.6 | 86.4 | 103 |
| HI0784 | 841173 | 841502 | ribosomal protein L22 (rpL22) (*Escherichia coli*) | 91.8 | 97.3 | 110 |
| HI0781 | 839722 | 840018 | ribosomal protein L23 (rpL23) (*Escherichia coli*) | 71.7 | 82.8 | 99 |
| HI0791 | 844761 | 845069 | ribosomal protein L24 (rpL24) (*Escherichia coli*) | 76.7 | 86.4 | 103 |
| HI1636 | 1692153 | 1692437 | ribosomal protein L25 (rpL25) (*Escherichia coli*) | 61.9 | 77.4 | 84 |
| HI0881 | 931428 | 931788 | ribosomal protein L27 (rpL27) (*Escherichia coli*) | 87.1 | 90.6 | 85 |
| HI0953 | 1010494 | 1010261 | ribosomal protein L28 (rpL28) (*Escherichia coli*) | 85.7 | 94.8 | 77 |
| HI0787 | 842654 | 842842 | ribosomal protein L29 (rpL29) (*Escherichia coli*) | 75.6 | 87.1 | 62 |
| HI0779 | 838461 | 839104 | ribosomal protein L3 (rpL3) (*Escherichia coli*) | 85.2 | 92.3 | 209 |
| HI0798 | 847813 | 847989 | ribosomal protein L30 (rpL30) (*Escherichia coli*) | 79.7 | 56.4 | 59 |
| HI0760 | 821826 | 821617 | ribosomal protein L31 (rpL31) (*Escherichia coli*) | 71.4 | 85.7 | 70 |
| HI0159 | 174441 | 174274 | ribosomal protein L32 (rpL32) (*Escherichia coli*) | 77.2 | 86.0 | 57 |
| HI0952 | 1010246 | 1010079 | ribosomal protein L33 (rpL33) (*Escherichia coli*) | 81.5 | 90.7 | 54 |
| HI1000 | 1063233 | 1063364 | ribosomal protein L34 (rpL34) (*Escherichia coli*) | 86.4 | 93.2 | 44 |
| HI1322 | 1395095 | 1395289 | ribosomal protein L35 (rpL35) (*Escherichia coli*) | 75.0 | 90.6 | 32 |
| HI0760 | 839722 | 839776 | ribosomal protein L4 (rpL4) (*Escherichia coli*) | 83.8 | 83.0 | 201 |
| HI0792 | 845090 | 845626 | ribosomal protein L5 (rpL5) (*Escherichia coli*) | 90.5 | 96.1 | 179 |
| HI0795 | 846391 | 846921 | ribosomal protein L6 (rpL6) (*Escherichia coli*) | 75.1 | 90.4 | 177 |
| HI0643 | 681915 | 682283 | ribosomal protein L7/L12 (rpL7/L12) (*Escherichia coli*) | 82.0 | 91.8 | 121 |
| HI0546 | 567819 | 567173 | ribosomal protein L9 (rpL9) (*Escherichia coli*) | 72.5 | 85.9 | 149 |
| HI1223 | 1289629 | 1291274 | ribosomal protein S1 (rpS1) (*Escherichia coli*) | 79.3 | 88.7 | 557 |
| HI0778 | 838108 | 838461 | ribosomal protein S10 (rpS10) (*Escherichia coli*) | 98.1 | 99.0 | 103 |
| HI0802 | 850416 | 850802 | ribosomal protein S11 (rpS11) (*Escherichia coli*) | 92.2 | 96.1 | 129 |
| HI0601 | 850045 | 850397 | ribosomal protein S13 (rpS13) (*Escherichia coli*) | 86.4 | 93.2 | 118 |
| HI0793 | 845641 | 845943 | ribosomal protein S14 (rpS14) (*Escherichia coli*) | 89.9 | 94.9 | 99 |
| HI1331 | 1405806 | 1406072 | ribosomal protein S15 (rpS15) (*Escherichia coli*) | 80.9 | 86.5 | 89 |
| HI1473 | 1554091 | 1553825 | ribosomal protein S15 (rpS15) (*Escherichia coli*) | 80.9 | 86.6 | 89 |
| HI0205 | 218422 | 218177 | ribosomal protein S16 (rpS16) (*Escherichia coli*) | 70.7 | 85.4 | 82 |
| HI0788 | 842845 | 843099 | ribosomal protein S17 (rpS17) (*Escherichia coli*) | 85.7 | 94.0 | 84 |
| HI0547 | 567883 | 567839 | ribosomal protein S18 (rpS18) (*Escherichia coli*) | 92.0 | 94.7 | 75 |

-continued

| | | | | | | |
|---|---|---|---|---|---|---|
| HI0783 | 840886 | 841158 | ribosomal protein S19 (rpS19) (*Escherichia coli*) | 90.1 | 97.9 | 91 |
| HI0915 | 967259 | 968041 | ribosomal protein S2 (rpS2) (*Escherichia coli*) | 82.2 | 89.2 | 241 |
| HI0533 | 553446 | 553858 | ribosomal protein S21 (rpS21) (*Escherichia coli*) | 83.1 | 87.3 | 71 |
| HI0785 | 841523 | 842227 | ribosomal protein S3 (rpS3) (*Escherichia coli*) | 87.2 | 93.2 | 233 |
| HI0803 | 850833 | 851450 | ribosomal protein S4 (rpS4) (*Escherichia coli*) | 89.3 | 94.7 | 206 |
| HI0797 | 847306 | 847803 | ribosomal protein S5 (rpS5) (*Escherichia coli*) | 92.8 | 95.8 | 166 |
| HI0549 | 568586 | 568592 | ribosomal protein S6 (rpS6) (*Escherichia coli*) | 76.8 | 87.2 | 125 |
| HI1537 | 1604087 | 1603182 | ribosomal protein S6 modification protein (nmK) (*Escherichia coli*) | 45.3 | 69.0 | 272 |
| HI0582 | 599803 | 599336 | ribosomal protein S7 (rpS7) (*Escherichia coli*) | 89.7 | 94.2 | 155 |
| HI0794 | 845983 | 846372 | ribosomal protein S8 (rpS8) (*Escherichia coli*) | 86.2 | 90.8 | 130 |
| HI1446 | 1530328 | 1529939 | ribosomal protein S9 (rpS9) (*Haemophilus somnus*) | 94.5 | 98.5 | 130 |
| HI0010 | 11292 | 10826 | ribosomal-protein-alanine acetyltransferase (nml) (*Escherichia coli*) | 55.9 | 73.1 | 144 |
| HI0583 | 600334 | 599963 | streptomycin resistance protein (strA) (*Haemophylis influenzae*) | 100.0 | 100.0 | 124 |
| Amino acyl tRNA Synthetases, tRNA modification | | | | | | |
| HI0816 | 865547 | 862926 | alanyl-tRNA synthetase (alaS) (*Escherichia coli*) | 68.2 | 82.6 | 873 |
| HI1589 | 1648885 | 1650415 | arginyl-tRNA synthetase (argS) (*Escherichia coli*) | 71.2 | 83.5 | 577 |
| HI1305 | 1382405 | 1380975 | asparaginyl-tRNA synthetase (asnS) (*Escherichia coli*) | 80.6 | 90.8 | 665 |
| HI0319 | 348931 | 347168 | aspertyl-tRNA synthetase (aspS) (*Escherichia coli*) | 76.2 | 85.5 | 585 |
| HI0078 | 85367 | 83991 | cys-tRNA synthetase (cysS) (*Escherichia coli*) | 75.7 | 87.0 | 461 |
| HI0710 | 753356 | 754738 | cysteinyl-tRNA (ser) selenium transferase (retA) (*Escherichia coli*) | 58.8 | 75.6 | 454 |
| HI1357 | 1431798 | 1433466 | glutaminyl-tRNA synthetase (glnS) (*Escherichia coli*) | 75.7 | 86.9 | 547 |
| HI0276 | 308282 | 308843 | glutamyl-tRNA synthetase (gllX) (*Escherichia coli*) | 72.4 | 84.3 | 464 |
| HI0929 | 985024 | 984119 | glycyl-tRNA synthetase alpha chain (glyO) (*Escherichia coli*) | 90.6 | 94.6 | 290 |
| HI0926 | 983066 | 981002 | glycyl-tRNA synthetase beta chain (glyS) (*Escherichia coli*) | 69.7 | 81.9 | 689 |
| HI0371 | 392076 | 393344 | histidine-tRNA synthetase (hisS) (*Escherichia coli*) | 66.8 | 79.1 | 421 |
| HI0964 | 1021072 | 1018250 | isoleucyl-tRNA ligase (ileS) (*Escherichia coli*) | 66.0 | 78.5 | 834 |
| HI0923 | 976547 | 979129 | leucyl-tRNA synthetase (leuS) (*Escherichia coli*) | 72.3 | 82.2 | 859 |
| HI1214 | 1276435 | 1276930 | lysyl-tRNA synthetase (lysU) (*Escherichia coli*) | 70.2 | 84.3 | 505 |
| HI0838 | 885271 | 886269 | lysyl-tRNA synthetase analog (genX) (*Escherichia coli*) | 62.7 | 78.5 | 331 |
| HI0625 | 662613 | 663566 | methionyl-tRNA formyltransferase (fmt) (*Escherichia coli*) | 65.0 | 77.4 | 313 |
| HI1279 | 1353301 | 1351256 | methionyl-tRNA synthetase (metG) (*Escherichia coli*) | 69.0 | 83.3 | 677 |
| HI0396 | 416276 | 415697 | peptidyl-tRNA hydrolase (pth) (*Escherichia coli*) | 64.2 | 80.5 | 190 |
| HI1314 | 1387890 | 1388876 | phenylalanyl-tRNA synthetase beta-subunit (pheS) (*Escherichia coli*) | 75.0 | 82.0 | 327 |
| HI1315 | 1388713 | 1391097 | phenylalanyl-tRNA synthetase beta-subunit (pheT) (*Escherichia coli*) | 65.3 | 80.1 | 795 |
| HI0731 | 781970 | 783684 | prolyl-tRNA synthetase (proS) (*Escherichia coli*) | 74.9 | 86.8 | 570 |
| HI1615 | 1709685 | 1708879 | pseudouridylate synthetase I (hisT) (*Escherichia coli*) | 69.2 | 82.7 | 260 |
| HI0246 | 273589 | 272501 | queuosine biosynthesis protein (queA) (*Escherichia coli*) | 72.5 | 55.7 | 346 |
| HI0201 | 215333 | 216439 | selenium metabolism protein (selD) (*Escherichia coli*) | 66.1 | 80.6 | 330 |
| HI0110 | 117234 | 118520 | seryl-tRNA synthetase (serS) (*Escherichia coli*) | 77.6 | 56.5 | 430 |
| HI1370 | 1453876 | 1455804 | threonyl-tRNA synthetase (thrS) (*Escherichia coli*) | 77.9 | 86.1 | 842 |
| HI0245 | 272154 | 271009 | transfer RNA-guanine transglycosylase (tgt) (*Escherichia coli*) | 81.3 | 91.5 | 374 |
| HI0203 | 217564 | 216827 | tRNA (guanine-N1)-methyltransferase (M1G-methyltransferase) (trmD) (*Escherichia coli*) | 83.2 | 93.0 | 244 |
| HI0650 | 894301 | 895369 | tRNA (uracil-5-)-methyltransferase (trmA) (*Escherichia coli*) | 64.6 | 80.4 | 362 |
| HI0088 | 71519 | 72451 | tRNA delta(2)-isopentenylpyrophosphate transferase (trpX) (*Escherichia coli*) | 69.8 | 87.4 | 300 |
| HI1612 | 1671420 | 1672667 | tRNA nucleolidyltransferase (coa) (*Escherichia coli*) | 59.4 | 73.4 | 464 |
| HI0242 | 270097 | 269807 | tRNA-guanine-transglycosylase (tgt) (*Escherichia coli*) | 62.4 | 81.7 | 92 |
| HI0658 | 678958 | 677957 | tryptophanyl-tRNA synthetase (trpS) (*Escherichia coli*) | 78.1 | 86.2 | 334 |
| HI1616 | 1676533 | 1675341 | tyrosyl tRNA synthetase (tyrS) (*Thiobacillus lericoxidana*) | 53.6 | 72.6 | 398 |
| HI1396 | 1490259 | 1487398 | valyl-tRNA synthetase (vetS) (*Escherichia coli*) | 70.8 | 83.3 | 951 |
| Nucleoproteins | | | | | | |
| HI0187 | 200140 | 200544 | DNA binding protein (probable) (*Bacillus subtilis*) | 43.4 | 64.2 | 106 |
| HI1496 | 1568481 | 1568685 | DNA-binding protein (rdgB) (*Ervinis carotovora*) | 42.4 | 60.8 | 67 |
| HI1593 | 1855153 | 1855554 | DNA-binding protein H-NS (hns) (*Escherichia coli*) | 47.4 | 65.2 | 136 |
| HI0432 | 453511 | 453104 | DNA-binding protein HU-ALPHA (NS2) (HU-2) (*Escherichia coli*) | 78.9 | 86.7 | 90 |
| Proteins - transition and modification | | | | | | |
| HI0648 | 883035 | 883757 | disulfide oxidoreductase (por) (*Haemophilus influenzae*) | 100.0 | 100.0 | 205 |
| HI0987 | 1042200 | 1041082 | DNA processing chain A (dprA) (*Escherichia coli*) | 44.8 | 80.2 | 358 |
| HI0916 | 968177 | 968025 | elongation factor EF-Ts (tsf) (*Escherichia coli*) | 71.4 | 85.0 | 260 |
| HI0580 | 597082 | 595901 | elongation factor EF-Tu (duplicate) (tufS) (*Escherichia coli*) | 92.6 | 95.9 | 384 |
| HI0634 | 671167 | 672348 | elongation factor EF-Tu (duplicate) (tufS) (*Escherichia coli*) | 92.6 | 95.9 | 384 |
| HI0581 | 599249 | 597150 | elongation factor G (fusA) (*Escherichia coli*) | 84.8 | 92.0 | 704 |
| HI0330 | 355817 | 355054 | elongation factor P (efp) (*Escherichia coli*) | 75.0 | 85.6 | 188 |
| HI0069 | 72460 | 75402 | glutamate-ammonia-ligase adenylyltransferase (ginE) (*Escherichia coli*) | 52.5 | 69.7 | 914 |
| HI1321 | 1394551 | 1394954 | initiation factor 3 (infC) (*Escherichia coli*) | 82.6 | 94.8 | 134 |
| HI0580 | 569019 | 568788 | initiation factor lf-1 (infA) (*Escherichia coli*) | 94.4 | 96.6 | 72 |
| HI1287 | 1360021 | 1362507 | initiation factor lf-2 (infB) (*Escherichia coli*) | 70.9 | 84.6 | 842 |
| HI1155 | 1218859 | 1220211 | maturation antibiotic MccB17 (prrbA) (*Escherichia coli*) | 80.8 | 76.7 | 450 |
| HI1728 | 1794724 | 1793921 | methionine aminopeptidase (map) (*Escherichia coli*) | 84.3 | 79.8 | 282 |
| HI0430 | 450570 | 451100 | oxido-reductase (dabB) (*Escherichia coli*) | 43.8 | 68.8 | 174 |
| HI1215 | 1279684 | 1278589 | peptide chain release factor 2 (prfB) (*Salmonella typhrimunum*) | 81.7 | 93.7 | 385 |
| HI1741 | 1811636 | 1813216 | peptide-chain-relase factor 3 (prfC) (*Escherichia coli*) | 86.0 | 93.4 | 527 |
| HI0079 | 85470 | 85976 | peptidyl-prolyl cis-trans isomerase B (ppiB) (*Escherichia coli*) | 71.3 | 80.5 | 83 |
| HI1567 | 1831427 | 1830345 | polypeptide chain release factor 1 (prfA) (*Salmonella typhrimunum*) | 72.5 | 88.3 | 360 |

-continued

| | | | | | | |
|---|---|---|---|---|---|---|
| HI0624 | 862011 | 862517 | polypeptide deformylase (formylmethionine deformylase) (def) (*Escherichia coli*) | 65.1 | 79.9 | 179 |
| HI0810 | 857270 | 856716 | ribosome releasing factor (frr) (*Escherichia coli*) | 68.1 | 84.9 | 185 |
| HI0575 | 593158 | 592940 | rotamase, peptidyl prolyl cis-trans isomearase (alyD) (*Escherichia coli*) | 50.7 | 73.1 | 87 |
| HI0701 | 745982 | 745413 | rotamase, peptidyl prolyl cis-trans isomearase (alyD) (*Escherichia coli*) | 68.3 | 79.4 | 187 |
| HI1334 | 1408450 | 1408923 | transcription elongation factor (greA) (*Escherichia coli*) | 79.7 | 89.9 | 158 |
| HI0711 | 754738 | 756593 | translation factor (selB) (*Escherichia coli*) | 44.0 | 64.7 | 606 |
| HI1216 | 1279817 | 1280500 | xprA protein (xprA) (*Escherichia coli*) | 45.4 | 67.4 | 227 |
| Degradation of proteins, peptides, glycopeptides | | | | | | |
| HI0877 | 927500 | 928801 | aminopeptidase A (pepA) (*Rickettsia prowazakil*) | 39.6 | 57.9 | 313 |
| HI1711 | 1775967 | 1777439 | aminopeptidase a/1 (pepA) (*Escherichia coli*) | 57.3 | 77.5 | 497 |
| HI1620 | 1682194 | 169586 | aminopeptidase N (pepN) (*Escherichia coli*) | 60.9 | 75.6 | 864 |
| HI0818 | 867554 | 886265 | aminopeptidase P (pepP) (*Escherichia coli*) | 54.6 | 73.6 | 436 |
| HI0716 | 762461 | 763039 | ATP-dependent clp protease protaclytac component (clpP) (*Escherichia coli*) | 71.0 | 88.1 | 193 |
| HI0717 | 763052 | 764284 | ATP-dependent protease ATPase subunit (clpX) (*Escherichia coli*) | 70.2 | 83.2 | 413 |
| HI0661 | 906379 | 908946 | ATP-dependent protease binding subunit(clpS) (*Escherichia coli*) | 77.4 | 88.6 | 867 |
| HI0421 | 440910 | 442289 | collagenase activity collagenase (prtC) (*Porphyromonas gingivatis*) | 31.1 | 53.4 | 206 |
| HI0151 | 166695 | 165811 | HFLC protein (hllC) (*Escherichia coli*) | 56.5 | 78.2 | 329 |
| HI0248 | 274175 | 276400 | IgA1 protease (iga1) (*Haemophilus influenzae*) | 29.8 | 51.5 | 759 |
| HI0992 | 1047674 | 1053118 | IgA1 protease (iga1) (*Haemophilus influenzae*) | 99.8 | 89.9 | 1702 |
| HI0249 | 278527 | 276401 | IgA1 protease (iga1) (*Haemophilus influenzae*) | 45.2 | 62.5 | 791 |
| HI1327 | 1402067 | 1403869 | lon protease (lon) (*Bacillus brevis*) | 24.2 | 46.6 | 714 |
| HI0215 | 229004 | 231046 | oligopeptidase A (prtC) (*Escherichia coli*) | 72.0 | 64.8 | 679 |
| HI0877 | 716670 | 718121 | peptidase D (pepD) (*Escherichia coli*) | 96.9 | 72.2 | 485 |
| HI0688 | 806842 | 607865 | peptidase E (pepE) (*Escherichia coli*) | 41.4 | 80.0 | 214 |
| HI1361 | 1423832 | 1425067 | peptidase T (pepT) (*Salmonella typhimunum*) | 53.3 | 71.4 | 399 |
| HI1202 | 1336467 | 1335070 | periplasmicserine protease Do and heat shock protein (htrA) (*Escherichia coli*) | 55.8 | 73.9 | 469 |
| HI1603 | 1664836 | 1663212 | probable ATP-dependent protease (ams) (*Escherichia coli*) | 80.0 | 92.2 | 460 |
| HI0724 | 768169 | 768784 | proline dipeptidase (pepO) (*Escherichia coli*) | 53.7 | 70.2 | 204 |
| HI0137 | 161209 | 161901 | protease (prtH) (*Porphyromones gingivitas*) | 52.6 | 64.9 | 57 |
| HI1547 | 1813228 | 1611384 | protease V (appA) (*Escherichia coli*) | 43.7 | 64.0 | 807 |
| HI0152 | 167827 | 166898 | protease specific for phage lembda ctl repressor (hllK) (*Escherichia coli*) | 55.8 | 72.6 | 396 |
| HI1688 | 1751031 | 1752089 | putative protease (schS) (*Escherichia coli*) | 53.3 | 74.5 | 348 |
| HI0632 | 553214 | 552189 | alaloglycoprotease (gcp) (*Psateurella haemolyeca*) | 81.8 | 91.5 | 319 |
| Transport binding proteins | | | | | | |
| Amino acids, peptides, amines | | | | | | |
| HI1183 | 1247387 | 1246659 | arginine transport ATP-binding protein artP (artP) (*Escherichia coli*) | 65.8 | 83.1 | 242 |
| HI1180 | 1245260 | 1244570 | arginine transport system permease protein (artM) (*Escherichia coli*) | 55.7 | 79.9 | 218 |
| HI1181 | 1245916 | 1245283 | arginine transport system permease protein (artO) (*Escherichia coli*) | 59.0 | 77.8 | 229 |
| HI0254 | 284235 | 283756 | biopolymer transport protein (subB) (*Haemophilus influenzae*) | 96.0 | 99.7 | 150 |
| HI0253 | 283779 | 283339 | biopolymer transport protein (subD) (*Escherichia coli*) | 29.8 | 55.1 | 118 |
| HI1734 | 1801710 | 1800520 | branched chain as transport system II carrier protein (brcB) (*Pesudomones aeruginosa*) | 28.4 | 49.8 | 279 |
| HI0866 | 936618 | 934149 | D-alanine permease (degA) (*Alteromones heloplaridis*) | 43.2 | 65.6 | 527 |
| HI1199 | 1251117 | 1250128 | dipeptide transport ATP-binding protein (dppD) (*Escherichia coli*) | 74.2 | 84.0 | 328 |
| HI1187 | 1250122 | 1249142 | dipeptide transport ATP-binding protein (dppF) (*Escherichia coli*) | 78.4 | 87.1 | 325 |
| HI1126 | 1189626 | 1188709 | dipeptide transport system permease protein (dppB) (*Escherichia coli*) | 34.1 | 80.7 | 337 |
| HI1190 | 1283029 | 1282031 | dipeptide transport system permease protein (dppB) (*Escherichia coli*) | 61.1 | 79.2 | 337 |
| HI1189 | 1252013 | 1251130 | dipeptide transport system permease protein (dppC) (*Escherichia coli*) | 63.8 | 83.3 | 287 |
| HI1636 | 1601926 | 1603137 | glutamate permease (gltS) (*Escherichia coli*) | 53.9 | 73.0 | 391 |
| HI1061 | 1146102 | 1146389 | glutamine transport system permease protein (glnP) (*Escherichia coli*) | 37.8 | 59.0 | 272 |
| HI1062 | 1146859 | 1148089 | glutamine-binding pertplasmic protein (glnH) (*Escherichia coli*) | 28.4 | 48.2 | 222 |
| HI0410 | 429066 | 428283 | glucine-specific transport protein (ltvG) (*Escherichia coli*) | 28.1 | 55.2 | 250 |
| HI0227 | 266066 | 254375 | membrane-associated component, LIV-# transport system (brnO) (*Salmonella typhimunum*) | 32.9 | 80.4 | 425 |
| HI0214 | 228528 | 226987 | oligopeptide binding protein (oppA) (*Escherichia coli*) | 31.7 | 53.6 | 473 |
| HI1127 | 1191333 | 1190710 | oligopeptide binding protein (oppA) (*Escherichia coli*) | 52.6 | 66.0 | 527 |
| HI1124 | 1187751 | 1186783 | oligopeptide transport ATP-binding protein (oppD) (*Salmonella typhimunum*) | 77.2 | 85.0 | 320 |
| HI1123 | 1186783 | 1185758 | oligopeptide transport ATP-binding protein (oppF) (*Salmonella typhimunum*) | 71.5 | 83.9 | 329 |
| HI1125 | 1188696 | 1187764 | oligopeptide transport system permease protein (oppC)C (*Salmonella typhimunum*) | 71.1 | 87.4 | 300 |
| HI1644 | 1702355 | 1704049 | peptide transport periplasmic protein (sapA) (*Salmonella typhimunum*) | 33.3 | 63.8 | 504 |
| HI1647 | 1705898 | 1706944 | peptide transport system ATP-binding protein (sapD) (*Salmonella typhimunum*) | 62.4 | 80.0 | 330 |
| HI1162 | 1248838 | 1245922 | periplasmic arginine-binding protein (ard) (*Pasteurella haemolydes*) | 58.6 | 73.4 | 234 |
| HI1157 | 1221270 | 1222588 | proton glutamate symport protein (gltP) (*Bacillus caldotanax*) | 28.6 | 83.6 | 396 |
| HI0692 | 611820 | 610616 | putrescine transport protein (potE) (*Escherichia coli*) | 77.3 | 96.0 | 434 |
| HI0291 | 324543 | 323308 | serine transporter (adaC) (*Escherichia coli*) | 61.0 | 77.8 | 411 |
| HI1350 | 1423563 | 1422421 | aspermidine/putrescine transport ATP-binding protein (potA) (*Escherichia coli*) | 68.1 | 83.1 | 378 |
| HI1349 | 1422434 | 1421577 | spermidine/putrescine transport system permease protein (potB) (*Escherichia coli*) | 61.5 | 83.6 | 275 |
| HI1348 | 1421548 | 1420808 | spermidine/putrescine transport system permease protein (potC) (*Escherichia coli*) | 72.4 | 88.9 | 243 |

-continued

| | | | | | | |
|---|---|---|---|---|---|---|
| HI0500 | 514110 | 513175 | spermidine/putrescine-binding periplasmic protein precursor (potD) (*Escherichia coli*) | 59.2 | 75.2 | 309 |
| HI1347 | 1420732 | 1419596 | spermidine/putrescine-binding periplasmic protein precursor (potD) (*Escherichia coli*) | 54.1 | 71.5 | 330 |
| HI0289 | 320539 | 321792 | tryptophan-specific permease (mtr) (*Escherichia coli*) | 55.8 | 72.5 | 396 |
| HI0479 | 497529 | 499028 | tyrosine-specific transport protein (tyrP) (*Escherichia coli*) | 48.1 | 68.2 | 401 |
| HI0530 | 551559 | 550342 | tyrosine-specific transport protein (tyrP) (*Escherichia coli*) | 45.4 | 65.4 | 404 |
| Cations | | | | | | |
| HI0255 | 284871 | 284407 | bacteriolerntin comigratory protein (bcp) (*Escherichia coli*) | 62.3 | 79.9 | 154 |
| HI1275 | 1347862 | 1348650 | ferric enterobactin transport ATP-binding protein (fepC) (*Escherichia coli*) | 29.4 | 51.3 | 238 |
| HI1475 | 1555193 | 1554435 | ferric enterobactin transport ATP-binding protein (fepC) (*Escherichia coli*) | 33.2 | 54.8 | 220 |
| HI1471 | 1549654 | 1551853 | ferrichrome-iron receptor (fhuA) (*Escherichia coli*) | 26.4 | 48.9 | 710 |
| HI1388 | 1479930 | 148/0475 | ferritin like protein (rsgA) (*Escherichia coli*) | 57.4 | 79.0 | 162 |
| HI1369 | 1480494 | 1480988 | ferritin like protein (rsgA) (*Escherichia coli*) | 57.3 | 73.8 | 164 |
| HI0363 | 385804 | 384887 | iron(III) dicitrate transport ATP-binding protein FECE (*Escherichia coli*) | 35.9 | 56.4 | 220 |
| HI1274 | 1347324 | 1347861 | iron(III) dicitrate transport system permease protein (fecD) (*Escherichia coli*) | 36.0 | 64.0 | 255 |
| HI1037 | 1099321 | 1100265 | magnesium and cobalt transport protein (corA) (*Escherichia coli*) | 70.3 | 84.8 | 316 |
| HI0097 | 103798 | 104679 | major ferric iron binding protein precursor (fbp) (*Neisseria gonorrhoses*) | 69.7 | 82.3 | 293 |
| HI1051 | 1114308 | 1114635 | mercuric transport protein (merT) (*Pseudomonas aeruginosa*) | 25.0 | 55.2 | 99 |
| HI1052 | 1114651 | 1114926 | mercury scavenger protein (merP) (*Pseudomonas fluorescens*) | 29.3 | 45.7 | 91 |
| HI0294 | 327396 | 327193 | mercury scavenger protein (merP) (*Pseudomonas fluorescens*) | 32.5 | 67.2 | 67 |
| HI1531 | 1594953 | 1594219 | molybdate-binding periplasmic protein precursor (modB) (*Azotobacter vinelendii*) | 21.7 | 43.0 | 245 |
| HI0226 | 254880 | 253681 | NA(+)/H(+) antiporter 1 (nhaA) (*Escherichia coli*) | 52.5 | 74.6 | 380 |
| HI0429 | 448992 | 450557 | na+/H+ antiporter (nhaB) (*Escherichia coli*) | 70.6 | 87.5 | 501 |
| HI1110 | 1171933 | 1170530 | Na+/H+ antiporter (nhaC) (*Bacillus firmus*) | 37.5 | 62.0 | 382 |
| HI0088 | 104899 | 106317 | periplasmic-binding-protein-dependent iron transport protein (sfuB) (*Serratia marcescens*) | 38.1 | 59.5 | 457 |
| HI1479 | 1556763 | 1558167 | periplasmic-binding-protein-dependent iron transport protein (sfuC) (*Serratia marcescens*) | 39.9 | 50.0 | 197 |
| HI0913 | 964424 | 966276 | potassium efflux system (kefC) (*Escherichia coli*) | 40.9 | 65.7 | 594 |
| HI0282 | 326934 | 324769 | potassium/copper-transportING ATPase A (copA) (*Enterococcus laecalis*) | 42.9 | 64.4 | 723 |
| HI1355 | 1429787 | 1428276 | sodium/proline-symporter (proline permease ) (putP) (*Escherichia coli*) | 62.8 | 79.1 | 489 |
| HI0252 | 283326 | 282517 | tonB protein (tonB) (*Haemophilus influenzae*) | 96.2 | 96.5 | 261 |
| HI0627 | 664922 | 666362 | TRK system potassium uptake protein (trkA) (*Escherichia coli*) | 65.8 | 83.4 | 458 |
| Carbohydrates, organic alcohols & acids | | | | | | |
| HI0020 | 22097 | 20661 | 2-oxoglutarate/malate translocator (SODIT1) (*Spinacia oleraosa*) | 35.8 | 59.6 | 452 |
| HI0624 | 872694 | 873940 | D-galactose-binding periplasmic protein (mglB) (*Escherichia coli*) | 57.6 | 81.2 | 329 |
| HI1113 | 1176024 | 1174516 | D-xylose transport ATP-binding protein (xylG) (*Escherichia coli*) | 71.5 | 85.8 | 501 |
| HI1114 | 1177073 | 1176078 | D-xylose-binding periplasmic protein (rbsB) (*Escherichia coli*) | 76.0 | 88.4 | 328 |
| HI1718 | 1785264 | 1783300 | enzyme I (ptaI) (*Salmonella typhimurium*) | 70.2 | 84.3 | 574 |
| HI0182 | 194818 | 193967 | formate transporter (formate channel) (*Escherichia coli*) | 53.2 | 73.4 | 263 |
| HI0450 | 471781 | 470265 | fructose-permease IIA/FPR component (fruB) (*Escherichia coli*) | 51.5 | 65.3 | 374 |
| HI0448 | 469337 | 467870 | fructose-permease IIBC component (FruA) (*Escherichia coli*) | 57.2 | 72.2 | 552 |
| HI0614 | 643282 | 6428551 | fucose operon protein (fucU) (*Escherichia coli*) | 66.3 | 80.0 | 94 |
| HI0692 | 733673 | 734464 | glpF protein (glpF) (*Escherichia coli*) | 73.6 | 97.2 | 258 |
| HI1019 | 1080518 | 1081194 | glpF protein (glpF) (*Escherichia coli*) | 30.6 | 54.6 | 208 |
| HI1017 | 1078404 | 1079887 | gluconate permease (gntP) (*Bacillus subtilis*) | 29.1 | 56.4 | 442 |
| HI1717 | 1783237 | 1782740 | glucose phosphotransferase enzyme III-glc (cir) (*Escherichia coli*) | 73.2 | 83.3 | 169 |
| HI0688 | 729474 | 730914 | glycerol-3-phosphatase transporter (glpT) (*Escherichia coli*) | 64.5 | 78.9 | 445 |
| HI0504 | 517869 | 519347 | high affinity nbose transport protein (rbsA) (*Escherichia coli*) | 71.1 | 85.4 | 494 |
| HI0505 | 519363 | 520331 | high affinity nbose transport protein (rbsC) (*Escherichia coli*) | 68.0 | 86.5 | 303 |
| HI0503 | 517436 | 517852 | high affinity nbose transport protein (rbsD) (*Escherichia coli*) | 59.0 | 78.4 | 139 |
| HI0612 | 642139 | 640856 | L-fucose permease (fucP) (*Escherichia coli*) | 35.6 | 57.9 | 413 |
| HI1221 | 1288578 | 1286983 | L-lactate permease (lctP) (*Escherichia coli*) | 30.2 | 53.9 | 532 |
| HI1735 | 1802527 | 1801757 | lactam utilization protein (lamB) (*Emencella ridulans*) | 41.3 | 60.3 | 130 |
| HI0825 | 874009 | 875526 | mglA protein (mglA) (*Escherichia coli*) | 73.9 | 84.6 | 506 |
| HI0826 | 875545 | 876553 | mglC protein (mglC) (*Escherichia coli*) | 79.2 | 90.2 | 336 |
| HI0506 | 520354 | 521229 | periplasmic ribos-binding protein (rbsB) (*Escherichia coli*) | 73.9 | 86.6 | 291 |
| HI1719 | 1785361 | 1785107 | phosphohistidinoprotein-hexose phosphotransferase (ptsH) (*Escherichia coli*) | 77.6 | 88.2 | 85 |
| HI0830 | 878480 | 878773 | potassium channel homolog (kch) (*Escherichia coli*) | 67.7 | 80.2 | 96 |
| HI0154 | 170140 | 168807 | putative aspartate transport protein (dcuA) (*Escherichia coli*) | 46.4 | 69.9 | 436 |
| HI0748 | 803858 | 805175 | putative aspartate transport protein (dcuA) (*Escherichia coli*) | 42.6 | 70.1 | 435 |
| HI1112 | 1174509 | 1173385 | ribose transport permease protein (xylH) (*Escherichia coli*) | 69.8 | 84.1 | 371 |
| HI1696 | 1759373 | 1760743 | sodium- and chloride-dependent GABA tranporter (*Homo sapiens*) | 29.3 | 52.6 | 471 |
| HI0738 | 790926 | 789403 | sodium-dependent noradrenaline transporter (*Homo sapiens*) | 31.1 | 54.2 | 523 |
| Nucleosides, punnes & pyrimidines | | | | | | |
| HI1069 | 1151815 | 1151024 | ribonucleotide transport ATP-binding protein (ridI) (*Mycobacterium leprae*) | 42.2 | 61.5 | 244 |
| HI1230 | 1296319 | 1295078 | uracil permease (uraA) (*Escherichia coli*) | 37.2 | 61.8 | 400 |
| Anions | | | | | | |
| HI1104 | 1164213 | 1165028 | cysteine synthetase (cysZ) (*Escherichia coli*) | 53.7 | 75.3 | 190 |
| HI1697 | 1761825 | 1760773 | hydrophilic membrane-bound protein (modC) (*Escherichia coli*) | 55.9 | 74.5 | 263 |
| HI1698 | 1762501 | 1761815 | hydrophobic membrane-bound protein (modB) (*Escherichia coli*) | 65.9 | 84.8 | 223 |

-continued

| | | | | | | |
|---|---|---|---|---|---|---|
| HI1384 | 1477430 | 1476585 | integral membrane protein (petA) (*Escherichia coli*) | 59.5 | 77.8 | 272 |
| HI0358 | 380045 | 380764 | nitrate transporter ATPase component (nasD) (*Klebsiella pneumoniae*) | 34.9 | 57.8 | 254 |
| HI1383 | 1475710 | 1476584 | peripheral membrane protein B (pslB) (*Escherichia coli*) | 77.0 | 85.8 | 256 |
| HI1385 | 1478379 | 1477435 | peripheral membrane protein C (pslC) (*Escherichia coli*) | 57.3 | 78.7 | 300 |
| HI1386 | 1479246 | 1478473 | periplasmic phosphate-binding protein (pslS) (*Escherichia coli*) | 49.8 | 67.7 | 256 |
| HI1387 | 1479247 | 1479929 | periplasmic phosphate-binding protein (pslS) (*Escherichia coli*) | 63.8 | 75.4 | 69 |
| HI1610 | 1869474 | 1870733 | phosphate permease(YBR295C) (*Saccharodiryces cerevisise*) | 35.6 | 60.0 | 551 |
| Other | | | | | | |
| HI0060 | 62584 | 60804 | ATP dependent translocator homolog (mabA) (*Haemophilus influenzae*) | 100.0 | 100.0 | 458 |
| HI0623 | 653683 | 662010 | ATP-binding protein (abc) (*Escherichia coli*) | 74.0 | 56.5 | 200 |
| HI1625 | 1686470 | 1686186 | cystic fibrosis transmembrane conductance regulator (*Bos laurus*) | 35.3 | 60.8 | 233 |
| HI0855 | 899042 | 900688 | hame-binding lipoprotein (dppA) (*Haemophilus influenzae*) | 98.9 | 99.3 | 547 |
| HI0256 | 295839 | 298353 | hame-hemopexin-binding protein (hxuA) (*Haemophilus influenzae*) | 82.1 | 89.5 | 928 |
| HI1476 | 1556199 | 1555189 | hemin permease (hemU) (*Yersinis enterocolitica*) | 36.1 | 62.7 | 325 |
| HI0264 | 291684 | 293862 | hemin receptor precursor (hemR) (*Yersinis enterocolitica*) | 28.5 | 45.9 | 678 |
| HI1712 | 1779487 | 1777481 | high-affinity choline transport protein (betT) (*Escherichia coli*) | 34.7 | 61.6 | 653 |
| HI0663 | 705327 | 703054 | lactolerrin binding protein (lbpA) (*Neissena meningitidis*) | 30.2 | 47.9 | 763 |
| HI0610 | 637954 | 639336 | Na+/sulfate cotransporter (*Rattus norvegicus*) | 34.4 | 57.8 | 562 |
| HI0977 | 1032420 | 1033671 | pantothenate permease (panF) (*Escherichia coli*) | 60.2 | 77.9 | 478 |
| HI0714 | 780739 | 757488 | transferrin binding protein 1 precursor (tbp1) (*Neissena menigitidis*) | 29.9 | 48.6 | 894 |
| HI0996 | 1059604 | 1056869 | transferrin binding protein 1 precursor (tbp1) (*Neissena menigitidis*) | 51.2 | 69.5 | 865 |
| HI1220 | 1286725 | 1283987 | transferrin binding protein 1 precursor (tbp1) (*Neissena menigitidis*) | 28.4 | 46.8 | 902 |
| HI0997 | 1061509 | 1059635 | transferrin binding protein 2 precursor (tbp2) (*Neissena menigitidis*) | 39.9 | 54.7 | 692 |
| HI0975 | 1029676 | 1030542 | transferrin-binding protein (tfbA) (*Actinobacillus pleuropneumoniae*) | 28.9 | 48.0 | 578 |
| HI1571 | 1633105 | 1633993 | transferrin-binding protein 1 (tbp1) (*Neissena menigitidis*) | 41.3 | 59.5 | 727 |
| HI0637 | 678956 | 674098 | transferrin-binding protein 1 (tbp2) (*Neissena gonorrhosae*) | 31.6 | 51.7 | 828 |
| HI0665 | 706622 | 708309 | transport ATP-binding protein (cydD) (*Escherichia coli*) | 26.4 | 54.0 | 561 |
| HI1160 | 1226897 | 1225140 | transport ATP-binding protein (cydD) (*Escherichia coli*) | 50.7 | 73.5 | 588 |
| Cellular processes | | | | | | |
| Chaperones | | | | | | |
| HI0544 | 565037 | 565324 | chaperonin (groES) (mop-B) (*Escherichia coli*) | 87.5 | 94.8 | 96 |
| HI0545 | 565360 | 566993 | heat shock protein (groEL) (mopA) (*Haemophilus ducreyi*) | 89.8 | 94.9 | 547 |
| HI1241 | 1310497 | 1311678 | heat shock protein (dnaJ) (*Escherichia coli*) | 68.0 | 82.5 | 376 |
| HI0104 | 111572 | 109680 | heat shock protein C62.5 (htpG) (*Escherichia coli*) | 75.4 | 88.3 | 621 |
| HI0375 | 396463 | 394607 | hac66 protein (hsc68) (*Escherichia coli*) | 69.2 | 82.0 | 616 |
| HI1210 | 1308539 | 1310443 | hsp70 protein (dnaK) (*Escherichia coli*) | 78.5 | 88.2 | 638 |
| Cell division | | | | | | |
| HI0771 | 831200 | 831853 | cell division ATP-binding protein (ttsE) (*Escherichia coli*) | 64.1 | 78.3 | 216 |
| HI1211 | 1275245 | 1274358 | cell division inhibitor (sulA) (*Vibno cholerae*) | 33.9 | 55.7 | 116 |
| HI1145 | 1210058 | 1211332 | cell division protein (ftsA) (*Escherichia coli*) | 52.8 | 74.2 | 420 |
| HI1338 | 1410017 | 1412129 | cell division protein (ftsH) (*Escherichia coli*) | 75.2 | 87.8 | 624 |
| HI1470 | 1549516 | 1548374 | cell division protein (ftsH) (*Escherichia coli*) | 77.8 | 88.3 | 369 |
| HI1337 | 1409390 | 1410016 | cell division protein (ftsJ) (*Escherichia coli*) | 81.7 | 90.4 | 208 |
| HI1134 | 1196901 | 1197221 | cell division protein (ftsL) (*Escherichia coli*) | 36.6 | 60.4 | 101 |
| HI1144 | 1209275 | 1210036 | cell division protein (ftsO) (*Escherichia coli*) | 40.6 | 56.5 | 231 |
| HI1140 | 1204467 | 1205646 | cell division protein (ftsW) (*Escherichia coli*) | 52.3 | 74.9 | 374 |
| HI0770 | 829937 | 831178 | cell division protein (ftsY) (*Escherichia coli*) | 66.0 | 81.1 | 497 |
| HI1146 | 1211419 | 1212681 | cell division protein (ftsZ) (*Escherichia coli*) | 67.2 | 83.1 | 306 |
| HI1377 | 1465224 | 1469780 | cell division protein (multB) (*Escherichia coli*) | 61.4 | 77.3 | 1455 |
| HI1356 | 1429903 | 1431375 | cytoplasmic axial filament protein (cafA) (*Escherichia coli*) | 71.0 | 86.3 | 488 |
| HI0772 | 831866 | 832795 | ftsX protein (ftsX) (*Escherichia coli*) | 43.5 | 69.9 | 292 |
| HI1067 | 1128811 | 1129221 | muliB suppressor protein (smbA) (*Escherichia coli*) | 77.4 | 90.2 | 235 |
| HI1135 | 1197237 | 1199067 | penicillin-binding protein 3 (ltsl) (*Escherichia coli*) | 52.8 | 70.7 | 564 |
| Protein, peptide secretion | | | | | | |
| HI0016 | 17278 | 15485 | GTP-binding membrane protein (lapA) (*Escherichia coli*) | 85.6 | 91.0 | 597 |
| HI1472 | 1551915 | 1553681 | colicin V secretion ATP-binding protein (cvsV) (*Escherichia coli*) | 29.9 | 56.0 | 373 |
| HI1008 | 1070885 | 1071397 | lipoprotein signal peptidase (lspA) (*Escherichia coli*) | 51.3 | 71.5 | 158 |
| HI1648 | 1706947 | 1707753 | peptide transport system ATP-binding protein SAPF (sapF) (*Escherichia coli*) | 49.8 | 70.8 | 264 |
| HI0718 | 764525 | 764842 | preprotein translocase (secE) (*Escherichia coli*) | 40.6 | 62.3 | 106 |
| HI0800 | 848348 | 849760 | preprotein translocase SECY subunit (secY) (*Escherichia coli*) | 74.7 | 86.9 | 443 |
| HI0241 | 269734 | 267887 | protein-export membrane protein (secD) (*Escherichia coli*) | 59.6 | 77.3 | 615 |
| HI0240 | 267876 | 266902 | protein-export membrane protein (secF) (*Escherichia coli*) | 48.0 | 73.0 | 302 |
| HI0447 | 466800 | 467135 | protein-export membrane protein (secG) (*Escherichia coli*) | 58.9 | 81.3 | 110 |
| HI0745 | 801965 | 801459 | protein-export protein (secB) (*Escherichia coli*) | 56.2 | 80.8 | 145 |
| HI0911 | 961135 | 963837 | secA protein (secA) (*Escherichia coli*) | 68.0 | 81.7 | 896 |
| HI0015 | 15473 | 14427 | signal peptidase I (lepB) (*Escherichia coli*) | 46.3 | 65.1 | 319 |
| HI0106 | 114073 | 112688 | signal recognition particle protein (54 homolog) (lth) (*Escherichia coli*) | 79.9 | 90.9 | 452 |
| HI0715 | 781040 | 762335 | trigger factor (tig) (*Escherichia coli*) | 64.4 | 80.3 | 432 |
| HI0298 | 330445 | 329756 | type 4 prepilin-like protein specific leader peptidase (hopD) (*Escherichia coli*) | 27.2 | 49.0 | 208 |
| HI0299 | 331681 | 330445 | xcpS protein (xcpS) (*Pseudomonas putide*) | 29.2 | 56.7 | 396 |
| Detoxification | | | | | | |
| HI0830 | 985290 | 986813 | KW20 catalase (hlrtE) (*Haemophilus influenzae*) | 99.2 | 99.4 | 506 |

-continued

| ID | Start | End | Description | % | % | Len |
|---|---|---|---|---|---|---|
| HI1090 | 1152892 | 1152248 | superoxide dierrulase (sodA) (*Haemophilus influenzae*) | 99.0 | 99.5 | 209 |
| HI1004 | 1065726 | 1057108 | thiophene and furan oxidation protein (thdF) (*Escherichia coli*) | 73.8 | 85.4 | 451 |

Cell killing

| ID | Start | End | Description | % | % | Len |
|---|---|---|---|---|---|---|
| HI0303 | 334601 | 335697 | hemolysin (SyC) (*Serpulina hyodysentenae*) | 36.9 | 57.5 | 252 |
| HI1664 | 1723070 | 1723648 | hemolysin, 21 kDa (hly) (*Actinobacillus pleuropneumonise*) | 54.5 | 72.4 | 156 |
| HI1376 | 1464493 | 1465221 | killing protein (lucA) (*Escherichia coli*) | 69.0 | 83.6 | 222 |
| HI1375 | 1463019 | 1464443 | killing protein suppressor (lucB) (*Escherichia coli*) | 66.9 | 83.0 | 440 |
| HI1053 | 1116898 | 1115057 | leukotosun secretion ATP-binding protein (tktB) (*Actinobacillus actinomycetemcornitans*) | 34.2 | 55.1 | 512 |

Transformation

| ID | Start | End | Description | % | % | Len |
|---|---|---|---|---|---|---|
| HI0436 | 456360 | 455674 | corn101A protein (cornF) (*Haemophilus influenzae*) | 100.0 | 100.0 | 229 |
| HI1010 | 1072519 | 1072854 | competence locus E (cornE1) (*Bacillus subtilis*) | 46.7 | 70.0 | 59 |
| HI0603 | 622277 | 622927 | tfoX protein (tfxO) (*Haemophilus influenzae*) | 99.5 | 99.5 | 217 |
| HI0443 | 462729 | 463571 | transformation gene cluster hypothetical protein (GB:M62809_1) (corn) (*Haemophilus influenzae*) | 100.0 | 100.0 | 281 |
| HI0435 | 455595 | 455002 | transformation gene cluster hypothetical protein (GB:M62809_10) (corn) (*Haemophilus influenzae*) | 99.5 | 99.5 | 198 |
| HI0442 | 460047 | 462638 | transformation gene cluster hypothetical protein (GB:M62809_2) (corn) (*Haemophilus influenzae*) | 100.0 | 100.0 | 864 |
| HI0441 | 460047 | 462638 | transformation gene cluster hypothetical protein (GB:M62809_3) (corn) (*Haemophilus influenzae*) | 100.0 | 100.0 | 265 |
| HI0440 | 459150 | 458647 | transformation gene cluster hypothetical protein (GB:M62809_4) (corn) (*Haemophilus influenzae*) | 100.0 | 100.0 | 168 |
| HI0439 | 456647 | 458129 | transformation gene cluster hypothetical protein (GB:M62809_5) (corn) (*Haemophilus influenzae*) | 100.0 | 100.0 | 173 |
| HI0438 | 458129 | 457719 | transformation gene cluster hypothetical protein (GB:M62809_6) (corn) (*Haemophilus influenzae*) | 100.0 | 100.0 | 137 |
| HI0437 | 457706 | 458365 | transformation gene cluster hypothetical protein (GB:M62809_7) (corn) (*Haemophilus influenzae*) | 99.8 | 99.8 | 441 |

Other categories

Colicin-related functions

| ID | Start | End | Description | % | % | Len |
|---|---|---|---|---|---|---|
| HI0384 | 403297 | 402017 | colicin tolerance protein (tolB) (*Escherichia coli*) | 83.9 | 78.1 | 409 |
| HI1209 | 1272281 | 1272769 | colicin V productin protein (pur regulon) (cvpA) (*Escherichia coli*) | 84.7 | 79.5 | 158 |
| HI0387 | 405650 | 4004967 | inner membrane protein (tolO) (*Escherichia coli*) | 68.8 | 83.3 | 221 |
| HI0386 | 404892 | 404476 | inner membrane protein (tolR) (*Escherichia coli*) | 61.8 | 78.7 | 138 |
| HI0385 | 404457 | 403342 | outer membrane integrity protein (tolA) (*Escherichia coli*) | 42.6 | 57.1 | 406 |
| HI1681 | 1753823 | 1756079 | outer membrane integrity protein (tolA) (*Escherichia coli*) | 26.9 | 47.7 | 345 |

Phage-related functions and prophages

| ID | Start | End | Description | % | % | Len |
|---|---|---|---|---|---|---|
| HI1483 | 1566955 | 1567509 | E16 protein (muE16) (*Bacteriophage mu*) | 28.5 | 52.8 | 143 |
| HI1508 | 1576485 | 1576922 | G protein (muG) (*Bacteriophage mu*) | 38.3 | 52.5 | 147 |
| HI1574 | 1636594 | 1636181 | G protein (muG) (*Bacteriophage mu*) | 33.3 | 54.0 | 138 |
| HI1488 | 1564685 | 1565191 | gam protein (*Bacteriophage mu*) | 57.1 | 73.8 | 188 |
| HI0071 | 78159 | 78860 | heat shock protein B253 (grpE) (*Escherichia coli*) | 45.9 | 86.5 | 193 |
| HI0413 | 432108 | 431836 | host factor-1 (HF-1) (hfq) (*Escherichia coli*) | 90.5 | 97.3 | 74 |
| HI1509 | 1577156 | 1575220 | I protein (mul) (*Bacteriophage mu*) | 50.0 | 55.4 | 58 |
| HI1485 | 1563429 | 1564289 | MuB protein (muB) (*Bacteriophage mu*) | 48.4 | 70.4 | 277 |
| HI1521 | 1584995 | 1586385 | N protein (muN) (*Bacteriophage mu*) | 31.5 | 52.1 | 452 |
| HI1522 | 1586368 | 1587105 | P protein (*Bacteriophage mu*) | 39.5 | 37.3 | 220 |
| HI1418 | 1505940 | 1505428 | terminase subunit 1 (Bacteriophage SF6) | 32.3 | 52.3 | 128 |
| HI1483 | 1560600 | 1562660 | transposase A (muA) (*Bacteriophage mu*) | 40.8 | 50.1 | 596 |

Transposon-related functions

| ID | Start | End | Description | % | % | Len |
|---|---|---|---|---|---|---|
| HI1106 | 1168078 | 1166803 | insertion sequence IS1016(V-4) hypothetical protein (G8:X58176_2) (*Haemophilus influenzae*) | 43.6 | 56.7 | 39 |
| HI1020 | 1081916 | 1081346 | IS1016-V6 protein (IS1016-V6) (*Haemophilus influenzae*) | 91.7 | 93.8 | 191 |
| HI1332 | 1408795 | 1406150 | IS1016-V6 protein (IS1016-V6) (*Haemophilus influenzae*) | 54.7 | 74.7 | 170 |
| HI1583 | 1645515 | 1645991 | IS1016-V6 protein (IS1016-V6) (*Haemophilus influenzae*) | 45.4 | 61.2 | 153 |

Drug/analog sensitivity

| ID | Start | End | Description | % | % | Len |
|---|---|---|---|---|---|---|
| HI0697 | 947919 | 951014 | acriflavine resistance protein (acrB) (*Escherichia coli*) | 32.7 | 55.0 | 1027 |
| HI0302 | 333614 | 334165 | ampD signalling protein (ampD) (*Escherichia coli*) | 56.1 | 75.1 | 172 |
| HI1245 | 1315822 | 1314629 | bicyclomycin resistance protein (bcr) (*Escherichia coli*) | 42.6 | 68.7 | 383 |
| HI1629 | 1688581 | 1689111 | mercury resistance regulatory protein (merR2) (*Thiobacillus ferrooxidans*) | 37.7 | 57.5 | 105 |
| HI0650 | 692523 | 691900 | modulator of drug activity (mda66) (*Escherichia coli*) | 58.1 | 75.4 | 191 |
| HI0699 | 953570 | 952041 | multidrug resistance protein (amrB) (*Escherichia coli*) | 67.7 | 84.8 | 499 |
| HI0900 | 954752 | 953583 | multidrug resistance protein (amrA) (*Escherichia coli*) | 46.5 | 66.3 | 389 |
| HI0036 | 37441 | 39472 | multidrug resistance protein (md1) (*Escherichia coli*) | 29.0 | 51.2 | 1094 |
| HI1467 | 1543471 | 1544832 | nodulation protein T (nodT) (*Rhizobium leguminosarum*) | 20.1 | 46.3 | 390 |
| HI0551 | 569189 | 570049 | rRNA (adenosine-N6,N6-)-dimethyltransferase (ksgA) (*Escherichia coli*) | 69.3 | 81.5 | 269 |
| HI0513 | 527345 | 526362 | tellurrie resistance protein (tehA) (*Escherichia coli*) | 38.9 | 62.0 | 317 |
| HI1278 | 1351140 | 1350283 | tellurrie resistance protein (tehB) (*Escherichia coli*) | 55.2 | 70.6 | 194 |

Radiation sensitivity

| ID | Start | End | Description | % | % | Len |
|---|---|---|---|---|---|---|
| HI0954 | 1011412 | 1010711 | radC protein (radC) (*Escherichia coli*) | 49.8 | 71.7 | 219 |

-continued

Adaptations, atypical conditions

| | | | | | | |
|---|---|---|---|---|---|---|
| HI1532 | 1596570 | 1595143 | autotrophic growth protein (aut) (*Alcaligenes autrophus*) | 45.0 | 50.9 | 154 |
| HI0722 | 766921 | 767769 | heat shock protein (htpX) (*Escherichia coli*) | 66.3 | 82.1 | 288 |
| HI1533 | 1596655 | 1597599 | heat shock protein B (ibpB) (*Escherichia coli*) | 55.9 | 71.2 | 304 |
| HI0947 | 1003887 | 1004906 | htrA-like protein (htrA) (*Escherichia coli*) | 55.2 | 72.6 | 262 |
| HI0903 | 956705 | 957292 | invasion protein (invA) (*Bartonella bacilliformis*) 39.5 | | 60.5 | 187 |
| HI1550 | 1615090 | 1614485 | NAD(P)H:menadione oxidoreductase (*Nus musculus*) | 35.9 | 54.9 | 200 |
| HI0460 | 479443 | 478505 | survival protein (surA) (*Escherichia coli*) | 33.0 | 58.5 | 424 |
| HI0617 | 866160 | 865738 | uspA protein (uspA) (*Escherichia coli*) | 68.6 | 87.1 | 140 |
| HI0323 | 350541 | 350774 | virulence plasmid protein (vagC) (*Salmonella dublin*) | 35.9 | 57.8 | 62 |
| HI1254 | 1326770 | 1327090 | virulence associated protein A (vapA) (*Dichelobacter nodosus*) | 40.8 | 57.7 | 71 |
| HI0324 | 350774 | 351175 | virulence associated protein C (vapC) (*Dichelobacter nodosus*) | 35.4 | 56.9 | 128 |
| HI0949 | 1007984 | 1007589 | virulence associated protein C (vapC) (*Dichelobacter nodosus*) | 40.9 | 60.6 | 131 |
| HI0452 | 472751 | 472479 | virulence associated protein D (vapD) (*Dichelobacter nodosus*) | 40.7 | 67.0 | 91 |
| HI1310 | 1385051 | 1385680 | virulence plasmid protein (migA) (*Shewanella colwalliana*) | 23.8 | 56.3 | 124 |

Undetermined

| | | | | | | |
|---|---|---|---|---|---|---|
| HI1164 | 1230321 | 1229906 | 15 kDs protein (P15) (*Escherichia coli*) | 49.3 | 68.4 | 136 |
| HI0085 | 89585 | 88593 | 2-hydroxyaciddehydrogenases homolog (ddh) (*Zymomorias mobilis*) | 51.5 | 72.8 | 324 |
| HI0462 | 480185 | 480973 | beta-lactamase regulatory homolog (mazG) (*Escherichia coli*) | 48.3 | 72.6 | 257 |
| HI1576 | 1738223 | 1737753 | conjugative transfer co-repressor (tinO) (*Escherichia coli*) | 32.5 | 51.9 | 76 |
| HI0309 | 340851 | 340591 | delta-I-pyrroline-5-carboxylate reductase (proC) (*Pseudomonas aeruginosa*) | 44.0 | 60.1 | 267 |
| HI1555 | 1620490 | 1619810 | devA protein (devA) (*Anabaena* sp.) | 42.7 | 66.4 | 219 |
| HI0558 | 576002 | 575514 | devB protein (devB) (*Anabaena* sp.) | 32.7 | 51.5 | 156 |
| HI1342 | 1415087 | 1415473 | embryonic abundant protein, group 3 (*Triticum aestivum*) | 33.3 | 50.0 | 102 |
| HI0939 | 996457 | 996658 | extragenic supressor (suhB) (*Escherichia coli*) | 64.7 | 80.2 | 258 |
| HI0370 | 390960 | 392063 | GCPE protein (protein E) (ppcE) (*Escherichia coli*) | 88.2 | 93.9 | 362 |
| HI0095 | 102616 | 101864 | GerC2 protein (gerC2) (*Bacillus subtilis*) | 32.9 | 55.2 | 191 |
| HI0689 | 712892 | 711894 | glpX protein (glpX) (*Escherichia coli*) | 69.2 | 83.4 | 325 |
| HI1015 | 1076616 | 1077389 | glyoxylate-induced protein (*Escherichia coli*) | 39.1 | 57.8 | 258 |
| HI0499 | 511702 | 513099 | halU protein (halU) (*Escherichia coli*) | 80.4 | 90.1 | 443 |
| HI0498 | 511230 | 511754 | halV protein (halV) (*Escherichia coli*) | 79.8 | 89.0 | 172 |
| HI1120 | 1184041 | 1182516 | ilv-related protein (*Escherichia coli*) | 59.7 | 77.0 | 504 |
| HI0287 | 319073 | 317784 | isochorismate synthase (entC) (*Bacillus subtilis*) | 31.5 | 48.9 | 311 |
| HI1624 | 1666217 | 1665567 | membrane associated ATPase (cbrO) (*Propionibacterium freudenreichi*) | 33.7 | 52.7 | 184 |
| HI0463 | 481901 | 481029 | membrane protein (lapB) (*Pasteurella haemolytica*) | 34.2 | 556.0 | 221 |
| HI1122 | 1184867 | 1185742 | membrane protein (lapB) (*Pasteurella haemolytica*) | 63.1 | 80.2 | 216 |
| HI0590 | 608642 | 609874 | N-carbamyl-L-amino acid amidohydrolase (*Bacillus stearothemophilus*) | 35.9 | 59.2 | 406 |
| HI0380 | 399796 | 398579 | nitrogen fixation protein (nifS) (*Anabaena* sp.) | 48.2 | 67.0 | 679 |
| HI1296 | 1375045 | 1373735 | nitrogen fixation protein (nifS) (*Mycobacterium leprae*) | 33.4 | 56.2 | 402 |
| HI1346 | 1418236 | 1417523 | nitrogen fixation protein (nifS) (*Mycobacterium leprae*) | 36.8 | 58.5 | 186 |
| HI0379 | 398591 | 398139 | nitrogen fixation protein (nifU) (*Klebsiella pneumoniae*) | 50.8 | 74.2 | 122 |
| HI0167 | 180354 | 181565 | nitrogen fixation protein (rnfE) (*Rhodobacter capsulatus*) | 30.1 | 47.9 | 292 |
| HI1692 | 1756087 | 1757180 | nitrogen fixation protein (rnfE) (*Rhodobacter capsulatus*) | 32.7 | 59.5 | 290 |
| HI0129 | 143015 | 144800 | nitrogenase C (nitC) (*Clostridium pasteunanum*) | 27.1 | 52.6 | 248 |
| HI1480 | 1559124 | 1558768 | nitrogenase C (nitC) (*Clostridium pasteunanum*) | 40.9 | 60.2 | 92 |
| HI0359 | 381523 | 382464 | nmtl protein (nmtl) (*Aspergileus parasiticus*) | 25.6 | 54.7 | 289 |
| HI1299 | 1375415 | 1374882 | partitioning system protein (parB) (Plasmid RP4) | 43.6 | 67.7 | 141 |
| HI0224 | 252941 | 252168 | rarD protein (rarD) (*Escherichia coli*) | 26.5 | 53.0 | 230 |
| HI0682 | 721733 | 720840 | rarD protein (rarD) (*Escherichia coli*) | 27.1 | 55.0 | 289 |
| HI0918 | 970839 | 970249 | skp protein (skp) (*Pasteurella multocida*) | 55.5 | 76.4 | 191 |
| HI0983 | 1038375 | 1037593 | small protein (ampB) (*Escherichia coli*) | 78.8 | 91.3 | 180 |
| HI1598 | 1661488 | 1659882 | spolllE protein (spolllE) (*Coxiella burneta*) | 56.1 | 74.5 | 504 |
| HI0898 | 951407 | 952018 | suppressor protein (msgA) (*Escherichia coli*) | 30.2 | 56.1 | 254 |
| HI1080 | 1145382 | 1144612 | surfactin (afpo) (*Bacillus subtilis*) | 58.2 | 77.9 | 246 |
| HI0753 | 811790 | 811296 | toxR regulon (tagD) (*Vibrio cholerae*) | 45.7 | 64.0 | 164 |
| HI1412 | 1502860 | 1501311 | traN protein (traN) (Plasmid RP4) | 40.2 | 61.5 | 233 |
| HI0658 | 708305 | 708960 | transport ATP-binding protein (cydC) (*Escherichia coli*) | 26.3 | 51.7 | 536 |
| HI1159 | 1225137 | 1223410 | transport ATP-binding protein (cydC) (*Escherichia coli*) | 48.5 | 70.1 | 568 |
| HI1582 | 1627239 | 1626295 | vanH protein (vanH) (Transposon Tn1546) | 39.7 | 57.1 | 251 |
| HI0632 | 668489 | 669433 | mucoid status locus protein (mucB) (*Pseudomonas aeruginosa*) | 25.4 | 51.8 | 309 |
| HI0172 | 183553 | 184785 | phenolhydroxylase (ORF6) (*Acinetobacter calcoacaticus*) | 33.0 | 56.9 | 313 |
| HI1390 | 1481177 | 1481266 | plasma protease C1 inhibitor (*Homo sapiens*) | 75.0 | 79.2 | 23 |

KNOWN.before

| | |
|---|---|
| HI0060 | ATP dependent translocator homolog (msbA) |
| HI0140 | outer membrane protein P2 (ompP2) |
| HI0251 | single-stranded DNA binding protein (sab) |
| HI0252 | tonB protein (tonB) |
| HI0266 | heme-hemopexin-binding protein (hxuA) |
| HI0351 | adenylate kinase (ATP-AMP transphosphorylase) (ack) |
| HI0352 | hypothetical protein (SP:P24326) |

KNOWN.before -continued

| | |
|---|---|
| HI0353 | udp-glucose 4-epimerase (galactowaldenase) (galE) |
| HI0354 | hypothetical protein (SP:P24324) |
| HI0383 | PC protein (15kd peptidoglycan-associated outer membrane lipoprotein) (pal) |
| HI0403 | outer membrane protein P1 (ompP1) |
| HI0435 | transformation gene cluster hypothetical protein (GB:M62809_10) (com) |
| HI0436 | com 101A protein (comF) |
| HI0437 | transformation gene cluster hypothetical protein (GB:M62809_7) (com) |
| HI0438 | transformation gene cluster hypothetical protein (GB:M62809_6) (com) |
| HI0439 | transformation gene cluster hypothetical protein (GB:M62809_5) (com) |
| HI0440 | transformation gene cluster hypothetical protein (GB:M62809_4) (com) |
| HI0441 | transformation gene cluster hypothetical protein (GB:M62809_3) (com) |
| HI0442 | transformation gene cluster hypothetical protein (GB:M62809_2) (com) |
| HI0443 | transformation gene cluster hypothetical protein (GB:M62809_1) (com) |
| HI0514 | HincII endonuclease (HincII) |
| HI0515 | modification methlyase HincII (hincIIM) |
| HI0552 | lipooligsaccharide biosynthesis protein |
| HI0583 | streptomycin resistance protein (strA) |
| HI0602 | recombinase (recA) |
| HI0603 | tfoX protein (tfoX) |
| HI0606 | adenylate cyclase (cysA) |
| HI0622 | 28 kDa membrane protein (hlpA) |
| HI0691 | protein D (hpd) |
| HI0695 | lipoprotein (hel) |
| HI0820 | aldose 1-epimerase precursor (mutarotase) (mro) |
| HI0821 | galactokinase (galK) |
| HI0822 | galactose-1-phosphate uridylytransferase (galT) |
| HI0823 | galactose operon repressor (galS) |
| HI0847 | hypothetical protein (GB:M94205_1) |
| HI0848 | disulfide oxidoreductase (por) |
| HI0855 | heme-binding lipoprotein (dppA) |
| HI0919 | protective surface antigen D15 |
| HI0930 | KW20 catalase (hktE) |
| HI0959 | cyclic AMP receptor protein (crp) |
| HI1090 | superoxide dismutase (sodA) |
| HI1167 | outer membrane protein P5 (ompA) |
| HI1191 | DNA helicase II (uvrD) |
| HI1397 | HindIII modification methyltransferase (hindIIIM) |
| HI1398 | HindIII restriction endonuclease (hindIIIR) |
| HI1402 | DNA polymerase III, chi subunit (holC) |
| HI1545 | lic-1 operon protein (licC) |
| HI1548 | lic-1 operon protein (licD) |
| HI1585 | 15 kd peptidoglycan-associated lipoprotein (lpp) |
| HI1594 | formyltetrahydrofolate hydrolase (purU) |
| HI1595 | enolpyruvylshikimatephosphatesynthase (aroA) |
| HI1699 | lag locus hypothetical protein (GB:M94855_8) |
| HI1700 | lag locus hypothetical protein (GB:M94855_7) |
| HI1701 | lag locus hypothetical protein (GB:M94855_6) |
| HI1702 | lag locus hypothetical protein (GB:M94855_5) |
| HI1703 | lag locus hypothetical protein (GB:M94855_4) |
| HI1704 | lag locus hypothetical protein (GB:M94855_3) |
| HI1705 | lag locus hypothetical protein (GB:M94855_2) |
| HI1706 | lag locus hypothetical protein (GB:M94855_1) |

UNKNOWNS

| | | |
|---|---|---|
| HI0003 | 3249 | 2464 |
| HI0004 | 3729 | 3268 |
| HI0012 | 11778 | 12767 |
| HI0017 | 17829 | 17449 |
| HI0019 | 20239 | 18819 |
| HI0021 | 23349 | 22102 |
| HI0028 | 29582 | 29307 |
| HI0033 | 35298 | 34834 |
| HI0034 | 35660 | 35355 |
| HI0035 | 37440 | 35788 |
| HI0040 | 43059 | 42286 |
| HI0042 | 44594 | 43923 |
| HI0043 | 45858 | 44597 |
| HI0044 | 46386 | 45721 |
| HI0045 | 47261 | 46710 |
| HI0046 | 47328 | 47687 |
| HI0050 | 51426 | 50224 |
| HI0051 | 51998 | 51504 |
| HI0052 | 53023 | 52040 |
| HI0053 | 54078 | 53053 |
| HI0056 | 56966 | 56256 |
| HI0059 | 60728 | 59733 |
| HI0065 | 67839 | 68312 |
| HI0072 | 78167 | 77313 |
| HI0073 | 79220 | 78879 |
| HI0074 | 79653 | 79216 |
| HI0077 | 83046 | 83909 |
| HI0080 | 85983 | 86411 |
| HI0081 | 86556 | 87341 |
| HI0082 | 87601 | 87864 |
| HI0083 | 87882 | 88094 |
| HI0090 | 96604 | 97314 |

-continued

| UNKNOWNS | | |
|---|---|---|
| HI0091 | 96493 | 97360 |
| HI0092 | 99761 | 98505 |
| HI0093 | 100989 | 99886 |
| HI0094 | 101511 | 101194 |
| HI0096 | 102950 | 103522 |
| HI0100 | 107807 | 107415 |
| HI0101 | 108091 | 107654 |
| HI0103 | 109598 | 109257 |
| HI0105 | 111789 | 112625 |
| HI0107 | 114405 | 115612 |
| HI0108 | 115744 | 116634 |
| HI0109 | 117067 | 116729 |
| HI0112 | 119485 | 119847 |
| HI0114 | 122424 | 122311 |
| HI0115 | 128606 | 130242 |
| HI0116 | 130860 | 130246 |
| HI0117 | 131552 | 131800 |
| HI0120 | 134883 | 134380 |
| HI0121 | 138357 | 134999 |
| HI0125 | 140096 | 141409 |
| HI0126 | 142556 | 141573 |
| HI0127 | 142955 | 143011 |
| HI0128 | 142716 | 142584 |
| HI0130 | 145160 | 144804 |
| HI0131 | 145840 | 145136 |
| HI0134 | 147247 | 148419 |
| HI0135 | 148422 | 149609 |
| HI0136 | 151208 | 149695 |
| HI0144 | 159021 | 158125 |
| HI0146 | 160156 | 159932 |
| HI0147 | 160966 | 161952 |
| HI0148 | 161966 | 163664 |
| HI0149 | 164031 | 165167 |
| HI0150 | 165574 | 165762 |
| HI0153 | 168744 | 168040 |
| HI0160 | 174988 | 174467 |
| HI0163 | 178311 | 177715 |
| HI0165 | 179007 | 180080 |
| HI0166 | 180130 | 180348 |
| HI0168 | 181582 | 182313 |
| HI0169 | 182316 | 182567 |
| HI0I70 | 182570 | 182938 |
| HI0I71 | 182945 | 183537 |
| HI0173 | 184932 | 185969 |
| HI0174 | 185975 | 186232 |
| HI0175 | 186247 | 187500 |
| HI0176 | 188281 | 187550 |
| HI0177 | 189257 | 188286 |
| HI0178 | 189385 | 190150 |
| HI0179 | 190715 | 190236 |
| HI0183 | 195295 | 196233 |
| HI0184 | 196413 | 197855 |
| HI0185 | 198872 | 198048 |
| HI0188 | 200705 | 201555 |
| HI0189 | 201568 | 202335 |
| HI0196 | 208646 | 206611 |
| HI0199 | 213460 | 214224 |
| HI0204 | 218138 | 217605 |
| HI0206 | 218715 | 219485 |
| HI0211 | 225095 | 225199 |
| HI0218 | 234170 | 234697 |
| HI0220 | 238722 | 238084 |
| HI0228 | 256953 | 256489 |
| HI0229 | 257403 | 257032 |
| HI0231 | 259913 | 260654 |
| HI0233 | 262997 | 264382 |
| HI0234 | 264390 | 264539 |
| HI0235 | 264822 | 264679 |
| HI0236 | 265239 | 265033 |
| HI0238 | 265736 | 266389 |
| HI0239 | 266350 | 266781 |
| HI0243 | 270426 | 270208 |
| HI0244 | 270941 | 270426 |
| HI0247 | 274159 | 273716 |
| HI0257 | 285979 | 286623 |
| HI0258 | 286796 | 286879 |
| HI0259 | 286880 | 288054 |

-continued

| UNKNOWNS | | |
|---|---|---|
| HI0260 | 288240 | 288058 |
| HI0261 | 288839 | 288180 |
| HI0262 | 289503 | 288919 |
| HI0267 | 298808 | 298450 |
| HI0268 | 298891 | 299487 |
| HI0272 | 304213 | 303284 |
| HI0273 | 305079 | 304216 |
| HI0277 | 309032 | 310684 |
| HI0278 | 311516 | 310710 |
| HI0279 | 311998 | 311516 |
| HI0280 | 312417 | 312004 |
| HI0281 | 312664 | 312371 |
| HI0283 | 315199 | 312886 |
| HI0284 | 315200 | 316061 |
| HI0286 | 318836 | 319252 |
| HI0293 | 327115 | 326912 |
| HI0295 | 327473 | 327856 |
| HI0301 | 333498 | 333052 |
| HI0305 | 337302 | 338036 |
| HI0306 | 338038 | 338593 |
| HI0307 | 338596 | 339012 |
| HI0308 | 339973 | 339068 |
| HI0310 | 340854 | 342017 |
| HI0312 | 343117 | 343401 |
| HI0313 | 343271 | 343092 |
| HI0317 | 346507 | 345770 |
| HI0318 | 347143 | 346670 |
| HI0320 | 349180 | 349665 |
| HI0321 | 349721 | 350002 |
| HI0322 | 349996 | 350444 |
| HI0325 | 351245 | 351649 |
| HI0327 | 352729 | 354078 |
| HI0328 | 354114 | 354374 |
| HI0329 | 354653 | 354697 |
| HI0331 | 355655 | 356688 |
| HI0335 | 359242 | 360555 |
| HI0338 | 363320 | 363910 |
| HI0340 | 364253 | 365296 |
| HI0342 | 367615 | 368352 |
| HI0343 | 368440 | 368781 |
| HI0344 | 368990 | 369516 |
| HI0345 | 369512 | 369790 |
| HI0346 | 369815 | 372311 |
| HI0347 | 372389 | 373205 |
| HI0348 | 373208 | 374068 |
| HI0349 | 374068 | 374517 |
| HI0352 | 377303 | 376029 |
| HI0354 | 379329 | 376637 |
| HI0355 | 379330 | 380044 |
| HI0357 | 380765 | 381167 |
| HI0358 | 381227 | 381171 |
| HI0361 | 384039 | 383227 |
| HI0365 | 386932 | 387009 |
| HI0366 | 387928 | 387053 |
| HI0367 | 388154 | 389323 |
| HI0368 | 389428 | 389964 |
| HI0369 | 390039 | 390947 |
| HI0372 | 393384 | 393975 |
| HI0373 | 394223 | 394032 |
| HI0376 | 397168 | 396485 |
| HI0377 | 397743 | 397222 |
| HI0378 | 398079 | 397759 |
| HI0381 | 400309 | 399860 |
| HI0382 | 401087 | 400365 |
| HI0388 | 406077 | 405670 |
| HI0390 | 408337 | 409044 |
| HI0391 | 409072 | 409620 |
| HI0393 | 413144 | 412599 |
| HI0394 | 414371 | 413637 |
| HI0395 | 415645 | 414557 |
| HI0397 | 416445 | 416750 |
| HI0398 | 416758 | 417967 |
| HI0400 | 419468 | 420118 |
| HI0402 | 421340 | 421056 |
| HI0406 | 425499 | 424210 |
| HI0407 | 426365 | 425502 |
| HI0414 | 433167 | 432202 |

-continued

| UNKNOWNS | | |
|---|---|---|
| HI0417 | 437163 | 437957 |
| HI0418 | 437953 | 438759 |
| HI0419 | 438773 | 439450 |
| HI0420 | 439396 | 440738 |
| HI0422 | 442434 | 442730 |
| HI0423 | 443077 | 442916 |
| HI0425 | 444797 | 445516 |
| HI0426 | 446607 | 445555 |
| HI0433 | 454103 | 453516 |
| HI0434 | 454932 | 454142 |
| HI0444 | 463691 | 464053 |
| HI0451 | 472389 | 471856 |
| HI0453 | 472951 | 472763 |
| HI0454 | 474321 | 473026 |
| HI0455 | 474896 | 474375 |
| HI0456 | 475705 | 474926 |
| HI0458 | 477453 | 476743 |
| HI0466 | 485905 | 486561 |
| HI0468 | 488712 | 487873 |
| HI0469 | 489585 | 488725 |
| HI0471 | 491037 | 492317 |
| HI0478 | 497647 | 497796 |
| HI0489 | 507333 | 506959 |
| HI0490 | 507449 | 508048 |
| HI0491 | 508051 | 508521 |
| HI0492 | 508274 | 508038 |
| HI0493 | 508854 | 509354 |
| HI0494 | 509815 | 509856 |
| HI0495 | 509856 | 510253 |
| HI0496 | 510797 | 510306 |
| HI0497 | 511011 | 510814 |
| HI0502 | 516228 | 517265 |
| HI0509 | 523382 | 523930 |
| HI0510 | 524561 | 524076 |
| HI0511 | 525540 | 524816 |
| HI0512 | 525587 | 526303 |
| HI0521 | 542216 | 540966 |
| HI0522 | 543103 | 542318 |
| HI0523 | 544656 | 543115 |
| HI0524 | 544869 | 545522 |
| HI0525 | 546551 | 545484 |
| HI0528 | 549859 | 549044 |
| HI0554 | 571956 | 572576 |
| HI0556 | 575147 | 574608 |
| HI0557 | 575547 | 575211 |
| HI0559 | 576210 | 576091 |
| HI0562 | 578540 | 580381 |
| HI0563 | 581038 | 580382 |
| HI0564 | 581352 | 581744 |
| HI0567 | 584110 | 583439 |
| HI0570 | 587757 | 587551 |
| HI0572 | 591096 | 590482 |
| HI0574 | 592124 | 592846 |
| HI0576 | 593256 | 593978 |
| HI0577 | 594070 | 594732 |
| HI0578 | 594735 | 595112 |
| HI0579 | 595480 | 595764 |
| HI0587 | 607340 | 606504 |
| HI0588 | 607798 | 607361 |
| HI0591 | 610092 | 610508 |
| HI0594 | 614632 | 614441 |
| HI0595 | 616566 | 616775 |
| HI0596 | 616702 | 615176 |
| HI0599 | 619155 | 619970 |
| HI0600 | 620322 | 619999 |
| HI0619 | 650498 | 651154 |
| HI0626 | 663588 | 664921 |
| HI0628 | 666387 | 666770 |
| HI0629 | 666863 | 667117 |
| HI0635 | 672600 | 672893 |
| HI0636 | 672899 | 673879 |
| HI0638 | 677932 | 677545 |
| HI0640 | 679087 | 679701 |
| HI0649 | 691619 | 690906 |
| HI0652 | 694996 | 694787 |
| HI0655 | 696806 | 697567 |
| HI0658 | 699494 | 698946 |

-continued

| UNKNOWNS | | |
|---|---|---|
| HI0660 | 701972 | 700059 |
| HI0661 | 702429 | 702136 |
| HI0663 | 702781 | 702425 |
| HI0664 | 706058 | 705867 |
| HI0667 | 711078 | 710050 |
| HI0668 | 711395 | 711078 |
| HI0670 | 713054 | 713269 |
| HI0672 | 713806 | 714236 |
| HI0673 | 715017 | 714544 |
| HI0674 | 715691 | 714544 |
| HI0675 | 715969 | 715694 |
| HI0679 | 719498 | 719061 |
| HI0689 | 731017 | 731928 |
| HI0690 | 732026 | 732334 |
| HI0696 | 737789 | 738508 |
| HI0698 | 743511 | 739619 |
| HI0699 | 744964 | 743524 |
| HI0700 | 745259 | 744239 |
| HI0702 | 746523 | 746065 |
| HI0703 | 746632 | 747648 |
| HI0704 | 747649 | 748418 |
| HI0706 | 749008 | 749188 |
| HI0708 | 749180 | 749148 |
| HI0720 | 765555 | 766304 |
| HI0721 | 766361 | 766750 |
| HI0723 | 768095 | 767817 |
| HI0725 | 768792 | 770060 |
| HI0726 | 776311 | 776868 |
| HI0727 | 776875 | 777312 |
| HI0732 | 786122 | 783778 |
| HI0733 | 786625 | 786245 |
| HI0734 | 786731 | 786582 |
| HI0735 | 787647 | 786715 |
| HI0737 | 788457 | 789167 |
| HI0742 | 799457 | 800908 |
| HI0743 | 801060 | 801386 |
| HI0744 | 801027 | 800965 |
| HI0746 | 802425 | 801982 |
| HI0755 | 816503 | 817618 |
| HI0757 | 819456 | 818531 |
| HI0758 | 820676 | 819447 |
| HI0762 | 823117 | 823388 |
| HI0763 | 823404 | 824474 |
| HIC764 | 825768 | 825091 |
| HI0768 | 829290 | 828811 |
| HI0769 | 829882 | 829304 |
| HI0774 | 835432 | 834092 |
| H10775 | 836100 | 835432 |
| HI0777 | 836970 | 837914 |
| HI0789 | 843493 | 844095 |
| HI0808 | 854572 | 855375 |
| HI0809 | 856603 | 855413 |
| HI0812 | 860092 | 859214 |
| HI0819 | 868114 | 867569 |
| HI0827 | 876702 | 877433 |
| HI0828 | 877442 | 877996 |
| HI0829 | 877999 | 878480 |
| HI0833 | 881059 | 881640 |
| HI0839 | 887221 | 886541 |
| HI0840 | 887844 | 887278 |
| HI0841 | 888779 | 887757 |
| HI0842 | 888896 | 889111 |
| HI0843 | 889116 | 890870 |
| HI0844 | 891071 | 891898 |
| HI0845 | 891925 | 892059 |
| HI0847 | 892866 | 893129 |
| HI0849 | 893822 | 894164 |
| HI0851 | 895374 | 896144 |
| HI0852 | 896141 | 896572 |
| HI0853 | 896977 | 897510 |
| HI0854 | 897510 | 898898 |
| HI0856 | 900867 | 901625 |
| HI0857 | 902112 | 901768 |
| HI0859 | 905088 | 905367 |
| HI0860 | 905688 | 906248 |
| HI0862 | 909728 | 908989 |
| HI0863 | 912130 | 909785 |

-continued

| UNKNOWNS | | |
|---|---|---|
| HI0864 | 912029 | 912325 |
| HI0866 | 915792 | 913945 |
| HI0868 | 918419 | 918538 |
| HI0871 | 920692 | 921248 |
| HI0872 | 921338 | 921439 |
| HI0873 | 922696 | 923613 |
| HI0876 | 927351 | 926155 |
| HI0880 | 931427 | 930509 |
| HI0883 | 932310 | 933296 |
| HI0884 | 933350 | 934084 |
| HI0888 | 938667 | 939088 |
| HI0892 | 943890 | 944319 |
| HI0893 | 944315 | 944518 |
| HI0904 | 957295 | 958086 |
| HI0905 | 957488 | 957174 |
| HI0908 | 959765 | 960283 |
| HI0909 | 960628 | 960317 |
| HI0910 | 960708 | 961007 |
| HI0914 | 966380 | 967141 |
| HI0920 | 974685 | 973357 |
| HI0922 | 976298 | 975582 |
| HI0927 | 983767 | 983405 |
| HI0928 | 984057 | 983800 |
| HI0931 | 988229 | 987051 |
| HI0932 | 988650 | 988233 |
| HI0933 | 989308 | 988826 |
| HI0935 | 991961 | 990760 |
| HI0936 | 993112 | 991961 |
| HI0937 | 993639 | 993112 |
| HI0938 | 995848 | 993642 |
| HI0940 | 996553 | 997110 |
| HI0941 | 997170 | 997883 |
| HI0942 | 997888 | 998566 |
| HI0943 | 998544 | 998846 |
| HI0945 | 1002315 | 1002762 |
| HI0950 | 1008217 | 1007887 |
| HI0957 | 1013248 | 1013899 |
| HI0958 | 1013924 | 1014091 |
| HI0860 | 1016378 | 1015203 |
| HI0861 | 1017426 | 1016374 |
| HI0862 | 1017780 | 1017433 |
| HI0863 | 1018172 | 1017783 |
| HI0865 | 1022036 | 1021104 |
| HI0866 | 1023806 | 1022077 |
| HI0867 | 1023983 | 1024175 |
| HI0868 | 1024843 | 1024944 |
| HI0869 | 1024817 | 1024254 |
| HI0876 | 1030808 | 1031712 |
| HI0878 | 1033994 | 1034883 |
| HI0879 | 1034889 | 1035440 |
| HI0881 | 1036523 | 1037512 |
| HI0886 | 1041067 | 1040252 |
| HI0888 | 1042709 | 1044301 |
| HI0890 | 1045812 | 1047047 |
| HI0898 | 1061807 | 1062044 |
| HI0899 | 1062383 | 1063049 |
| HI1002 | 1063710 | 1063987 |
| HI1003 | 1063970 | 1065592 |
| HI1005 | 1067238 | 1067478 |
| HI1006 | 1067384 | 1069165 |
| HI1007 | 1069256 | 1070812 |
| HI1009 | 1071385 | 1072339 |
| HI1012 | 1073835 | 1074737 |
| HI1013 | 1074743 | 1075961 |
| HI1016 | 1077448 | 1078392 |
| HI1018 | 1079980 | 1080315 |
| HI1021 | 1082175 | 1083170 |
| HI1022 | 1083178 | 1084791 |
| HI1023 | 1084738 | 1085422 |
| HI1026 | 1089488 | 1088792 |
| HI1028 | 1091055 | 1090208 |
| HI1029 | 1091088 | 1092257 |
| HI1030 | 1093581 | 1092598 |
| HI1031 | 1094889 | 1093515 |
| HI1032 | 1095371 | 1094889 |
| HI1033 | 1096441 | 1095446 |
| HI1034 | 1096517 | 1097420 |

-continued

| UNKNOWNS | | |
|---|---|---|
| HI1036 | 1098535 | 1099023 |
| HI1038 | 1100258 | 1100810 |
| HI1039 | 1101878 | 1100997 |
| HI1040 | 1102257 | 1103456 |
| HI1041 | 1103535 | 1103386 |
| HI1045 | 1108332 | 1107835 |
| HI1046 | 1108943 | 1108335 |
| HI1050 | 1113190 | 1114304 |
| HI1055 | 1117964 | 1118322 |
| HI1056 | 1119807 | 1118428 |
| HI1057 | 1121238 | 1119698 |
| HI1058 | 1123210 | 1123287 |
| HI1060 | 1123448 | 1122668 |
| HI1065 | 1127038 | 1126827 |
| HI1066 | 1128454 | 1127000 |
| HI1072 | 1135048 | 1133604 |
| HI1073 | 1135234 | 1134995 |
| HI1074 | 1137513 | 1135257 |
| HI1075 | 1137884 | 1137513 |
| HI1076 | 1138337 | 1137888 |
| HI1084 | 1148702 | 1148448 |
| HI1085 | 1149040 | 1148726 |
| HI1086 | 1149665 | 1149054 |
| HI1087 | 1150228 | 1149728 |
| HI1088 | 1151024 | 1150242 |
| HI1091 | 1153141 | 1153776 |
| HI1092 | 1153784 | 1154446 |
| HI1093 | 1154507 | 1155244 |
| HI1094 | 1155289 | 1155489 |
| HI1095 | 1155489 | 1158007 |
| HI1096 | 1156007 | 1157950 |
| HI1097 | 1158092 | 1158634 |
| HI1098 | 1158637 | 1160013 |
| HI1099 | 1160451 | 1160492 |
| HI1100 | 1160501 | 1160632 |
| HI1101 | 1160637 | 1160942 |
| HI1103 | 1164060 | 1163077 |
| HI1107 | 1166804 | 1168024 |
| HI1121 | 1184774 | 1184115 |
| HI1128 | 1191629 | 1192577 |
| HI1129 | 1193461 | 1193234 |
| HI1131 | 1195069 | 1195242 |
| HI1132 | 1195447 | 1195899 |
| HI1133 | 1195933 | 1196895 |
| HI1149 | 1215838 | 1214972 |
| HI1150 | 1216338 | 1215847 |
| HI1151 | 1217066 | 1216344 |
| HI1152 | 1217588 | 1217073 |
| HI1153 | 1218198 | 1217572 |
| HI1154 | 1218770 | 1218237 |
| HI1156 | 1220425 | 1220951 |
| HI1158 | 1223159 | 1222595 |
| HI1165 | 1231243 | 1230773 |
| HI1168 | 1235872 | 1236231 |
| HI1171 | 1238778 | 1239119 |
| HI1172 | 1239729 | 1239166 |
| HI1176 | 1242816 | 1243383 |
| HI1178 | 1244125 | 1244051 |
| HI1179 | 1244360 | 1244142 |
| HI1184 | 1246098 | 1247517 |
| HI1185 | 1248305 | 1248859 |
| HI1186 | 1248934 | 1249107 |
| HI1193 | 1256974 | 1256552 |
| HI1194 | 1257654 | 1257067 |
| HI1195 | 1257810 | 1257950 |
| HI1198 | 1260250 | 1261479 |
| HI1201 | 1263689 | 1264309 |
| HI1202 | 1264360 | 1265430 |
| HI1205 | 1267550 | 1268050 |
| HI1206 | 1270263 | 1268131 |
| HI1208 | 1271751 | 1272191 |
| HI1218 | 1282515 | 1283219 |
| HI1219 | 1283219 | 1283904 |
| HI1225 | 1291759 | 1292049 |
| HI1226 | 1292052 | 1293239 |
| HI1237 | 1306218 | 1306673 |
| HI1238 | 1307299 | 1306835 |

-continued

| UNKNOWNS | | |
|---|---|---|
| HI1239 | 1308273 | 1307173 |
| HI1243 | 1313696 | 1313037 |
| HI1244 | 1313794 | 1314591 |
| HI1246 | 1318522 | 1315827 |
| HI1247 | 1317233 | 1318616 |
| HI1249 | 1319911 | 1321851 |
| HI1151 | 1325506 | 1324541 |
| HI1252 | 1326129 | 1325512 |
| HI1253 | 1326454 | 1326758 |
| HI1255 | 1327256 | 1328923 |
| HI1255 | 1328946 | 1329326 |
| HI1257 | 1329334 | 1330392 |
| HI1258 | 1330818 | 1330839 |
| HI1259 | 1330839 | 1331300 |
| HI1260 | 1331300 | 1331470 |
| HI1265 | 1339879 | 1339148 |
| HI1268 | 1346269 | 1345733 |
| HI1269 | 1346269 | 1346836 |
| HI1270 | 1348824 | 1346241 |
| HI1271 | 1348849 | 1347025 |
| HI1272 | 1347022 | 1347135 |
| HI1273 | 1347135 | 1347323 |
| HI1276 | 1348850 | 1349453 |
| HI1283 | 1356439 | 1356654 |
| HI1284 | 1356655 | 1357185 |
| HI1285 | 1355080 | 1358502 |
| HI1289 | 1367227 | 1365851 |
| HI1291 | 1369084 | 1369447 |
| HI1292 | 1369450 | 1370385 |
| HI1294 | 1372453 | 1371617 |
| HI1295 | 1373365 | 1372583 |
| HI1296 | 1373601 | 1373359 |
| HI1297 | 1373735 | 1373532 |
| HI1300 | 1375530 | 1375949 |
| HI1301 | 1375971 | 1376663 |
| HI1303 | 1379236 | 1380176 |
| HI1304 | 1380896 | 1380210 |
| HI1309 | 1384563 | 1385051 |
| HI1312 | 1386755 | 1386510 |
| HI1313 | 1386780 | 1387538 |
| HI1317 | 1391445 | 1391927 |
| HI1318 | 1392096 | 1392410 |
| HI1319 | 1392802 | 1393383 |
| HI1320 | 1393468 | 1394280 |
| HI1326 | 1401970 | 1401527 |
| HI1329 | 1404808 | 1405533 |
| HI1330 | 1405533 | 1405067 |
| HI1335 | 1409063 | 1405968 |
| HI1336 | 1409263 | 1408968 |
| HI1340 | 1412995 | 1414329 |
| HI1341 | 1414391 | 1414882 |
| HI1343 | 1416879 | 1415557 |
| HI1344 | 1417517 | 1417009 |
| HI1345 | 1418133 | 1419509 |
| HI1352 | 1426118 | 1425637 |
| HI1354 | 1428276 | 1427314 |
| HI1358 | 1433535 | 1433996 |
| HI1367 | 1450229 | 1449365 |
| HI1369 | 1453591 | 1453010 |
| HI1371 | 1458706 | 1455929 |
| HI1372 | 1461329 | 1458813 |
| HI1378 | 1469827 | 1470732 |
| HI1379 | 1470738 | 1471610 |
| HI1391 | 1481365 | 1481808 |
| HI1394 | 1484556 | 1485584 |
| HI1399 | 1492391 | 1482023 |
| HI1400 | 1493035 | 1492616 |
| HI1401 | 1493171 | 1493004 |
| HI1404 | 1495447 | 1498052 |
| HI1405 | 1496978 | 1498157 |
| HI1407 | 1498433 | 1498230 |
| HI1408 | 1499014 | 1498489 |
| HI1409 | 1499168 | 1499050 |
| HI1410 | 1500612 | 1499515 |
| HI1411 | 1501028 | 1500676 |
| HI1413 | 1503610 | 1504026 |
| HI1414 | 1504094 | 1502787 |

-continued

| UNKNOWNS | | |
|---|---|---|
| HI1415 | 1505280 | 1504099 |
| HI1417 | 1506471 | 1505953 |
| HI1418 | 1506880 | 1506602 |
| HI1419 | 1507067 | 1506795 |
| HI1421 | 1507987 | 1507834 |
| HI1422 | 1506392 | 1508327 |
| HI1423 | 1509030 | 1508428 |
| HI1424 | 1509352 | 1509648 |
| HI1425 | 1509648 | 1509938 |
| HI1426 | 1510250 | 1509975 |
| HI1427 | 1510403 | 1510975 |
| HI1428 | 1511264 | 1511545 |
| HI1431 | 1513776 | 1514795 |
| HI1432 | 1514998 | 1515831 |
| HI1439 | 1521750 | 1522223 |
| HI1440 | 1522224 | 1525568 |
| HI1441 | 1525569 | 1525820 |
| HI1443 | 1526752 | 1528626 |
| HI1450 | 1533358 | 1533038 |
| HI1454 | 1536172 | 1536492 |
| HI1455 | 1536633 | 1536668 |
| HI1456 | 1537150 | 1536568 |
| HI1458 | 1538541 | 1537903 |
| HI1460 | 1540315 | 1539812 |
| HI1462 | 1541101 | 1541340 |
| HI1468 | 1547394 | 1546060 |
| HI1474 | 1554422 | 1554078 |
| HI1477 | 1557241 | 1556189 |
| HI1481 | 1560071 | 1559355 |
| HI1482 | 1560378 | 1560563 |
| HI1484 | 1562720 | 1562989 |
| HI1486 | 1563395 | 1562928 |
| HI1487 | 1564353 | 1564667 |
| HI1489 | 1565191 | 1565349 |
| HI1490 | 1565824 | 1566042 |
| HI1491 | 1566045 | 1566215 |
| HI1492 | 1566221 | 1566778 |
| HI1494 | 1567509 | 1568060 |
| HI1495 | 1568255 | 1568467 |
| HI1497 | 1568697 | 1569200 |
| HI1498 | 1569285 | 1569566 |
| HI1500 | 1569836 | 1570093 |
| HI1501 | 1570093 | 1570344 |
| HI1502 | 1570465 | 1570689 |
| HI1503 | 1570599 | 1571015 |
| HI1504 | 1571343 | 1571909 |
| HI1505 | 1571912 | 1573435 |
| HI1506 | 1573450 | 1575009 |
| HI1507 | 1575103 | 1576344 |
| HI1510 | 1578223 | 1579146 |
| HI1511 | 1579232 | 1579486 |
| HI1512 | 1579501 | 1579614 |
| HI1513 | 1579620 | 1580042 |
| HI1514 | 1580012 | 1580593 |
| HI1515 | 1580609 | 1580797 |
| HI1516 | 1580800 | 1582260 |
| HI1517 | 1582273 | 1582626 |
| HI1518 | 1582642 | 1583022 |
| HI1519 | 1583106 | 1584996 |
| HI1520 | 1584526 | 1584371 |
| HI1523 | 1587316 | 1587624 |
| HI1524 | 1587664 | 1588209 |
| HI1525 | 1588221 | 1588625 |
| HI1526 | 1588625 | 1589892 |
| HI1527 | 1589781 | 1590284 |
| HI1528 | 1590287 | 1592155 |
| HI1529 | 1592772 | 1593659 |
| HI1530 | 1593826 | 1593975 |
| HI1540 | 1605903 | 1606442 |
| HI1541 | 1606426 | 1607595 |
| HI1542 | 1607568 | 1607912 |
| HI1548 | 1613326 | 1613877 |
| HI1549 | 1614482 | 1613931 |
| HI1551 | 1618455 | 1615214 |
| HI1552 | 1616740 | 1617159 |
| HI1554 | 1619807 | 1618580 |
| HI1558 | 1622639 | 1621995 |

-continued

UNKNOWNS

| | | |
|---|---|---|
| HI1561 | 1626292 | 1625114 |
| HI1564 | 1628971 | 1628171 |
| HI1566 | 1630319 | 1629652 |
| HI1568 | 1631692 | 1631537 |
| HI1569 | 1632481 | 1631948 |
| HI1570 | 1632603 | 1632517 |
| HI1572 | 1633105 | 1633257 |
| HI1575 | 1636870 | 1636721 |
| HI1576 | 1637376 | 1636870 |
| HI1577 | 1637498 | 1637439 |
| HI1586 | 1647922 | 1647857 |
| HI1587 | 1648198 | 1648028 |
| HI1588 | 1649605 | 1648189 |
| HI1592 | 1654749 | 1653193 |
| HI1596 | 1659183 | 1657846 |
| HI1597 | 1659861 | 1659247 |
| HI1599 | 1661805 | 1661453 |
| HI1600 | 1662311 | 1661643 |
| HI1601 | 1662648 | 1662328 |
| HI1604 | 1665779 | 1664724 |
| HI1605 | 1666807 | 1668094 |
| HI1606 | 1667750 | 1668800 |
| HI1607 | 1668067 | 1667793 |
| HI1608 | 1668561 | 1668109 |
| HI1609 | 1668769 | 1669416 |
| HI1611 | 1670802 | 1671410 |
| HI1613 | 1672733 | 1673359 |
| HI1614 | 1673350 | 1674312 |
| HI1618 | 1678655 | 1677464 |
| HI1626 | 1686816 | 1686318 |
| HI1627 | 1687436 | 1686819 |
| HI1628 | 1687921 | 1687439 |
| HI1630 | 1688617 | 1687937 |
| HI1631 | 1689671 | 1689177 |
| HI1632 | 1690500 | 1690647 |
| HI1633 | 1690388 | 1689675 |
| HI1634 | 1690881 | 1691282 |
| HI1637 | 1693111 | 1692542 |
| HI1643 | 1702265 | 1700876 |
| HI1649 | 1707765 | 1708781 |
| HI1653 | 1711962 | 1712854 |
| HI1654 | 1712909 | 1713433 |
| HI1656 | 1715839 | 1716046 |
| HI1657 | 1716442 | 1718767 |
| HI1658 | 1717744 | 1717196 |
| HI1659 | 1718225 | 1717860 |
| HI1660 | 1720257 | 1719409 |
| HI1661 | 1720329 | 1722053 |
| HI1662 | 1722056 | 1722412 |
| HI1663 | 1722425 | 1723010 |
| HI1668 | 1732543 | 1731989 |
| HI1670 | 1733232 | 1732596 |
| HI1671 | 1733482 | 1733283 |
| HI1672 | 1733818 | 1733528 |
| HI1673 | 1735404 | 1733836 |
| HI1675 | 1737711 | 1737588 |
| HI1677 | 1738407 | 1739658 |
| HI1678 | 1739641 | 1742283 |
| HI1683 | 1745073 | 1745741 |
| HI1685 | 1747304 | 1747841 |
| HI1686 | 1750100 | 1747940 |
| HI1687 | 1750833 | 1750177 |
| HI1689 | 1752080 | 1753086 |
| HI1690 | 1753041 | 1753819 |
| HI1693 | 1757163 | 1757783 |
| HI1694 | 1757788 | 1758492 |
| HI1707 | 1770253 | 1770983 |
| HI1709 | 1774757 | 1773684 |
| HI1710 | 1775850 | 1774744 |
| HI1715 | 1782227 | 1781885 |
| HI1716 | 1782482 | 1782345 |
| HI1720 | 1786580 | 1785523 |
| HI1721 | 1788831 | 1787176 |
| HI1723 | 1788842 | 1788747 |
| HI1724 | 1789761 | 1788979 |
| HI1726 | 1792471 | 1793034 |
| HI1727 | 1793205 | 1793862 |
| HI1729 | 1794880 | 1795201 |
| HI1730 | 1795181 | 1795556 |
| HI1736 | 1803407 | 1802481 |
| HI1737 | 1804046 | 1803407 |
| HI1742 | 1813828 | 1813296 |
| HI1743 | 1813980 | 1813634 |
| HI1744 | 1814881 | 1813980 |

TABLE 3

Whole Genome Sequencing Strategy

| Stage | Description |
|---|---|
| Random small insert and large Insert library construction | Randomly sheared genomic DNA on the order of 2 kb and 15–20 kb respectively |
| Library Plating | Verify random nature of library and maximize random selection of small insert and large insert clones for template production |
| High-throughout DNA sequencing | Sequence sufficient number of sequence fragments from both ends for 6X coverage |
| Assembly | Assemble random sequence fragments and identify repeat regions |
| Gap closure | |
| a. Physical gaps | Order all contigs (fingerprints, peptide links, lambda clones, PCR) and provide templates for closure |
| b. Sequence gaps | Complete the genome sequence by primer walking |
| Editing | Visual inspection and resolution of sequence ambiguities, including frameshifts |
| Annotation | Identification and description of all predicted coding regions (putative identifications, starts and stops, role assignments, operons, regulatory regions) |

TABLE 4

The theory of shotgun sequencing follows from the application of the equation for the Poisson distribution $p_1 \approx m^1 c^{m/st}$ where x is the number of occurrences of an event and m is the mean number of occurrences. The numbers below predict the assembly of a 1.9 Mb genome with an average sequence fragment size of 460 bp.

| N | % unsequenced | bp unsequenced | DS Gaps | Avg. Gap Length |
|---|---|---|---|---|
| 250 | 94.44 | 1794304 | 236 | 7600 |
| 500 | 89.18 | 1694487 | 446 | 3800 |
| 1,000 | 79.54 | 1511204 | 795 | 1900 |
| 2,000 | 63.26 | 1201967 | 1265 | 950 |
| 3,000 | 50.32 | 956009 | 1509 | 633 |
| 5,000 | 31.83 | 604785 | 1592 | 380 |
| 10,000 | 10.13 | 192508 | 1013 | 190 |
| 15,000 | 3.23 | 61277 | 484 | 127 |
| 20,000 | 1.03 | 19505 | 205 | 95 |
| 25,000 | 0.33 | 6209 | 82 | 76 |
| 30,000 | 0.10 | 1976 | 31 | 63 |
| 50,000 | 0.00 | 20 | 1 | 38 |

TABLE 5

Summary of features of whole genome sequencing of *H. influenzae* Rd

| Description | Number |
|---|---|
| Double stranded templates | 19,687 |
| Forward sequencing reactions (M13-21 primer) | 19,346 |
| # Successful (%) | 16,240 (84%) |
| Average edited read length | 485 bp |
| Reverse sequencing reactions (M13RP1 primer) | 9297 |
| # Successful (%) | 7,744 (83%) |
| Average edited read length | 444 bp |
| Sequence fragments in random assembly | 24,304 |
| Total # of base pairs | 11,631,485 |
| #of contigs | 140 |
| Physical gas closure | 42 |
| PCR | 37 |
| Southern analysis | 15 |
| Lambda clones | 23 |
| Peptide links | 2 |
| Terminator sequencing reactions* | 3,102 |
| # Successful (%) | 2,024 (65%) |
| Average edited read length | 375 bp |
| Genome Size | 1,830,121 bp |
| # of N's in sequence (%) | 188 (0.01%) |
| Coordinates of proposed origin of replication | 602,483–602,764 |
| G/C content | 38% |
| # of rRNA | 6 |
| rrnA, rrnC, rrnD (spacer region) | 723 bp |
| rrnB, rrnE, rrnF (spacer region) | 478 bp |
| # of tRNA genes identified | 54 |
| Number of Predicted Coding Regions | 1,749 |
| # Unassigned role (%) | 724 (41%) |
| No database match | 384 |
| Match hypothetical proteins | 340 |
| #Assigned role (%) | 1025 (59%) |
| Amino acid metabolism | 71 (6.9%) |
| Fatty acid/phospholipid metabolism | 24 (2.3%) |
| Biosynthesis of cofacters, prosthetic groups, and carriers | 54 (5.3%) |
| Purines, pyrimidines, nucleosides, nucleotides | 54 (5.3%) |
| Central intermediary metabolism | 31 (3.0%) |
| Energy metabolism | 99 (9.7%) |
| Cell envelope | 82 (8.0%) |
| Regulatory functions | 63 (6.1%) |
| Replication | 88 (8.6%) |
| Transcription | 27 (2.5%) |
| Translation | 146 (14.2%) |
| Transport/binding proteins | 145 (14.1%) |
| Cellular processes | 42 (4.1%) |
| Other | 99 (9.7%) |

*Includes gap closure, walks on rRNA repeats, and random end-sequencing of lambda clones for assembly confirmation

TABLE 6

Two component systems in *H. influenzae* Rd

| ID | Location | Best Match | % ID | % Sim | Length (bp) |
|---|---|---|---|---|---|
| Sensors: | | | | | |
| HI0221 | 239,378 | arcB (*E. coli*) | 39.5 | 63.9 | 200 |
| HI0269 | 299,541 | narQ (*E. coli*) | 38.1 | 68.0 | 562 |
| HI1713 | 1,781,143 | basS (*E. coli*) | 27.7 | 51.5 | 250 |
| HI1381 | 1,475,017 | phoR (*E. coli*) | 38.1 | 61.6 | 280 |
| Regulators: | | | | | |
| HI0728 | 777,934 | narP (*E. coli*) | 59.3 | 77.0 | 209 |
| HI0839 | 887,011 | cpxR (*E. coli*) | 51.9 | 73.0 | 229 |
| HI0886 | 936,624 | arcA (*E. coli*) | 77.2 | 87.8 | 236 |
| HI1382 | 1,475,502 | phoB (*E. coli*) | 52.9 | 71.4 | 228 |
| HI1714 | 1,781,799 | basR (*E. coli*) | 43.5 | 59.3 | 219 |

SEQUENCE LISTING

The patent contains a lengthy "Sequence Listing" section. A copy of the "Sequence Listing" is available in electronic form from the USPTO web site (http://seqdata.uspto.gov/sequence.html?DocID=05226676B1). An electronic copy of the "Sequence Listing" will also be available from the USPTO upon request and payment of the fee set forth in 37 CFR 1.19(b)(3).

What is claimed is:

1. An isolated polynucleotide fragment comprising a nucleic acid sequence encoding an amino acid sequence encoded by an ORF selected from the group consisting of:
   (a) HI0140, represented by nucleotides 153446–154522 of SEQ ID NO:1;
   (b) HI1585, represented by nucleotides 1647247–1647711 of SEQ ID NO:1;
   (c) HI1167, represented by nucleotides 1234699–1235757 of SEQ ID NO:1;
   (d) HI0714, represented by nucleotides 757488–760739 of SEQ ID NO:1;
   (e) HI0403, represented by nucleotides 421547–422923 of SEQ ID NO:1;
   (f) HI1545, represented by nucleotides 1609845–1610543 of SEQ ID NO:1;
   (g) HI1545, represented by nucleotides 1611384–1613228 of SEQ ID NO:1;
   (h) HI1688, represented by nucleotides 1751031–1752089 of SEQ ID NO:1; and
   (i) HI0918, represented by nucleotides 970249–970839 of SEQ ID NO:1.

2. The isolated polynucleotide of claim 1, wherein said ORF is (a).

3. The isolated polynucleotide of claim 2, wherein said nucleic acid sequence is identical to the nucleic acid sequence of HI0140.

4. The isolated polynucleotide of claim 1, wherein said ORF is (b).

5. The isolated polynucleotide of claim 4, wherein said nucleic acid sequence is identical to the nucleic acid sequence of HI1585.

6. The isolated polynucleotide of claim 1, wherein said ORF is (c).

7. The isolated polynucleotide of claim 6, wherein said nucleic acid sequence is identical to the nucleic acid sequence of HI1167.

8. The isolated polynucleotide of claim 1, wherein said ORF is (d).

9. The isolated polynucleotide of claim 8, wherein said nucleic acid sequence is identical to the nucleic acid sequence of HI0714.

10. The isolated polynucleotide of claim 1, wherein said ORF is (e).

11. The isolated polynucleotide of claim 10, wherein said nucleic acid sequence is identical to the nucleic acid sequence of HI0403.

12. The isolated polynucleotide of claim 11, wherein said ORF is (f).

13. The isolated polynucleotide of claim 12, wherein said nucleic acid sequence is identical to the nucleic acid sequence of HI1545.

14. The isolated polynucleotide of claim 11, wherein said ORF is (g).

15. The isolated polynucleotide of claim 14, wherein said nucleic acid sequence is identical to the nucleic acid sequence of HI1547.

16. The isolated polynucleotide of claim 11, wherein said ORF is (h).

17. The isolated polynucleotide of claim 16, wherein said nucleic acid sequence is identical to the nucleic acid sequence of HI1688.

18. The isolated polynucleotide of claim 1, wherein said ORF is (i).

19. The isolated polynucleotide of claim 18, wherein said nucleic acid sequence is identical to the nucleic acid sequence of HI0918.

20. The isolated polynucleotide of claim 14, wherein said polynucleotide comprises a heterologous polynucleotide sequence.

21. The isolated polynucleotide of claim 20, wherein said heterologous polynucleotide sequence encodes a heterologous polypeptide.

22. A method for making a recombinant vector comprising inserting the isolated polynucleotide of claim 1 into a vector.

23. A nucleic acid sequence complimentary to the polynucleotide of claim 1.

24. A recombinant vector comprising the isolated polynucleotide of claim 1.

25. The recombinant vector of claim 24, wherein said polynucleotide is operably associated with a heterologous regulatory sequence that controls gene expression.

26. A recombinant host cell comprising the isolated polynucleotide of claim 1.

27. The recombinant host cell of claim 26, wherein said polynucleotide is operably associated with a heterologous regulatory sequence that controls gene expression.

28. A method for producing a polypeptide, comprising:
   (a) culturing a host cell under conditions suitable to produce a polypeptide encoded by the polynucleotide of claim 1, and
   (b) recovering the polypeptide from the cell culture.

29. An isolated polynucleotide comprising a nucleic acid sequence encoding at least 15 contiguous amino acid residues of an amino acid sequence encoded by an ORF selected from the group consisting of:
   (a) HI0714, represented by nucleotides 757488–760739 of SEQ ID NO:1; and
   (b) HI1688, represented by nucleotides 1751031–1752089 of SEQ ID NO:1.

30. The isolated polynucleotide of claim 29, wherein said ORF is (a).

31. The isolated polynucleotide of claim 29, wherein said ORF is (b).

32. An isolated polynucleotide complementary to the polynucleotide of claim 29.

33. The isolated polynucleotide of claim 29, wherein said polynucleotide comprises a heterologous polynucleotide sequence.

34. The isolated polynucleotide of claim 33, wherein said heterologous polynucleotide sequence encodes a heterologous polypeptide.

35. A method for making a recombinant vector comprising inserting the isolated polynucleotide of claim 29 into a vector.

36. A recombinant vector comprising the isolated polynucleotide of claim 29.

37. The recombinant vector of claim 36, wherein said polynucleotide is operably associated with a heterologous regulatory sequence that controls gene expression.

38. A recombinant host cell comprising the isolated polynucleotide of claim 29.

39. The recombinant host cell of claim 38, wherein said polynucleotide is operably associated with a heterologous regulatory sequence that controls gene expression.

40. A method for producing a polypeptide, comprising:
   (a) culturing a host cell under conditions suitable to produce a polypeptide encoded by the polynucleotide of claim 29; and
   (b) recovering the polypeptide from the cell culture.

41. The isolated polynucleotide of claim 29, wherein said polynucleotide comprises a nucleic acid sequence encoding at least 30 contiguous amino acid residues of an amino acid sequence encoded by an ORF selected from the group consisting of:
- (a) HI0714, represented by nucleotides 757488–760739 of SEQ ID NO:1; and
- (b) HI1688, represented by nucleotides 1751031–1752089 of SEQ ID NO:1.

42. The isolated polynucleotide of claim 41, wherein said ORF is (a).

43. The isolated polynucleotide of claim 41, wherein said ORF is (b).

44. An isolated polynucleotide complementary to the polynucleotide of claim 41.

45. The isolated polynucleotide of claim 41, wherein said polynucleotide comprises a heterologous polynucleotide sequence.

46. The isolated polynucleotide of claim 45, wherein said heterologous polynucleotide sequence encodes a heterologous polypeptide.

47. A method for making a recombinant vector comprising inserting the isolated polynucleotide of claim 41, into a vector.

48. A recombinant vector comprising the isolated polynucleotide of claim 41.

49. The recombinant vector of claim 48, wherein said polynucleotide is operably associated with a heterologous regulatory sequence that controls gene expression.

50. A recombinant host cell comprising the isolated polynucleotide of claim 41.

51. The recombinant host cell of claim 50, wherein said polynucleotide is operably associated with a heterologous regulatory sequence that controls gene expression.

52. A method for producing a polypeptide, comprising:
- (a) culturing a host cell under conditions suitable to produce a polypeptide encoded by the polynucleotide of claim 41; and
- (b) recovering the polypeptide from the cell culture.

53. An isolated polynucleotide fragment comprising a nucleic acid sequence which hybridizes under hybridization conditions, comprising hybridization in 5× SSPC and 50% formamide at 50–65° C. and washing in a wash buffer consisting of 0.5× SSPC at 50–60° C., to the complementary strand of an ORF selected from the group consisting of:
- (a) HI0714, represented by nucleotides 757488–760739 of SEQ ID NO:1; and
- (b) HI1688, represented by nucleotides 1751031–1752089 of SEQ ID NO:1.

54. The isolated polynucleotide of claim 53, wherein said ORF is (a).

55. The isolated polynucleotide of claim 53, wherein said ORF is (b).

56. An isolated polynucleotide complementary to the polynucleotide of claim 53.

57. The isolated polynucleotide of claim 53, wherein said polynucleotide comprises a heterologous polynucleotide sequence.

58. The isolated polynucleotide of claim 57, wherein said heterologous polynucleotide sequence encodes a heterologous polypeptide.

59. A method for making a recombinant vector comprising inserting the isolated polynucleotide of claim 53 into a vector.

60. A recombinant vector comprising the isolated polynucleotide of claim 53.

61. The recombinant vector of claim 60, wherein said polynucleotide is operably associated with a heterologous regulatory sequence that controls gene expression.

62. A recombinant host cell comprising the isolated polynucleotide of claim 53.

63. The recombinant host cell of claim 62, wherein said polynucleotide is operably associated with a heterologous regulatory sequence that controls gene expression.

64. A method for producing a polypeptide, comprising:
- (a) culturing a host cell under conditions suitable to produce a polypeptide encoded by the polynucleotide of claim 53; and
- (b) recovering the polypeptide from the cell culture.

65. An isolated polynucleotide comprising at least 50 contiguous nucleotides of an ORF selected from the group consisting of:
- (a) HI0714, represented by nucleotides 757488–760739 of SEQ ID NO:1; and
- (b) HI1688, represented by nucleotides 1751031–1752089 of SEQ ID NO:1.

66. The isolated polynucleotide of claim 65, wherein said ORF is (a).

67. The isolated polynucleotide of claim 65, wherein said ORF is (b).

68. An isolated polynucleotide complementary to the polynucleotide of claim 65.

69. The isolated polynucleotide of claim 65, wherein said polynucleotide comprises a heterologous polynucleotide sequence.

70. The isolated polynucleotide of claim 69, wherein said heterologous polynucleotide sequence encodes a heterologous polypeptide.

71. A method for making a recombinant vector comprising inserting the isolated polynucleotide of claim 65 into a vector.

72. A recombinant vector comprising the isolated polynucleotide of claim 65.

73. The recombinant vector of claim 72, wherein said polynucleotide is operably associated with a heterologous regulatory sequence that controls gene expression.

74. A recombinant host cell comprising the isolated polynucleotide of claim 65.

75. The recombinant host cell of claim 74, wherein said polynucleotide is operably associated with a heterologous regulatory sequence that controls gene expression.

76. A method for producing a polypeptide, comprising:
- (a) culturing a host cell under conditions suitable to produce a polypeptide encoded by the polynucleotide of claim 65; and
- (b) recovering the polypeptide from the cell culture.

77. An isolated polynucleotide comprising at least 100 contiguous nucleotides of an ORF selected from the group consisting of:
- (a) HI0714, represented by nucleotides 757488–760739 of SEQ ID NO:1; and
- (b) HI1688, represented by nucleotides 1751031–1752089 of SEQ ID NO:1.

78. The isolated polynucleotide of claim 77, wherein said ORF is (a).

79. The isolated polynucleotide of claim 77, wherein said ORF is (b).

80. An isolated polynucleotide complementary to the polynucleotide of claim 77.

81. The isolated polynucleotide of claim 77, wherein said polynucleotide is a heterologous polynucleotide sequence.

82. The isolated polynucleotide of claim 81, wherein said heterologous polynucleotide encodes a heterologous polypeptide.

83. A method for making a recombinant vector comprising inserting the isolated polynucleotide of claim 77, into a vector.

84. A recombinant vector comprising the isolated polynucleotide of claim 77.

85. The recombinant vector of claim 84, wherein said polynucleotide is operably associated with a heterologous regulatory sequence that controls gene expression.

86. A recombinant host cell comprising the isolated polynucleotide of claim 77.

87. The recombinant host cell of claim 86, wherein said polynucleotide is operably associated with a heterologous regulatory sequence that controls gene expression.

88. A method for producing a polypeptide, comprising:
(a) culturing a host cell under conditions suitable to produce a polypeptide encoded by the polynucleotide of claim 77; and
(b) recovering the polypeptide from the cell culture.

* * * * *